US010570412B2

(12) United States Patent
Schultheiss et al.

(10) Patent No.: US 10,570,412 B2
(45) Date of Patent: Feb. 25, 2020

(54) **METHOD OF INCREASING RESISTANCE AGAINST SOYBEAN RUST IN TRANSGENIC PLANTS BY INCREASING THE

(51) Int. Cl.
C07K 14/415 (2006.01)
C12N 9/02 (2006.01)
(52) U.S. Cl.
CPC ......... *C12N 9/1007* (2013.01); *C12N 9/1048* (2013.01); *C12Y 114/11* (2013.01); *C12Y 201/01104* (2013.01)

(56) References Cited

U.S. PATENT DOCUMENTS

| | | | |
|---|---|---|---|
| 2005/0108791 A1* | 5/2005 | Edgerton | C07K 14/415 800/284 |
| 2007/0214517 A1 | 9/2007 | Alexandrov et al. | |
| 2007/0256192 A1* | 11/2007 | Herbers | C12N 9/90 800/279 |
| 2009/0100536 A1 | 4/2009 | Adams et al. | |
| 2016/0068856 A1 | 3/2016 | Schultheiss et al. | |
| 2018/0010144 A1 | 1/2018 | Schultheiss et al. | |

FOREIGN PATENT DOCUMENTS

| | | |
|---|---|---|
| WO | WO-2011/140329 A1 | 11/2011 |
| WO | WO-2012/127373 A1 | 9/2012 |

OTHER PUBLICATIONS

Azelmat, Jabrane, et al. "Synthesis and evaluation of antibacterial and anti-inflammatory properties of naturally occurring coumarins." Phytochemistry Letters 13 (2015): 399-405. (Year: 2015).*
Cai, Xueting, et al. "Synthesis and biological evaluation of scopoletin derivatives." Bioorganic & medicinal chemistry 21.1 (2013): 84-92. (Year: 2013).*
Darla, Mark Manidhar, et al. "Synthesis and bio-evaluation of novel 7-hydroxy coumarin derivatives via Knoevenagel reaction." Research on Chemical Intermediates 41.2 (2015): 1115-1133. (Year: 2015).*
Shen, Qiong, et al. "Hydroxycoumarin derivatives: Novel and potent α-glucosidase inhibitors." Journal of medicinal chemistry 53.23 (2010): 8252-8259. (Year: 2010).*
Kontogiorgis, Christos A., and Dimitra J. Hadjipavlou-Litina. "Synthesis and antiinflammatory activity of coumarin derivatives." Journal of medicinal chemistry 48.20 (2005): 6400-6408. (Year: 2005).*
Witaicenis, Aline, et al. "Antioxidant and intestinal anti-inflammatory effects of plant-derived coumarin derivatives." Phytomedicine 21.3 (2014): 240-246. (Year: 2014).*
McArthur, John B., and Xi Chen. "Glycosyltransferase engineering for carbohydrate synthesis." Biochemical Society Transactions 44.1 (2016): 129-142. (Year: 2016).*
Lin, Yuheng, et al. "Combinatorial biosynthesis of plant-specific coumarins in bacteria." Metabolic engineering 18 (2013): 69-77. (Year: 2013).*
Kai, Kosuke, et al. "Accumulation of coumarins in Arabidopsis thaliana." Phytochemistry 67.4 (2006): 379-386. (Year: 2006).*
Peterson, Joseph K., et al. "Biological activities and contents of scopolin and scopoletin in sweetpotato clones." HortScience 38.6 (2003): 1129-1133 (Year: 2003).*
Sun, Huanhuan, et al. "Scopoletin is a phytoalexin against Alternaria alternata in wild tobacco dependent on jasmonate signalling." Journal of experimental botany 65.15 (2014): 4305-4315. (Year: 2014).*
Cai, Xueting, et al. "Synthesis and biological evaluation of scopoletin derivatives." Bioorganic & medicinal chemistry 21.1 (2013): 84-92. (Year: 2013).*
Darla, Mark Manidhar, et al. "Synthesis and bio-evaluation of novel 7-hydroxy coumarin derivatives via Knoevenagel reaction." Research on Chemical Intermediates 41.2 (2015): 1115-1133. (Year: 2015).*
Khunnawutmanotham, Nisachon, et al. "Synthesis and anti-acetylcholinesterase activity of scopoletin derivatives." Bioorganic chemistry 65 (2016): 137-145. (Year: 2016).*
Shen, Qiong, et al. "Hydroxycoumarin derivatives: Novel and potent α-glucosidase inhibitors." Journal of medicinal chemistry 53.23 (2010): 8252-8259. (Year: 2010).*
Kontogiorgis, Christos A., and Dimitra J. Hadjipavlou-Litina. "Synthesis and antiinflammatory activity of coumarin derivatives." Journal of medicinal chemistry 48.20 (2005): 6400-6408. (Year: 2005).*
Witaicenis, Aline, et al. "Antioxidant and intestinal anti-inflammatory effects of plant-derived coumarin derivatives." Phytomedicine 21.3 (2014): 240-246. (Year: 2014).*
Sun, Xinxiao, et al. "Structural insights into substrate specificity of Feruloyl-CoA 6'-Hydroxylase from Arabidopsis thaliana." Scientific reports 5 (2015): 10355. (Year: 2015).*
McArthur, John B., and Xi Chen. "Glycosyltransferase engineering for carbohydrate synthesis." Biochemical Society Transactions 44.1 (2016): 129-142. (Year: 2016).*
Levee, V., and A. Seguin. "Inducible expression of the heterologous PAL2 promoter from bean in white pine (*Pinus strobus*) transgenic cells." Tree physiology 21.10 (2001): 665-672. (Year: 2001).*
Nicole Beate Schmid: "Identification and characterization of Arabidopsis genes involved in tolerance to Fe deficiency mediated chlorosis", Dissertation zur Erlangung des Doktorgrades der Naturmwissenschaften, May 28, 2014 (May 28, 2014), XP002740757, submitted in IDS (Year: 2014).*
Jeandet, Philippe, et al. "Modulation of phytoalexin biosynthesis in engineered plants for disease resistance." International journal of molecular sciences 14.7 (2013): 14136-14170. (Year: 2013).*
Sanzani, Simona M., Leonardo Schena, and Antonio Ippolito. "Effectiveness of phenolic compounds against citrus green mould." Molecules 19.8 (2014): 12500-12508. (Year: 2014).*
Carpinella, Maria C., Carlos G. Ferrayoli, and Sara M. Palacios. "Antifungal synergistic effect of scopoletin, a hydroxycoumarin isolated from *Melia azedarach* L. fruits." Journal of agricultural and food chemistry 53.8 (2005): 2922-2927. (Year: 2005).*
Lin, Yuheng, et al. "Combinatorial biosynthesis of plant-specific coumarins in bacteria." Metabolic engineering 18 (2013): 69-77. (Year: 2013).*
Kai, Kosuke, et al. "Scopoletin is biosynthesized via ortho-hydroxylation of feruloyl CoA by a 2-oxoglutarate-dependent dioxygenase in Arabidopsis thaliana." The Plant Journal 55.6 (2008): 989-999. (Year: 2008).*
Ahl Goy et al., Accumulation of scopoletin is associated with the high disease resistance of the hybrid Nicotiana glutinosa x Nicotiana debneyi, Planta, 191:200-6 (1993).
Database Geneseq [Online], "Amino Acid Sequence SEQ ID 18550", XP002740752, Retrieved from EBI accession No. GSP:AWJ45345, Database accession No. AWJ45345, Oct. 29, 2009.
Database Geneseq [Online], "Arabidopsis Thaliana Amino Acid Sequence SEQ ID 81044", XP002740753, retrieved from EBI accession No. GSP:ARM81672, Database accession No. ARM81672.
Database Geneseq [Online], "Arabidopsis Thaliana Glucosyltransferase (GTase) A961 Protein", XP002740756, retrieved from EBI accession No. GSP:AAE07511, Database accession No. AAE07511 (Jun. 15, 2007).
Database Geneseq [Online], "Arabidopsis Thaliana Protein, SEQ ID 1605.", XP002740755, retrieved from EBI accession No. GSP:AWW66938, Database accession No. AWW66938, Nov. 12, 2009.
Database Geneseq [Online], "Plant Biomass-Modulating DNA Encoded Protein SEQ :78.", XP002740754, retrieved from EBI accession No. GSP:AZP53437, Database accession No. AZP53437, Jan. 5, 2012.
European Search Report for EP Patent Application No. 15153820.4, Completed on Jun. 15, 2015, 5 pages.
Fourcroy et al., Involvement of the ABCG37 transporter in secretion of scopoletin and derivatives by Arabidopsis roots in response to iron deficiency, New Phytol., 201(1):155-67 (2014).
Fraissinet-Tachet et al., Two tobacco genes induced by infection, elicitor and salicylic acid encode glucosyltransferases acting on phenylpropanoids and benzoic acid derivatives, including salicylic acid, FEBS Lett., 437(3):319-23 (1998).
Gielen et al., The complete nucleotide sequence of the TL-DNA of the Agrobacterium tumefaciens plasmid pTiAch5, EMBO J., 3(4):835-46 (1984).

(56) References Cited

OTHER PUBLICATIONS

Gnonlonfin et al., Review scopoletin—a coumarin phytoalexin with medicinal properties, Crit. Rev. Plant Sci., 31:1, 47-56 (2012).
Herbers et al., Functional analysis of a leucine aminopeptidase from *Solanum tuberosum* L, Planta, 194(2):230-40 (1994).
International Application No. PCT/EP2016/052019, International Search Report and Written Opinion, dated Mar. 29, 2016.
Kai et al., Scopoletin is biosynthesized via ortho-hydroxylation of feruloyl CoA by a 2-oxoglutarate-dependent dioxygenase in Arabidopsis thaliana, Plant J., 55(6):989-99 (2008).
Kawalleck et al., Polyubiquitin gene expression and structural properties of the ubi4-2 gene in Petroselinum crispum, Plant Mol. Biol., 21(4):673-84 (1993).
Lee et al., Novel plant transformation vectors containing the superpromoter, Plant Physiol., 145(4):1294-300 (2007).
Lim et al., Evolution of substrate recognition across a multigene family of glycosyltransferases in Arabidopsis, Glycobiology, 13(3):139-45 (2003).
Schmid, "Identification and Characterization of Arabidopsis Genes Involved in Tolerance to Fe Deficiency-Mediated Chlorosis", Dissertation zur Erlangung des Doktorgrades der Naturwissenschaften der Naturwissenschaftlichen Faukultät I—Biowissenschaften—der Martin-Luther-Universität Halle-Wittenberg (Apr. 8, 1983).
Shimizu, 2-Oxoglutarate-dependent dioxygenases in the biosynthesis of simple coumarins, Front Plant Sci., 5:549 (2014).
Sun et al., Scopoletin is a phytoalexin against Alternaria alternata in wild tobacco dependent on jasmonate signalling, J. Exp. Bot., 65(15):4305-15 (2014).
Tal et al., The metabolism of sunflower phytoalexins ayapin and scopoletin: plant-fungus interactions, Plant Physiol., 81(1):167-72 (1986).

\* cited by examiner

Figure 6

| | |
|---|---|
| SEQ-ID-No. 1 | DNA-sequence F6H1 |
| SEQ-ID-No. 2 | Protein-sequence F6H1 |
| SEQ-ID-No. 3 | DNA-sequence CCoAOMT1 |
| SEQ-ID-No. 4 | Protein-sequence CCoAOMT1 |
| SEQ-ID-No. 5 | DNA-sequence ABCG37 |
| SEQ-ID-No. 6 | Protein-sequence ABCG37 |
| SEQ-ID-No. 7 | DNA-sequence UGT71C1 |
| SEQ-ID-No. 8 | Protein-sequence UGT71C1 |
| SEQ-ID-No. 9, 11, 13, 15, 17, 19, 21 | Further examples DNA-sequence F6H1 |
| SEQ-ID-No. 10, 12, 14, 16, 18, 20, 22 | Further examples protein-sequence F6H1 |
| SEQ-ID-No. 23, 25, 27, 29, 31, 33, 35, 37, 39, 41, 43, 45, 47 | Further examples DNA-sequence CCoAOMT1 |
| SEQ-ID-No. 24, 26, 28, 30, 31, 34, 36, 38, 40, 42, 44, 46, 48 | Further examples protein-sequence CCoAOMT1 |
| SEQ-ID-No. 49, 51, 53 | Further examples DNA-sequence ABCG37 |
| SEQ-ID-No. 50, 52, 54 | Further examples protein-sequence ABCG37 |
| SEQ-ID-No. 55, 57, 59, 61 | Further examples DNA-sequence UGT71C1 |
| SEQ-ID-No. 56, 58, 60, 62 | Further examples protein-sequence UGT71C1 |
| SEQ-ID-No. 63 | Domains protein-sequence F6H1 |
| SEQ-ID-No.64 | Domains protein-sequence CCoAOMT1 |
| SEQ-ID-No.65, 66, 67, 68 | Domains protein-sequence ABCG37 |
| SEQ-ID-No. 69, 70 | Domains protein-sequence UGT71C1 |
| SEQ-No. 71 | vector: OmegaFlagF6H1_in_pB2GW7 |
| SEQ-No. 72 | vector: F6H1_in_pB2GW7 |
| SEQ-No. 73 | vector: F6H1_in_soy_transformation_vector |
| SEQ-No. 74 | vector: F6H1+CCoAOMT1_in_soy_transformation_vector |
| SEQ-No. 75 | vector: F6H1+CCoAOMT1+ABCG37_in_soy_transformation_vector |
| SEQ-No. 76 | Cloning primer: F6H1_attB1 forward primer |

Figure 6 continued

| SEQ-No. 77 | Cloning primer: F6H1_attB2 reverse primer |
| --- | --- |
| SEQ-No. 78 | Cloning primer: Ω-FLAG-attB1 forward Primer |
| SEQ-No. 79 | Cloning primer: Ω-FLAG-attB5r reverse Primer |
| SEQ-No. 80 | Cloning primer: F6H1-attB5 forward Primer |
| SEQ-No. 81 | Primer for expression analysis: F6H1_RT_F |
| SEQ-No. 82 | Primer for expression analysis: F6H1_RT_R |
| SEQ-No. 83 | Primer for expression analysis: CCoAOMT1_RT_F |
| SEQ-No. 84 | Primer for expression analysis CCoAOMT1_RT_R |
| SEQ-No. 85 | Primer for expression analysis: ABCG37_RT_F |
| SEQ-No. 86 | Primer for expression analysis: ABCG37_RT_R |
| SEQ-No. 87 | Primer for expression analysis: UGT71C1_RT_R |
| SEQ-No. 88 | Primer for expression analysis: UGT71C1_RT_R |

Figure 7a F6H1 (At3g13610) gene sequence atggctccaacactcttgacaacccaattctcaaatccagctgaagtaaccgactttgtagtctacaaaggaaatggtgttaagg
gtttatcagaaacaggaatcaaagctcttccagaacaatacattcagccacttgaagaacgactcatcaacaaattcgtcaacg
aaacagatgaagccattccagttatcgatatgtcgaaccctgatgaggacagagtcgctgaagctgtttgtgatgctgctgagaa
atgggggttctttcaagtgatcaatcatggagttcctttggaagttcttgatgacgtcaaggctgcgactcacaagttcttcaatctcc
ctgttgaagagaagcgcaagttcactaaagagaattcgctgtcgacgactgttaggtttgggacgagttttagtcctcttgcagag
caagcgcttgagtggaaagattatctcagcctcttctttgtctctgaagctgaagctgaacagttctggcctgatatctgcaggaatg
aaacgttagagtacattaacaagtcaaagaagatggtgaggaggcttctagagtatttgggaaagaatctcaatgttaaagagc
ttgacgagacgaaagaatcactctttatgggctcgattcgagtcaaccttaactactacccatctgccctaatccggacctaaca
gttggtgttggtcgccactcagacgtctcttctctcaccattctcttacaagaccagatcggtggtctacacgtgcgttctctggcttca
gggaactgggttcacgtgcctccggttgctggatcttttgtgatcaacatcggagatgcgatgcagatcatgagcaatggtctgta
caagagcgtggagcatcgtgtcttagccaatggttacaataatagaatctctgttcctatctttgtgaacccaaaaccagagtcagt
tattggtcctctacctgaggtgattgcaaacggagaggaaccgatttacagagacgtcctgtactctgattacgtcaagtatttcttc
aggaaggcacacgatggaaagaaaaccgtcgattacgccaagatctga Figure 7b F6H1 (At3g13610) protein sequence

```
MAPTLLTTQFSNPAEVTDFVVYKGNGVKGLSETGIKALPEQYIQPLEERL  50
INKFVNETDEAIPVIDMSNPDEDRVAEAVCDAAEKWGFFQVINHGVPLEV 100
LDDVKAATHKFFNLPVEEKRKFTKENSLSTTVRFGTSFSPLAEQALEWKD 150
YLSLFFVSEAEAEQFWPDICRNETLEYINKSKKMVRRLLEYLGKNLNVKE 200
LDETKESLFMGSIRVNLNYYPICPNPDLTVGVGRHSDVSSLTILLQDQIG 250
GLHVRSLASGNWVHVPPVAGSFVINIGDAMQIMSNGLYKSVEHRVLANGY 300
NNRISVPIFVNPKPESVIGPLPEVIANGEEPIYRDVLYSDYVKYFFRKAH 350
DGKKTVDYAKI*
```

Figure 8a CCoAOMT1 (At4g34050) gene sequence

Atggcgacgacaacaacagaagcaacgaagacatcatcgaccaatggagaagatcagaagcagtctcagaatcttcgac
atcaagaagttggtcacaagagtctcttacagagcgatgatctctaccagtatatactggagacaagtgtgtatcctagagaacc
agaatcaatgaaggaactcagggaagtgacagcaaaacatccatggaacataatgaccacatcagctgatgaaggacagtt
cttaaacatgcttatcaagctcgttaacgccaagaacacaatggagatcggagtttacactggctactctcttctcgccaccgctct
tgctctccctgaagacggcaaaattctggctatggatgtcaacagagagaattacgaattgggtttaccgatcattgagaaagcc
ggcgttgctcacaagatcgacttcagggaaggccctgctcttcccgttcttgatgaaatcgttgctgacgagaagaaccatggaa
catatgactttatattcgttgatgctgacaaagacaactacatcaactaccacaagcgtttgatcgatcttgtgaaaattggaggag
tgattggctacgacaacactctgtggaatggttctgtcgtggctcctcctgatgcaccaatgaggaagtacgttcgttactacagag
actttgttcttgagcttaacaaggctcttgctgctgaccctcggatcgagatctgtatgctccctgttggtgatggaatcactatctgcc
gtcggatcagttga Figure 8b CCoAOMT1 (At4g34050) protein sequence

```
MATTTTEATKTSSTNGEDQKQSQNLRHQEVGHKSLLQSDDLYQYILETSV 50
YPREPESMKELREVTAKHPWNIMTTSADEGQFLNMLIKLVNAKNTMEIGV 100
YTGYSLLATALALPEDGKILAMDVNRENYELGLPIIEKAGVAHKIDFREG 150
PALPVLDEIVADEKNHGTYDFIFVDADKDNYINYHKRLIDLVKIGGVIGY 200
DNTLWNGSVVAPPDAPMRKYVRYYRDFVLELNKALAADPRIEICMLPVGD 250
GITICRRIS*
```

Figure 9a ABCG37 (PDR9; AT3G53480) gene sequence atggctcatatggttggagcagacgatattgagtcattgagagtagagcttgcagagatcggaagaagcatcagatcatcattcc
ggagacatacttcgagtttcagaagcagctcttcaatatatgaagttgaaaatgatggtgatgttaatgatcatgatgcagagtatg
ctctgcaatgggctgagattgagagattaccaactgtcaagcgaatgagatcgactctccttgatgatggcgatgagtccatgac
cgagaaaggaagaagagtcgttgatgtcacaaagcttggagccgtggaacgtcatctgatgattgagaaactcatcaaacac
attgagaatgataatctcaagttgctcaagaaaatcaggagaagaatagacagagtcgggatggagttaccgaccatagaag
tgaggtacgagagtttaaaagtggtggccgagtgcgaggttgtcgaagggaaggcacttccaacactgtggaacactgctaag
cgtgttttatctgaactggtgaagctcactggtgcaaaaacacatgaagccaagataaacattattaatgatgttaatggcattata
aagccaggaaggttaacactgttgcttggtcctcctagctgcggaaaaacaactttgttaaaggccttgtctggaaatttagaaaa
caatctaaagtgttcaggtgaaatatcttacaatggacacagactggatgagtttgttcctcagaaaacttcagcgtacataagtc
aatatgatctgcacattgcagagatgacagtgagggagacagttgacttctcagctcgttgtcagggcgttggtagccgaacag
atattatgatggaagttagtaaaagagaaaaggaaaaaggaatcattcctgacacagaagtggatgcttacatgaaagcaatt
tctgttgaaggactccaaagaagtctgcaaacagattacattttgaagattctcggacttgatatttgtgcagaaatattgattggag
atgtgatgaggagaggtatatcaggaggtcaaaagaagcgtcttaccacagctgagatgatcgttggcccgacaaaggctctg
tttatggatgaaataacaaatggcctagacagctccacagcttttcagattgtcaaatctcttcagcagtttgctcacatatcaagcg
ctactgtacttgtttcgcttcttcaacccgccccagaatcctatgacctctttgatgacattatgctgatggccaaaggaagaatcgtg
tatcatggtccacgcggtgaagtccttaacttctttgaggattgtggattccgatgccctgaaaggaagggtgttgcagactttctcc
aggaggttatatccaaaaaagatcaagcacaatactggtggcacgaggatttaccttacagttttgtctcggtagaaatgttgtcg
aagaagttcaaggacttgagtattgggaaaaagatcgaagacactctgtcaaagccatatgatagatccaaaagccataagg
atgctttgtccttcagtgtgtattctcttccaaactgggagctgttcatagcatgcatatcaagagagtatcttctcatgaagagaaac
tatttcgtctatattttcaagactgctcagcttgttatggccgcattcatcactatgacagtgtttatccgaacacggatgggtattgata
tcattcatggaaattcttacatgagtgccctcttttcgccctcattatacttcttgttgacggattcccagagttgtctatgacggctcaa
cgtctagccgtgttttataagcagaagcagttgtgtttctatcctgcatgggcgtatgcaatccctgcaacagtgttaaaggtccctct
ctcgttctttgaatctctcgtttggacctgcctctcatactatgtcattggatacacccctgaagcatccaggttcttcaagcagttcatt
ctactctttgctgttcacttcacctcgatatccatgttccggtgtctagctgcaatcttccagacagtagttgcttcaatcacagctggc
agttttggtatattattcacatttgtctttgccggtttcgtcattccaccaccttctatgccagcatggctcaagtgggggtttctgggcaaa
tcctttgagttacggtgagattgggttatcagtaaacgagtttcttgctccaaggtggaatcagatgcaacccaataattttaccttag
gacgaaccatactccaaacccgtggaatggactacaacggttacatgtactgggtatcattatgtgccttgttgggtttcactgtgct
cttcaacatcattttcactctggctctaacgttcttgaaatcacccacatcatctcgagccatgatttcgcaagacaaactctctgag
ctgcaaggaacagaaaagtcaacagaagattcttctgtcaggaaaaagaccacagactcccctgtaaagaccgaagaaga
agacaaaatggtcttaccattcaagcctctcactgtaacatttcaagacttgaactatttcgttgacatgccagtggagatgagag
accaaggatatgatcagaagaaactacaacttctctcagatatcacaggagctttccgtcccggaatcctaacggcactaatgg
gagtgagtggagctggaaaaaccactcttctcgacgttctagccggaaggaaaacaagcggatacatcgaaggagacatta

Figure 9a (continued):

gaatcagtggcttccctaaagtccaagaaacattcgctagagtctcaggctactgtgaacaaacagatattcactcaccaaaca
tcactgtagaagaatccgtaatctactcggcttggcttcgtctagctcctgagatcgatgccacaacaaaaaccaaattcgtgaa
gcaagtgcttgagacgatcgaattagatgagattaaagattcattggtgggagtcaccggagttagtggattatcgacggagca
aaggaagagattgacgattgcggtggagttggtggcgaatccgtcgattatatttatggatgagccaacgacggggctagacg
caagagcagctgccattgttatgagagctgtgaagaacgtcgctgatactggacgaaccatcgtctgtactattcatcagcctagt
atcgacattttgaagccttcgacgagctggtgcttcttaaaagaggtggtcgcatgatctacacaggaccattaggccaacattc
acgtcacattatcgagtattttgagagtgttcctgaaattcctaaaataaaagacaaccacaatccagcaacatggatgcttgatg
ttagttcacagtcggtagaaattgaacttggtgtcgatttcgcaaaaatctaccatgactctgctctttacaagcgaaactcagagct
tgtgaaacagttgagccagccagattcaggatcaagtgatatacagtttaagagaacctttgcacaaagctggtggggacaatt
caaatctattctatggaaaatgaacttgtcttattggagaagcccttcttataacctaatgcgtatgatgcacactttagtctcttctttg
atcttcggcgcacttttctggaaacaaggccaaaatctagatactcaacagagtatgttcacagtatttggagcgatctacggtttg
gtactcttcttagggataaacaattgtgcatcagctcttcaatatttcgaaacagagagaaatgttatgtaccgggaaagattcgca
gggatgtactcagcgactgcttatgcattgggtcaagtggtgactgagatacctatatattcatacaagctgccgagtttgtgatcg
taacatatccaatgatcggtttctatccttcagcctacaaagtcttttggtcactctactctatgttttgctcactactcactttcaactacc
ttgcgatgttcctcgtctccatcacgccaaacttcatggttgccgcgattcttcaatcgctcttttatgttggtttcaaccttttttcggggttt
ttgatcccccaaacgcaagtaccagggtggtggatttggttatattatctaacaccaacgtcttggacactcaacgggtttatctcgt
cccaatacggcgatattcatgaagagatcaatgtctttggacaatccacgacggttgcaagattcttgaaagactattttggatttc
atcatgacctttggcggttaccgcggttgttcaaatcgcttttcccattgccttagcttctatgtttgcattcttcgtgggcaaactcaact
tccaacgaagatga

Figure 9b ABCG37 (PDR9; AT3G53480) protein sequence

```
MAHMVGADDIESLRVELAEIGRSIRSSFRRHTSSFRSSSSIYEVENDGDV  50
NDHDAEYALQWAEIERLPTVKRMRSTLLDDGDESMTEKGRRVVDVTKLGA  100
VERHLMIEKLIKHIENDNLKLLKKIRRRIDRVGMELPTIEVRYESLKVVA  150
ECEVVEGKALPTLWNTAKRVLSELVKLTGAKTHEAKINIINDVNGIIKPG  200
RLTLLLGPPSCGKTTLLKALSGNLENNLKCSGEISYNGHRLDEFVPQKTS  250
AYISQYDLHIAEMTVRETVDFSARCQGVGSRTDIMMEVSKREKEKGIIPD  300
TEVDAYMKAISVEGLQRSLQTDYILKILGLDICAEILIGDVMRRGISGGQ  350
KKRLTTAEMIVGPTKALFMDEITNGLDSSTAFQIVKSLQQFAHISSATVL  400
VSLLQPAPESYDLFDDIMLMAKGRIVYHGPRGEVLNFFEDCGFRCPERKG  450
VADFLQEVISKKDQAQYWWHEDLPYSFVSVEMLSKKFKDLSIGKKIEDTL  500
SKPYDRSKSHKDALSFSVYSLPNWELFIACISREYLLMKRNYFVYIFKTA  550
QLVMAAFITMTVFIRTRMGIDIIHGNSYMSALFFALIILLVDGFPELSMT  600
AQRLAVFYKQKQLCFYPAWAYAIPATVLKVPLSFFESLVWTCLSYYVIGY  650
TPEASRFFKQFILLFAVHFTSISMFRCLAAIFQTVVASITAGSFGILFTF  700
VFAGFVIPPPSMPAWLKWGFWANPLSYGEIGLSVNEFLAPRWNQMQPNNF  750
TLGRTILQTRGMDYNGYMYWVSLCALLGFTVLFNIIFTLALTFLKSPTSS  800
RAMISQDKLSELQGTEKSTEDSSVRKKTTDSPVKTEEEDKMVLPFKPLTV  850
TFQDLNYFVDMPVEMRDQGYDQKKLQLLSDITGAFRPGILTALMGVSGAG  900
KTTLLDVLAGRKTSGYIEGDIRISGFPKVQETFARVSGYCEQTDIHSPNI  950
TVEESVIYSAWLRLAPEIDATTKTKFVKQVLETIELDEIKDSLVGVTGVS  1000
GLSTEQRKRLTIAVELVANPSIIFMDEPTTGLDARAAAIVMRAVKNVADT  1050
GRTIVCTIHQPSIDIFEAFDELVLLKRGGRMIYTGPLGQHSRHIIEYFES  1100
VPEIPKIKDNHNPATWMLDVSSQSVEIELGVDFAKIYHDSALYKRNSELV  1150
KQLSQPDSGSSDIQFKRTFAQSWWGQFKSILWKMNLSYWRSPSYNLMRMM  1200
HTLVSSLIFGALFWKQGQNLDTQQSMFTVFGAIYGLVLFLGINNCASALQ  1250
YFETERNVMYRERFAGMYSATAYALGQVVTEIPYIFIQAAEFVIVTYPMI  1300
GFYPSAYKVFWSLYSMFCSLLTFNYLAMFLVSITPNFMVAAILQSLFYVG  1350
FNLFSGFLIPQTQVPGWWIWLYYLTPTSWTLNGFISSQYGDIHEEINVFG  1400
QSTTVARFLKDYFGFHHDLLAVTAVVQIAFPIALASMFAFFVGKLNFQRR  1450
*
```

Figure 10a UGT71C1 (At2g29750) gene sequence atggggaagcaagaagatgcagagctcgtcatcatacctttcccttctccggacacattctcgcaacaatcgaactcgccaaa
cgtctcataagtcaagacaatcctcggatccacaccatcaccatcctctattggggattacctttattcctcaagctgacacaatc
gctttcctccgatccctagtcaaaaatgagcctcgtatccgtctcgttacgttgcccgaagtccaagaccctccaccaatggaact
ctttgtggaatttgccgaatcttacattcttgaatacgtcaagaaaatggttcccatcatcagagaagctctctccactctcttgtcttcc
cgcgatgaatcgggttcagttcgtgtggctggattggttcttgacttcttctgcgtccctatgatcgatgtaggaaacgagtttaatctc
ccttcttacattttcttgacgtgtagcgcagggttcttgggtatgatgaagtatcttccagagagacaccgcgaaatcaaatcggaa
ttcaaccggagcttcaacgaggagttgaatctcattcctggttatgtcaactctgttcctactaaggttttgccgtcaggtctattcatg
aaagagacctacgagccttgggtcgaactagcagagaggtttcctgaagctaagggtattttggttaattcatacacagctctcg
agccaaacggttttaaatatttcgatcgttgtccggataactacccaaccatttacccaatcgggccgatattatgctccaacgacc
gtccgaatttggactcatcggaacgagatcggatcataacttggctagatgaccaacccgagtcatcggtcgtgttcctctgtttcg
ggagcttgaagaatctcagcgctactcagatcaacgagatagctcaagccttagagatcgttgactgcaaattcatctggtcgttt
cgaaccaacccgaaggagtacgcgagcccttacgaggctctaccacacgggttcatggaccgggtcatggatcaaggcattg
tttgtggttgggctcctcaagttgaaatcctagcccataaagctgtgggaggattcgtatctcattgtggttggaactcgatattggag
agtttgggtttcggcgttccaatcgccacgtggccgatgtacgcggaacaacaactaaacgcgttcacgatggtgaaggagctt
ggtttagccttggagatgcggttggattacgtgtcggaagatggagatatagtgaaagctgatgagatcgcaggaaccgttagat
ctttaatggacggtgtggatgtgccgaagagtaaagtgaaggagattgctgaggcgggaaaagaagctgtggacggtggatct
tcgtttcttgcggttaaaagattcatcggtgacttgatcgacggcgtttctataagtaagtag

Figure 10b UGT71C1 (At2g29750) protein sequence

```
MGKQEDAELVIIPFPFSGHILATIELAKRLISQDNPRIHTITILYWGLPF  50
IPQADTIAFLRSLVKNEPRIRLVTLPEVQDPPPMELFVEFAESYILEYVK 100
KMVPIIREALSTLLSSRDESGSVRVAGLVLDFFCVPMIDVGNEFNLPSYI 150
FLTCSAGFLGMMKYLPERHREIKSEFNRSFNEELNLIPGYVNSVPTKVLP 200
SGLFMKETYEPWVELAERFPEAKGILVNSYTALEPNGFKYFDRCPDNYPT 250
IYPIGPILCSNDRPNLDSSERDRIITWLDDQPESSVVFLCFGSLKNLSAT 300
QINEIAQALEIVDCKFIWSFRTNPKEYASPYEALPHGFMDRVMDQGIVCG 350
WAPQVEILAHKAVGGFVSHCGWNSILESLGFGVPIATWPMYAEQQLNAFT 400
MVKELGLALEMRLDYVSEDGDIVKADEIAGTVRSLMDGVDVPKSKVKEIA 450
EAGKEAVDGGSSFLAVKRFIGDLIDGVSISK*
```

METHOD OF INCREASING RESISTANCE AGAINST SOYBEAN RUST IN TRANSGENIC PLANTS BY INCREASING THE SCOPOLETIN CONTENT

This application is a National Stage application of International Application No. PCT/EP2016/052019, filed Feb. 1, 2016, which claims priority to European Patent Application No. 15153820.4, filed on Feb. 4, 2015.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "76603_Seqlisting.txt", which was created on Aug. 1, 2017 and is 43,652 bytes in size. The subject matter of the Sequence Listing is incorporated herein in its entirety by reference.

SUMMARY OF THE INVENTION

The present invention relates to a method of increasing resistance against fungal pathogens, in particular soybean rust and/or *Fusarium graminearum* and/or *Fusarium verticillioides*, in plants, plant parts, and/or plant cells. This is achieved by increasing the content of scopoletin and/or a derivative thereof, in particular by increasing the expression of F6H1 in a plant, plant part and/or plant cell. This can also be achieved by application of a formulation or solution containing scopoletin and/or a derivative thereof.

Furthermore, the invention relates to recombinant expression vector constructs comprising a sequence that is identical or homologous to a sequence encoding F6H1 protein.

BACKGROUND OF THE INVENTION

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man. Alternatively, natural occurring fungicides produced by the plants after fungal infection can be synthesized and applied to the plants.

Resistance generally describes the ability of a plant to prevent, or at least curtail the infestation and colonization by a harmful pathogen. Different mechanisms can be discerned in the naturally occurring resistance, with which the plants fend off colonization by phytopathogenic organisms (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host is seriously hampered in development or dies off. An incompatible interaction occurs on the other hand when the pathogen infects the plant but is inhibited in its growth before or after weak development of symptoms (mostly by the presence of R genes of the NBS-LRR family, see below). In the latter case, the plant is resistant to the respective pathogen (Schopfer and Brennicke, vide supra). However, this type of resistance is mostly specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular, such a resistance works for different strains of the pathogen.

Fungi are distributed worldwide. Approximately 100 000 different fungal species are known to date. Thereof rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant. To counteract plants have developed physical barriers, such as wax layers, and chemical compounds having antifungal effects to inhibit spore germination, hyphal growth or penetration.

The soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyl cell. During the penetration process the plasmamembrane of the penetrated mesophyll cell stays intact.

*Fusarium* species are important plant pathogens that attacks a wide range of plant species including many important crops such as maize and wheat. They cause seed rots, seedling blights as well as root rots, stalk rots and ear rots. Pathogens of the genus *Fusarium* infect the plants via infected seeds, roots or silks or they penetrate the plant via wounds or natural openings and cracks. After a very short establishment phase the *Fusarium* fungi start to secrete mycotoxins such as trichothecenes, zearalenone and fusaric acid into the infected host tissues leading to cell death and maceration of the infected tissue. Nourishing from dead tissue the fungus then starts to spread through the infected plant leading to severe yield losses and decreases in quality of the harvested grain.

Biotrophic phytopathogenic fungi depend for their nutrition on the metabolism of living cells of the plants. This type of fungi belong to the group of biotrophic fungi, like many rust fungi, powdery mildew fungi or oomycete pathogens like the genus *Phytophthora* or *Peronospora*. Necrotrophic phytopathogenic fungi depend for their nutrition on dead cells of the plants, e.g. species from the genus *Fusarium, Rhizoctonia* or *Mycospaerella*. Soybean rust has occupied an intermediate position, since it penetrates the epidermis directly, whereupon the penetrated cell becomes necrotic. After the penetration, the fungus changes over to an obligatory-biotrophic lifestyle. The subgroup of the biotrophic fungal pathogens which follows essentially such an infection strategy are heminecrotrohic.

Scopoletin and scopolin are antimicrobial phenolic hydroxycumarins that accumulate in different plants upon infection with various pathogens such as fungi or bacteria or in response to insect feeding damage, mechanical injury, dehydration or various other abiotic stresses.

Scopoletin shows broad antimicrobial activity and can inhibit development and growth of various fungi or bacteria in vitro (Goy, P. A., Signer, H., Reist, R., Aichholz, R., Blum, W., Schmidt, E., and Kessmann, H. (1993). Accumulation of scopoletin is associated with the high disease resistance of the hybrid *Nicotiana glutinosa×Nicotiana debneyi*. Planta 41: 200-206; Tal, B. and Robeson, D. J. (1986b). The Metabolism of Sunflower Phytoalexins Ayapin and Scopoletin: Plant-Fungus Interactions. Plant Physiology 82: 167-172.).

Scopoletin and its glucoside scopolin originate from the phenylpropanoid pathway (FIG. 1; (Kai, K., Mizutani, M., Kawamura, N., Yamamoto, R., Tamai, M., Yamaguchi, H., Sakata, K., and Shimizu, B. (2008). Scopoletin is biosynthesized via ortho-hydroxylation of feruloyl CoA by a 2-oxoglutarate-dependent dioxygenase in *Arabidopsis thaliana*. Plant Journal 55: 989-99).

Key steps of scopletin/scopolin synthesis comprise ortho hydroxylation of feruloyl-CoA, trans/cis isomeration of the side chain, lactonization and—considering scopolin synthesis—glycosylation (Kai et al., 2008). In *Arabidopsis* it has recently been shown that scopoletin production depends on ortho hydroxylation of feruloyl-CoA by the Fe(II)- and 2-oxoglutarate-dependent dioxygenase F6H1 (At3g13610). E-Z isomerisation of the side chain and lactonization were found to occur spontaneously. (Kai et al., 2008).

In planta accumulating scopoletin can finally be glucosylated to produce scopolin. Several *Arabidopsis* glucosyltransferases (e.g. UGT71C1) (Lim, E.-K., Baldauf, S., Li, Y., Elias, L., Worrall, D., Spencer, S. P., Jackson, R. G., Taguchi, G., Ross, J., and Bowles, D. J. (2003). Evolution of substrate recognition across a multigene family of glycosyltransferases in *Arabidopsis*. Glycobiology 13: 139-45.) as well as two different tobacco glucosyltransferases (Togt1 and Togt2) (Fraissinet-Tachet, L., Baltz, R., Chong, J., Kauffmann, S., Fritig, B., and Saindrenan, P. (1998). Two tobacco genes induced by infection, elicitor and salicylic acid encode glucosyltransferases acting on phenylpropanoids and benzoic acid derivatives, including salicylic acid. FEBS letters 437: 319-23) have been identified that can catalyze glycosylation of scopoletin in vitro.

Scopolin is generally regarded a less potent antimicrobial agent than scopoletin. Following pathogen-induced mechanical injury or hypersensitive reactions (HR), decompartimentalization of scopolin containing cells might lead to the release of scopolin from vacuoles into the cytoplasm and subsequent hydrolysis of the glucose conjugate by β-glucosidases.

Scopoletin and its glucoside scopolin are widely distributed among the plant kingdom and have been detected in various plant organs of approximately 80 different plant families. Interestingly, scopoletin biosynthesis seems to be lost in several economically important crops (e.g. *Glycine max, Zea mays, Triticum aestivum, Oryza sativa* etc.), indicating that the ability to synthesize this antimicrobial substance might have been lost during breeding. However, this does not apply to sweet potato, tobacco, sunflower, cotton or cassava since scopoletin has been shown to accumulate in these crops in response to infection (summarized by Gnonlonfin, G. J. B., Sanni, A., and Brimer, L. (2012). Review Scopoletin—A Coumarin Phytoalexin with Medicinal Properties. Critical Reviews in Plant Sciences 31: 47-56).

Soybean rust has become increasingly important in recent times. The disease may be caused by the biotrophic rusts *Phakopsora pachyrhizi* (Sydow) and *Phakopsora meibomiae* (Arthur). They belong to the class Basidiomycota, order Uredinales, family Phakopsoraceae. Both rusts infect a wide spectrum of leguminosic host plants. *P. pachyrhizi*, also referred to as Asian rust, is the more aggressive pathogen on soy (*Glycine max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant soybean accessions, six dominant R-genes of the NBS-LRR family, which mediate resistance of soy to *P. pachyrhizi*, were discovered. The resistance was lost rapidly, as *P. pachyrhizi* develops new virulent races.

Increasing resistance to *Fusarium* is one of the most important goals in maize breeding. Despite having a great natural diversity in interaction phenotypes with *Fusarium* species, resistance seems to be distributed over many weak QTLs with low heritability. Therefore only little progress was made in increasing resistance against *Fusarium* by breeding.

In recent years, fungal diseases, e.g. soybean rust and *Fusarium graminearum* have gained in importance as pest in agricultural production. There was therefore a demand in the prior art for developing methods to control fungi and to provide fungal resistant plants.

Much research has been performed on the field of powdery and downy mildew infecting the epidermal layer of plants. However, the problem to cope with soybean rust which infects the mesophyll or *Fusarium* fungi that infect inaccessible inner tissues remains unsolved.

The object of the present invention is inter alia to provide a method of increasing resistance against fungal pathogens, preferably against fungal pathogens of the family Phakopsoraceae, more preferably against fungal pathogens of the genus *Phakopsora*, most preferably against *Phakopsora pachyrhizi* (Sydow) and/or *Phakopsora meibomiae* (Arthur), also known as soybean rust.

A further object of the present invention is inter alia to provide a method of increasing resistance against fungal pathogens, preferably against fungal pathogens of the genus *Fusarium*, most preferably against *Fusarium graminearum* and/or *Fusarium verticillioides*.

Surprisingly, we found that fungal pathogens, in particular of the genus *Phakopsora*, for example soybean rust and/or of the genus *Fusarium*, for example *Fusarium graminearum* and/or *Fusarium verticillioides*, can be controlled by increased production or increased accumulation of scopoletin or derivatives thereof in a plant and by direct application of scopoletin or derivatives thereof to the plant.

Surprisingly, we found that fungal pathogens, in particular of the genus *Phakopsora*, for example soybean rust and of the genus *Fusarium*, for example *Fusarium graminearum* and/or *Fusarium verticillioides*, can be controlled by increased expression of the F6H1 protein, optionally in combination with one or more proteins selected from the group consisting of CCoAOMT1, ABCG37 and UGT71C1.

The present invention therefore provides a method of increasing resistance against fungal pathogens, preferably against fungal pathogens of the family Phakopsoraceae and/or Nectriaceae, more preferably against fungal pathogens of the genus *Phakopsora* and/or *Fusarium*, most preferably against *Phakopsora pachyrhizi* (Sydow), *Phakopsora meibomiae* (Arthur), *Fusarium graminearum* and/or *Fusarium verticillioides* in transgenic plants, plant parts, or transgenic plant cells by increasing the production and/or accumulation of scopoletin and/or derivatives thereof or by exogenous application of scopoletin and/or derivatives thereof to plants, plant parts, or plant cells.

A further object is to provide transgenic plants resistant against fungal pathogens, preferably of the family Phakopsoraceae and/or Nectriaceae, more preferably against fungal pathogens of the genus *Phakopsora* and/or *Fusarium*, most preferably against *Phakopsora pachyrhizi* (Sydow), *Phakopsora meibomiae* (Arthur), *Fusarium graminearum* and/or *Fusarium verticillioides*, a method for producing such plants as well as a recombinant vector construct useful for the above methods.

The present invention also refers to a recombinant vector construct and a transgenic plant, plant part, or plant cell comprising exogenous nucleic acids or fragment thereof which lead to enhanced production of scopoletin and/or derivatives thereof. Furthermore, a method for the production of a transgenic plant, plant part or plant cell using the nucleic acids of the present invention is claimed herein. In addition, the use of a nucleic acid or the recombinant vector of the present invention for the transformation of a plant, plant part, or plant cell is claimed herein.

The present invention also refers to method for applying a scopoletin and/or derivatives to a surface of a plant, plant part or plant cell as well as plant surface or plant part surface coated with scopoletin and/or derivatives.

The objects of the present invention, as outlined above, are achieved by the subject-matter of the main claims. Preferred embodiments of the invention are defined by the subject matter of the dependent claims.

BRIEF DESCRIPTION OF THE SEVERAL VIEWS OF THE DRAWINGS FIGURES

FIG. 1 shows the key steps of the scopoletin and scopolin synthesis in *Arabidopsis thaliana* (as proposed by Kai et al, Plant J. 2008 September; 55(6):989-99)

(a) 3-O-methylation of the caffeate unit occurs mainly via CCoAOMT1 using caffeoyl CoA. Ortho-hydroxylation of feruloyl CoA is catalyzed by F6H1, followed by trans/cis isomerization of the side chain and lactonization to form scopoletin. C3H, p-coumarate 3-hydroxylase; 4CL, 4-coumarate:CoA ligase.

(b) An ionic mechanism of trans/cis isomerization of the side chain and lactonization is proposed for the thioester.

FIG. 2*a* shows the schematic illustration of plant transformation vectors harboring p35S::F6H1 (At3g13610) for transient production of scopoletin in *N. benthamiana* leaves (see example 3).

FIG. 2*b* shows the schematic illustration of plant transformation vectors harboring P35S::FLAG-tag:F6H1 (At3g13610) for expression of FLAG-tagged F6H1 used for transient production of scopoletin in *N. benthamiana* leaves (see example 3)

FIG. 2*c* shows the schematic illustration of plant transformation vectors harboring pUbi: F6H1 (At3g13610) for stable production of scopoletin in soybean plants (see examples 6-10).

FIG. 3 shows the schematic illustration of plant transformation vectors harboring pUbi F6H1 (AT3G13610)+pSUPER CCoAOMT1 (At4g34050) for stable production of scopoletin in soybean plants (see examples 7-11).

FIG. 4 shows the schematic illustration of plant transformation vectors harboring pUbi F6H1 (AT3G13610)+pSUPER CCoAOMT1 (At4g34050)+pGlyma14g06680 ABCG37 (PDR9; AT3G53480) for stable production of scopoletin in soybean plants (see examples 7-11).

FIG. 5 shows the schematic illustration of plant transformation vectors harboring pUbi F6H1 (AT3G13610)+pSUPER UGT71C1 (At2g29750) for stable production of scopoletin in soybean plants (see examples 7-11).

FIG. 6 contains a brief description of the sequences of the sequence listing.

FIG. 7*a* shows the nucleotide sequence of the F6H1 (At3g13610) gene from *Arabidopsis thaliana* having SEQ ID No: 1.

FIG. 7*b* shows the protein sequence of the F6H1 (At3g13610) gene from *Arabidopsis thaliana* having SEQ ID No: 2.

FIG. 8*a* shows the nucleotide sequence of the CCoAOMT1 (At4g34050) gene from *Arabidopsis thaliana* having SEQ ID No: 3.

FIG. 8*b* shows the protein sequence of the CCoAOMT1 (At4g34050) gene from *Arabidopsis thaliana* having SEQ ID No: 4.

FIG. 9*a* shows the nucleotide sequence of the ABCG37 (PDR9; AT3G53480) gene from *Arabidopsis thaliana* having SEQ ID No: 5.

FIG. 9*b* shows the protein sequence of the ABCG37 (PDR9; AT3G53480) gene from *Arabidopsis thaliana* having SEQ ID No: 6.

FIG. 10*a* shows the nucleotide sequence of the UGT71C1 gene from *Arabidopsis thaliana* having SEQ ID No:7.

FIG. 10*b* shows the protein sequence of the UGT71C1 gene from *Arabidopsis thaliana* having SEQ ID No: 8.

FIG. 11 shows the scoring system used to determine the level of diseased leaf area of wildtype and transgenic soy plants against the rust fungus *P. pachyrhizi* ((as described in GODOY, C. V., KOGA, L. J. & CANTERI, M. G. Diagrammatic scale for assessment of soybean rust severity. Fitopatologia Brasileira 31:063-068. 2006.)

FIG. 12*a* shows the production of scopoletin in transiently transformed *N. benthamiana* leaves by overexpression of F6H1. Leaves of *Nicotiana benthamiana* were transiently transformed by infiltrated with *Agrobacterium tumefaciens* AGL01 harboring one of the plasmids shown in FIGS. 2*a* and 2*b* (see example 3). Scopoletin produced by transiently transformed *N. benthamiana* leaves was identified and quantified by HPLC as described in example 3b.

Untransformed (wildtype) *N. benthamiana* is not able to produce Scopoletin. Transient expression of the F6H1 enzyme (original sequence (F6H1, FIG. 2a) or FLAG-tagged (Omega-F6H1-FLAG; FIG. 2b) leads to the production and accumulation of scopoletin in leaves of *N. benthamiana* (independent on the construct used.

FIG. 12b shows the enhancement of the production of scopoletin and scopolin in transiently transformed *N. benthamiana* leaves by co-overexpression of F6H1 and CCoAOMT1. Leaves of *Nicotiana benthamiana* were transiently transformed by infiltrating with *Agrobacterium tumefaciens* harboring plasmids containing the F6H1 gene or F6H1 gene and the CCoAOMT1 gene (see FIG. 2b and example 3). Untransformed (wildtype) *N. benthamiana* is not able to produce scopoletin. Transient expression of the F6H1 enzyme (Omega-F6H1-FLAG) leads to the production and accumulation of scopoletin. Transient co-overexpression of the F6H1 enzyme in combination with CCoAOMT1 (Omega-F6H1-FLAG+CCoAOMT1) leads to an enhanced production and accumulation of scopoletin in comparison to F6H1 alone, as visible in a larger peak area in the HPLC chromatograph. This results shows that the F6H1 accumulation could be enhanced by coexpression of CCoAOMT1.

FIG. 13 Scopoletin inhibits the germination of ASR (Asian soy rust) spores in vivo. Leaves of *Arabidopsis* Col-0 wildtype plants were treated with 1 mM Scopoletin either 6 h before inoculation (bi) with *P. pachyrhizi* (stripped bar) or in parallel with the inoculation with *P. Pachyrhizi* (black bar) (plants not treated with Scopoletin, light grey bar): Germination of ASR spores was assessed microscopically 48 hours after infection (see example 6.1) Quantitative microscopic analysis showed that the germination of spores of *Phakopsora pachyrhizi* is strongly inhibited by the presence of 1 mM Scopoletin on the leaves of *Arabidopsis thaliana* independent of the application method (co-application or pre-treatment).

FIG. 14a Scopoletin inhibits the germination of ASR spores in vitro.

Spores of *Phakopsora pachyrhizi* were germinated on glass slides in water containing 0 (grey dotted bar), 10 µM (vertically striped bar), 100 µM (diagonally striped bar), 500 µM (horizontally striped bar) and 1 mM (black bar) scopoletin. Morphological status of spores was determined microscopically 6 h after inoculation (see example 5a). Quantitative microscopic analysis showed that the germination and appressorium formation of *Phakopsora pachyrhizi* is strongly inhibited by the presence of scopoletin in a dose dependent manner.

FIG. 14b Scopoletin reduces soybean rust disease symptoms in planta.

Leaves of soybean plants were treated with 10 µM, 100 µM or 1 mM scopoletin in parallel with the inoculation with *P. pachyrhizi* (Co-application). Plants not treated with Scopoletin are marked as control (see example 6.2). The diseased leaf area was assessed according to FIG. 11 and as described in example 10.

Quantitative analysis of the ratio of the infected leaf area showed that the diseased leaf area caused by *Phakopsora pachyrhizi* infection is strongly reduced in a dose dependent manner by co-application of scopoletin.

FIG. 14c Scopoletin reduces soybean rust disease symptoms in planta.

Primary leaves (grey dotted bars) or first trifoliate leaves (vertically striped bars) and second trifoliate leaves (diagonally striped bars) of soy plants were treated with 1 mM scopoletin either 6 h before inoculation with *P. pachyrhizi* (Pre-treatment) or in parallel with the inoculation with *P. Pachyrhizi* (Co-application). Plants not treated with scopoletin are marked "ASR-only")(see example 6.2). The diseased leaf area was assessed according to FIG. 11 and as described in example 10.

Quantitative analysis of the ratio of the infected leaf area showed that the diseased leaf area caused by *Phakopsora pachyrhizi* infection is strongly reduced by the either pre-treatment or co-application of 1 mM scopoletin on primary leaves (grey dotted bars) and first trifoliate leaves (vertically striped bars) and second trifoliate leaves (diagonally striped bars).

FIG. 15 shows the impact of scopoletin on the growth of *Fusarium graminearum* (in-vitro) *Fusarium graminearum* fungus is grown on PDA plates containing either 1 mM Scopoletin (solved in methanol) or methanol alone as control. The growth rate of the *Fusarium graminearum* in mm/day was determined microscopically (see example 5b).

The presence of 1 mM scopoletin in the agar leads to a reduction of the *Fusarium graminearum* growth rate per day by 61% in comparison to *Fusarium graminearum* grown on PDA+methanol, indicating that scopoletin is also toxic against *Fusarium graminearum*.

FIG. 16 shows soybean leaves expressing F6H1 enzyme in comparison to wildtype control. Expression of F6H1 enzyme is leading to accumulation of the antifungal molecule Scopoletin as visible by fluorescence under UV light. Elicitation of fluorescence was done by a B-100AP UV lamp (UVP LLC, Upland, Canada) using 365 nm longwave UV.

FIG. 17 shows the result of the scoring of 25 transgenic soy plants (derived from 5 independent events) accumulating Scopoletin by overexpression of F6H1 enzyme (construct see FIG. 2c) compared with wildtype plants.

DETAILED DESCRIPTION OF THE INVENTION

Figure 1:
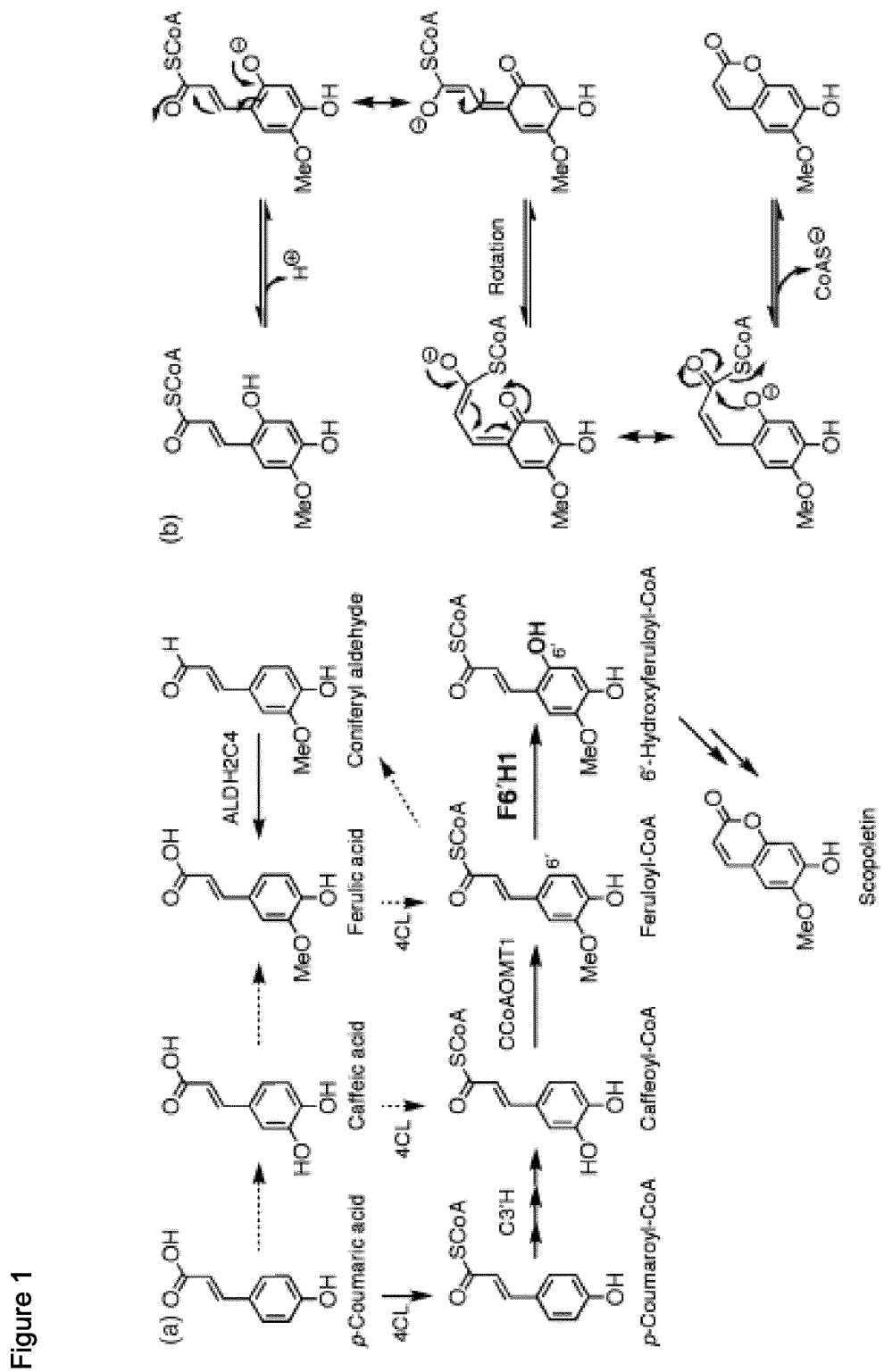

The present invention may be understood more readily by reference to the following detailed description of the preferred embodiments of the invention and the examples included herein.

Definitions

Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, "a" or "an" can mean one or more, depending upon the context in which it is used. Thus, for example, reference to "a cell" can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

"Homologues" of a protein encompass peptides, oligopeptides, polypeptides, proteins and/or enzymes having amino acid substitutions, deletions and/or insertions relative to the unmodified protein in question and having the same, essentially the same biological activity or similar as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has the same, essentially the same or similar biological activity as the unmodified protein coded by the unmodified nucleic acid from which they are derived. In particular, homologues of a nucleic acid may encompass substitutions on the basis of the degenerative amino acid code.

The terms "identity", "homology" and "similarity" are used herein interchangeably. "Identity" or "homology" or "similarity" between two nucleic acids sequences or amino acid sequences refers in each case over at least 70%, at least 80% or at least 90% of the entire length of the respective F6H1, CCoAOMT, ABCG37 and/or UGT71C1 nucleic acid sequence or the respective F6H1, CCoAOMT, ABCG37 and/or UGT71C1 amino acid sequence, preferably over the entire length of the respective F6H1, CCoAOMT, ABCG37 and/or UGT71C1 nucleic acid sequence or the respective F6H1, CCoAOMT, ABCG37 and/or UGT71C1 amino acid sequence.

Preferably, "percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the region being compared and multiplying the result by 100.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity or similarity or homology and performs a statistical analysis of the identity or similarity or homology between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity/homology/identity may also be determined using one of the methods available in the MatGAT software package (Campanella et al., BMC Bioinformatics. 2003 Jul. 10; 4:29. MatGAT: an application that generates similarity/homology/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

The sequence identity may also be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:
Multiple Alignment Parameter:
Gap opening penalty 10
Gap extension penalty 10
Gap separation penalty range 8
Gap separation penalty off
% identity for alignment delay 40
Residue specific gaps off
Hydrophilic residue gap off
Transition weighing 0
Pairwise Alignment Parameter:
FAST algorithm on
K-tuple size 1
Gap penalty 3
Window size 5
Number of best diagonals 5

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index.html# and the following settings
DNA Gap Open Penalty 15.0
DNA Gap Extension Penalty 6.66
DNA Matrix Identity
Protein Gap Open Penalty 10.0
Protein Gap Extension Penalty 0.2
Protein matrix Gonnet
Protein/DNA ENDGAP −1
Protein/DNA GAPDIST 4

Sequence identity between the nucleic acid or protein useful according to the present invention and the F6H1, CCoAOMT, ABCG37 and UGT71C1 nucleic acids and the F6H1, CCoAOMT, ABCG37 and UGT71C1 proteins may be optimized by sequence comparison and alignment algorithms known in the art (see Gribskov and Devereux, Sequence Analysis Primer, Stockton Press, 1991, and references cited therein) and calculating the percent difference between the nucleotide or protein sequences by, for example, the Smith-Waterman algorithm as implemented in the BESTFIT software program using default parameters (e.g., University of Wisconsin Genetic Computing Group).

A "deletion" refers to removal of one or more amino acids from a protein or to the removal of one or more nucleic acids from DNA, ssRNA and/or dsRNA.

An "insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or beta-sheet structures).

On the nucleic acid level a substitution refers to a replacement of one or more nucleotides with other nucleotides within a nucleic acid, wherein the protein coded by the modified nucleic acid has essentially the same or a similar function. In particular homologues of a nucleic acid encompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues. The amino acid substitutions are preferably conservative amino acid substitutions. Conservative substitution tables are well known in the art (see for example Taylor W. R. (1986) The classification of amino acid conservation J Theor Biol., 119:205-18 and Table 1 below).

TABLE 1

Examples of conserved amino acid substitutions

| Residue | Conservative Substitutions | Residue | Conservative Substitutions |
|---------|---------------------------|---------|---------------------------|
| A | G, V, I, L, M | L | M, I, V, A, G |
| C | S, T | N | Q |
| E | D | Q | N |
| D | E | P | |
| G | A, V, I, L, M | S | T, C |
| F | Y, W | R | K, H |
| I | V, A, G, L, M | T | S, C |
| H | R, K | W | Y, F |
| K | R, H | V | I, A, G, L, M |
| M | L, I, V, A, G | Y | F, W |

Amino acid substitutions, deletions and/or insertions may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

The terms "encode" or "coding for" is used for the capability of a nucleic acid to contain the information for the amino acid sequence of a protein via the genetic code, i.e., the succession of codons each being a sequence of three nucleotides, which specify which amino acid will be added next during protein synthesis. The terms "encode" or "coding for" therefore includes all possible reading frames of a nucleic acid. Furthermore, the terms "encode" or "coding for" also applies to a nucleic acid, which coding sequence is interrupted by non-coding nucleic acid sequences, which are removed prior translation, e.g., a nucleic acid sequence comprising introns.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

The nucleic acids according to the present invention may comprise domains as defined herein below when analysed with the software tool InterProScan (version 4.8, (see Zdobnov E. M. and Apweiler R.; "InterProScan—an integration platform for the signature-recognition methods in InterPro."; Bioinformatics, 2001, 17(9): 847-8; InterPro database, release 42 (Apr. 4, 2013)).

As used herein the terms "fungal-resistance", "resistant to a fungus" and/or "fungal-resistant" mean reducing, preventing, or delaying an infection by fungi. Preferably fungal resistance is soybean rust-resistance and/or *fusarium*-resistance. The term "resistance" refers to fungal resistance. Resistance does not imply that the plant necessarily has 100% resistance to infection. In preferred embodiments, enhancing or increasing fungal resistance means that resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant. Preferably the wild type plant is a plant of a similar, more preferably identical, genotype as the plant having increased resistance to fungi, in particular soy-rust and or *fusarium*, but does not comprise an exogenous F6H1 nucleic acid optionally in combination with one or more nucleic acids selected from the group consisting of CCoAOMT, ABCG37 and UGT71C1 nucleic acids. Preferably, the wildtype plant is not capable to produce more than 10 μM scopoletin and/or a derivative thereof, more preferably more than 5 μM scopoletin and/or a derivative thereof, most preferably the wildtype plant is not capable to produce scopoletin and/or a derivative thereof.

As used herein the terms "soybean rust-resistance", "resistant to a soybean rust", "soybean rust-resistant", "rust-resistance", "resistant to a rust", or "rust-resistant" mean reducing or preventing or delaying an infection of a plant, plant part, or plant cell by Phacopsoracea, in particular *Phakopsora*, more particularly soybean rust or Asian Soybean Rust (ASR), more particularly *Phakopsora pachyrhizi, Phakopsora meibomiae* and/or *Fusarium solani*—also known as, as compared to a wild type plant, wild type plant part, or wild type plant cell.

As used herein the terms "*fusarium*-resistance", "resistant to a *fusarium*", or "*fusarium*-resistant" mean reducing or preventing or delaying an infection of a plant, plant part, or plant cell by *Fusarium*, in particular *Fusarium graminearum, Fusarium sporotrichioides, Fusarium pseudograminearum, Fusarium culmorum, Fusarium poae, Fusarium verticillioides (Fusarium moniliforme), Fusarium subglutinans, Fusarium proliferatum, Fusarium fujikuroi), Fusarium avenaceum, Fusarium oxysporum, Fusarium virguliforme* and/or *Fusarium solani* as compared to a wild type plant, wild type plant part, or wild type plant cell.

The level of fungal resistance of a plant can be determined in various ways, e.g. by scoring/measuring the infected leaf area or three-dimensional space in relation to the overall area or three-dimensional space. Another possibility to determine the level of resistance is to count the number of *fusarium* colonies on the plant or to measure the amount of spores produced by these colonies. Another way to resolve the degree of fungal infestation is to specifically measure the amount of fungal DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens *Phakopsora pachyrhizi* and *P. meibomiae*, Phytopathology 92(2) 217-227). (Nicolaisen M, Suproniene S, Nielsen L K, Lazzaro I, Spliid N H, Justesen A F. 2009 Real-time PCR for quantification of eleven individual *Fusarium* species in cereals. J Microbiol Methods. 2009 March; 76(3): 234-40.) Another way of evaluating fungal biomass is to biochemically determining the amount of fungal specific compounds, such as ergosterol or chitin (L. M. Reid, R. W. Nicol, T. Ouellet, M. Savard, J. D. Miller, J. C. Young, D. W. Stewart, and A. W. Schaafsma (1999) Interaction of *Fusarium graminearum* and *F. moniliforme* in Maize Ears: Disease Progress, Fungal Biomass, and Mycotoxin Accumulation Phytopathology 89(11) 1028-1037; CA Roberts, R R Marquardt, A A Frohlich, R L McGraw, R G Rotter, J C Henning (1991) Chemical and spectral quantification of mold in contaminated barley; Cereal Chemistry 68(3):272-275).

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: $Tm=81.5+0.41(\% G+C)$, when a nucleic acid molecule is in aqueous solution at 1 M NaCl (see e.g., Anderson and Young, Quantitative Filter Hybridization, in Nucleic Acid Hybridization (1985). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contigous nucleotides or more, 150 contigous nucleotides or more, 200 contigous nucleotides or more or 250 contigous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole nucleic acids of exogenous F6H1, CCoAOMT, ABCG37 genes and UGT71C1, respectively. Alternatively, preferred hybridization conditions encompass hybridisation at 65° C. in 1×SSC or at 42° C. in 1×SSC and 50% formamide, followed by washing at 65° C. in 0.3×SSC or hybridisation at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the exogenous F6H1 nucleic acid optionally in combination one or more nucleic acid selected from CCoAOMT, ABCG37 and UGT71C1 nucleic acids. In one embodiment, the seeds can develop into plants with increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

Reference herein to an "endogenous" nucleic acid and/or protein refers to the nucleic acid and/or protein in question as found in a plant in its natural form (i.e., without there being any human intervention).

The term "exogenous" nucleic acid refers to a nucleic acid that has been introduced in a plant by means of genetechnology. An "exogenous" nucleic acid can either not occur in a plant in its natural form, be different from the nucleic acid in question as found in a plant in its natural form, or can be identical to a nucleic acid found in a plant in its natural form, but integrated not within their natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the present invention includes an exogenous F6H1 nucleic acid optionally in combination one or more exogenous nucleic acid(s) selected from CCoAOMT, ABCG37 and UGT71C1 nucleic acids integrated at any genetic loci and optionally the plant may also include the endogenous gene within the natural genetic background. Preferably the plant, plant part or plant cell does not include endogenous F6H1 nucleic acid optionally in combination with one or more endogenous nucleic acid(s) selected from CCoAOMT, ABCG37 and UGT71C1.

For the purposes of the invention, "recombinant" means with regard to, for example, a nucleic acid sequence, a nucleic acid molecule, an expression cassette or a vector construct comprising F6H1 nucleic acid optionally in combination with any one or more of CCoAOMT, ABCG37 and/or UGT71C1 nucleic acid(s), all those constructions brought about by man by genetechnological methods in which either
(a) the sequences of the F6H1, CCoAOMT, ABCG37 and/or UGT71C1 nucleic acids or a part thereof, or
(b) genetic control sequence(s) which are operably linked with the F6H1, CCoAOMT, ABCG37 and/or UGT71C1 nucleic acid sequences according to the invention, for example a promoter, or
(c) a) and b)
are not located in their natural genetic environment within the genome of the wildtype plant or have been modified by man by genetechnological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

For instance, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

The term "isolated nucleic acid" or "isolated protein" refers to a nucleic acid or protein that is not located in its natural environment, in particular its natural cellular environment. Thus, an isolated nucleic acid or isolated protein is essentially separated from other components of its natural environment. However, the skilled person in the art is aware that preparations of an isolated nucleic acid or an isolated protein can display a certain degree of impurity depending on the isolation procedure used. Methods for purifying nucleic acids and proteins are well known in the art. The isolated gene may be isolated from an organism or may be manmade, for example by chemical synthesis. In this regard, a recombinant nucleic acid may also be in an isolated form.

As used herein, the term "transgenic" refers to an organism, e.g., a plant, plant cell, callus, plant tissue, or plant part that exogenously contains the nucleic acid, recombinant construct, vector or expression cassette described herein or a part thereof which is preferably introduced by non-essentially biological processes, preferably by Agrobacteria transformation. The recombinant construct or a part thereof is stably integrated into a chromosome, so that it is passed on to successive generations by clonal propagation, vegetative propagation or sexual propagation. Preferred successive generations are transgenic too. Essentially biological processes may be crossing of plants and/or natural recombination.

Preferably, the nucleic acids according to the invention or used according to the invention comprise
F6H1 nucleic acid,
F6H1 and CCoAOMT nucleic acids,
F6H1 and ABCG37 nucleic acids, or
F6H1 and UGT71C1 nucleic acids, or
F6H1, CCoAOMT and ABCG37 nucleic acids or
F6H1, CCoAOMT, ABCG37 and UGT71C1 nucleic acids.

A transgenic plant, plants cell or tissue for the purposes of the invention is thus understood as meaning that an exogenous F6H1 nucleic acid optionally in combination with one or more nucleic acids selected from the group consisting of CCoAOMT, ABCG37 and UGT71C1 nucleic acids is integrated into the genome by means of genetechnology.

A recombinant construct, vector or expression cassette for the purposes of the invention comprises a F6H1 nucleic acid optionally in combination with one or more nucleic acids selected from the group consisting of CCoAOMT, ABCG37 and UGT71C1 nucleic acids and is prepared by means of genetechnology.

A "wild type" plant, "wild type" plant part, or "wild type" plant cell means that said plant, plant part, or plant cell does not express exogenous F6H1, CCoAOMT, ABCG37 and UGT71C1 nucleic acids and exogenous F6H1, CCoAOMT, ABCG37 and UGT71C1 proteins. Preferably, the wildtype plant is not capable to produce more than 10 µM scopoletin and/or a derivative thereof, more preferably not more than 5 µM scopoletin and/or a derivative thereof and most preferably the wildtype plant is not capable to produce scopoletin and/or a derivative thereof. A derivative of scopoletin is e.g. scopolin. Preferably, the wildtype plant plant does not express endogenous F6H1, CCoAOMT, ABCG37 and/or UGT71C1 nucleic acids and endogenous F6H1, CCoAOMT, ABCG37 and/or UGT71C1 proteins.

Natural locus means the location on a specific chromosome and/or the location between certain genes and/or the same sequence background as in the original plant which is transformed.

Preferably, the transgenic plant, plant cell or tissue thereof expresses the F6H1 nucleic acids optionally in combination with one or more nucleic acids selected from the group consisting of CCoAOMT, ABCG37 and UGT71C1 nucleic acids. Preferably, the transgenic plant, plant cell or tissue thereof is transformed with recombinant vector constructs comprising F6H1 nucleic acids optionally in combination with one or more nucleic acids selected from the group consisting of CCoAOMT, ABCG37 and UGT71C1 nucleic acids described herein. F6H1, CCoAOMT, ABCG37 and/or UGT71C1 nucleic acids may be located on the same vector or different recombinant vectors.

The term "expression" or "gene expression" means the transcription of a specific gene or specific genes or specific genetic vector construct. The term "expression" or "gene expression" in particular means the transcription of a gene or genes or genetic vector construct into structural RNA (rRNA, tRNA), or mRNA with or without subsequent translation of the latter into a protein. The process includes transcription of DNA and processing of the resulting RNA product. The term "expression" or "gene expression" can also include the translation of the mRNA and therewith the synthesis of the encoded protein, i.e., protein expression.

The term "increased expression" or "enhanced expression" or "overexpression" or "increase of content" as used herein means any form of expression that is additional to the original wild-type expression level. For the purposes of this invention, the original wild-type expression level might also be zero (absence of expression).

Methods for increasing expression of genes or gene products are well documented in the art and include, for example, overexpression driven by appropriate promoters, the use of transcription enhancers or translation enhancers, or RNAa (Li et al 2006, PNAS 103(46) 17337-42). Isolated nucleic acids which serve as promoter or enhancer elements may be introduced in an appropriate position (typically upstream) of a non-heterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

The term "functional fragment" refers to any nucleic acid or protein which comprises merely a part of the fulllength nucleic acid or fulllength protein, respectively, but still provides the essentially same or similar function, e.g., increased fungal resistance and/or the same, essentially the same or similar biological activity when expressed in a plant. Preferably, the fragment comprises at least 70%, at least 80%, at least 90% at least 95%, at least 98%, at least 99% of the original sequence. Preferably, the functional fragment comprises contiguous nucleic acids or amino acids as in the original nucleic acid or original protein, respectively. In one embodiment the fragment of any of the F6H1, CCoAOMT, ABCG37 and/or UGT71C1 nucleic acids has an identity as defined above over a length of at least 70%, at least 75%, at least 90% of the nucleotides of the respective F6H1, CCoAOMT, ABCG37 and/or UGT71C1 nucleic acid.

The term "the same biological activity", "essentially the same biologicla activity", "similar biological activity" or increased biological activity preferably means leading to an increased production and/or accumulation compared to the wildtype plant, wild type plant part, or wild type plant cell of more than 0.1 µM, preferably more than 1 µM, preferably more than 2 µM, more preferably more than 5 µM, most preferably more than 10 µM scopoletin and/or a derivative thereof when F6H1 and optionally CCoAOMT, ABCG37 and/or UGT71C1 nucleic acids or fragments thereof are expressed in a plant.

The term "splice variant" as used herein encompasses variants of a nucleic acid sequence in which selected introns and/or exons or parts thereof have been excised, replaced, displaced or added, or in which introns have been shortened or lengthened. Thus, a splice variant can have one or more or even all introns removed or added or partially removed or partially added. According to this definition, a cDNA is considered as a splice variant of the respective intron-containing genomic sequence and vice versa. Such splice variants may be found in nature or may be manmade. Methods for predicting and isolating such splice variants are well known in the art (see for example Foissac and Schiex (2005) BMC Bioinformatics 6: 25).

The wildtype plant may express the respective endogenous F6H1, CCoAOMT, ABCG37 and/or UGT71C1 nucleic acids. As far as overexpression of exogenous F6H1, CCoAOMT, ABCG37 and/or UGT71C1 nucleic acids is concerned, for the purposes of this invention, the original wild-type expression level of the corresponding endogenous nucleic acids might also be zero (absence of expression).

With respect to a vector construct and/or the recombinant nucleic acid molecules, the term "operatively linked" is intended to mean that the nucleic acid to be expressed is linked to the regulatory sequence, including promoters, terminators, enhancers and/or other expression control elements (e.g. polyadenylation signals), in a manner which allows for expression of the nucleic acid (e.g. in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of nucleic acid desired, and the like.

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The host genome includes the nucleic acid contained in the nucleus as well as the nucleic acid contained in the plastids, e.g., chloroplasts, and/or mitochondria. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

Detailed Description

F6H1, CCoAOMT, ABCG37 and/or UGT71C1 nucleic acids

The F6H1 nucleic acid to be overexpressed in order to achieve increased resistance to fungal pathogens, e.g., of the family Phacopsoraceae, for example soybean rust, or of the genus of *Fusarium*, in particular *Fusarium graminearum* and/or *Fusarium verticillioides*, is preferably a nucleic acid consisting of or comprising a nucleic acid selected from the group consisting of:

(i) a nucleic acid having in increasing order of preference at least 70%, at least 75%, at least 80%, at least 85%, at least 90%, at least 95%, at least 96%, at least 97%, at least 98%, at least 99% or 100% sequence identity to the nucleic acid sequence represented by SEQ ID NO: 1 or a functional fragment, or a splice variant thereof;

(ii) a nucleic acid encoding a F6H1 protein comprising an amino acid sequence having in increasing order of preference at least 70%, at least 75%, at least 80%, at least 85%, at least 90%, at least 95%, at least 96%, at least 97%, at least 98%, at least 99% or 100% sequence identity to the amino acid sequence represented by SEQ ID NO: 2 or a functional fragment; preferably the F6H1 protein has the essentially same or similar biological activity as a F6H1 protein encoded by SEQ ID NO: 2; preferably the F6H1 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a F6H1 protein; preferably wherein the nucleic acid molecule codes for a polypeptide which has essentially identical properties to the polypeptide described in SEQ ID NO: 2; preferably the encoded protein confers enhanced fungal resistance relative to control plants; and (iv) a nucleic acid encoding the same F6H1 protein as the F6H1 nucleic acids of (i) to (iii) above, but differing from the F6H1 nucleic acids of (i) to (iii) above due to the degeneracy of the genetic code.

The F6H1 nucleic acid to be overexpressed in order to achieve increased resistance to fungal pathogens is for example a nucleic acid selected from SEQ ID No. 1, 9, 11, 13, 15, 17, 19 and 21. The F6H1 nucleic acid to be overexpressed in order to achieve increased resistance to fungal pathogens is for example a nucleic acid encoding a F6H1 protein selected from SEQ ID No. 2, 10, 12, 14, 16, 18, 20 and 22.

The F6H1 protein may comprise a domain as defined in SEQ ID No. 63, and having least 90%, at least 91%, at least 92%, at least 93%, at least 94%, at least 95%, at least 96%, at least 97%, at least 98%, at least 99% or 100% sequence identity to the protein sequence represented by the respective sequence.

The CCoAOMT nucleic acid to be overexpressed in order to achieve increased resistance to fungal pathogens, e.g., of the family Phacopsoraceae, for example soybean rust, or of the genus of *Fusarium*, in particular *Fusarium graminearum* and/or *Fusarium verticillioides*, is preferably a nucleic acid consisting of or comprising a nucleic acid selected from the group consisting of:

(i) a nucleic acid having in increasing order of preference at least 70%, at least 75%, at least 80%, at least 85%, at least 90%, at least 95%, at least 96%, at least 97%, at least 98%, at least 99% or 100% sequence identity to the nucleic acid sequence represented by SEQ ID NO: 3 or a functional fragment, or a splice variant thereof;

(ii) a nucleic acid encoding a CCoAOMT protein comprising an amino acid sequence having in increasing order of preference at least 70%, at least 75%, at least 80%, at least 85%, at least 90%, at least 95%, at least 96%, at least 97%, at least 98%, at least 99% or 100% sequence identity to the amino acid sequence represented by SEQ ID NO: 4 or a functional fragment; preferably the protein has essentially the same or similar biological activity as a CCoAOMT protein encoded by SEQ ID NO: 4; preferably the CCoAOMT protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a CCoAOMT protein; preferably wherein the nucleic acid molecule codes for a polypeptide which has essentially identical properties to the polypeptide described in SEQ ID NO: 4; preferably the encoded protein confers enhanced fungal resistance relative to control plants; and (iv) a nucleic acid encoding the same CCoAOMT protein as the CCoAOMT nucleic acids of (i) to (iii) above, but differing from the CCoAOMT nucleic acids of (i) to (iii) above due to the degeneracy of the genetic code.

The CCoAOMT nucleic acid to be overexpressed in order to achieve increased resistance to fungal pathogens is for example a nucleic acid selected from SEQ ID No. 3, 23, 25, 27, 29, 31, 33, 35, 37, 39, 41, 43, 45 and 47. The CCoAOMT nucleic acid to be overexpressed in order to achieve increased resistance to fungal pathogens is for example a nucleic acid encoding a CCoAOMT protein selected from SEQ ID No. 4, 24, 26, 28, 30, 32, 34, 36, 38, 40, 42, 44, 46 and 48.

The CCoAOMT protein may comprise a domain as defined in SEQ ID No. 64, having least 90%, at least 91%, at least 92%, at least 93%, at least 94%, at least 95%, at least 96%, at least 97%, at least 98%, at least 99% or 100% sequence identity to the protein sequence represented by the respective sequence.

The ABCG37 nucleic acid to be overexpressed in order to achieve increased resistance to fungal pathogens, e.g., of the family Phacopsoraceae, for example soybean rust, or of the genus of *Fusarium*, in particular *Fusarium graminearum* and/or *Fusarium verticillioides*, is preferably a nucleic acid consisting of or comprising a nucleic acid selected from the group consisting of:

(i) a nucleic acid having in increasing order of preference at least 70%, at least 75%, at least 80%, at least 85%, at least 90%, at least 95%, at least 96%, at least 97%, at least 98%, at least 99% or 100% sequence identity to the nucleic acid sequence represented by SEQ ID NO: 5 or a functional fragment thereof, or a splice variant thereof;

(ii) a nucleic acid encoding a ABCG37 protein comprising an amino acid sequence having in increasing order of preference at least 70%, at least 75%, at least 80%, at least 85%, at least 90%, at least 95%, at least 96%, at least 97%, at least 98%, at least 99% or 100% sequence identity to the amino acid sequence represented by SEQ ID NO: 6 or a functional fragment thereof; preferably the protein has essentially the same or similar biological activity as a ABCG37 protein encoded by SEQ ID NO: 6; preferably the ABCG37 protein confers enhanced fungal resistance relative to control plants;
(iii) a nucleic acid molecule which hybridizes with a complementary sequence of any of the nucleic acid molecules of (i) or (ii) under high stringency hybridization conditions; preferably encoding a ABCG37 protein; preferably wherein the nucleic acid molecule codes for a polypeptide which has essentially identical properties to the polypeptide described in SEQ ID NO: 6; preferably the encoded protein confers enhanced fungal resistance relative to control plants; and
(iv) a nucleic acid encoding the same ABCG37 protein as the ABCG37 nucleic acids of (i) to (iii) above, but differing from the ABCG37 nucleic acids of (i) to (iii) above due to the degeneracy of the genetic code.

The ABCG37 nucleic acid to be overexpressed in order to achieve increased resistance to fungal pathogens is for example a nucleic acid selected from SEQ ID No. 5, 49, 51 and 53. The ABCG37 nucleic acid to be overexpressed in order to achieve increased resistance to fungal pathogens is for example a nucleic acid encoding a ABCG37 protein selected from SEQ ID No. 6, 50, 52 and 54.

The ABCG37 protein may comprise at least one domain selected from the group as defined in SEQ ID No. 65, 66, 67 and/or 68 having least 90%, at least 91%, at least 92%, at least 93%, at least 94%, at least 95%, at least 96%, at least 97%, at least 98%, at least 99% or 100% sequence identity to the protein sequence represented by the respective sequence.

The UGT71C1 nucleic acid to be overexpressed in order to achieve increased resistance to fungal pathogens, e.g., of the family Phacopsoraceae, for example soybean rust, or of the genus of *Fusarium*, in particular *Fusarium graminearum* and/or *Fusarium verticillioides*, is preferably a nucleic acid consisting of or comprising a nucleic acid selected from the group consisting of:
(i) a nucleic acid having in increasing order of preference at least 70%, at least 75%, at least 80%, at least 85%, at least 90%, at least 95%, at least 96%, at least 97%, at least 98%, at least 99% or 100% sequence identity to the nucleic acid sequence represented by SEQ ID NO: 7 or a functional fragment thereof, or a splice variant thereof;
(ii) a nucleic acid encoding a UGT71C1 protein comprising an amino acid sequence having in increasing order of preference at least 70%, at least 75%, at least 80%, at least 85%, at least 90%, at least 95%, at least 96%, at least 97%, at least 98%, at least 99% or 100% sequence identity to the amino acid sequence represented by SEQ ID NO: 8 or a functional fragment thereof; preferably the protein has essentially the same or similar biological activity as a UGT71C1 protein encoded by SEQ ID NO: 8; preferably the UGT71C1 protein confers enhanced fungal resistance relative to control plants;
(iii) a nucleic acid molecule which hybridizes with a complementary sequence of any of the nucleic acid molecules of (i) or (ii) under high stringency hybridization conditions; preferably encoding a UGT71C1 protein; preferably wherein the nucleic acid molecule codes for a polypeptide which has essentially identical properties to the polypeptide described in SEQ ID NO: 8; preferably the encoded protein confers enhanced fungal resistance relative to control plants; and
(iv) a nucleic acid encoding the same UGT71C1 protein as the UGT71C1 nucleic acids of (i) to (iii) above, but differing from the UGT71C1 nucleic acids of (i) to (iii) above due to the degeneracy of the genetic code.

The UGT71C1 nucleic acid to be overexpressed in order to achieve increased resistance to fungal pathogens is for example a nucleic acid selected from SEQ ID No. 55, 57, 59 and 61. The UGT71C1 nucleic acid to be overexpressed in order to achieve increased resistance to fungal pathogens is for example a nucleic acid encoding an ABCG37 protein selected from SEQ ID No. 56, 58, 60 and 62.

The UGT71C1 protein may comprise at least one domain selected from the group as defined in SEQ ID No. 69 and/or 70 having least 90%, at least 91%, at least 92%, at least 93%, at least 94%, at least 95%, at least 96%, at least 97%, at least 98%, at least 99% or 100% sequence identity to the protein sequence represented by the respective sequence.

Percentages of identity of a nucleic acid are indicated with reference to the entire nucleotide region given in a sequence specifically disclosed herein.

Preferably the portion of the F6H1 nucleic acid fragment is about 500-600, about 600-700, about 700-800, about 800-900, about 900-1000, or about 1000-1086 nucleotides, preferably consecutive nucleotides, preferably counted from the 5' or 3' end of the nucleic acid, in length, of the nucleic acid sequences given in SEQ ID NO: 1.

Preferably the portion of the CCoAOMT nucleic acid fragment is about 400-500 about 500-600, about 600-700, about 700-780, preferably consecutive nucleotides, preferably counted from the 5' or 3' end of the nucleic acid, in length, of the nucleic acid sequences given in SEQ ID NO: 3.

Preferably the portion of the ABCG37 nucleic acid fragment is about 2500-2600, about 2600-2700, about 2700-2800 about 2800-2900, about 2900-3000, about 3000-3100, about 3100-3200, about 3200-3300, about 3300-3400, about 3400-3500, about 3500-3600, about 3600-3700, about 3700-3800, about 3800-3900, about 3900-4000, about 4000-4100, about 4100-4200, or about 4300-4353 nucleotides, preferably consecutive nucleotides, preferably counted from the 5' or 3' end of the nucleic acid, in length, of the nucleic acid sequences given in SEQ ID NO: 5.

Preferably the portion of the UGT71C1 nucleic acid fragment is about 500-600, about 600-700, about 700-800 about 800-900, about 900-1000, about 1000-1100, about 1100-1200, about 1200-1300, about 1300-1400 or about 1400-1446 nucleotides, preferably consecutive nucleotides, preferably counted from the 5' or 3' end of the nucleic acid, in length, of the nucleic acid sequences given in SEQ ID NO: 7.

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The F6H1, CCoAOMT, ABCG37 and/or UGT71C1 nucleic acids described herein are useful in the constructs, methods, plants, harvestable parts and products of the invention.

F6H1, CCoAOMT, ABCG37 and/or UGT71C1 Proteins

In one embodiment of the invention, the F6H1 protein is encoded by a nucleic acid comprising an exogenous nucleic acid having
(i) a nucleic acid having in increasing order of preference at least 70%, at least 75%, at least 80%, at least 85%, at least 90%, at least 95%, at least 96%, at least 97%, at least 98%, at least 99% or 100% sequence identity with SEQ ID NO: 1 a functional fragment thereof, or a splice variant thereof; or by
(ii) an exogenous nucleic acid encoding a protein comprising an amino acid sequence having at least F6H1 homology with SEQ ID NO: 2, a functional fragment thereof, preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a F6H1 protein; preferably wherein the nucleic acid molecule codes for a polypeptide which has essentially identical properties to the polypeptide described in SEQ ID NO: 2; preferably the encoded protein confers enhanced fungal resistance relative to control plants; or by
(iv) an exogenous nucleic acid encoding the same F6H1 protein as the nucleic acids of (i) to (iii) above, but differing from the nucleic acids of (i) to (iii) above due to the degeneracy of the genetic code.

In one embodiment of the invention, the CCoAOMT protein is encoded by a nucleic acid comprising an exogenous nucleic acid having
(i) a nucleic acid having in increasing order of preference at least 70%, at least 75%, at least 80%, at least 85%, at least 90%, at least 95%, at least 96%, at least 97%, at least 98%, at least 99% or 100% sequence identity with SEQ ID NO: 3 a functional fragment thereof, or a splice variant thereof; or by
(ii) an exogenous nucleic acid encoding a protein comprising an amino acid sequence having at least CCoAOMT homology with SEQ ID NO: 4, a functional fragment thereof, preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a CCoAOMT protein; preferably wherein the nucleic acid molecule codes for a polypeptide which has essentially identical properties to the polypeptide described in SEQ ID NO: 4; preferably the encoded protein confers enhanced fungal resistance relative to control plants; or by
(iv) an exogenous nucleic acid encoding the same CCoAOMT protein as the nucleic acids of (i) to (iii) above, but differing from the nucleic acids of (i) to (iii) above due to the degeneracy of the genetic code.

In one embodiment of the invention, the ABCG37 protein is encoded by a nucleic acid comprising an exogenous nucleic acid having
(i) a nucleic acid having in increasing order of preference at least 70%, at least 75%, at least 80%, at least 85%, at least 90%, at least 95%, at least 96%, at least 97%, at least 98%, at least 99% or 100% sequence identity with SEQ ID NO: 5 a functional fragment thereof, or a splice variant thereof; or by
(ii) an exogenous nucleic acid encoding a protein comprising an amino acid sequence having at least ABCG37 homology with SEQ ID NO: 6, a functional fragment thereof, preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a ABCG37 protein; preferably wherein the nucleic acid molecule codes for a polypeptide which has essentially identical properties to the polypeptide described in SEQ ID NO: 6; preferably the encoded protein confers enhanced fungal resistance relative to control plants; or by
(iv) an exogenous nucleic acid encoding the same ABCG37 protein as the nucleic acids of (i) to (iii) above, but differing from the nucleic acids of (i) to (iii) above due to the degeneracy of the genetic code.

In one embodiment of the invention, the UGT71C1 protein is encoded by a nucleic acid comprising an exogenous nucleic acid having
(i) a nucleic acid having in increasing order of preference at least 70%, at least 75%, at least 80%, at least 85%, at least 90%, at least 95%, at least 96%, at least 97%, at least 98%, at least 99% or 100% sequence identity with SEQ ID NO: 7 a functional fragment thereof, or a splice variant thereof; or by
(ii) an exogenous nucleic acid encoding a protein comprising an amino acid sequence having at least UGT71C1 homology with SEQ ID NO: 8, a functional fragment thereof, preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a UGT71C1 protein; preferably wherein the nucleic acid molecule codes for a polypeptide which has essentially identical properties to the polypeptide described in SEQ ID NO: 8; preferably the encoded protein confers enhanced fungal resistance relative to control plants; or by
(iv) an exogenous nucleic acid encoding the same UGT71C1 protein as the nucleic acids of (i) to (iii) above, but differing from the nucleic acids of (i) to (iii) above due to the degeneracy of the genetic code.

Preferably, the F6H1 polypeptide comprises about 200-225, about 225-250, about 250-275, about 275-300, about 300-325, about 325-350, or about 350-362 amino acid residues, preferably consecutive amino acid residues, preferably counted from the N-terminus or C-terminus of the amino acid sequence, or up to the full length of any of the amino acid sequences encoded by the nucleic acid sequences set out in SEQ ID NO: 1.

Preferably, the CCoAOMT polypeptide comprises about 100-125, about 125-150, about 150-175, about 175-200, about 200-225, about 225-250, or about 250-260 amino acid residues, preferably consecutive amino acid residues, preferably counted from the N-terminus or C-terminus of the amino acid sequence, or up to the full length of any of the amino acid sequences encoded by the nucleic acid sequences set out in SEQ ID NO: 3.

Preferably, the ABCG37 polypeptide comprises about 1100-1125, about 1125-1150, about 1150-1175, about 1175-1200, about 1200-1225, about 1200-1225, about 1225-1250, about 1250-1275, about 1275-1300, about 1300-1325, about 1325-1350, about 1350-1375, about 1375-1400, about 1400-1425, or about 1425-1451 amino acid residues, preferably consecutive amino acid residues, preferably counted from the N-terminus or C-terminus of the amino acid sequence, or up to the full length of any of the amino acid sequences encoded by the nucleic acid sequences set out in SEQ ID NO: 5.

Preferably, the UGT71C1 polypeptide comprises about 225-250, about 250-275, about 275-300, about 300-325, about 325-350, about 350-375, about 375-400, about 400-425, about 425-450, about 450-475, or about 475-482 amino acid residues, preferably consecutive amino acid residues, preferably counted from the N-terminus or C-terminus of the amino acid sequence, or up to the full length of any of the amino acid sequences encoded by the nucleic acid sequences set out in SEQ ID NO: 7.

The F6H1, CCoAOMT, ABCG37 and/or UGT71C1 proteins described herein are useful in the constructs, methods, plants, harvestable parts and products of the invention.

Methods for Increasing Fungal Resistance

One embodiment of the present invention is a method according to the present invention for increasing fungal resistance in a plant, a plant part, or a plant cell, wherein the method comprises the step of increasing the production of scopoletin and/or a derivative thereof in the plant, plant part, or plant cell in comparison to a wild type plant, wild type plant part, or wild type plant cell. The derivative of the scopoletin may be the scopolin.

Scopoletin is defined by the structural formula:

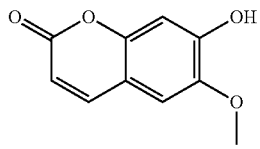

Scopolin is defined by the structural formula:

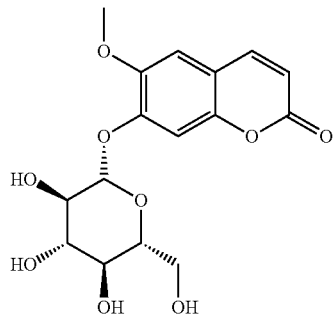

One embodiment of the present invention is a method for increasing fungal resistance in a plant, a plant part, or a plant cell, wherein the method comprises increasing the expression and/or biological activity of a F6H1 protein in the plant, plant part, or plant cell in comparison to a wild type plant, wild type plant part, or wild type plant cell, wherein said F6H1 protein is encoded by as defined above. In a preferred embodiment said method further comprises increasing the expression and/or biological activity of at least one or more additional protein(s) selected from the group consisting of a CCoAOMT1 protein, a ABCG37 protein and a UGT71C1 protein in the plant, plant part, or plant cell in comparison to a wild type plant, wild type plant part, or wild type plant cell, wherein said CCoAOMT1 protein, a ABCG37 protein and a UGT71C1 protein are defined as above. Preferably, said method comprises increasing the productions and/or accumulation of scopoletin and/or a derivative thereof in a plant, plant part or plant cell.

One embodiment of the invention is a method for increasing fungal resistance, preferably resistance to Phacopsoracea and/or *Fusarium*, in a plant, plant part, or plant cell by increasing the expression and/or biological activity of a F6H1 protein, and optionally in combination with increasing the expression and/or biological activity of one or more of the protein(s) selected from the group consisting of CCoAOMT, ABCG37 and/or UGT71C1 protein(s) or a functional fragment, homologue thereof in comparison to wild-type plants, wild-type plant parts or wild-type plant cells. Preferably, the F6H1 protein is expressed from an exogenous nucleic acid. Preferably, F6H1 protein and one or more the proteins selected from the group consisting of CCoAOMT, ABCG37 and/or UGT71C1 protein(s), are expressed from an exogenous nucleic acid.

One embodiment of the invention is a method for increasing fungal resistance in a plant, a plant part, or a plant cell comprises (a) stably transforming a plant cell with an expression cassette comprising an exogenous nucleic acid encoding a F6H1 protein,
(b) regenerating the plant from the plant cell; and
(c) expressing said exogenous nucleic acid.

A preferred method according to the present invention comprises (a) stably transforming a plant cell with expression cassette
  (s) comprising an exogenous nucleic acid encoding a F6H1 protein and encoding one or more exogenous nucleic acid(s) encoding CCoAOMT1, ABCG37 and/or UGT71C1 protein(s),
(b) regenerating the plant from the plant cell; and
(c) expressing said exogenous nucleic acids,
  optionally wherein the nucleic acid(s) which codes for a CCoAOMT1, ABCG37 and/or UGT71C1 protein(s) is expressed in an amount and for a period sufficient to generate or to increase fungal resistance in said plant.

Preferably the nucleic acid(s) encoding F6H1, CCoAOMT1, ABCG37 and/or UGT71C1 protein(s) are in functional linkage with a promoter. Preferably, the promoter is a constitutive, pathogen inducible, preferably fungal inducible, mesophyll-specific promoter and/or epidermis-specific promoter and/or stalk specific, ear or kernel specific promoter Preferably, the production of scopoletin and/or a derivative thereof in the plant, plant part, or plant cell in comparison to a wild type plant, wild type plant part, or wild type plant cell is increased.

In preferred embodiments, the protein amount and/or biological activity of the F6H1 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the F6H1 nucleic acid.

In preferred embodiments, the protein amount and/or biological activity of the CCoAOMT protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the CCoAOMT nucleic acid.

In preferred embodiments, the protein amount and/or biological activity of the ABCG37 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the ABCG37 nucleic acid.

In preferred embodiments, the protein amount and/or biological activity of the UGT71C1 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the UGT71C1 nucleic acid.

The exogenous nucleic acid encoding F6H1, CCoAOMT1, ABCG37 and/or UGT71C1 are located on the same or different expression cassettes. Preferably, one expression cassette comprises exogenous nucleic acid encoding F6H1 and optionally in combination with one or more exogenous nucleic acid encoding CCoAOMT1, ABCG37 and/or UGT71C1. Preferably, the expression cassette comprises exogenous nucleic acid encoding

F6H1,

F6H1 and CCoAOMT1,

F6H1 and ABCG37,

F6H1 and UGT71C1,

F6H1, CCoAOMT1 and ABCG37

F6H1, CCoAOMT1 and UGT71C1,

F6H1, UGT71C1 and ABCG37 or

F6H1, CCoAOMT1, ABCG37 and UGT71C1 proteins.

In another embodiment the exogenous nucleic acid encoding

F6H1 and CCoAOMT1,

F6H1 and ABCG37,

F6H1 and UGT71C1 or

F6H1, CCoAOMT1 and ABCG37

F6H1, CCoAOMT1 and UGT71C1

F6H1, UGT71C1 and ABCG37 or

F6H1, CCoAOMT1, ABCG37 and UGT71C1 proteins are located on different expression cassettes.

The fungal pathogens or fungus-like pathogens (such as, for example, Chromista) can belong to the group comprising Plasmodiophoramycota, Oomycota, Ascomycota, Chytridiomycetes, Zygomycetes, Basidiomycota or Deuteromycetes (Fungi imperfecti). Pathogens which may be mentioned by way of example, but not by limitation, are those detailed in Tables 2 and 3, and the diseases which are associated with them.

TABLE 2

Diseases caused by biotrophic and/or heminecrotrophic phytopathogenic fungi

| Disease | Pathogen |
|---|---|
| Leaf rust | Puccinia recondita |
| Yellow rust | P. striiformis |
| Powdery mildew | Erysiphe graminis/Blumeria graminis |
| Rust (common corn) | Puccinia sorghi |
| Rust (Southern corn) | Puccinia polysora |
| Tobacco leaf spot | Cercospora nicotianae |
| Rust (soybean) | Phakopsora pachyrhizi, P. meibomiae |
| Rust (tropical corn) | Physopella pallescens, P. zeae = Angiopsora zeae |

TABLE 3

Diseases caused by necrotrophic and/or hemibiotrophic fungi and Oomycetes

| Disease | Pathogen |
|---|---|
| Plume blotch | Septoria (Stagonospora) nodorum |
| Leaf blotch | Septoria tritici |
| Ear fusarioses | Fusarium spp. |
| Late blight | Phytophthora infestans |
| Anthrocnose leaf blight | Colletotrichum graminicola (teleomorph: Glomerella graminicola Politis); |
| Anthracnose stalk rot | Glomerella tucumanensis (anamorph: Glomerella falcatum Went) |
| Curvularia leaf spot | Curvularia clavata, C. eragrostidis, =C. maculans (teleomorph: Cochliobolus eragrostidis), Curvularia inaequalis, C. intermedia (teleomorph: Cochliobolus intermedius), Curvularia lunata (teleomorph: Cochliobolus lunatus), Curvularia pallescens (teleomorph: Cochliobolus pallescens), Curvularia senegalensis, C. tuberculata (teleomorph: Cochliobolus tuberculatus) |
| Didymella leaf spot | Didymella exitalis |
| Diplodia leaf spot or streak | Stenocarpella macrospora = Diplodialeaf macrospora |
| Brown stripe downy mildew | Sclerophthora rayssiae var. zeae |
| Crazy top downy mildew | Sclerophthora macrospora = Sclerospora macrospora |
| Green ear downy mildew (graminicola downy mildew) | Sclerospora graminicola |
| Leaf spots, minor | Alternaria alternata, Ascochyta maydis, A. tritici, A. zeicola, Bipolaris victoriae = Helminthosporium victoriae (teleomorph: Cochliobolus victoriae), C. sativus (anamorph: Bipolaris sorokiniana = H. sorokinianum = H. sativum), Epicoccum nigrum, Exserohilum prolatum = Drechslera prolata (teleomorph: Setosphaeria prolata) Graphium penicillioides, Leptosphaeria maydis, Leptothyrium zeae, Ophiosphaerella herpotricha, (anamorph: Scolecosporiella sp.), Paraphaeosphaeria michotii, Phoma sp., Septoria zeae, S. zeicola, S. zeina |
| Northern corn leaf blight (white blast, crown stalk rot, stripe) | Setosphaeria turcica (anamorph: Exserohilum turcicum = Helminthosporium turcicum) |
| Northern corn leaf spot Helminthosporium ear rot (race 1) | Cochliobolus carbonum (anamorph: Bipolaris zeicola = Helminthosporium carbonum) |
| Phaeosphaeria leaf spot | Phaeosphaeria maydis = Sphaerulina maydis |
| Rostratum leaf spot (Helminthosporium leaf disease, ear and stalk rot) | Setosphaeria rostrata, (anamorph: xserohilum rostratum = Helminthosporium rostratum) |
| Java downy mildew | Peronosclerospora maydis = Sclerospora maydis |
| Philippine downy mildew | Peronosclerospora philippinensis = Sclerospora philippinensis |
| Sorghum downy mildew | Peronosclerospora sorghi = Sclerospora sorghi |
| Spontaneum downy mildew | Peronosclerospora spontanea = Sclerospora spontanea |
| Sugarcane downy mildew | Peronosclerospora sacchari = Sclerospora sacchari |
| Sclerotium ear rot (southern blight) | Sclerotium rolfsii Sacc. (teleomorph: Athelia rolfsii) |

TABLE 3-continued

Diseases caused by necrotrophic and/or hemibiotrophic fungi and Oomycetes

| Disease | Pathogen |
|---|---|
| Seed rot-seedling blight | Bipolaris sorokiniana, B. zeicola = Helminthosporium carbonum, Diplodia maydis, Exserohilum pedicillatum, Exserohilum turcicum = Helminthosporium turcicum, Fusarium avenaceum, F. culmorum, F. moniliforme, Gibberella zeae (anamorph: F. graminearum), Macrophomina phaseolina, Penicillium spp., Phomopsis sp., Pythium spp., Rhizoctonia solani, R. zeae, Sclerotium rolfsii, Spicaria sp. |
| Selenophoma leaf spot | Selenophoma sp. |
| Yellow leaf blight | Ascochyta ischaemi, Phyllosticta maydis (teleomorph: Mycosphaerella zeae-maydis) |
| Zonate leaf spot | Gloeocercospora sorghi |

Preferred fungal pathogens are of the order Pucciniales, in particular the family Phacopsoracea, in particular the genus *Phakopsora*, more particularly the species *Phakopsora pachyrhizi* and/or *Phakopsora meibomiae*—also known as soybean rust or Asian Soybean Rust (ASR) and/or preferred fungal pathogens are of the family Nectriaceae, in particular the genus *Fusarium*, in particular the species *Fusarium graminearum, Fusarium sporotrichioides, Fusarium pseudograminearum, Fusarium culmorum, Fusarium poae, Fusarium verticillioides* (*Fusarium moniliforme*), *Fusarium subglutinans, Fusarium proliferatum, Fusarium fujikuroi*), *Fusarium avenaceum, Fusarium oxysporum, Fusarium virguliforme* and/or *Fusarium solani*. Most preferred is *fusarium graminearum* and/or *fusarium verticolloides*.

F6H1, CCoAOMT1, ABCG37 and/or UGT71C1 expression constructs and vector constructs One embodiment of the present invention is a recombinant vector construct comprising the nucleic acid encoding F6H1 protein as defined above operably linked with a promoter and a transcription termination sequence.

One embodiment of the present invention is a recombinant vector construct comprising the nucleic acid encoding CCoAOMT1 protein as defined above operably linked with a promoter and a transcription termination sequence.

One embodiment of the present invention is a recombinant vector construct comprising the nucleic acid encoding ABCG37 protein as defined above operably linked with a promoter and a transcription termination sequence.

One embodiment of the present invention is a recombinant vector construct comprising the nucleic acid encoding UGT71C1 protein as defined above operably linked with a promoter and a transcription termination sequence.

In one embodiment the nucleic acid encoding F6H1 protein, CCoAOMT1 protein, ABCG37 and/or UGT71C1 protein are located on the same recombinant vector construct. In another embodiment the nucleic acid encoding F6H1 protein, CCoAOMT1 protein and/or ABCG37 protein are located on different vector constructs. Preferably, one expression cassette comprises the exogenous nucleic acid(s) encoding F6H1 and optionally in combination with exogenous nucleic acids encoding one or more selected from the group of the exogenous nucleic acid(s) CCoAOMT1, ABCG37 and/or UGT71C1. Preferably, the recombinant vector construct comprises exogenous nucleic acid encoding.

F6H1,
F6H1 and CCoAOMT1,
F6H1 and ABCG37,
F6H1 and UGT71C1,
F6H1, CCoAOMT1 and ABCG37
F6H1, CCoAOMT1 and UGT71C1
F6H1, UGT71C1 and ABCG37 or
F6H1, CCoAOMT1, ABCG37 and UGT71C1 proteins.

Promoters according to the present invention may be constitutive, inducible, in particular pathogen-inducible, developmental stage-preferred, cell type-preferred, tissue-preferred or organ-preferred. Examples for suitable promoters and terminators are:

p-PcUbi::F6H1::t-ocs
p-SUPER::CCoAOMT1::t-nos
p-Glyma14g06680::ABCG37::t-StCATHD
p-SUPER::UGT71C1::t-nos The PcUbi promoter regulates constitutive expression of the ubi4-2 gene (accession number X64345) of Petroselinum crispum (Kawalleck, P., Somssich, I. E., Feldbrügge, M., Hahlbrock, K., & Weisshaar, B. (1993). Polyubiquitin gene expression and structural properties of the ubi4-2 gene in Petroselinum crispum. Plant molecular biology, 21(4), 673-684. The p-Super promoter consists of three identical Octapine Synthase Enhancers followed by a MAS promoter (Lee et al., 2007 Plant Physiology Vol145 Issue 4 1294-1300). The p-Glyma14g06680 promoter has been identified in a screen for genes that are predominantly expressed in the leaf of soybean. The promoter regulates the expression of the gene Glyma14g06680, which is most likely a water channel protein (WO12127373) T-ocs and t-NOS terminators are both derived from *Agrobacterium* (Gielen, J., et al. "The complete nucleotide sequence of the TL-DNA of the *Agrobacterium tumefaciens* plasmid pTiAch5." The EMBO journal 3.4 (1984): 835. T-ocs is the terminator of the octopine synthase gene and t-NOS is the terminator of the nopaline synthase gene of *Agrobacterium tumefaciens* The StCATHD-pA is the terminator of the cathepsin D inhibitor gene from *Solanum tuberosum* (t-StCat) (Herbers et al. 1994)

One type of recombinant vector construct is a "plasmid," which refers to a circular double stranded DNA loop into which additional DNA segments can be ligated. Another type of vector is a viral vector, wherein additional DNA segments can be ligated into the viral genome. Certain vector constructs are capable of autonomous replication in a host plant cell into which they are introduced. Other vector constructs are integrated into the genome of a host plant cell upon introduction into the host cell, and thereby are replicated along with the host genome. In particular the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

Transgenic Organisms; Transgenic Plants, Plant Parts, and Plant Cells

A preferred embodiment is a transgenic plant, transgenic plant part, or transgenic plant cell overexpressing an exogenous F6H1 protein, optionally in combination with overexpressing one or more of CCoAOMT1 protein, ABCG37 protein and/or UGT71C1 protein encoded by a nucleic acid as defined above.

In preferred embodiments the biological activity of the F6H1 protein optional the biological activity of one or more of CCoAOMT1 protein, ABCG37 protein and/or UGT71C1 protein is increased in said transgenic plant, transgenic plant part, or transgenic plant cell.

In preferred embodiments, the protein amount of a F6H1 protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the F6H1 nucleic acid.

In preferred embodiments, the protein amount of a CCoAOMT1 protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the CCoAOMT1 nucleic acid.

In preferred embodiments, the protein amount of a ABCG37 protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the ABCG37 nucleic acid.

In preferred embodiments, the protein amount of a UGT71C1 protein in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the ABCG37 nucleic acid.

On preferred embodiments the amount of F6H1 protein in combination with CCoAOMT1 and/or ABCG37 and/or UGT71C1 in the transgenic plant is increased by at least 10%, at least 20%, at least 30%, at least 40%, at least 50%, at least 60%, at least 70%, at least 80%, at least 90%, or at least 95% or more in comparison to a wild type plant that is not transformed with the respective nucleic acid(s).

More preferably, the transgenic plant, transgenic plant part, or transgenic plant cell according to the present invention has been obtained by transformation with one or more recombinant vector construct(s) described herein. In one embodiment a transgenic plant, transgenic plant part, or transgenic plant cell is transformed with one or more recombinant vector construct(s) as described, wherein the nucleic acid(s) encoding a F6H1 protein, and/or a CCoAOMT1 protein, and/or a ABCG37 protein and/or a UGT71C1 protein are located on the same recombinant vector construct or different vector constructs. Preferably, the recombinant vector construct comprises exogenous nucleic acid encoding F6H1 and CCoAOMT1, F6H1 and ABCG37, F6H1 and UGT71C1 or F6H1, CCoAOMT1, ABCG37 and UGT71C1 proteins.

A preferred embodiment comprises a transgenic plant, transgenic plant part, or transgenic plant cell overexpressing an exogenous F6H1 protein optionally in combination with one or more additional exogenous protein(s) selected from the group consisting of a CCoAOMT1 protein, an ABCG37 protein and an UGT71C1 protein, wherein the nucleic acid encodings the respective protein(s) is operably linked with a promoter and a transcription termination sequence.

Suitable methods for transforming or transfecting host cells including plant cells are well known in the art of plant biotechnology. Any method may be used to transform the recombinant expression vector into plant cells to yield the transgenic plants of the invention. General methods for transforming dicotyledonous plants are disclosed, for example, in U.S. Pat. Nos. 4,940,838; 5,464,763, and the like. Methods for transforming specific dicotyledonous plants, for example, cotton, are set forth in U.S. Pat. Nos. 5,004,863; 5,159,135; and 5,846,797. Soy transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of Agrobacterium (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). Agrobacterium based transformation techniques (especially for dicotyledonous plants) are well known in the art. The Agrobacterium strain (e.g., Agrobacterium tumefaciens or Agrobacterium rhizogenes) comprises a plasmid (Ti or Ri plasmid) and a T-DNA element which is transferred to the plant following infection with Agrobacterium. The T-DNA (transferred DNA) is integrated into the genome of the plant cell. The T-DNA may be localized on the Ri- or Ti-plasmid or is separately comprised in a so-called binary vector. Methods for the Agrobacterium-mediated transformation are described, for example, in Horsch R B et al. (1985) Science 225:1229. The Agrobacterium-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The genetically modified plant cells can be regenerated via all methods with which the skilled worker is familiar. Suitable methods can be found in the abovementioned publications by S. D. Kung and R. Wu, Potrykus or Höfgen and Willmitzer.

After transformation, plant cells or cell groupings may be selected for the presence of one or more markers which are encoded by plant-expressible genes co-transferred with the gene of interest, following which the transformed material is regenerated into a whole plant.

To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. The transformed plants may also be directly selected by screening for the presence of the F6H1, CCoAOMT1, ABCG37 and/or UGT71C1 protein nucleic acid(s).

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques or crossed with appropriate tester lines to generate hybrids. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion). Preferably, constructs or vectors or expression cassettes are not present in the genome of the original plant or are present in the genome of the transgenic plant not at their natural locus of the genome of the original plant.

Preferably, the transgenic plant of the present invention or the plant obtained by the method of the present invention has increased resistance against fungal pathogens, preferably rust pathogens (i.e., fungal pathogens of the order Pucciniales), preferably against fungal pathogens of the family Phacopsoraceae, more preferably against fungal pathogens of the genus *Phacopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Preferably, the plant, plant part, or plant cell is a plant or derived from a plant selected from the group consisting of beans, soya, pea, clover, kudzu, lucerne, lentils, lupins, vetches, groundnut, rice, wheat, barley, *arabidopsis*, lentil, banana, canola, cotton, potatoe, corn, sugar cane, alfalfa, and sugar beet.

In one embodiment of the present invention the plant is selected from the group consisting of beans, soy, pea, clover, kudzu, lucerne, lentils, lupins, vetches, and/or groundnut. Preferably, the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. sativum), also called smooth or round-seeded peas; marrowfat pea (*Pisum sativum* L. convar. medullare Alef. emend. C. O. Lehm), sugar pea (*Pisum sativum* L. convar. axiphium Alef emend. C. O. Lehm), also called snow pea, edible-podded pea or mangetout, (*Pisum granda sneida* L. convar. sneidulo p. shneiderium)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (*Lens*) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna* subterrane (L.) Verdc.), rice bean (*Vigna umbellata* (Thunb.) Ohwi & H. Ohashi), *Vigna* vexillata (L.) A. Rich., *Vigna unguiculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.); goa bean (*Psophocarpus tetragonolobus* (L.) DC.), African yam bean (*Sphenostylis stenocarpa* (Hochst. ex A. Rich.) Harms), Egyptian black bean, dolichos bean, lablab bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.).

Further preferred is a plant selected from the group consisting of beans, soya, pea, clover, kudzu, lucerne, lentils, lupins, vetches, and groundnut. Most preferably, the plant, plant part, or plant cell is or is derived from soy and/or corn.

Preferably, the transgenic plant of the present invention or the plant obtained by the method of the present invention is a soybean plant and has increased resistance against fungal pathogens of the order Pucciniales (rust), preferably, of the family Phacopsoraceae, more preferably against fungal pathogens of the genus *Phacopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Preferably, the transgenic plant of the present invention or the plant obtained by the method of the present invention is a corn plant and has increased resistance against fungal pathogens of the family Nectriaceae, in particular the genus *Fusarium*, in particular the species *Fusarium graminearum, Fusarium sporotrichioides, Fusarium pseudograminearum, Fusarium culmorum, Fusarium poae, Fusarium verticillioides (Fusarium moniliforme), Fusarium subglutinans, Fusarium proliferatum, Fusarium fujikuroi), Fusarium avenaceum, Fusarium oxysporum, Fusarium virguliforme* and/or *Fusarium solani*. Most preferred is *fusarium graminearum* and/or *fusarium* verticolloides.

Methods for the Production of Transgenic Plants

One embodiment according to the present invention provides a method for the production of a transgenic plant, transgenic plant part, or transgenic plant cell having increased fungal resistance, comprising introducing a) exogenous nucleic acid encoding the nucleic acid encoding F6H1 protein wherein said F6H1 protein is encoded a nucleic acid as defined above operably linked with a promoter and a transcription termination sequence, and further optionally introducing one or more nucleic acids selected from the group consisting of b) exogenous nucleic acids encoding CCoAOMT1 protein as defined above operably linked with a promoter and a transcription termination sequence, c) exogenous nucleic acids encoding ABCG37 protein as defined above operably linked with a promoter and a transcription termination sequence, and
d) exogenous nucleic acids encoding UGT71C1 protein as defined above operably linked with a promoter and a transcription termination sequence
into a plant, a plant part, or a plant cell,
wherein the exogenous nucleic acid encoding F6H1, CCoAMT1, ABCG37 and/or UGT71C1 protein are located on the same or different vector constructs,
generating a transgenic plant, transgenic plant part, or transgenic plant cell from the plant, plant part or plant cell; and
expressing the protein(s) encoded by the recombinant vector construct(s).

In one embodiment, the present invention refers to a method for the production of a transgenic plant, transgenic plant part, or transgenic plant cell having increased fungal resistance, comprising
(a) introducing a recombinant vector construct according to the present invention into a plant, a plant part or a plant cell and
(b) generating a transgenic plant from the plant, plant part or plant cell and optionally
(c) expressing the F6H1 protein and one or more proteins selected from the group consisting of CCoAMT1, ABCG37 and/or UGT71C1 protein(s).

Preferably, said introducing and expressing does not comprise an essentially biological process.

Preferably, the method for the production of the transgenic plant, transgenic plant part, or transgenic plant cell further comprises the step of selecting a transgenic plant expressing F6H1 protein and one or more proteins selected from the group consisting of CCoAMT1, ABCG37 and/or UGT71C1 protein(s).

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises a nucleic acid encoding F6H1 protein and one or more nucleic acids encoding proteins selected from the group consisting of CCoAMT1, ABCG37 and/or UGT71C1 protein(s) operably linked with a promoter and a transcription termination sequence.

Preferably, the step of harvesting the seeds of the transgenic plant and planting the seeds and growing the seeds to plants is repeated more than one time, preferably, 1, 2, 3, 4, 5, 6, 7, 8, 9, 10, 15, 20, 25, 30, 35, 40, 45, or 50 times.

The transgenic plants may be selected by known methods as described above (e.g., by screening for the presence of one or more markers which are encoded by plant-expressible genes co-transferred with the F6H1, CCoAMT1, ABCG37 and/or UGT71C1 gene(s) or by directly screening for the FF6H1, CCoAMT1, ABCG37 and/or UGT71C1 nucleic acid(s)).

Furthermore, the use of the exogenous F6H1 nucleic acid optionally in combination with one or more nucleic acids selected from the group consisting of CCoAMT1, ABCG37 and/or UGT71C1 nucleic acid(s) or use of the recombinant vector construct comprising the F6H1 nucleic acid optionally in combination with one or more nucleic acid(s) selected from the group CCoAMT1, ABCG37 and/or UGT71C1 nucleic acid(s) for the transformation of a plant, plant part, or plant cell to provide a fungal resistant plant, plant part, or plant cell is provided.

Harvestable Parts and Products

Harvestable parts of the transgenic plant according to the present invention are part of the invention. Preferably, the harvestable parts comprise the F6H1 nucleic acid optionally in combination with one or more nucleic acids selected from the group consisting of CCoAMT1, ABCG37 and/or UGT71C1 nucleic acid(s) or F6H1 protein optionally in combination with one or more protein(s) selected from the group consisting of CCoAMT1, ABCG37 and UGT71C1 protein(s). The harvestable parts may be seeds, roots, leaves and/or flowers. Preferred parts of soy plants are soy beans. Preferred parts of corn plants are corn grains.

Products derived from a transgenic plant according to the present invention, parts thereof or harvestable parts thereof are part of the invention. A preferred product is oil, preferably, corn oil or soybean oil.

Preferred parts of soy plants are soy beans comprising the F6H1 nucleic acid optionally in combination with one or more nucleic acids selected from the group consisting of CCoAMT1, ABCG37 and/or UGT71C1 nucleic acid(s) or F6H1 protein optionally in combination with one or more protein(s) selected from the group consisting of CCoAMT1, ABCG37 and UGT71C1 protein(s).

Preferred parts of corn plants are soy grains comprising the F6H1 nucleic acid optionally in combination with one or more nucleic acids selected from the group consisting of CCoAMT1, ABCG37 and/or UGT71C1 nucleic acid(s) or F6H1 protein optionally in combination with one or more protein(s) selected from the group consisting of CCoAMT1, ABCG37 and UGT71C1 protein(s).

In a preferred embodiment a product is derived from the plant described above or from the harvestable part of the plant described above, wherein the product is preferably soybean oil and/or corn oil.

Preferably the soybean oil comprise the F6H1 nucleic acid optionally in combination with one or more nucleic acids selected from the group consisting of CCoAMT1, ABCG37 and/or UGT71C1 nucleic acid(s) or F6H1 protein optionally in combination with one or more protein(s) selected from the group consisting of CCoAMT1, ABCG37 and UGT71C1 protein(s).

Preferably the corn oil comprises the F6H1 nucleic acid optionally in combination with one or more nucleic acids selected from the group consisting of CCoAMT1, ABCG37 and/or UGT71C1 nucleic acid(s) or F6H1 protein optionally in combination with one or more protein(s) selected from the group consisting of CCoAMT1, ABCG37 and UGT71C1 protein(s).

Methods for Manufacturing a Product

In one embodiment the method for the production of a product comprises
a) growing the plants of the invention or obtainable by the methods of invention and
b) producing said product from or by the plants of the invention and/or parts, e.g. seeds, of these plants.

In a further embodiment the method comprises the steps a) growing the plants of the invention, b) removing the harvestable parts as defined above from the plants and c) producing said product from or by the harvestable parts of the invention.

Preferably the products obtained by said method comprises an exogenous nucleic acid(s) and/or protein(s) according to the invention.

Method for the production of a product comprising
a) growing a plant according to the invention or obtainable by the method according to the invention and b) producing said product from or by the plant and/or part, preferably seeds, of the plant, wherein the product comprise the F6H1 nucleic acid optionally in combination with one or more nucleic acids selected from the group consisting of CCoAMT1, ABCG37 and/or UGT71C1 nucleic acid(s) or the proteins encoded by said nucleic acids.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Methods for Breeding/Methods for Plant Improvement/ Methods Plant Variety Production The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the F6H1 nucleic acid optionally in combination with nucleic acids selected from the group consisting of CCoAMT1, ABCG37 and UGT71C1 nucleic acid(s). The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Thus, one embodiment of the present invention is a method for breeding a fungal resistant plant comprising the steps of (a) crossing a transgenic plant described herein or a plant obtainable by a method described herein with a second plant;
(b) obtaining a seed or seeds resulting from the crossing step described in (a);
(c) planting said seed or seeds and growing the seed or seeds to plants; and
(d) selecting from said plants the plants expressing a F6H1 protein optionally in combination with one or more proteins selected from the group consisting of, CCoAMT1, ABCG37 and UGT71C1 protein(s).

Another preferred embodiment is a method for plant improvement comprising (a) obtaining a transgenic plant by any of the methods of the present invention;
(b) combining within one plant cell the genetic material of at least one plant cell of the plant of (a) with the genetic material of at least one cell differing in one or more gene from the plant cells of the plants of (a) or crossing the transgenic plant of (a) with a second plant;
(c) obtaining seed from at least one plant generated from the one plant cell of (b) or the plant of the cross of step (b);
(d) planting said seeds and growing the seeds to plants; and
(e) selecting from said plants, plants expressing the nucleic acid encoding F6H1 protein optionally in combination with one or more protein(s) selected from the group consisting of CCoAMT1, ABCG37 and UGT71C1 protein(s); and optionally
(f) producing propagation material from the plants expressing the nucleic acid encoding F6H1 protein optionally in combination with one or more protein(s) selected from the group consisting of CCoAMT1, ABCG37 and UGT71C1 protein(s).

The transgenic plants may be selected by known methods as described above (e.g., by screening for the presence of one or more markers which are encoded by plant-expressible genes co-transferred with the F6H1, CCoAMT1, ABCG37 and/or UGT71C1 gene or screening for the F6H1, CCoAMT1, ABCG37 and/or UGT71C1 nucleic acid itself).

According to the present invention, the introduced F6H1 nucleic acid optionally in combination with one or more nucleic acids selected from the group consisting of CCoAMT1, ABCG37 and/or UGT71C1 nucleic acid may be maintained in the plant cell stably if it is incorporated into a non-chromosomal autonomous replicon or integrated into the plant chromosomes. Whether present in an extra-chromosomal non-replicating or replicating vector construct or a vector construct that is integrated into a chromosome, the exogenous F6H1, CCoAMT1, ABCG37 and/or UGT71C1 nucleic acid preferably resides in one or more a plant expression cassette. A plant expression cassette preferably contains regulatory sequences capable of driving gene expression in plant cells that are functional linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other functional linked sequences like translational enhancers such as the overdrive-sequence containing the 5'-untranslated leader sequence from tobacco mosaic virus increasing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

A preferred method according to the invention is a method for applying a scopoletin and/or a derivative thereof to a surface of a plant, plant part or plant cell, wherein the resistance to a fungal pathogen of the plant, plant part or plant cell is increased by applying scopoletin and/or a derivative thereof to the surface of the plant, plant part or plant cell in comparison to a plant, plant part or plant cell to which surface scopoletin and/or a derivative has not been applied, wherein the plant is soy and/or corn.

In one embodiment according to the invention a plant surface or plant part surface is coated with scopoletin and/or a derivative thereof, wherein the plant is soy and/or corn.

In one embodiment according to the invention a plant, plant part or plant cell has a surface coated with scopoletin and/or a derivative thereof. wherein the plant is soy and/or corn.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1

General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977).

Example 2

Figure 2A:
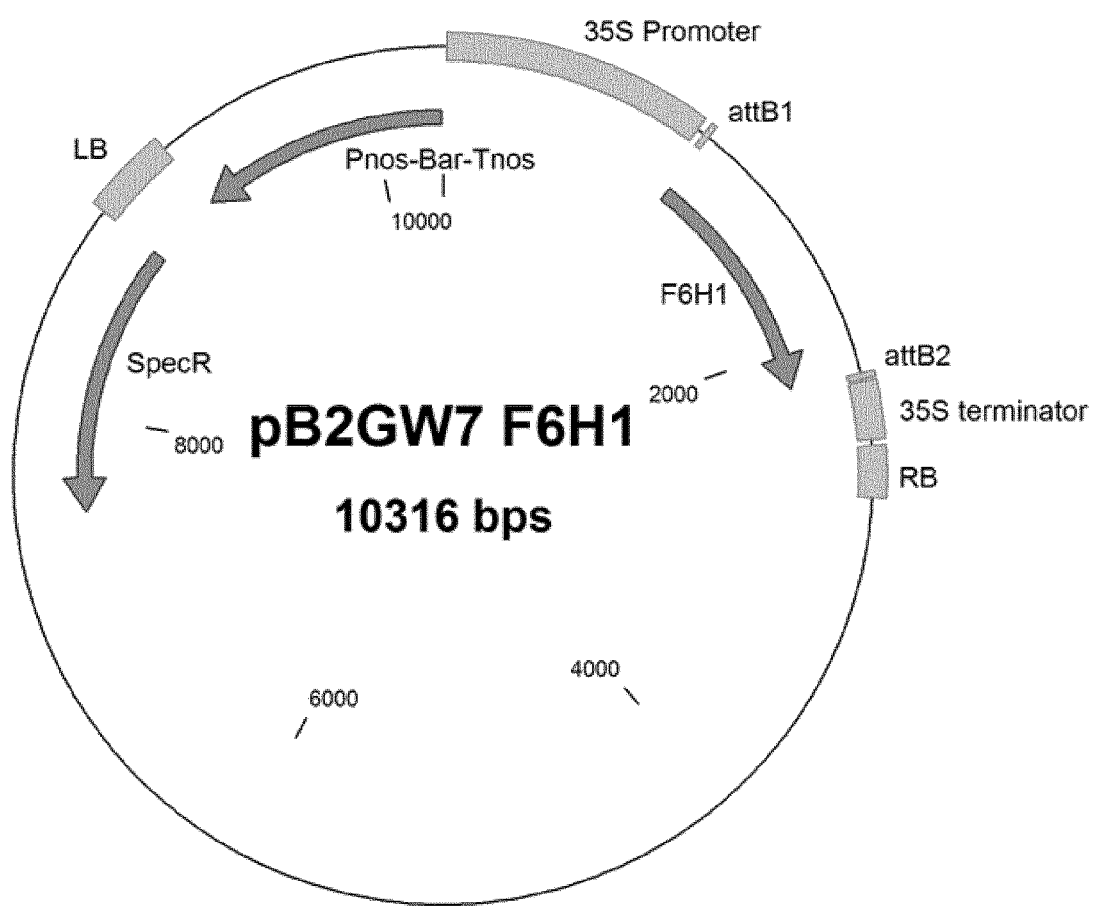
Figure 2B:
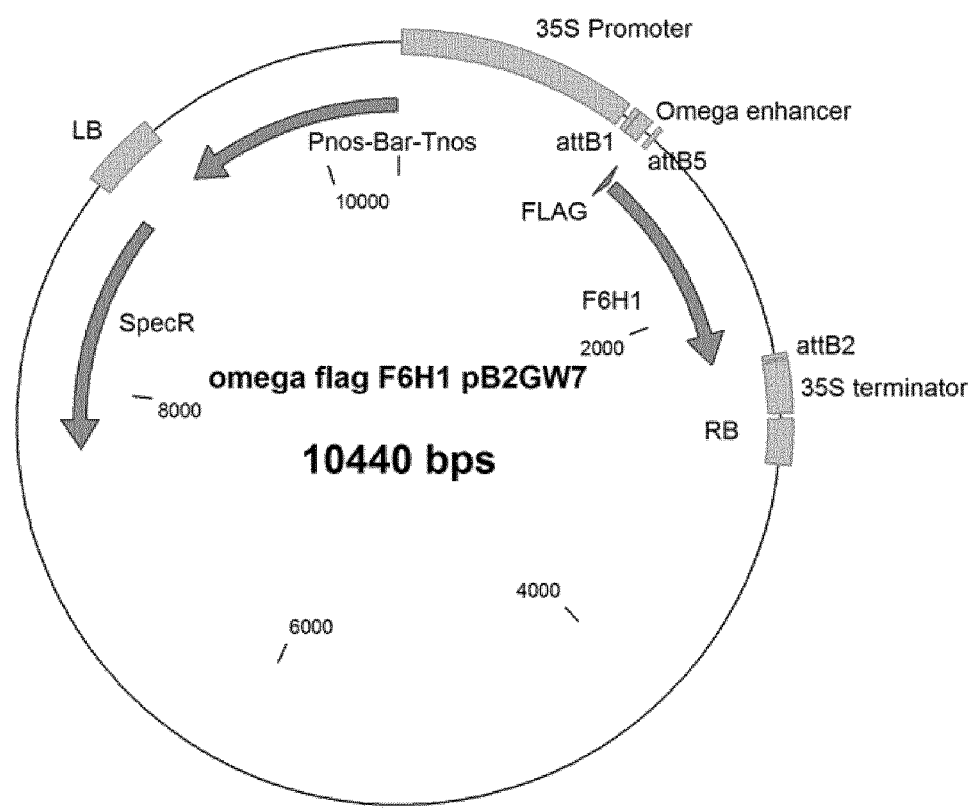

Cloning of Overexpression Vector Constructs for Transient *N. benthamiana* Transformation To obtain cDNA, RNA was extracted from leaf tissue of *Arabidopsis thaliana* pen2 mutants that had been inoculated with *P. pachyrhizi* two days before harvest. cDNA was produced using RevertAid H minus reverse trancriptase (Thermo Scientific). All steps of cDNA preparation and purification were performed according as described in the manual.

The SEQ-ID 1-sequence (F6H1) was amplified from the cDNA by PCR as described in the protocol of the Phusion High-Fidelity DNA Polymerase (Thermo Scientific) hot-start, Pfu Ultra, Pfu Turbo or Herculase DNA polymerase (Stratagene). The composition for the protocol of the Pfu Ultra, Pfu Turbo or Herculase DNA polymerase was as follows: 1×PCR buffer, 0.2 mM of each dNTP, 100 ng cDNA of *Arabidopsis thaliana* (var Columbia-0), 50 pmol forward primer, 50 pmol reverse primer, 1 u Phusion hot-start, Pfu Ultra, Pfu Turbo or Herculase DNA polymerase.

The amplification cycles were as follows:

1 cycle of 30 seconds at 98° C., followed by 35 cycles of in each case 10 seconds at 98° C., 30 seconds at 62° C. and 40 seconds at 72° C., followed by 1 cycle of 10 minutes at 72° C., then 4° C.

The following primer sequences were used to specifically amplify the F6H1 full-length ORF for cloning purposes:

```
i) F6H1_attB1 foward primer:
                                              (SEQ ID NO: 76)
5'-GGGGACAAGTTTGTACAAAAAAGCAGGCTTAATGGCTCCAACACTCT
TGAC-3' ii) F6H1_attB2 reverse primer:
                                              (SEQ ID NO: 77)
5'-GGGGACCACTTTGTACAAGAAAGCTGGGTATCAGATCTTGGCGTAAT
CG-3'
```

The amplified fragments were gel purified and cloned into the pDONR 207 entry vector (Invitrogen) using Gateway® cloning according to the manufacturer's instructions. Using this cloning technique the full-length F6H1 fragment is inserted in sense direction between the attL1 and attL2 recombination sites of the entry vector. To prepare an untagged F6H1 overexpression construct, a LR reaction (Gateway system, (Invitrogen, Life Technologies, Carlsbad, Calif., USA) was performed according to manufacturers protocol by using a pDONR207 vector containing the F6H1 fragment. As target a binary pB2GW7 (Ghent University, Belgium) vector was used, which is composed of: (1) a Spectinomycin resistance cassette for bacterial selection (2) a pVS1 origin for replication in Agrobacteria (3) a pBR322 origin of replication for stable maintenance in *E. coli* and (4) between the right and left border a bar selection gene under control of a pNos-promoter. The recombination reaction was transformed into competent *E. coli* (DH5alpha), mini-prepped and screened by specific restriction digestions. A positive clone from each the vector construct was sequenced and submitted to soy transformation (see FIG. 2*a*).

The amplified fragments were gel purified and to prepare a FLAG tagged F6H1 overexpression construct MultiSite Gateway® cloning was applied according to the manufacturer's manual. First, the Ω-FLAG sequence was PCR amplified from the vector pTA7002 (Shuqun Zhang, Columbia University, Missouri, USA) harboring the *Arabidopsis thaliana* MKK4 gene 5' flanked by a tobacco mosaic virus Ω translational enhancer and a FLAG Tag sequence using following primers (attB primer extensions underlined):

```
(i) Ω-FLAG-attB1 forward Primer:
                                              (SEQ ID NO: 78)
GGGGACAAGTTTGTACAAAAAAGCAGGCTCATATTTTTACAACAATTAC
CAACAACA (ii) Ω-FLAG-attB5r reverse Primer:
                                              (SEQ ID NO: 79)
GGGGACAACTTTTGTATACAAAGTTGTCTTGTCATCGTCGTCCTTGT
```

Second, the F6H1 full length coding sequence was PCR amplified from pen2 cDNA prepared as described above. Following primer sequences carrying 5"attB5 and attB2 extensions were used for F6H1 amplification by PCR (i) F6H1-attB5 forward Primer:
(SEQ ID NO: 80)
GGGGACAACTTTGTATACAAAAGTTGCAATGGCTCCAACACTCTTGAC (ii) F6H1-attB2 reverse Primer:
(SEQ ID NO: 77 see above)
GGGGACCACTTTGTACAAGAAAGCTGGGTATCAGATCTTGGCGTAATCG PCR products were gel purified and the attB1-Ω-FLAG-attB5r sequence introduced into pDONR221 P1-P5r via gateway cloning (BP reaction). Analogously the attB5-F6H1-attB2 sequence was cloned into pDONR 221 P5-P2. Recombination reactions were transformed into competent E. coli (DH5alpha). Following plasmid extraction both vectors were used for LR recombination with the pB2GW7 destination vector. The resulting expression clone containing both sequences (Ω-FLAG and F6H1) was screened by specific restriction digestions and sequenced prior to transformation (FIG. 2b).

Example 3a

Transient Transformation of N. benthamiana Leaves

Transient transformation of N. benthamiana leaves was done according to a slightly modified protocol from Popescu et al. 2007 (Popescu, S. C., Popescu, G. V., Bachan, S., Zhang, Z., Seay, M., Gerstein, M., Snyder, M., and Dinesh-Kumar, S. P. (2007). Differential binding of calmodulin-related proteinsto their targets revealed through high-density Arabidopsis protein microarrays Proc Natl Acad Sci USA 104, 4730-4735.) A single Agrobacterium (strain AGL01) carrying a DNA construct of interest (see FIGS. 2a and 2b) was cultured in YEB medium with appropriate antibiotics for 14-16 h at 28° C. Cells were harvested by centrifugation (5000 rpm 10 min), resuspended to an OD of 0.4-0.8 in buffer containing 10 mM MgCl2, 10 mM MES pH 5.6 and 150 µM acetosyringone and incubated for 2-5 h at room temperature. Agrobacteria transformed with the DNA construct of interest were then mixed with an equal volume of Agrobacteria containing the p19 silencing suppressor gene from tomato bushy stunt virus (TBSV) and 1:1 mixtures were syringae-infiltrated into leaves of 6-week-old N. benthamiana plants. Three days after Agrobacterium infiltration, leaves were frozen in liquid nitrogen and stored at −80° C. until analysis.

Example 3b

Figure 12A:
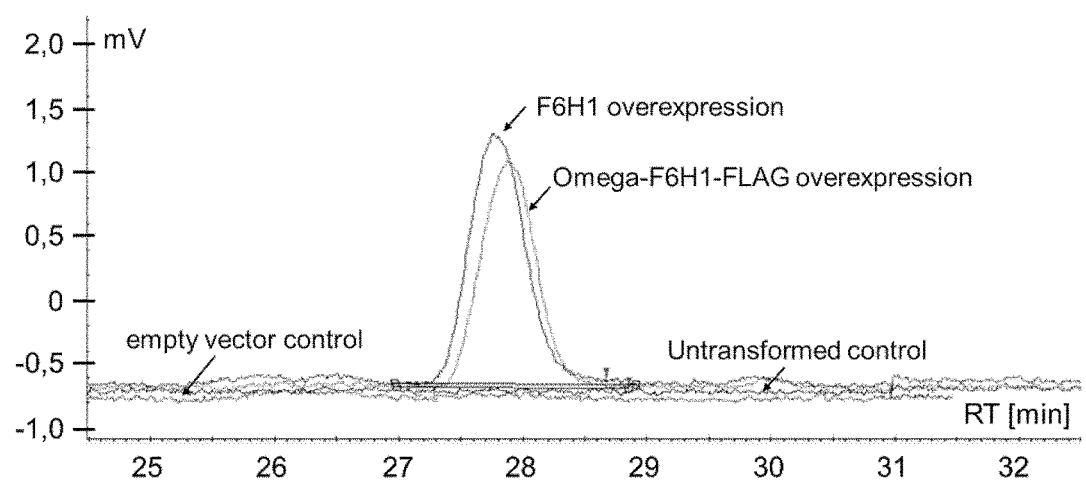
Figure 12B:
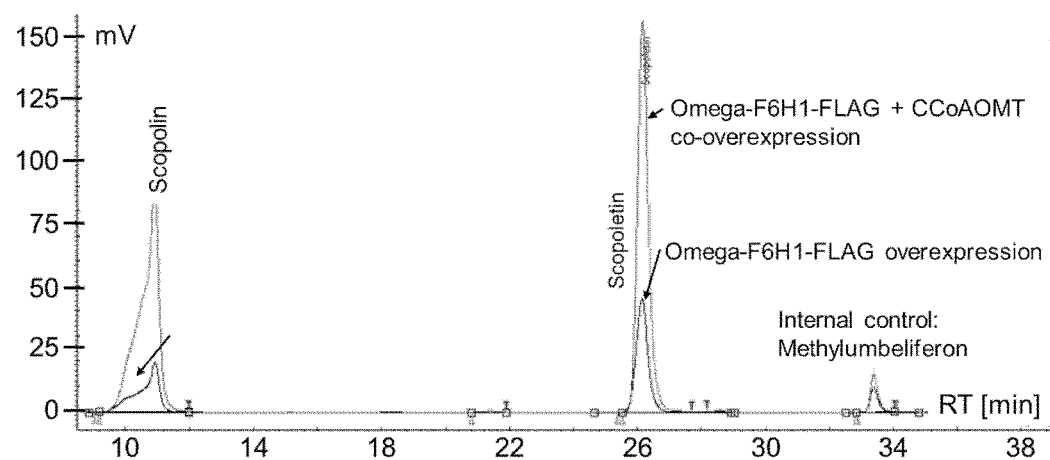
Figure 13:
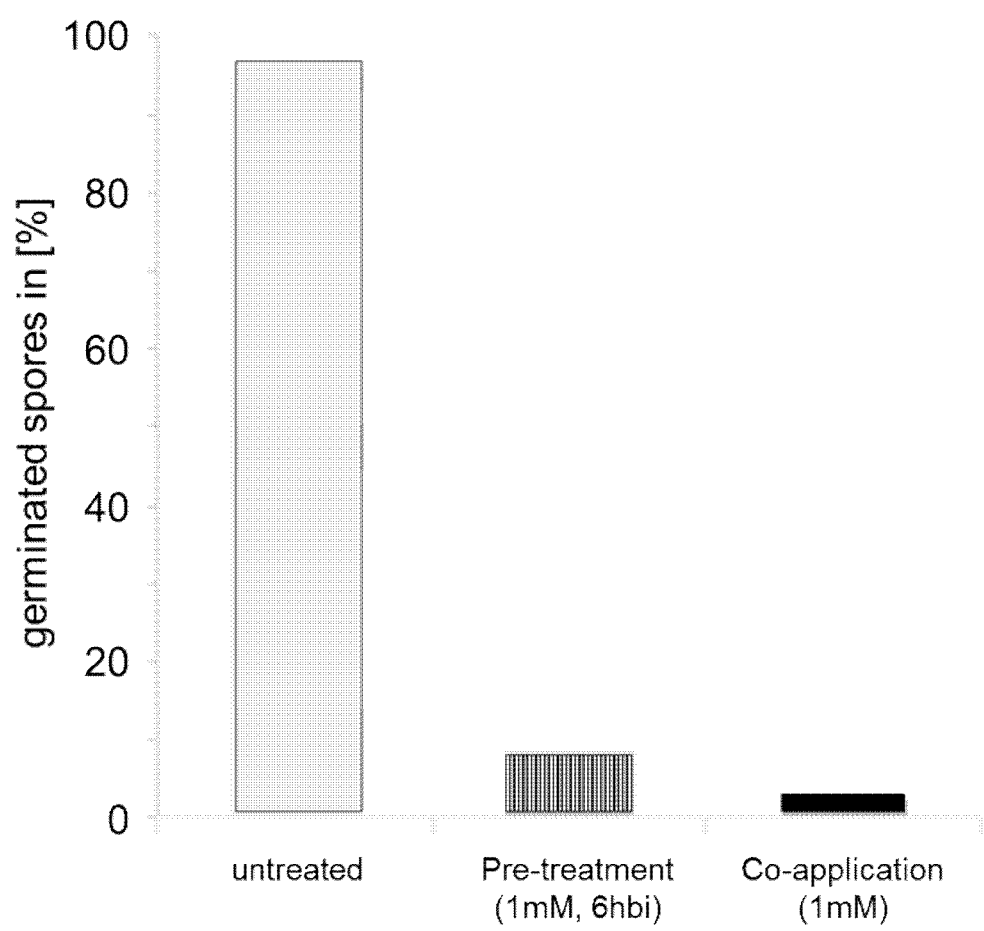

Scopoletin Extraction and HPLC Based Analytics
(FIGS. 12a and 12b)

Plant material was ground in liquid $N_2$ and extracted for 24 h with 90% (v/v) methanol (1 ml per 0.5 g fresh material) supplemented with 4-methylumbelliferone as an internal standard. Extracts were centrifuged for 10 min at 15,000 g. The supernatants were concentrated in a speed vac and the dried residue resolved in 150 µl 100% methanol. Samples (20 µl injection volume) were subsequently subjected to reverse-phase high-performance liquid chromatography (HPLC) analysis on a Nucleosil C18 column (EC 150/4.6 Nucleosil 100-5 C18; Macherey-Nagel) with a gradient mobile phase built with 1% (v/v) formic acid in water (A) and 1% (v/v) formic acid in methanol (B), and a flow rate of 1.0 ml/min at RT. The gradient program started at 15% B for 2 min, then increased linearly to 21.5% for 18 min followed by a linear increase to 55% B between 20 and 40 min. The gradient then increased to 95% B for 5 min. This proportion was maintained for 10 min and then returned to initial conditions in 5 min. Scopoletin was detected with a fluorescence detector with an excitation wavelength of 345 nm and an emission wavelength of 460 nm and identified by comparison with the pure reference compound (Scopoletin, SIGMA-ALDRICH).

Example 4

Determining Abundance of Gene Transcripts

Total RNA was extracted from leaves of the described Arabidopsis mutants as described by Chomczynski and Sacchi (1987). 1 µg RNA was transcribed to cDNA using random primers (9-mers) and RevertAid™ reverse transcriptase (Fermentas) according to manufacturer's instructions. Accumulation of gene transcripts was quantified in an ABI7300 using SYBR green (Invitrogen) at the following conditions for RT-qPCR: 50° C. for 2 min, 95° C. for 10 min, 95° C. for 15 s, 60° C. for 1 min, 95° C. for 15 s, 60° C. for 1 min, and 95° C. for 15 s (the third and fourth steps were repeated 40 times).

Primers specifically hybridizing to F6H1 gene (SEQ ID No 1):
F6H1_RT_F:
(SEQ ID NO: 81)
5'-CTCAGCCTCTTCTTTGTCTC-3

F6H1_RT_R:
(SEQ ID NO: 82)
5'-AAGCCTCCTCACCATCTTC-3'

Primers specifically hybridizing to CCoAOMT1 (SEQ ID No 3):
CCoAOMT1_RT_F:
(SEQ ID NO: 83)
5'-ATGGCGACGACAACAACAGAAGC-3

CCoAOMT1_RT_R:
(SEQ ID NO: 84)
5'-GCCAATCACTCCTCCAATTTTCACA-3'

-continued

```
Primers specifically hybridizing to ABCG37 (SEQ ID No 5):
ABCG37_RT_F:
                                                    (SEQ ID NO: 85)
5'-GATCGACTCTCCTTGATGATGGCGA-3

ABCG37_RT_R:
                                                    (SEQ ID NO: 86)
5-CGCACTCGGCCACCACTTTTAAACT-3'

Primers specifically hybridizing to UGT71C1 (SEQ ID No 7):
UGT71C1_RT_F:
                                                    (SEQ ID NO: 87)
5'-CTCGCAACAATCGAACTCGCCAAA-3

UGT71C1_RT_R:
                                                    (SEQ ID NO: 88)
5'-TCGGCAAATTCCACAAAGAGTTCCA-3'
```

All primers were designed according to standard criteria (Udvardi et al., 2008), off target search using Primer Blast tool at NCBI (http://www.ncbi.nlm.nih.gov/tools/primer-blast/)). Expression of the genes was normalized to Actin2. Data were analyzed using the ABI 7300 software and the expression relative to actin was calculated according to Livak and Schmittgen (2001) with $2^{-(Ct\ F6H1-Ct\ Actin2)}$.

Example 5

In Vitro Germination Tests

Example 5a

Growth Inhibition of *Phakopsora pachyrhizi*

Spores of *Phakopsora pachyrhizi* were resuspended in $H_2O$ supplemented with Tween-20 and 10 μM, 100 μM, 500 μM and 1 mM scopoletin. Spores of *Phakopsora pachyrhizi* resuspended in $H_2O$ supplemented with Tween-20 were used as control. All resuspended spores were transferred onto glass slides. After six hours incubation time the ASR spores were germinated and started to form appressoria.

The germination rate and appressoria formation rate was determined by quantitative microscopic analysis. Spores showing a visible germtube formation but no thickening of the germ tube tip were counted as "germinated", whereas the presence of a thickened germ tube tip indicated the formation of an appressoria (FIG. 14*a*).

Application of scopoletin to ASR spores decreases the germination and appressoria formation in a dose dependent manner. At 1 mM concentration scopoletin completely abolishes spore germination in-vitro.

Example 5b

Growth Inhibition of *Fusarium graminearum*

1 $cm^2$ Agar plugs from 7 day old *F. graminearum* cultures grown on potato dextrose agar (PDA) at 24° C. were placed on fresh PDA plates supplemented with 1 mM scopoletin in methanol or equal volumes of methanol lacking scopoletin as control. Fungal spores were stained by spraying Uvitex2 solution (0.1% Uvitex 2B (Polyscience, Warrington, UK) solved in 0.1 M Tris-/HCl-buffer, pH 8.5). Fungal growth was measured daily using a fluorescence microscope to determine the average growth rate of the fungus. 100 spores were counted per sample (see FIG. 15).

Example 6

In Vivo Spore Germination Tests 6.1 *Arabidopsis*

*Arabidopsis* seeds were sown on soil (type VM, Einheitserde Werkverband) and stratified at 4° C. for two days. Plants were grown at short day conditions (in a chamber at 8 h photoperiod, 120 μmol m-2 s-1 photon irradiance) 22° C., and 65% humidity. Five to six-week-old plants were inoculated with *P. pachyrhizi* as described below.

For pre-treatment experiments *Arabidopsis* plants were sprayed with—1 mM scopoletin (solved in $H_2O$, 0.01% Tween-20); incubated for 6 h at short day conditions and subsequently inoculated with 1 mg/ml *P. pachyrhizi* uredospores. For co-treatment experiments spores of *Phakopsora pachyrhizi* were solved in 0.01% Tween-20 supplemented with 1 mM scopoletin.

Following inoculation plants were covered with moistened plastic domes to ensure high humidity and incubated at short day conditions (see above). 24 h later plastic domes were removed and plants incubated at the same conditions for another 24 h. Leaves were harvested 2 dpi and destained on tissue soaked with a saturated (2.5 g/ml) chloralhydrate solution. Germination and penetration on destained leaves was determined by quantitative microscopic analysis. Spores showing a visible germtube formation are assigned to the category "germinated" Pretreated as well as co-treated plants showed a drastically reduced formation of germinated spores, proving the toxic effect of scopoletin against soybean rust fungus (FIG. 13). We never observed any phytotoxic effect of scopoletin leading to pleiotropic effects in *Arabidopsis*.

6.2 Soybean

Soy seeds were sown on soil (type VM, Einheitserde Werkverband) and grown at short day conditions in a chamber (at 8 h photoperiod, 120 μmol m-2 s-1 photon irradiance) 22° C., and 65% humidity. Five to six-week-old plants were inoculated with *P. pachyrhizi* as described below.

For co-treatment experiments spores of *Phakopsora pachyrhizi* were solved in 0.01% Tween-20 supplemented with 10 μM, 100 μM, 500 μM and 1 mM scopoletin (FIGS. 14*b* and *c*).

For pre-treatment experiments soy plants were sprayed with 1 mM scopoletin (solved in $H_2O$, 0.01% Tween-20); incubated for 6 h and subsequently inoculated with 1 mg/ml *P. pachyrhizi* uredospores (FIG. 14*c*).

Following inoculation plants were covered with moistened plastic domes to ensure high humidity and incubated at short day conditions (see above). 24 h later plastic domes were removed and plants incubated at the same conditions for another 11 days. At 12 dpi the diseased leaf area was rated on primary leaves, first and second trifoliate leaves by using the program Assess2.0 (Lobet G., Draye X., Périlleux C. 2013 An online database for plant image analysis software tools, Plant Methods, vol. 9 (38)). The average of the percentage of the leaf area showing fungal colonies or strong yellowing/browning on all leaves is considered as diseased leaf area.

Figure 14A:
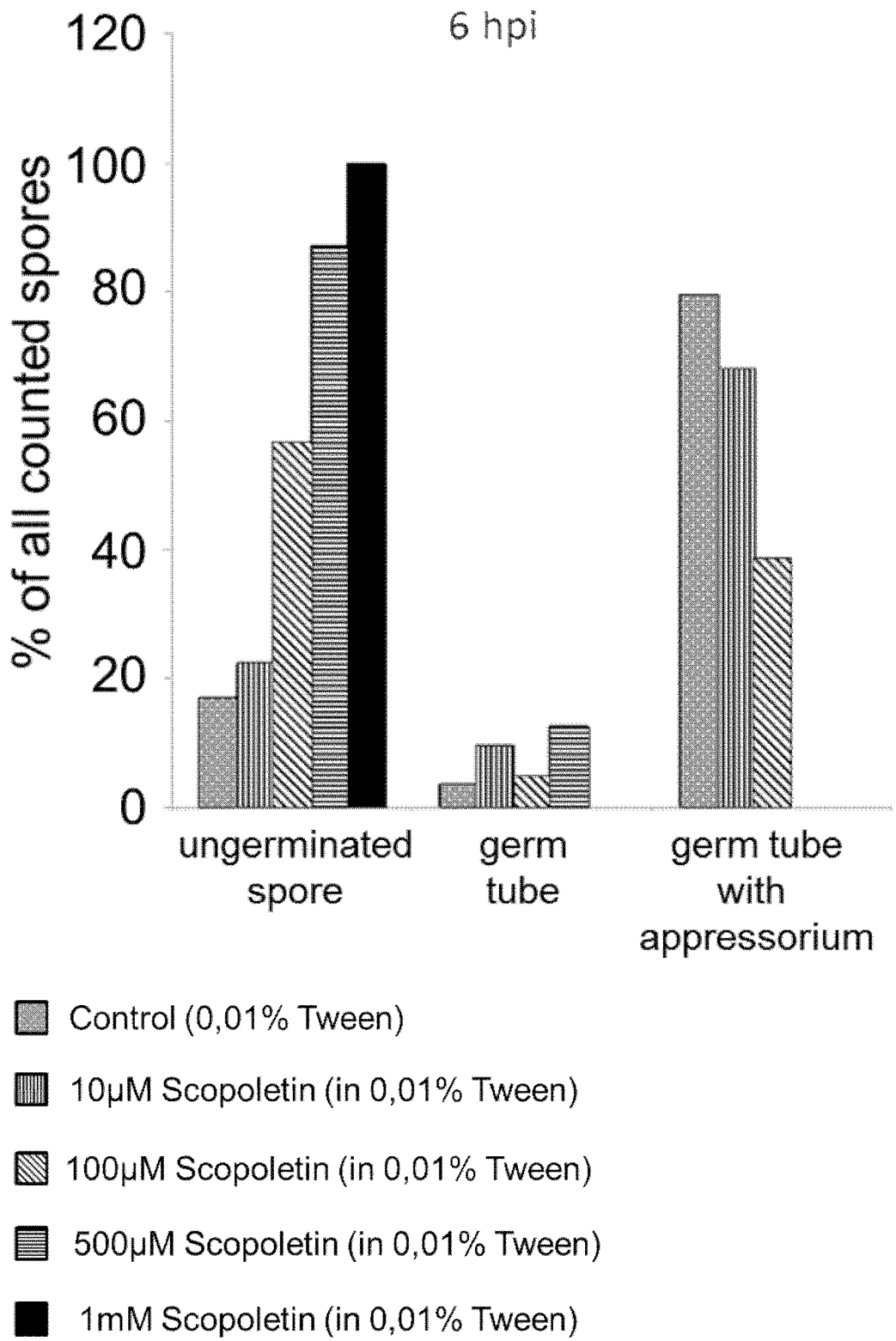
Figure 14B:
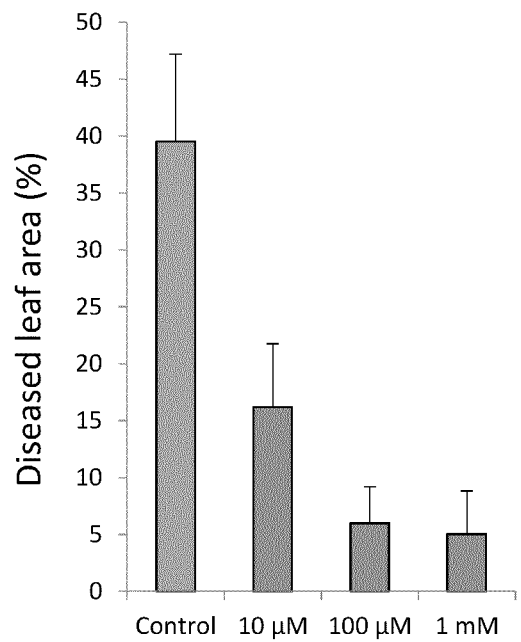
Figure 14C:
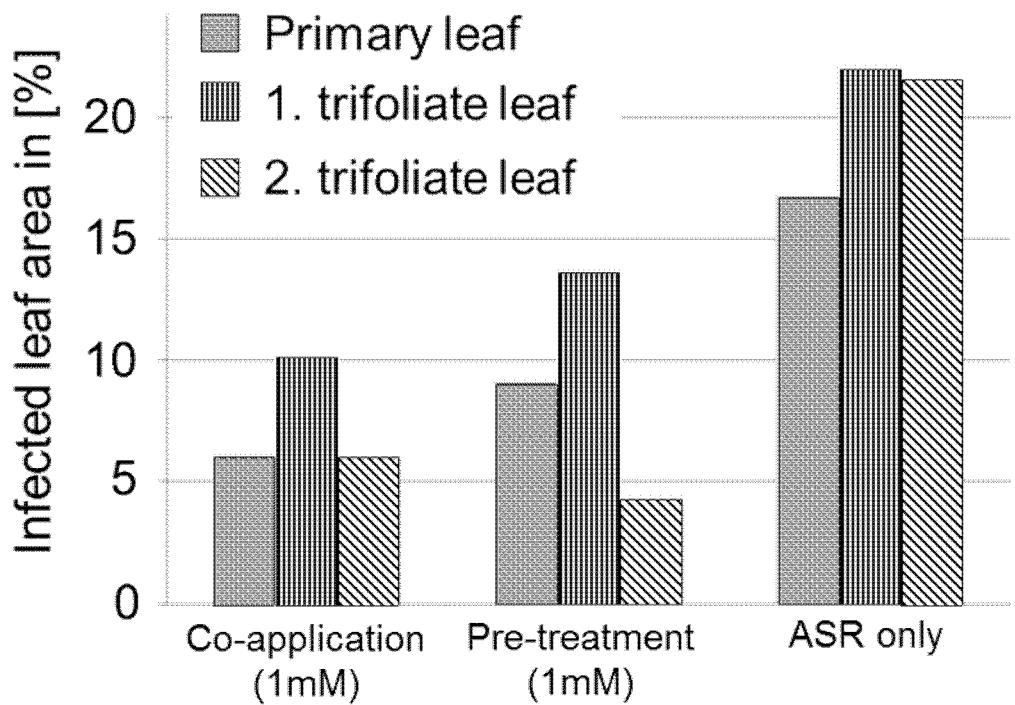
Figure 15:
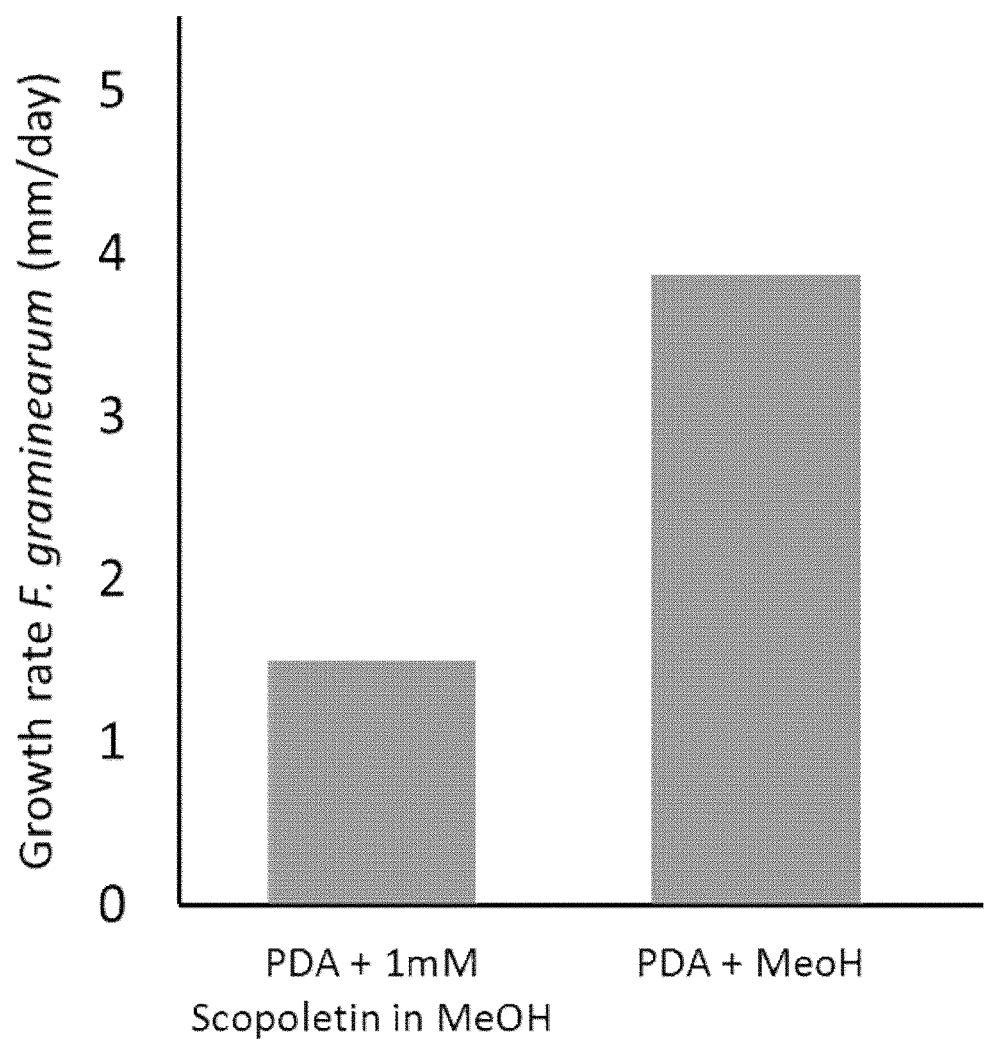

Pretreated as well as co-treated plants showed a drastically reduced formation of infected leaf area (FIGS. 14b and 14c) showing the potential of scopoletin to inhibit soybean rust disease. Any phytotoxic effect of scopoletin leading to pleiotropic effects in soybean was never observed, so the toxic effects are fungus specific.

Example 7

Cloning of Overexpression Vector Constructs for Stable Soybean Transformation

The DNA sequence of the F6H1 (AT3G13610, SEQ ID No: 1), CCoAOMT1 (At4g34050, SEQ ID No: 3), ABCG37 (PDR9; AT3G53480, SEQ ID No: 5) and UGT71C1 (SEQ ID No: 7) genes mentioned in this application were generated by DNA synthesis (Geneart, Regensburg, Germany).

The F6H1 DNA (as shown in SEQ ID No: 1) was synthesized in a way that a PacI restriction site is located in front of the start-ATG and a AscI restriction site downstream of the stop-codon. The synthesized DNA was digested using the restriction enzymes PacI and AscI (NEB Biolabs) and ligated in a PacI/AscI digested Gateway pENTRY-C vector (Invitrogen, Life Technologies, Carlsbad, Calif., USA) in a way that the full-length fragment is located in sense direction between the parsley ubiquitin promoter and the *Agrobacterium tumefaciens* derived octopine synthase terminator (t-OCS). The PcUbi promoter regulates constitutive expression of the ubi4-2 gene (accession number X64345) of Petroselinum crispum (Kawalleck et al. 1993 Plant Molecular Biology 21(4): 673-684).

Figure 2C:
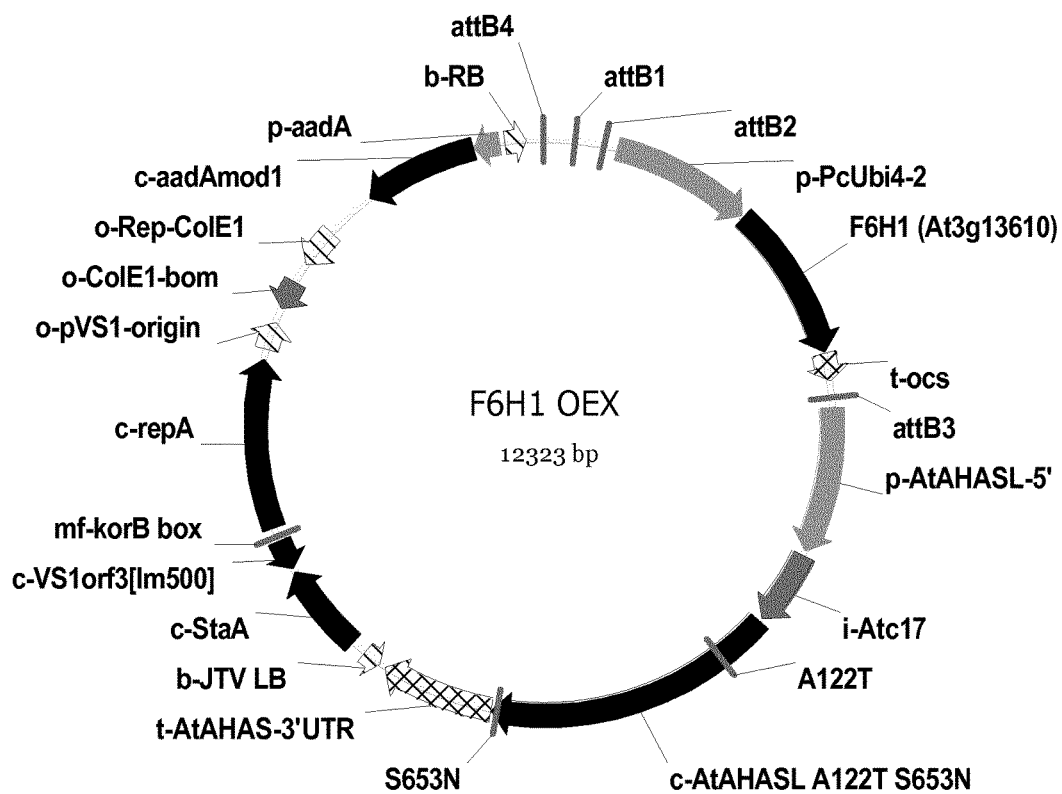

To obtain the binary plant transformation vector, a triple LR reaction (Gateway system, Invitrogen, Life Technologies, Carlsbad, Calif., USA) was performed according to manufacturer's protocol by using an empty pENTRY-A vector, an empty pENTRY-C, and the PcUbi promoter:: F6H1::OCS-terminator in the above described pENTRY-C vector. As target a binary pDEST vector was used which is composed of: (1) a Spectinomycin/Streptomycin resistance cassette for bacterial selection (2) a pVS1 origin for replication in Agrobacteria (3) a ColE1 origin of replication for stable maintenance in *E. coli* and (4) between the right and left border an AHAS selection under control of a AtAHASL-promoter (see FIG. 2c). The recombination reaction was transformed into *E. coli* (DH5alpha), mini-prepped and screened by specific restriction digestions. A positive clone from the vector construct (FIG. 2c) was sequenced and submitted soy transformation.

Figure 3:
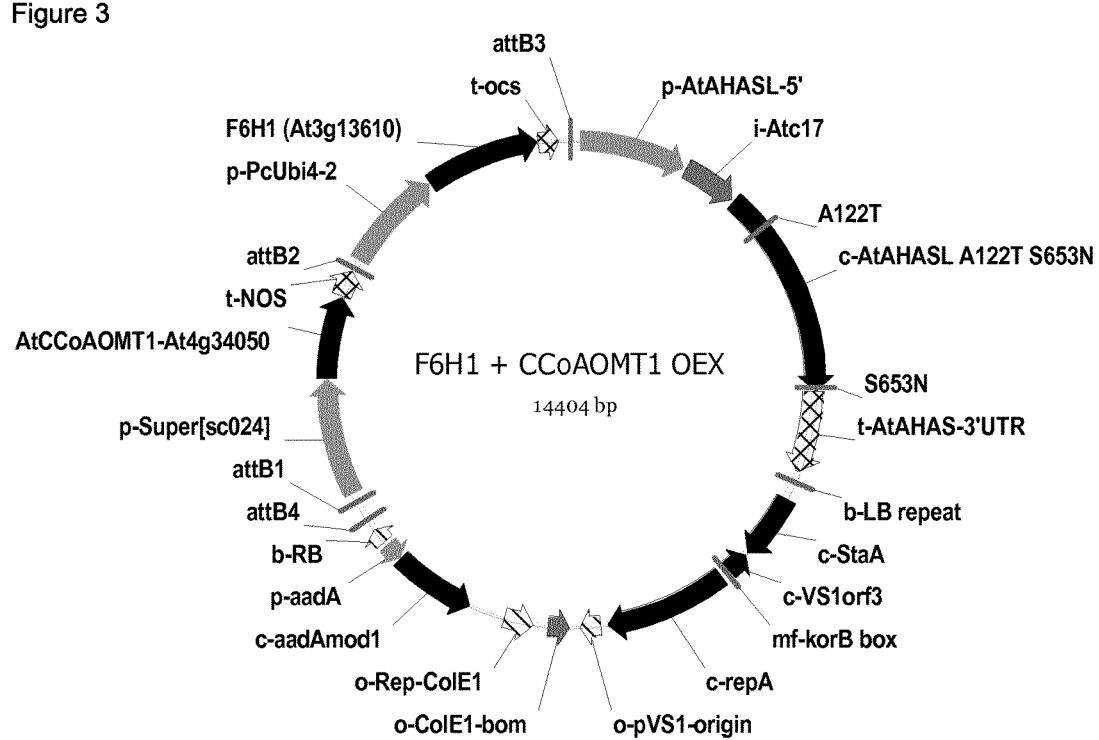

To obtain the F6H1-CCoAOMT1 double gene construct (FIG. 3) the CCoAOMT1 DNA (as shown in SEQ ID No: 3) was synthesized in a way that a PacI restriction site is located in front of the start-ATG and a AscI restriction site downstream of the stop-codon. The synthesized DNA was digested using the restriction enzymes PacI and AscI (NEB Biolabs) and ligated in a PacI/AscI digested Gateway pENTRY-B vector (Invitrogen, Life Technologies, Carlsbad, Calif., USA) in a way that the full-length fragment is located in sense direction between the pSuper promoter (Lee et al., 2007 Plant Physiology Vol 145 Issue 4 1294-1300) and the *Agrobacterium tumefaciens* derived nopaline synthase terminator (t-nos). The Super promoter consists of three identical Octapine Synthase Enhancers followed by a MAS promoter (Lee et al., 2007 Plant Physiology Vol 145 Issue 4 1294-1300).

To obtain the binary plant transformation vector containing F6H1 and CCoAOMT1, a triple LR reaction (Gateway system, Invitrogen, Life Technologies, Carlsbad, Calif., USA) was performed according to manufacturer's protocol by using an empty pENTRY-A vector, the pSuper promoter:: CCoAOMT1::nos-terminator in the above described pENTRY-B vector and the PcUbi promoter::F6H1::OCS-terminator in the above described pENTRY-C vector. As target a binary pDEST vector was used which is composed of: (1) a Spectinomycin/Streptomycin resistance cassette for bacterial selection (2) a pVS1 origin for replication in Agrobacteria (3) a ColE1 origin of replication for stable maintenance in *E. coli* and (4) between the right and left border an AHAS selection under control of a AtAHASL-promoter (see FIG. 3). The recombination reaction was transformed into *E. coli* (DH5alpha), mini-prepped and screened by specific restriction digestions. A positive clone from each vector construct was sequenced and submitted soy transformation.

Figure 5:
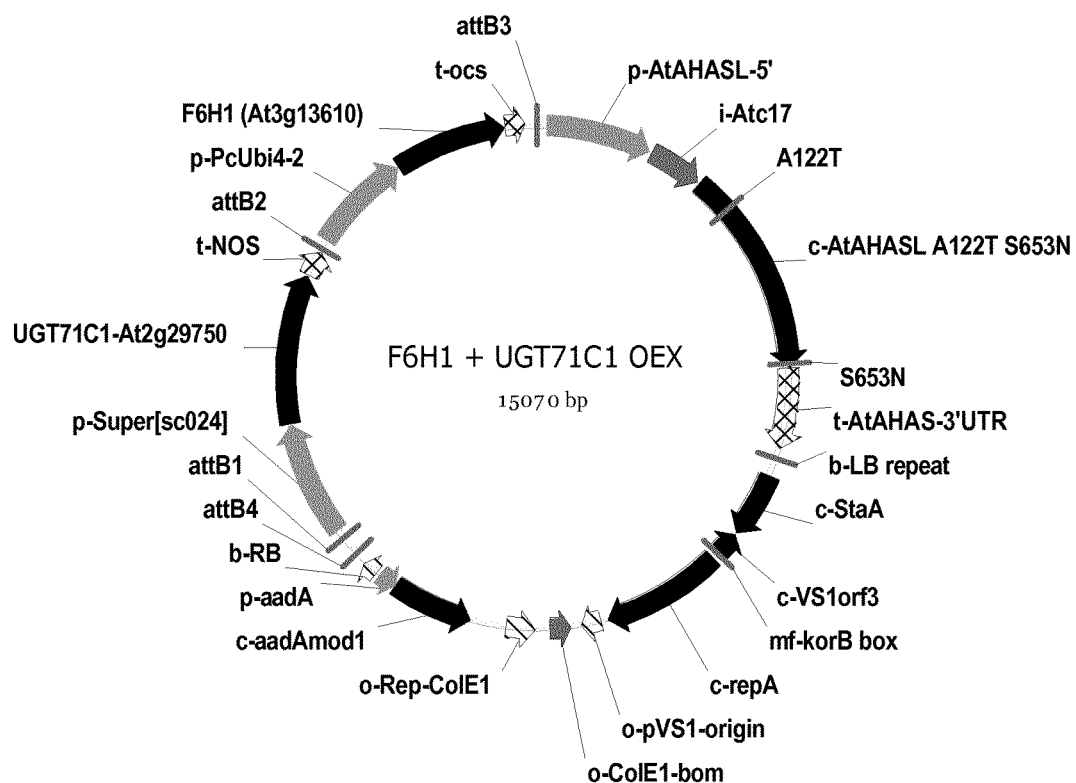

To obtain the F6H1-UGT71C1 double gene construct (FIG. 5) the UGT71C1 DNA (as shown in SEQ ID No: 7) was synthesized in a way that a PacI restriction site is located in front of the start-ATG and a AscI restriction site downstream of the stop-codon. The synthesized DNA was digested using the restriction enzymes PacI and AscI (NEB Biolabs) and ligated in a PacI/AscI digested Gateway pENTRY-B vector (Invitrogen, Life Technologies, Carlsbad, Calif., USA) in a way that the full-length fragment is located in sense direction between the pSuper promoter (Lee et al., 2007 Plant Physiology Vol 145 Issue 4 1294-1300) and the *Agrobacterium tumefaciens* derived nopaline synthase terminator (t-nos). The Super promoter consists of three identical Octapine Synthase Enhancers followed by a MAS promoter (Lee et al., 2007 Plant Physiology Vol 145 Issue 4 1294-1300).

To obtain the binary plant transformation vector containing F6H1 and UGT71C1, a triple LR reaction (Gateway system, Invitrogen, Life Technologies, Carlsbad, Calif., USA) was performed according to manufacturer's protocol by using an empty pENTRY-A vector, the pSuper promoter:: UGT71C1::nos-terminator in the above described pENTRY-B vector and the PcUbi promoter::F6H1::OCS-terminator in the above described pENTRY-C vector. As target a binary pDEST vector was used which is composed of: (1) a Spectinomycin/Streptomycin resistance cassette for bacterial selection (2) a pVS1 origin for replication in Agrobacteria (3) a ColE1 origin of replication for stable maintenance in *E. coli* and (4) between the right and left border an AHAS selection under control of a AtAHASL-promoter (see FIG. 5). The recombination reaction was transformed into *E. coli* (DH5alpha), mini-prepped and screened by specific restriction digestions. A positive clone from each vector construct was sequenced and submitted soy transformation.

Figure 4:
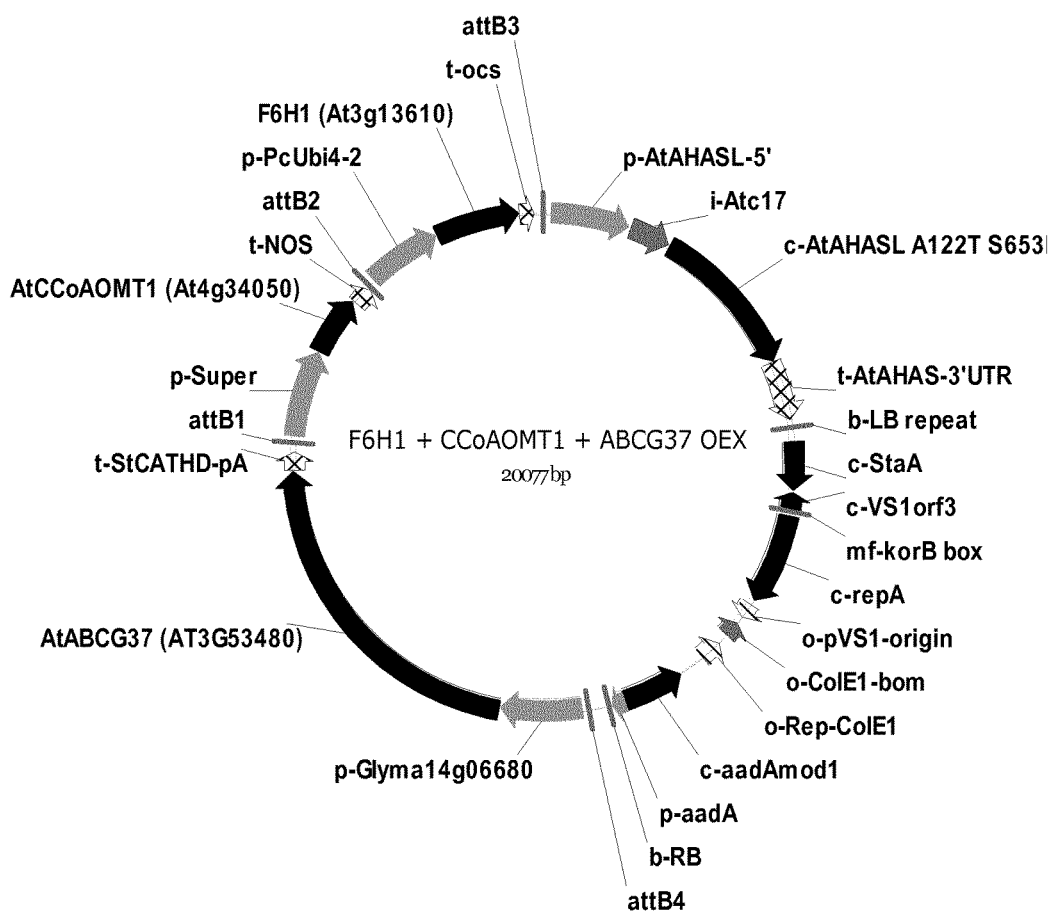

To obtain the F6H1-CCoAOMT1-ABCG37 (FIG. 4) triple gene construct the ABCG37 DNA (as shown in SEQ ID No 5) was synthesized in a way that a PacI restriction site is located in front of the start-ATG and a AscI restriction site downstream of the stop-codon.

The synthesized DNA was digested using the restriction enzymes PacI and AscI (NEB Biolabs) and ligated in a PacI/AscI digested Gateway pENTRY-A vector (Invitrogen, Life Technologies, Carlsbad, Calif., USA) in a way that the full-length fragment is located in sense direction between the pGlyma14g06680 promoter (see WO 2012/127373) and the *Solanum tuberosum* cathepsin D inhibitor (Herbers, Karin, Salomé Prat, and Lothar Willmitzer. "Functional analysis of a leucine aminopeptidase from *Solanum tuberosum* L." Planta 194.2 (1994): 230-240.). The pGlyma14g06680 promoter mediates a medium strong constitutive expression in soybean.

To obtain the binary plant transformation vector containing F6H1, CCoAOMT1 and ABCG37, a triple LR reaction (Gateway system, Invitrogen, Life Technologies, Carlsbad, Calif., USA) was performed according to manufacturer's protocol by using the Glyma14g06680 promoter::ABCG37::cathepsin inhibitor terminator in the pENTRY-A vector, as described above, the pSuper promoter::CCoAOMT1::nos-terminator in the above described pENTRY-B vector and the PcUbi promoter::F6H1::OCS-terminator in the above described pENTRY-C vector.

As target a binary pDEST vector was used which is composed of: (1) a Spectinomycin/Streptomycin resistance cassette for bacterial selection (2) a pVS1 origin for replication in Agrobacteria (3) a ColE1 origin of replication for stable maintenance in *E. coli* and (4) between the right and left border an AHAS selection under control of a AtAHASL-promoter (see FIG. 4). The recombination reaction was transformed into *E. coli* (DH5alpha), mini-prepped and screened by specific restriction digestions. A positive clone from each vector construct was sequenced and submitted for soy transformation.

Example 8

Soy Transformation

The expression vector constructs (see example 2) is transformed into soy.
8.1 Sterilization and Germination of Soy Seeds Virtually any seed of any soy variety can be employed in the method of the invention. A variety of soybean cultivar (including Jack, Williams 82, Jake, Stoddard, CD215 and Resnik) is appropriate for soy transformation. Soy seeds are sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds are removed and approximately 18 to 20 seeds are plated on solid GM medium with or without 5 µM 6-benzyl-aminopurine (BAP) in 100 mm Petri dishes. Seedlings without BAP are more elongated and roots develop especially secondary and lateral root formation. BAP strengthens the seedling by forming a shorter and stockier seedling.

Seven-day-old seedlings grown in the light (>100 µEinstein/m$^2$s) at 25 degreeC are used for explant material for the three-explant types. At this time, the seed coat was split, and the epicotyl with the unifoliate leaves are grown to, at minimum, the length of the cotyledons.

The epicotyl should be at least 0.5 cm to avoid the cotyledonary-node tissue (since soycultivars and seed lots may vary in the developmental time a description of the germination stage is more accurate than a specific germination time).

For inoculation of entire seedlings, see Method A (example 8.3. and 8.3.2) or leaf explants see Method B (example 8.3.3).

For method C (see example 8.3.4), the hypocotyl and one and a half or part of both cotyledons are removed from each seedling. The seedlings are then placed on propagation media for 2 to 4 weeks. The seedlings produce several branched shoots to obtain explants from. The majority of the explants originated from the plantlet growing from the apical bud. These explants are preferably used as target tissue.
8.2—Growth and Preparation of *Agrobacterium* Culture

*Agrobacterium* cultures are prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium YEP media: 10 g yeast extract. 10 g Bacto Peptone. 5 g NaCl. Adjust pH to 7.0, and bring final volume to 1 liter with H2O, for YEP agar plates add 20 g Agar, autoclave) and incubating at 25.degree C. until colonies appeared (about 2 days). Depending on the selectable marker genes present on the Ti or Ri plasmid, the binary vector, and the bacterial chromosomes, different selection compounds are be used for *A. tumefaciens* and *A. rhizogenes* selection in the YEP solid and liquid media. Various *Agrobacterium* strains can be used for the transformation method.

After approximately two days, a single colony (with a sterile toothpick) is picked and 50 ml of liquid YEP is inoculated with antibiotics and shaken at 175 rpm (25° C.) until an OD$_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP are inoculated with 5 µl to 3 ml of working *Agrobacterium* stock in a 500 ml Erlenmeyer flask. The flask is shaken overnight at 25° C. until the OD$_{600}$ is between 0.8 and 1.0. Before preparing the soy explants, the Agrobacteria ARE pelleted by centrifugation for 10 min at 5,500×g at 20° C. The pellet Is resuspended in liquid CCM to the desired density (OD$_{600}$ 0.5-0.8) and placed at room temperature at least 30 min before use.
8.3—Explant Preparation and Co-Cultivation (Inoculation)
8.3.1 Method A: Explant Preparation on the Day of Transformation.

Seedlings at this time had elongated epicotyls from at least 0.5 cm but generally between 0.5 and 2 cm. Elongated epicotyls up to 4 cm in length are successfully employed. Explants are then prepared with: i) with or without some roots, ii) with a partial, one or both cotyledons, all preformed leaves are removed including apical meristem, and the node located at the first set of leaves is injured with several cuts using a sharp scalpel.

This cutting at the node not only induces *Agrobacterium* infection but also distributes the axillary meristem cells and damaged pre-formed shoots. After wounding and preparation, the explants are set aside in a Petri dish and subsequently co-cultivated with the liquid CCM/*Agrobacterium* mixture for 30 minutes. The explants are then removed from the liquid medium and plated on top of a sterile filter paper on 15×100 mm Petri plates with solid co-cultivation medium. The wounded target tissues are placed such that they are in direct contact with the medium.
8.3.2 Modified Method A: Epicotyl Explant Preparation Soyepicotyl segments prepared from 4 to 8 d old seedlings are used as explants for regeneration and transformation. Seeds of soya cv. L00106CN, 93-41131 and Jack are germinated in 1/10 MS salts or a similar composition medium with or without cytokinins for 4 to 8 d. Epicotyl explants are prepared by removing the cotyledonary node and stem node from the stem section. The epicotyl is cut into 2 to 5 segments. Especially preferred are segments attached to the primary or higher node comprising axillary meristematic tissue.

The explants are used for *Agrobacterium* infection. *Agrobacterium* AGL1 harboring a plasmid with the gene of interest (GOI) and the AHAS, bar or dsdA selectable marker gene is cultured in LB medium with appropriate antibiotics overnight, harvested and resuspended in a inoculation medium with acetosyringone. Freshly prepared epicotyl segments are soaked in the *Agrobacterium* suspension for 30 to 60 min and then the explants were blotted dry on sterile filter papers. The inoculated explants are then cultured on a co-culture medium with L-cysteine and TTD and other chemicals such as acetosyringone for increasing T-DNA delivery for 2 to 4 d. The infected epicotyl explants are then placed on a shoot induction medium with selection agents such as imazapyr (for AHAS gene), glufosinate (for bar gene), or D-serine (for dsdA gene). The regenerated shoots are subcultured on elongation medium with the selective agent.

For regeneration of transgenic plants the segments are then cultured on a medium with cytokinins such as BAP, TDZ and/or Kinetin for shoot induction. After 4 to 8 weeks, the cultured tissues are transferred to a medium with lower concentration of cytokinin for shoot elongation. Elongated shoots are transferred to a medium with auxin for rooting and plant development. Multiple shoots are regenerated.

Many stable transformed sectors showing strong cDNA expression are recovered. Soybean plants are regenerated from epicotyl explants. Efficient T-DNA delivery and stable transformed sectors are demonstrated.

8.3.3 Method B: Leaf Explants

For the preparation of the leaf explant the cotyledon is removed from the hypocotyl. The cotyledons are separated from one another and the epicotyl is removed. The primary leaves, which consist of the lamina, the petiole, and the stipules, are removed from the epicotyl by carefully cutting at the base of the stipules such that the axillary meristems are included on the explant. To wound the explant as well as to stimulate de novo shoot formation, any pre-formed shoots are removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soy-explants. Wrap five plates with Parafilm™ "M" (American National Can, Chicago, Ill., USA) and incubate for three to five days in the dark or light at 25° C.

8.3.4 Method C: Propagated Axillary Meristem

For the preparation of the propagated axillary meristem explant propagated 3-4 week-old plantlets are used. Axillary meristem explants can be pre-pared from the first to the fourth node. An average of three to four explants could be obtained from each seedling. The explants are prepared from plantlets by cutting 0.5 to 1.0 cm below the axillary node on the internode and removing the petiole and leaf from the explant. The tip where the axillary meristems lie is cut with a scalpel to induce de novo shoot growth and allow access of target cells to the *Agrobacterium*. Therefore, a 0.5 cm explant included the stem and a bud.

Once cut, the explants are immediately placed in the *Agrobacterium* suspension for 20 to 30 minutes. After inoculation, the explants are blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soy-explants. Plates are wrapped with Parafilm™ "M" (American National Can, Chicago, Ill., USA) and incubated for two to three days in the dark at 25° C.

8.4—Shoot Induction

After 3 to 5 days co-cultivation in the dark at 25° C., the explants are rinsed in liquid SIM medium (to remove excess *Agrobacterium*) (SIM, see Olhoft et al 2007 A novel *Agrobacterium rhizogenes*-mediated transformation method of soy using primary-node explants from seedlings In Vitro Cell. Dev. Biol.—Plant (2007) 43:536-549; to remove excess *Agrobacterium*) or Modwash medium (1×B5 major salts, 1×B5 minor salts, 1×MSIII iron, 3% Sucrose, 1×B5 vitamins, 30 mM MES, 350 mg/L Timentin pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants are placed such that the target tissue was in direct contact with the medium. During the first 2 weeks, the explants could be cultured with or without selective medium. Preferably, explants are transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant is placed into the medium such that it is parallel to the surface of the medium (basipetal) with the explant partially embedded into the medium.

Wrap plates with Scotch 394 venting tape (3M, St. Paul, Minn., USA) are placed in a growth chamber for two weeks with a temperature averaging 25.degree. C. under 18 h light/6 h dark cycle at 70-100 µE/m$^2$s. The explants remains on the SIM medium with or without selection until de novo shoot growth occurred at the target area (e.g., axillary meristems at the first node above the epicotyl). Transfers to fresh medium can occur during this time. Explants are transferred from the SIM with or without selection to SIM with selection after about one week. At this time, there is considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation are removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

8.5—Shoot Elongation

After 2 to 4 weeks (or until a mass of shoots is formed) on SIM medium (preferably with selection), the explants are transferred to SEM medium (shoot elongation medium, see Olhoft et al 2007 A novel *Agrobacterium rhizogenes*-mediated transformation method of soy using primary-node explants from seedlings. In Vitro Cell. Dev. Biol.—Plant (2007) 43:536-549) that stimulates shoot elongation of the shoot primordia. This medium may or may not contain a selection compound.

After every 2 to 3 weeks, the explants are transferred to fresh SEM medium (preferably containing selection) after carefully removing dead tissue. The explants should hold together and not fragment into pieces and retain somewhat healthy. The explants are continued to be transferred until the explant dies or shoots elongate. Elongated shoots >3 cm are removed and placed into RM medium for about 1 week (Methods A and B), or about 2 to 4 weeks depending on the cultivar (Method C) at which time roots began to form. In the case of explants with roots, they are transferred directly into soil. Rooted shoots are transferred to soil and hardened in a growth chamber for 2 to 3 weeks before transferring to the greenhouse. Regenerated plants obtained using this method are fertile and produced on average 500 seeds per plant.

After 5 days of co-cultivation with *Agrobacterium tumefaciens* transient expression of the gene of interest (GOI) is widespread on the seedling axillary meristem explants especially in the regions wounding during explant preparation (Method A). Explants are placed into shoot induction medium without selection to see how the primary-node responds to shoot induction and regeneration. Thus far, greater than 70% of the explants were formed new shoots at this region. Expression of the GOI is stable after 14 days on SIM, implying integration of the T-DNA into the soybean genome. In addition, preliminary experiments results in the formation of cDNA expressing shoots forming after 3 weeks on SIM.

For Method C, the average regeneration time of a soybean plantlet using the propagated axillary meristem protocol is 14 weeks from explant inoculation. Therefore, this method has a quick regeneration time that leads to fertile, healthy soybean plants.

Example 9

Pathogen Assay for Soybean 9.1. Growth of Plants

10 T1 soy plants per event are potted and grown for 3-4 weeks in the Phytochamber (16 h-day-und 8 h-night-Rhythm at a temperature of 16° and 22° C. und a humidity of 75%) till the first 2 trifoliate leaves were fully expanded.

9.2 Inoculation

The plants are inoculated with spores of *P. pachyrhizi*.

In order to obtain appropriate spore material for the inoculation, soybean leaves which are infected with rust 15-20 days ago, are taken 2-3 days before the inoculation and transferred to agar plates (1% agar in H2O). The leaves are placed with their upper side onto the agar, which allowed the fungus to grow through the tissue and to produce very young spores. For the inoculation solution, the spores are knocked off the leaves and are added to a Tween-H2O solution. The counting of spores is performed under a light microscope by means of a Thoma counting chamber. For the inoculation of the plants, the spore suspension is added into a compressed-air operated spray flask and applied uniformly onto the plants or the leaves until the leaf surface is well moisturized. For macroscopic assays a spore density of $1\text{-}5\times10^5$ spores/ml is used. For the microscopy, a density of $>5\times10^5$ spores/ml is used. The inoculated plants are placed for 24 hours in a greenhouse chamber with an average of 22° C. and >90% of air humidity. The following cultivation is performed in a chamber with an average of 25° C. and 70% of air humidity.

Example 10

Microscopical Screening

For the evaluation of the pathogen development, the inoculated leaves of plants are stained with aniline blue 48 hours after infection.

The aniline blue staining serves for the detection of fluorescent substances. During the defense reactions in host interactions and non-host interactions, substances such as phenols, callose or lignin accumulate or are produced and are incorporated at the cell wall either locally in papillae or in the whole cell (hypersensitive reaction, HR). Complexes are formed in association with aniline blue, which lead e.g. in the case of callose to yellow fluorescence. The leaf material is transferred to falcon tubes or dishes containing destaining solution II (ethanol/acetic acid 6/1) and is incubated in a water bath at 90° C. for 10-15 minutes. The destaining solution II is removed immediately thereafter, and the leaves are washed 2× with water. For the staining, the leaves are incubated for 1.5-2 hours in staining solution II (0.05% aniline blue=methyl blue, 0.067 M di-potassium hydrogen phosphate) and analyzed by microscopy immediately thereafter.

The different interaction types are evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae can be recognized beneath the fungal appressorium by a green/yellow staining. The hypersensitive reaction (HR) is characterized by a whole cell fluorescence

Example 11

Evaluating the Susceptibility to Soybean Rust

The progression of the soybean rust disease is scored by the estimation of the diseased area (area which was covered by sporulating uredinia) on the backside (abaxial side) of the leaf. Additionally the yellowing of the leaf is taken into account. (for scheme see FIG. 11)

At all 50 T1 soybean plants per construct are inoculated with spores of *Phakopsora pachyrhizi*. The macroscopic disease symptoms of soy against *P. pachyrhizi* of the inoculated soybean plants are scored 14 days after inoculation.

The average of the percentage of the leaf area showing fungal colonies or strong yellowing/browning on all leaves is considered as diseased leaf area. At all 50 soybean T1 plants per construct (expression checked by RT-PCR) are evaluated in parallel to non-transgenic control plants. Non-transgenic soy plants grown in parallel to the transgenic plants are used as controls.

The expression of the F6H1 gene will lead to enhanced resistance of corn against *Phakopsora pachyrhizi.*

Example 12

Cloning of Overexpression Vector Constructs for Stable Corn Transformation

The DNA sequence of the F6H1 (AT3G13610), CCoAOMT1 (At4g34050) and ABCG37 (PDR9;

AT3G53480) genes mentioned in this application were generated by DNA synthesis (Geneart, Regensburg, Germany).

The F6H1 DNA (as shown in SEQ ID No: 1) was synthesized in a way that a PacI restriction site is located in front of the start-ATG and a AscI restriction site downstream of the stop-codon. The synthesized DNA was digested using the restriction enzymes PacI and AscI (NEB Biolabs) and ligated in a PacI/AscI digested Gateway pENTRY-C vector (Invitrogen, Life Technologies, Carlsbad, Calif., USA) in a way that the full-length fragment is located in sense direction between the maize ubiquitin promoter and the *Agrobacterium tumefaciens* derived octopine synthase terminator (t-OCS).

To obtain the binary plant transformation vector, a triple LR reaction (Gateway system, Invitrogen, Life Technologies, Carlsbad, Calif., USA) was performed according to manufacturer's protocol by using an empty pENTRY-A vector, an empty pENTRY-C, and the ZmUbi promoter::F6H1::OCS-terminator in the above described pENTRY-C vector. As target a binary pDEST vector was used which is composed of: (1) a Spectinomycin/Streptomycin resistance cassette for bacterial selection (2) a pVS1 origin for replication in Agrobacteria (3) a ColE1 origin of replication for stable maintenance in *E. coli* and (4) between the right and left border an AHAS selection (*Z. mays* acetohydroxyacid synthase (AHAS108) gene) under control of a Maize AHASL2 promoter. The recombination reaction was transformed into *E. coli* (DH5alpha), mini-prepped and screened by specific restriction digestions. A positive clone from the vector construct was sequenced and submitted to corn transformation.

To obtain the F6H1-CCoAOMT1 double gene construct the CCoAOMT1 DNA (as shown in SEQ ID No: 3) was synthesized in a way that a PacI restriction site is located in front of the start-ATG and a AscI restriction site downstream of the stop-codon. The synthesized DNA was digested using the restriction enzymes PacI and AscI (NEB Biolabs) and ligated in a PacI/AscI digested Gateway pENTRY-B vector (Invitrogen, Life Technologies, Carlsbad, Calif., USA) in a way that the full-length fragment is located in sense direction between the pSuper promoter (Lee et al., 2007 Plant Physiology Vol 145 Issue 4 1294-1300) and the *Agrobacterium tumefaciens* derived nopaline synthase terminator (t-nos). The Super promoter consists of three identical Octapine Synthase Enhancers followed by a MAS promoter (Lee et al., 2007 Plant Physiology Vol 145 Issue 4 1294-1300).

To obtain the binary plant transformation vector containing F6H1 and CCoAOMT1, a triple LR reaction (Gateway system, Invitrogen, Life Technologies, Carlsbad, Calif., USA) was performed according to manufacturer's protocol by using an empty pENTRY-A vector, the pSuper promoter::CCoAOMT1::nos-terminator in the above described pENTRY-B vector and the PcUbi promoter::F6H1::OCS-terminator in the above described pENTRY-C vector. As target a binary pDEST vector was used which is composed of: (1) a Spectinomycin/Streptomycin resistance cassette for bacterial selection (2) a pVS1 origin for replication in Agrobacteria (3) a ColE1 origin of replication for stable maintenance in *E. coli* and (4) between the right and left border an AHAS selection (*Z. mays* acetohydroxyacid synthase (AHAS108) gene) under control of a Maize AHASL2 promoter. The recombination reaction was transformed into *E. coli* (DH5alpha), mini-prepped and screened by specific restriction digestions. A positive clone from each vector construct was sequenced and submitted soy transformation.

To obtain the F6H1-UGT71C1 double gene construct the UGT71C1 DNA (as shown in SEQ ID No: 7) was synthesized in a way that a PacI restriction site is located in front of the start-ATG and a AscI restriction site downstream of the stop-codon. The synthesized DNA was digested using the restriction enzymes PacI and AscI (NEB Biolabs) and ligated in a PacI/AscI digested Gateway pENTRY-B vector (Invitrogen, Life Technologies, Carlsbad, Calif., USA) in a way that the full-length fragment is located in sense direction between the pSuper promoter (Lee et al., 2007 Plant Physiology Vol 145 Issue 4 1294-1300) and the *Agrobacterium tumefaciens* derived nopaline synthase terminator (t-nos). The Super promoter consists of three identical Octapine Synthase Enhancers followed by a MAS promoter (Lee et al., 2007 Plant Physiology Vol 145 Issue 4 1294-1300).

To obtain the binary plant transformation vector containing F6H1 and UGT71C1, a triple LR reaction (Gateway system, Invitrogen, Life Technologies, Carlsbad, Calif., USA) was performed according to manufacturer's protocol by using an empty pENTRY-A vector, the pSuper promoter::UGT71C1::nos-terminator in the above described pENTRY-B vector and the ZmUbi promoter::F6H1::OCS-terminator in the above described pENTRY-C vector. As target a binary pDEST vector was used which is composed of: (1) a Spectinomycin/Streptomycin resistance cassette for bacterial selection (2) a pVS1 origin for replication in Agrobacteria (3) a ColE1 origin of replication for stable maintenance in *E. coli* and (4) between the right and left border an AHAS selection (*Z. mays* acetohydroxyacid synthase (AHAS108) gene) under control of a Maize AHASL2 promoter. The recombination reaction was transformed into *E. coli* (DH5alpha), mini-prepped and screened by specific restriction digestions. A positive clone from the vector construct was sequenced and submitted to corn transformation.

To obtain the F6H1-CCoAOMT1-ABCG37 triple gene construct the ABCG37 DNA (as shown in SEQ ID No: 5) was synthesized in a way that a PacI restriction site is located in front of the start-ATG and a AscI restriction site downstream of the stop-codon. The synthesized DNA was digested using the restriction enzymes PacI and AscI (NEB Biolabs) and ligated in a PacI/AscI digested Gateway pENTRY-A vector (Invitrogen, Life Technologies, Carlsbad, Calif., USA) in a way that the full-length fragment is located in sense direction between the ScBV promoter (Bouhida, Mohammed, B. E. Lockhart, and Neil E. Olszewski. "An analysis of the complete sequence of a sugarcane bacilliform virus genome infectious to banana and rice." The Journal of general virology 74 (1993): 15-22.) and the *Solanum tuberosum* cathepsin D inhibitor (Herbers, Karin, Salomé Prat, and Lothar Willmitzer. "Functional analysis of a leucine aminopeptidase from *Solanum tuberosum* L." Planta 194.2 (1994): 230-240.). The ScBV promoter mediates a medium strong constitutive expression in corn.

To obtain the binary plant transformation vector containing F6H1, CCoAOMT1 and ABCG37, a triple LR reaction (Gateway system, Invitrogen, Life Technologies, Carlsbad, Calif., USA) was performed according to manufacturer's protocol by using the ScBV promoter::ABCG37::cathepsin inhibitor terminator in the pENTRY-A vector, as described above, the pSuper promoter::CCoAOMT1::nos-terminator in the above described pENTRY-B vector and the ZmUbi promoter::F6H1::OCS-terminator in the above described pENTRY-C vector.

As target a binary pDEST vector was used which is composed of: (1) a Spectinomycin/Streptomycin resistance cassette for bacterial selection (2) a pVS1 origin for replication in Agrobacteria (3) a ColE1 origin of replication for stable maintenance in *E. coli* and (4) between the right and left border an AHAS selection (*Z. mays* acetohydroxyacid synthase (AHAS108) gene) under control of a Maize AHASL2 promoter. The recombination reaction was transformed into *E. coli* (DH5alpha), mini-prepped and screened by specific restriction digestions. A positive clone from the vector construct was sequenced and submitted to corn transformation.

Example 13

Maize Transformation

*Agrobacterium* cells harboring a plasmid containing the gene of interest (see above) and the mutated maize AHAS gene were grown in YP medium supplemented with appropriate antibiotics for 1-2 days. One loop of *Agrobacterium* cells was collected and suspended in 1.8 ml M-LS-002 medium (LS-inf). The cultures were incubated while shaking at 1,200 rpm for 5 min-3 hrs. Corn cobs were harvested at 8-11 days after pollination. The cobs were sterilized in 20% Clorox solution for 5 min, followed by spraying with 70% Ethanol and then thoroughly rinsed with sterile water. Immature embryos 0.8-2.0 mm in size were dissected into the tube containing *Agrobacterium* cells in LS-inf solution.

The constructs were transformed into immature embryos by a protocol modified from Japan Tobacco *Agrobacterium* mediated plant transformation method (U.S. Pat. Nos. 5,591, 616; 5,731,179; 6,653,529; and U.S. Patent Application Publication No. 2009/0249514). Two types of plasmid vectors were used for transformation. One type had only one T-DNA border on each of left and right side of the border, and selectable marker gene and gene of interest were between the left and right T-DNA borders. The other type was so called "two T-DNA constructs" as described in Japan Tobacco U.S. Pat. No. 5,731,179. In the two DNA constructs, the selectable marker gene was located between one set of T-DNA borders and the gene of interest was included in between the second set of T-DNA borders. Either plasmid vector can be used. The plasmid vector was electroporated into *Agrobacterium*.

*Agrobacterium* infection of the embryos was carried out by inverting the tube several times. The mixture was poured onto a filter paper disk on the surface of a plate containing co-cultivation medium (M-LS-011). The liquid agro-solution was removed and the embryos were checked under a microscope and placed scutellum side up. Embryos were cultured in the dark at 22° C. for 2-4 days, and transferred to M-MS-101 medium without selection and incubated for four to seven days. Embryos were then transferred to M-LS-202 medium containing 0.75 µM imazethapyr and grown for three weeks at 27° C. to select for transformed callus cells.

Plant regeneration was initiated by transferring resistant calli to M-LS-504 medium supplemented with 0.75 µM imazethapyr and growing under light at 26° C. for two to three weeks. Regenerated shoots were then transferred to a rooting box with M-MS-618 medium (0.5 µM imazethapyr). Plantlets with roots were transferred to soil-less potting mixture and grown in a growth chamber for a week, then transplanted to larger pots and maintained in a greenhouse until maturity.

Transgenic maize plant production is also described, for example, in U.S. Pat. Nos. 5,591,616 and 6,653,529; U.S. Patent Application Publication No. 2009/0249514; and WO/2006136596, each of which are hereby incorporated by reference in their entirety.

Transformation of maize may be made using *Agrobacterium* transformation, as described in U.S. Pat. Nos. 5,591, 616; 5,731,179; U.S. Patent Application Publication No. 2002/0104132, and the like. Transformation of maize (*Zea mays* L.) can also be performed with a modification of the method described by Ishida et al. (Nature Biotech., 1996, 14:745-750). The inbred line A188 (University of Minnesota) or hybrids with A188 as a parent are good sources of donor material for transformation (Fromm et al., Biotech, 1990, 8:833), but other genotypes can be used successfully as well. Ears are harvested from corn plants at approximately 11 days after pollination (DAP) when the length of immature embryos is about 1 to 1.2 mm. Immature embryos are co-cultivated with *Agrobacterium tumefaciens* that carry "super binary" vectors and transgenic plants are recovered through organogenesis. The super binary vector system is described in WO 94/00977 and WO 95/06722. Vectors are constructed as described. Various selection marker genes are used including the maize gene encoding a mutated acetohydroxy acid synthase (AHAS) enzyme (U.S. Pat. No. 6,025,541). Similarly, various promoters are used to regulate the trait gene to provide constitutive, developmental, inducible, tissue or environmental regulation of gene transcription. Excised embryos can be used and can be grown on callus induction medium, then maize regeneration medium, containing imidazolinone as a selection agent. The Petri dishes are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the imidazolinone herbicides and which are PCR positive for the transgenes.

Example 14

*Fusarium* and *Colletotrichum* Resistance Screening

Transgenic maize plants expressing the F6H1 DNA alone or in combination with CCoAOMT1, ABCG37 or UGT71C1 (as described above) are grown in greenhouse or phyto-chamber under standard growing conditions in a controlled environment (20-25° C., 60-90% humidity).

Shortly after the transgenic maize plants enter the reproductive phase they are inoculated near the base of the stalk using a fungal suspension of spores ($10^5$ spores in PBS solution) of *Fusarium* ssp. or *Colletotrichum graminicola*. Plants are incubated for 2-4 weeks at 20-25° C. and 60-90% humidity.

For scoring the stalk rot disease, stalks are split and the progression of the disease is scored by observation of the characteristic brown to black color of the fungus as it grows up the stalk. Disease ratings are conducted by assigning a visual score. Per experiment the diseased leaf area of more than 10 transgenic plants (and wild-type plants as control) is scored. For analysis the average of the diseased leaf area of the non-transgenic mother plant is set to 100% to calculate the relative diseased leaf area of the transgenic lines The expression of the F6H1 gene will lead to enhanced resistance of corn against *Fusarium* ssp. and *Colletotrichum graminicola*.

Example 15

Evaluating the Effect of Scopoletin Accumulation and Susceptibility to Soybean Rust The effect on resistance of Scopoletin accumulation in leaves was evaluated. To achieve accumulation of Scopoeltin in leaves a F6H1 overexpression construct generated. The F6H1 overexpression construct (FIG. 2c) carries the coding sequence of the F6H1 enzyme (SEQ-ID-No. 1) under control of a constitutively and ubiquitously expressing promoter (as described in example 7). The construct was transformed into soybean as described in example 8 (Method C) and resulting T1 soybean seeds were planted and cultivated for 3 weeks as described in example 9.

The 5 best working independent events were selected for further analysis. As trait efficacy is varying depending on the T-DNA insertion site, the average of those 5 independent events is seen as a good measure to estimate the overall effect of F6H1 overexpression.

Figure 16:
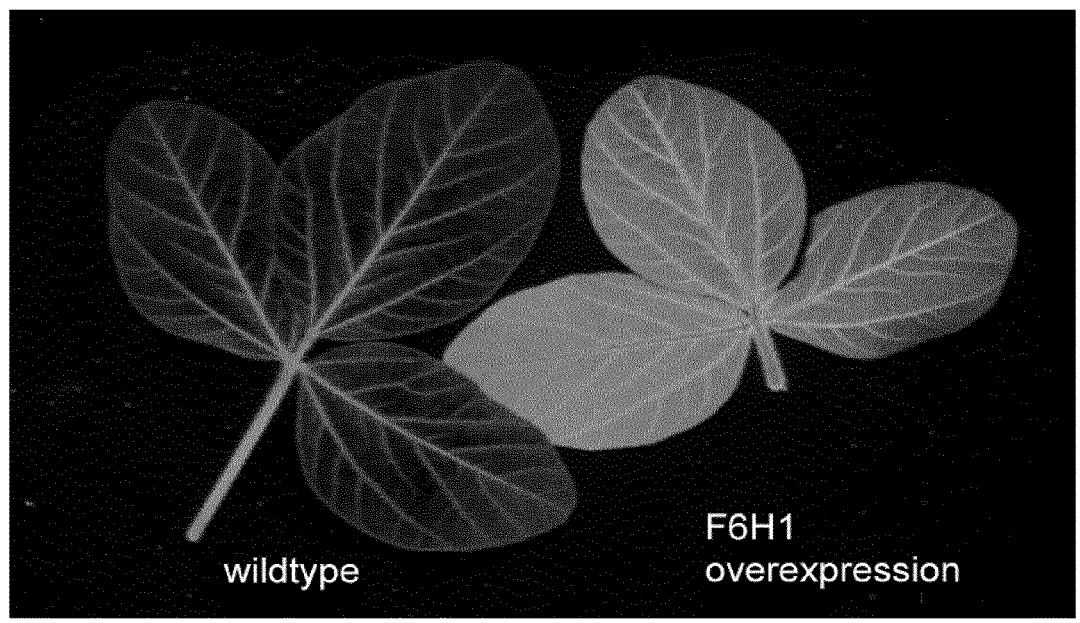

At all 5 transgenic plants were cultivated per event. Additionally 11 non-transgenic wild type soybean plants were grown in parallel as controls. Presence of the construct was confirmed by qPCR, and Scopoletin accumulation was confirmed by presence of fluorescence (FIG. 16). Elicitation of fluorescence was done using a B-100AP UV lamp (UVP LLC, Upland, Canada) using 365 nm longwave UV. Occurrence of fluorescence is a qualitative measure only (not quantitative)

Three weeks old plants (V1 stage) were inoculated with spores of *Phakopsora pachyrhizi* as described in example 9.

Figure 11:
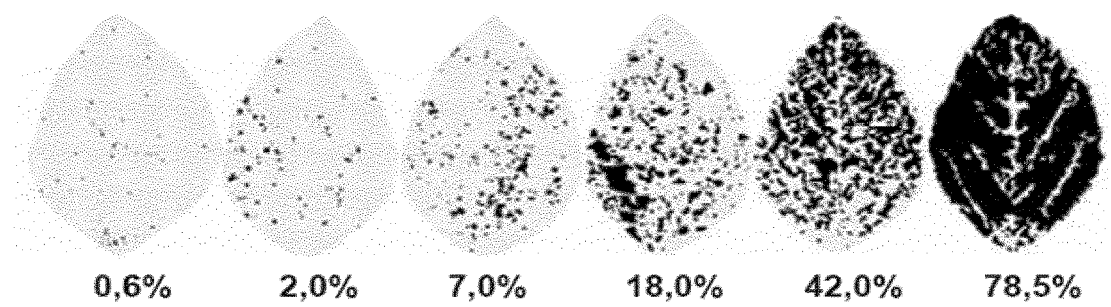

The progression of the soybean rust disease was scored 14 days after infection by visual rating of the diseased leaf area. Diseased leaf area is defined as area showing fungal colonies or strong yellowing/browning. The relative diseased area in percent is defined as diseased leaf area divided by overall leaf area (for scheme see FIG. 11).

Figure 17:
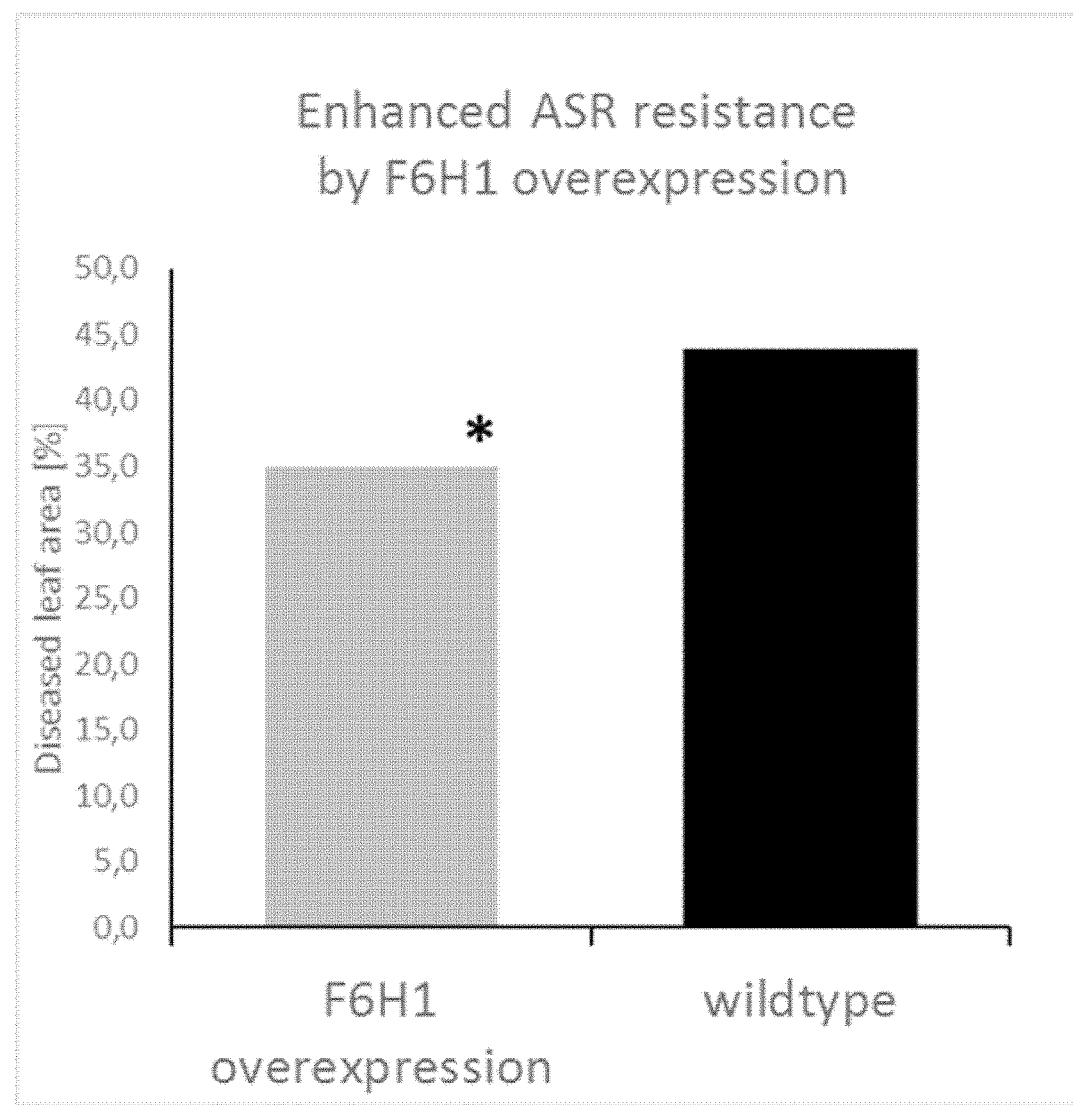

Evaluation of Scopoletin accumulating plants was done in parallel to the evaluation of the non-transformed wildtype controls. The average of the diseased leaf area for soybean plants transformed with the F6H1 overexpression construct (FIG. 2c) resulting in Scopoletin accumulation is shown in FIG. 17.

Expression of F6H1 (construct 1, FIG. 2c) leads to a relative diseased leaf area of 34.9%. In comparison to the wild type, which shows a relative diseased leaf area of 43.9%. So the expression of F6H1 (construct 1, FIG. 2c) leads to a significant ($p<0.05$, t-test, * FIG. 17) relative increase of soybean rust resistance of 20.6% in average over 5 independent events.

This data clearly indicates that the in-planta accumulation of Scopoletin leads to a lower disease of transgenic plants compared to non-transgenic wild type controls. So, the expression of F6H1 in soybean significantly ($p<0.05$) increases the resistance of soy against soybean rust.

The invention claimed is:

1. A method for reducing, preventing, or delaying biotrophic rust fungal infection in a plant, a plant part, or a plant cell, said method comprising:
   providing a transgenic plant, transgenic plant part, or transgenic plant cell with an exogenous nucleic acid encoding an F6H1 protein having an amino acid sequence with at least 90% identity to SEQ ID NO: 2, wherein the F6H1 protein increases the production and/or accumulation of scopoletin and/or scopolin in the plant, plant part, or plant cell in comparison to a wild type plant, wild type plant part, or wild type plant cell; and
   growing the transgenic plant, transgenic plant part, or transgenic plant cell in the presence of a biotrophic rust fungus, wherein biotrophic rust fungal infection is reduced, prevented, or delayed in the transgenic plant, transgenic plant part, or transgenic plant cell as compared to a wild type plant, wild type plant part, or wild type plant cell.

2. The method according to claim 1, wherein the transgenic plant, transgenic plant part, or transgenic plant cell further comprises one or more additional exogenous nucleic acid(s) encoding a protein(s) selected from the group consisting of a CCoAOMT1 protein, a ABCG37 protein and a UGT71C1 protein, (a) wherein said CCoAOMT1 protein is encoded by an exogenous nucleic acid encoding a protein having at least 90% identity with SEQ ID NO: 4; (b) wherein said ABCG37 protein is encoded by an exogenous nucleic acid encoding a protein having at least 90% identity with SEQ ID NO: 6: and (c) wherein said UGT71C1 protein is encoded by an exogenous nucleic acid encoding a protein having at least 90% identity with SEQ ID NO: 8 thereof.

3. A transgenic plant, transgenic plant part, or transgenic plant cell comprising an exogenous nucleic acid encoding an F6H1 protein having an amino acid sequence with at least 90% identity to SEQ ID NO: 2, wherein the F6H1 protein increases the production and/or accumulation of scopoletin and/or scopolin in the plant, plant part, or plant cell in comparison to a wild type plant, wild type plant part, or wild type plant cell and results in increased resistance to biotrophic rust fungal infection, and wherein the transgenic plant, transgenic plant part, or transgenic plant cell is selected from the group consisting of beans, soya, pea, clover, kudzu, lucerne, lentils, lupins, vetches, and groundnut.

4. The transgenic plant, transgenic plant part, or transgenic plant cell of claim 3 further comprising one or more additional exogenous protein(s) selected from the group consisting of a CCoAOMT1 protein, an ABCG37 protein, and an UGT71GC1 protein, (a) wherein said CCoAOMT1 protein is encoded by an exogenous nucleic acid coding for a protein having at least 90% identity with SEQ ID NO: 4, operably linked with a promoter and a transcription termination sequence, (b) wherein said ABCG37 protein is encoded by an exogenous nucleic acid coding for a protein having at least 90% identity with SEQ ID NO: 6, operably linked with a promoter and a transcription termination sequence, and (c) wherein said UGT71GC1 protein is encoded by an exogenous nucleic acid coding for a protein having at least 90% identity with SEQ ID NO: 8, operably linked with a promoter and a transcription termination sequence.

5. A harvestable part of the transgenic plant of claim 3, wherein the harvestable part of the transgenic plant comprises the exogenous nucleic acid encoding a F6H1 protein.

6. A product derived from the plant of claim 3, wherein the product comprises the exogenous nucleic acid encoding the F6H1 protein.

7. A method for the production of a product comprising
   a) growing a plant of claim 3 and
   b) producing said product from or by the plant and/or part of the plant,
   wherein the product comprises the exogenous nucleic acid encoding the F6H1 protein and/or the F6H1 protein.

8. Method according to claim 7, comprising
   a) growing the plant and removing the harvestable parts from the plant; and
   b) producing said product from or by the harvestable parts of the plant.

9. The method according to claim 1, wherein the biotrophic rust fungal infection is *Phakopsora meibomiae* and/or *Phakopsora pachyrhizi*.

10. The method according to claim 1, wherein the plant is selected from the group consisting of beans, soy, pea, clover, kudzu, lucerne, lentils, lupins, vetches, groundnut, rice, wheat, barley, arabidopsis, lentil, banana, canola, cotton, potatoe, corn, sugar cane, alfalfa, and sugar beet.

11. A method for breeding a fungal resistant plant comprising
   (i) crossing the plant of claim 3 with a second plant;
   (ii) obtaining seed from the cross of step (a);
   (iii) planting said seeds and growing the seeds to plants; and
   (iv) selecting from said plants plants expressing the exogenous F6H1 protein and optionally expressing a one or more additional protein(s) selected from the group consisting of CCoAMT1 protein, ABCG37 protein and UGT71C1 protein.

12. The method of claim 1, wherein the exogenous nucleic acid encodes an F6H1 protein with at least 95% identity to SEQ ID NO: 2.

13. The method of claim 1, wherein the exogenous nucleic acid encodes an F6H1 protein with at least 98% identity to SEQ ID NO: 2.

14. The method of claim 1, wherein the exogenous nucleic acid encodes an F6H1 protein with 100% identity to SEQ ID NO: 2.

15. The transgenic plant, transgenic plant part, or transgenic plant cell of claim 3, wherein the exogenous nucleic acid encodes an F6H1 protein with at least 95% identity to SEQ ID NO: 2.

16. The transgenic plant, transgenic plant part, or transgenic plant cell of claim 3, wherein the exogenous nucleic acid encodes an F6H1 protein with at least 98% identity to SEQ ID NO: 2.

17. The transgenic plant, transgenic plant part, or transgenic plant cell of claim 3, wherein the exogenous nucleic acid encodes an F6H1 protein with 100% identity to SEQ ID NO: 2.

* * * * *

UNITED STATES PATENT AND TRADEMARK OFFICE
CERTIFICATE OF CORRECTION

PATENT NO. : 10,570,412 B2
APPLICATION NO. : 15/548145
DATED : February 25, 2020
INVENTOR(S) : Holger Schultheiss et al.

It is certified that error appears in the above-identified patent and that said Letters Patent is hereby corrected as shown below:

In the Claims

Column 311, Line 26, Claim 2, "CCoAOMT1protein," should be -- CCoAOMT1 protein, --.

Column 311, Line 52, Claim 4, "UGT71GC1" should be -- UGT71C1 --.

Column 311, Line 60, Claim 4, "UGT71GC1" should be -- UGT71C1 --.

Signed and Sealed this
Sixteenth Day of April, 2024

Katherine Kelly Vidal
*Director of the United States Patent and Trademark Office*

SEQUENCE LISTING

```
<160> NUMBER OF SEQ ID NOS: 88

<210> SEQ ID NO 1
<211> LENGTH: 1086
<212> TYPE: DNA
<213> ORGANISM: Arabidopsis thaliana
<220> FEATURE:
<221> NAME/KEY: CDS
<222> LOCATION: (1)..(1086)

<400> SEQUENCE: 1 atg gct cca aca ctc ttg aca acc caa ttc tca aat cca gct gaa gta      48
Met Ala Pro Thr Leu Leu Thr Thr Gln Phe Ser Asn Pro Ala Glu Val
1               5                   10                  15 acc gac ttt gta gtc tac aaa gga aat ggt gtt aag ggt tta tca gaa      96
Thr Asp Phe Val Val Tyr Lys Gly Asn Gly Val Lys Gly Leu Ser Glu
                20                  25                  30 aca gga atc aaa gct ctt cca gaa caa tac att cag cca ctt gaa gaa     144
Thr Gly Ile Lys Ala Leu Pro Glu Gln Tyr Ile Gln Pro Leu Glu Glu
            35                  40                  45 cga ctc atc aac aaa ttc gtc aac gaa aca gat gaa gcc att cca gtt     192
Arg Leu Ile Asn Lys Phe Val Asn Glu Thr Asp Glu Ala Ile Pro Val
        50                  55                  60 atc gat atg tcg aac cct gat gag gac aga gtc gct gaa gct gtt tgt     240
Ile Asp Met Ser Asn Pro Asp Glu Asp Arg Val Ala Glu Ala Val Cys
65                  70                  75                  80 gat gct gct gag aaa tgg ggg ttc ttt caa gtg atc aat cat gga gtt     288
Asp Ala Ala Glu Lys Trp Gly Phe Phe Gln Val Ile Asn His Gly Val
                85                  90                  95 cct ttg gaa gtt ctt gat gac gtc aag gct gcg act cac aag ttc ttc     336
Pro Leu Glu Val Leu Asp Asp Val Lys Ala Ala Thr His Lys Phe Phe
                100                 105                 110 aat ctc cct gtt gaa gag aag cgc aag ttc act aaa gag aat tcg ctg     384
Asn Leu Pro Val Glu Glu Lys Arg Lys Phe Thr Lys Glu Asn Ser Leu
            115                 120                 125 tcg acg act gtt agg ttt ggg acg agt ttt agt cct ctt gca gag caa     432
Ser Thr Thr Val Arg Phe Gly Thr Ser Phe Ser Pro Leu Ala Glu Gln
        130                 135                 140
```

```
gcg ctt gag tgg aaa gat tat ctc agc ctc ttc ttt gtc tct gaa gct    480
Ala Leu Glu Trp Lys Asp Tyr Leu Ser Leu Phe Phe Val Ser Glu Ala
145                 150                 155                 160 gaa gct gaa cag ttc tgg cct gat atc tgc agg aat gaa acg tta gag    528
Glu Ala Glu Gln Phe Trp Pro Asp Ile Cys Arg Asn Glu Thr Leu Glu
                165                 170                 175 tac att aac aag tca aag aag atg gtg agg agg ctt cta gag tat ttg    576
Tyr Ile Asn Lys Ser Lys Lys Met Val Arg Arg Leu Leu Glu Tyr Leu
            180                 185                 190 gga aag aat ctc aat gtt aaa gag ctt gac gag acg aaa gaa tca ctc    624
Gly Lys Asn Leu Asn Val Lys Glu Leu Asp Glu Thr Lys Glu Ser Leu
        195                 200                 205 ttt atg ggc tcg att cga gtc aac ctt aac tac tac ccc atc tgc cct    672
Phe Met Gly Ser Ile Arg Val Asn Leu Asn Tyr Tyr Pro Ile Cys Pro
    210                 215                 220 aat ccg gac cta aca gtt ggt gtt ggt cgc cac tca gac gtc tct tct    720
Asn Pro Asp Leu Thr Val Gly Val Gly Arg His Ser Asp Val Ser Ser
225                 230                 235                 240 ctc acc att ctc tta caa gac cag atc ggt ggt cta cac gtg cgt tct    768
Leu Thr Ile Leu Leu Gln Asp Gln Ile Gly Gly Leu His Val Arg Ser
                245                 250                 255 ctg gct tca ggg aac tgg gtt cac gtg cct ccg gtt gct gga tct ttt    816
Leu Ala Ser Gly Asn Trp Val His Val Pro Pro Val Ala Gly Ser Phe
            260                 265                 270 gtg atc aac atc gga gat gcg atg cag atc atg agc aat ggt ctg tac    864
Val Ile Asn Ile Gly Asp Ala Met Gln Ile Met Ser Asn Gly Leu Tyr
        275                 280                 285 aag agc gtg gag cat cgt gtc tta gcc aat ggt tac aat aat aga atc    912
Lys Ser Val Glu His Arg Val Leu Ala Asn Gly Tyr Asn Asn Arg Ile
    290                 295                 300 tct gtt cct atc ttt gtg aac cca aaa cca gag tca gtt att ggt cct    960
Ser Val Pro Ile Phe Val Asn Pro Lys Pro Glu Ser Val Ile Gly Pro
305                 310                 315                 320 cta cct gag gtg att gca aac gga gag gaa ccg att tac aga gac gtc   1008
Leu Pro Glu Val Ile Ala Asn Gly Glu Glu Pro Ile Tyr Arg Asp Val
                325                 330                 335 ctg tac tct gat tac gtc aag tat ttc ttc agg aag gca cac gat gga   1056
Leu Tyr Ser Asp Tyr Val Lys Tyr Phe Phe Arg Lys Ala His Asp Gly
            340                 345                 350 aag aaa acc gtc gat tac gcc aag atc tga                           1086
Lys Lys Thr Val Asp Tyr Ala Lys Ile
        355                 360

<210> SEQ ID NO 2
<211> LENGTH: 361
<212> TYPE: PRT
<213> ORGANISM: Arabidopsis thaliana

<400> SEQUENCE: 2

Met Ala Pro Thr Leu Leu Thr Thr Gln Phe Ser Asn Pro Ala Glu Val
1               5                   10                  15

Thr Asp Phe Val Val Tyr Lys Gly Asn Gly Val Lys Gly Leu Ser Glu
            20                  25                  30

Thr Gly Ile Lys Ala Leu Pro Glu Gln Tyr Ile Gln Pro Leu Glu Glu
        35                  40                  45

Arg Leu Ile Asn Lys Phe Val Asn Glu Thr Asp Glu Ala Ile Pro Val
    50                  55                  60

Ile Asp Met Ser Asn Pro Asp Glu Asp Arg Val Ala Glu Ala Val Cys
65                  70                  75                  80
```

```
Asp Ala Ala Glu Lys Trp Gly Phe Phe Gln Val Ile Asn His Gly Val
             85                  90                  95

Pro Leu Glu Val Leu Asp Asp Val Lys Ala Ala Thr His Lys Phe Phe
            100                 105                 110

Asn Leu Pro Val Glu Glu Lys Arg Lys Phe Thr Lys Glu Asn Ser Leu
        115                 120                 125

Ser Thr Thr Val Arg Phe Gly Thr Ser Phe Ser Pro Leu Ala Glu Gln
130                 135                 140

Ala Leu Glu Trp Lys Asp Tyr Leu Ser Leu Phe Phe Val Ser Glu Ala
145                 150                 155                 160

Glu Ala Glu Gln Phe Trp Pro Asp Ile Cys Arg Asn Glu Thr Leu Glu
                165                 170                 175

Tyr Ile Asn Lys Ser Lys Lys Met Val Arg Arg Leu Leu Glu Tyr Leu
            180                 185                 190

Gly Lys Asn Leu Asn Val Lys Glu Leu Asp Glu Thr Lys Glu Ser Leu
        195                 200                 205

Phe Met Gly Ser Ile Arg Val Asn Leu Asn Tyr Tyr Pro Ile Cys Pro
210                 215                 220

Asn Pro Asp Leu Thr Val Gly Val Gly Arg His Ser Asp Val Ser Ser
225                 230                 235                 240

Leu Thr Ile Leu Leu Gln Asp Gln Ile Gly Gly Leu His Val Arg Ser
                245                 250                 255

Leu Ala Ser Gly Asn Trp Val His Val Pro Pro Val Ala Gly Ser Phe
            260                 265                 270

Val Ile Asn Ile Gly Asp Ala Met Gln Ile Met Ser Asn Gly Leu Tyr
        275                 280                 285

Lys Ser Val Glu His Arg Val Leu Ala Asn Gly Tyr Asn Asn Arg Ile
290                 295                 300

Ser Val Pro Ile Phe Val Asn Pro Lys Pro Glu Ser Val Ile Gly Pro
305                 310                 315                 320

Leu Pro Glu Val Ile Ala Asn Gly Glu Glu Pro Ile Tyr Arg Asp Val
                325                 330                 335

Leu Tyr Ser Asp Tyr Val Lys Tyr Phe Phe Arg Lys Ala His Asp Gly
            340                 345                 350

Lys Lys Thr Val Asp Tyr Ala Lys Ile
        355                 360

<210> SEQ ID NO 3
<211> LENGTH: 780
<212> TYPE: DNA
<213> ORGANISM: Arabidopsis thaliana
<220> FEATURE:
<221> NAME/KEY: CDS
<222> LOCATION: (1)..(780)

<400> SEQUENCE: 3 atg gcg acg aca aca aca gaa gca acg aag aca tca tcg acc aat gga    48
Met Ala Thr Thr Thr Thr Glu Ala Thr Lys Thr Ser Ser Thr Asn Gly
1               5                   10                  15 gaa gat cag aag cag tct cag aat ctt cga cat caa gaa gtt ggt cac    96
Glu Asp Gln Lys Gln Ser Gln Asn Leu Arg His Gln Glu Val Gly His
            20                  25                  30 aag agt ctc tta cag agc gat gat ctc tac cag tat ata ctg gag aca   144
Lys Ser Leu Leu Gln Ser Asp Asp Leu Tyr Gln Tyr Ile Leu Glu Thr
        35                  40                  45 agt gtg tat cct aga gaa cca gaa tca atg aag gaa ctc agg gaa gtg   192
```

```
Ser Val Tyr Pro Arg Glu Pro Glu Ser Met Lys Glu Leu Arg Glu Val
    50                  55                  60 aca gca aaa cat cca tgg aac ata atg acc aca tca gct gat gaa gga       240
Thr Ala Lys His Pro Trp Asn Ile Met Thr Thr Ser Ala Asp Glu Gly
65                  70                  75                  80 cag ttc tta aac atg ctt atc aag ctc gtt aac gcc aag aac aca atg       288
Gln Phe Leu Asn Met Leu Ile Lys Leu Val Asn Ala Lys Asn Thr Met
                    85                  90                  95 gag atc gga gtt tac act ggc tac tct ctt ctc gcc acc gct ctt gct       336
Glu Ile Gly Val Tyr Thr Gly Tyr Ser Leu Leu Ala Thr Ala Leu Ala
                100                 105                 110 ctc cct gaa gac ggc aaa att ctg gct atg gat gtc aac aga gag aat       384
Leu Pro Glu Asp Gly Lys Ile Leu Ala Met Asp Val Asn Arg Glu Asn
            115                 120                 125 tac gaa ttg ggt tta ccg atc att gag aaa gcc ggc gtt gct cac aag       432
Tyr Glu Leu Gly Leu Pro Ile Ile Glu Lys Ala Gly Val Ala His Lys
        130                 135                 140 atc gac ttc agg gaa ggc cct gct ctt ccc gtt ctt gat gaa atc gtt       480
Ile Asp Phe Arg Glu Gly Pro Ala Leu Pro Val Leu Asp Glu Ile Val
145                 150                 155                 160 gct gac gag aag aac cat gga aca tat gac ttt ata ttc gtt gat gct       528
Ala Asp Glu Lys Asn His Gly Thr Tyr Asp Phe Ile Phe Val Asp Ala
                165                 170                 175 gac aaa gac aac tac atc aac tac cac aag cgt ttg atc gat ctt gtg       576
Asp Lys Asp Asn Tyr Ile Asn Tyr His Lys Arg Leu Ile Asp Leu Val
                180                 185                 190 aaa att gga gga gtg att ggc tac gac aac act ctg tgg aat ggt tct       624
Lys Ile Gly Gly Val Ile Gly Tyr Asp Asn Thr Leu Trp Asn Gly Ser
            195                 200                 205 gtc gtg gct cct cct gat gca cca atg agg aag tac gtt cgt tac tac       672
Val Val Ala Pro Pro Asp Ala Pro Met Arg Lys Tyr Val Arg Tyr Tyr
        210                 215                 220 aga gac ttt gtt ctt gag ctt aac aag gct ctt gct gct gac cct cgg       720
Arg Asp Phe Val Leu Glu Leu Asn Lys Ala Leu Ala Ala Asp Pro Arg
225                 230                 235                 240 atc gag atc tgt atg ctc cct gtt ggt gat gga atc act atc tgc cgt       768
Ile Glu Ile Cys Met Leu Pro Val Gly Asp Gly Ile Thr Ile Cys Arg
                245                 250                 255 cgg atc agt tga                                                        780
Arg Ile Ser
```

<210> SEQ ID NO 4
<211> LENGTH: 259
<212> TYPE: PRT
<213> ORGANISM: Arabidopsis thaliana

<400> SEQUENCE: 4

```
Met Ala Thr Thr Thr Glu Ala Thr Lys Thr Ser Ser Thr Asn Gly
1               5                   10                  15

Glu Asp Gln Lys Gln Ser Gln Asn Leu Arg His Gln Glu Val Gly His
                20                  25                  30

Lys Ser Leu Leu Gln Ser Asp Leu Tyr Gln Tyr Ile Leu Glu Thr
            35                  40                  45

Ser Val Tyr Pro Arg Glu Pro Glu Ser Met Lys Glu Leu Arg Glu Val
    50                  55                  60

Thr Ala Lys His Pro Trp Asn Ile Met Thr Thr Ser Ala Asp Glu Gly
65                  70                  75                  80

Gln Phe Leu Asn Met Leu Ile Lys Leu Val Asn Ala Lys Asn Thr Met
                85                  90                  95
```

```
Glu Ile Gly Val Tyr Thr Gly Tyr Ser Leu Leu Ala Thr Ala Leu Ala
            100                 105                 110

Leu Pro Glu Asp Gly Lys Ile Leu Ala Met Asp Val Asn Arg Glu Asn
        115                 120                 125

Tyr Glu Leu Gly Leu Pro Ile Ile Glu Lys Ala Gly Val Ala His Lys
130                 135                 140

Ile Asp Phe Arg Glu Gly Pro Ala Leu Pro Val Leu Asp Glu Ile Val
145                 150                 155                 160

Ala Asp Glu Lys Asn His Gly Thr Tyr Asp Phe Ile Phe Val Asp Ala
                165                 170                 175

Asp Lys Asp Asn Tyr Ile Asn Tyr His Lys Arg Leu Ile Asp Leu Val
            180                 185                 190

Lys Ile Gly Gly Val Ile Gly Tyr Asp Asn Thr Leu Trp Asn Gly Ser
        195                 200                 205

Val Val Ala Pro Pro Asp Ala Pro Met Arg Lys Tyr Val Arg Tyr Tyr
    210                 215                 220

Arg Asp Phe Val Leu Glu Leu Asn Lys Ala Leu Ala Ala Asp Pro Arg
225                 230                 235                 240

Ile Glu Ile Cys Met Leu Pro Val Gly Asp Gly Ile Thr Ile Cys Arg
                245                 250                 255

Arg Ile Ser

<210> SEQ ID NO 5
<211> LENGTH: 4353
<212> TYPE: DNA
<213> ORGANISM: Arabidopsis thaliana
<220> FEATURE:
<221> NAME/KEY: CDS
<222> LOCATION: (1)..(4353)

<400> SEQUENCE: 5 atg gct cat atg gtt gga gca gac gat att gag tca ttg aga gta gag      48
Met Ala His Met Val Gly Ala Asp Asp Ile Glu Ser Leu Arg Val Glu
1               5                   10                  15 ctt gca gag atc gga aga agc atc aga tca tca ttc cgg aga cat act      96
Leu Ala Glu Ile Gly Arg Ser Ile Arg Ser Ser Phe Arg Arg His Thr
            20                  25                  30 tcg agt ttc aga agc agc tct tca ata tat gaa gtt gaa aat gat ggt     144
Ser Ser Phe Arg Ser Ser Ser Ser Ile Tyr Glu Val Glu Asn Asp Gly
        35                  40                  45 gat gtt aat gat cat gat gca gag tat gct ctg caa tgg gct gag att     192
Asp Val Asn Asp His Asp Ala Glu Tyr Ala Leu Gln Trp Ala Glu Ile
50                  55                  60 gag aga tta cca act gtc aag cga atg aga tcg act ctc ctt gat gat     240
Glu Arg Leu Pro Thr Val Lys Arg Met Arg Ser Thr Leu Leu Asp Asp
65                  70                  75                  80 ggc gat gag tcc atg acc gag aaa gga aga aga gtc gtt gat gtc aca     288
Gly Asp Glu Ser Met Thr Glu Lys Gly Arg Arg Val Val Asp Val Thr
                85                  90                  95 aag ctt gga gcc gtg gaa cgt cat ctg atg att gag aaa ctc atc aaa     336
Lys Leu Gly Ala Val Glu Arg His Leu Met Ile Glu Lys Leu Ile Lys
            100                 105                 110 cac att gag aat gat aat ctc aag ttg ctc aag aaa atc agg aga aga     384
His Ile Glu Asn Asp Asn Leu Lys Leu Leu Lys Lys Ile Arg Arg Arg
        115                 120                 125 ata gac aga gtc ggg atg gag tta ccg acc ata gaa gtg agg tac gag     432
Ile Asp Arg Val Gly Met Glu Leu Pro Thr Ile Glu Val Arg Tyr Glu
130                 135                 140
```

```
agt tta aaa gtg gtg gcc gag tgc gag gtt gtc gaa ggg aag gca ctt      480
Ser Leu Lys Val Val Ala Glu Cys Glu Val Val Glu Gly Lys Ala Leu
145                 150                 155                 160 cca aca ctg tgg aac act gct aag cgt gtt tta tct gaa ctg gtg aag      528
Pro Thr Leu Trp Asn Thr Ala Lys Arg Val Leu Ser Glu Leu Val Lys
                165                 170                 175 ctc act ggt gca aaa aca cat gaa gcc aag ata aac att att aat gat      576
Leu Thr Gly Ala Lys Thr His Glu Ala Lys Ile Asn Ile Ile Asn Asp
            180                 185                 190 gtt aat ggc att ata aag cca gga agg tta aca ctg ttg ctt ggt cct      624
Val Asn Gly Ile Ile Lys Pro Gly Arg Leu Thr Leu Leu Leu Gly Pro
        195                 200                 205 cct agc tgc gga aaa aca act ttg tta aag gcc ttg tct gga aat tta      672
Pro Ser Cys Gly Lys Thr Thr Leu Leu Lys Ala Leu Ser Gly Asn Leu
    210                 215                 220 gaa aac aat cta aag tgt tca ggt gaa ata tct tac aat gga cac aga      720
Glu Asn Asn Leu Lys Cys Ser Gly Glu Ile Ser Tyr Asn Gly His Arg
225                 230                 235                 240 ctg gat gag ttt gtt cct cag aaa act tca gcg tac ata agt caa tat      768
Leu Asp Glu Phe Val Pro Gln Lys Thr Ser Ala Tyr Ile Ser Gln Tyr
                245                 250                 255 gat ctg cac att gca gag atg aca gtg agg gag aca gtt gac ttc tca      816
Asp Leu His Ile Ala Glu Met Thr Val Arg Glu Thr Val Asp Phe Ser
            260                 265                 270 gct cgt tgt cag ggc gtt ggt agc cga aca gat att atg atg gaa gtt      864
Ala Arg Cys Gln Gly Val Gly Ser Arg Thr Asp Ile Met Met Glu Val
        275                 280                 285 agt aaa aga gaa aag gaa aaa gga atc att cct gac aca gaa gtg gat      912
Ser Lys Arg Glu Lys Glu Lys Gly Ile Ile Pro Asp Thr Glu Val Asp
    290                 295                 300 gct tac atg aaa gca att tct gtt gaa gga ctc caa aga agt ctg caa      960
Ala Tyr Met Lys Ala Ile Ser Val Glu Gly Leu Gln Arg Ser Leu Gln
305                 310                 315                 320 aca gat tac att ttg aag att ctc gga ctt gat att tgt gca gaa ata     1008
Thr Asp Tyr Ile Leu Lys Ile Leu Gly Leu Asp Ile Cys Ala Glu Ile
                325                 330                 335 ttg att gga gat gtg atg agg aga ggt ata tca gga ggt caa aag aag     1056
Leu Ile Gly Asp Val Met Arg Arg Gly Ile Ser Gly Gly Gln Lys Lys
            340                 345                 350 cgt ctt acc aca gct gag atg atc gtt ggc ccg aca aag gct ctg ttt     1104
Arg Leu Thr Thr Ala Glu Met Ile Val Gly Pro Thr Lys Ala Leu Phe
        355                 360                 365 atg gat gaa ata aca aat ggc cta gac agc tcc aca gct ttt cag att     1152
Met Asp Glu Ile Thr Asn Gly Leu Asp Ser Ser Thr Ala Phe Gln Ile
    370                 375                 380 gtc aaa tct ctt cag cag ttt gct cac ata tca agc gct act gta ctt     1200
Val Lys Ser Leu Gln Gln Phe Ala His Ile Ser Ser Ala Thr Val Leu
385                 390                 395                 400 gtt tcg ctt ctt caa ccc gcc cca gaa tcc tat gac ctc ttt gat gac     1248
Val Ser Leu Leu Gln Pro Ala Pro Glu Ser Tyr Asp Leu Phe Asp Asp
                405                 410                 415 att atg ctg atg gcc aaa gga aga atc gtg tat cat ggt cca cgc ggt     1296
Ile Met Leu Met Ala Lys Gly Arg Ile Val Tyr His Gly Pro Arg Gly
            420                 425                 430 gaa gtc ctt aac ttc ttt gag gat tgt gga ttc cga tgc cct gaa agg     1344
Glu Val Leu Asn Phe Phe Glu Asp Cys Gly Phe Arg Cys Pro Glu Arg
        435                 440                 445 aag ggt gtt gca gac ttt ctc cag gag gtt ata tcc aaa aaa gat caa     1392
Lys Gly Val Ala Asp Phe Leu Gln Glu Val Ile Ser Lys Lys Asp Gln
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 450 |     |     |     |     | 455 |     |     |     |     | 460 |     |     |      |
| gca | caa | tac | tgg | tgg | cac | gag | gat | tta | cct | tac | agt | ttt | gtc | tcg | gta | 1440 |
| Ala | Gln | Tyr | Trp | Trp | His | Glu | Asp | Leu | Pro | Tyr | Ser | Phe | Val | Ser | Val |      |
| 465 |     |     |     | 470 |     |     |     |     | 475 |     |     |     |     | 480 |     |      |
| gaa | atg | ttg | tcg | aag | aag | ttc | aag | gac | ttg | agt | att | ggg | aaa | aag | atc | 1488 |
| Glu | Met | Leu | Ser | Lys | Lys | Phe | Lys | Asp | Leu | Ser | Ile | Gly | Lys | Lys | Ile |      |
|     |     |     |     | 485 |     |     |     |     | 490 |     |     |     |     | 495 |     |      |
| gaa | gac | act | ctg | tca | aag | cca | tat | gat | aga | tcc | aaa | agc | cat | aag | gat | 1536 |
| Glu | Asp | Thr | Leu | Ser | Lys | Pro | Tyr | Asp | Arg | Ser | Lys | Ser | His | Lys | Asp |      |
|     |     |     | 500 |     |     |     |     | 505 |     |     |     |     | 510 |     |     |      |
| gct | ttg | tcc | ttc | agt | gtg | tat | tct | ctt | cca | aac | tgg | gag | ctg | ttc | ata | 1584 |
| Ala | Leu | Ser | Phe | Ser | Val | Tyr | Ser | Leu | Pro | Asn | Trp | Glu | Leu | Phe | Ile |      |
| 515 |     |     |     |     |     | 520 |     |     |     |     | 525 |     |     |     |     |      |
| gca | tgc | ata | tca | aga | gag | tat | ctt | ctc | atg | aag | aga | aac | tat | ttc | gtc | 1632 |
| Ala | Cys | Ile | Ser | Arg | Glu | Tyr | Leu | Leu | Met | Lys | Arg | Asn | Tyr | Phe | Val |      |
|     | 530 |     |     |     |     | 535 |     |     |     |     | 540 |     |     |     |     |      |
| tat | att | ttc | aag | act | gct | cag | ctt | gtt | atg | gcc | gca | ttc | atc | act | atg | 1680 |
| Tyr | Ile | Phe | Lys | Thr | Ala | Gln | Leu | Val | Met | Ala | Ala | Phe | Ile | Thr | Met |      |
| 545 |     |     |     |     | 550 |     |     |     |     | 555 |     |     |     |     | 560 |      |
| aca | gtg | ttt | atc | cga | aca | cgg | atg | ggt | att | gat | atc | att | cat | gga | aat | 1728 |
| Thr | Val | Phe | Ile | Arg | Thr | Arg | Met | Gly | Ile | Asp | Ile | Ile | His | Gly | Asn |      |
|     |     |     |     | 565 |     |     |     |     | 570 |     |     |     |     | 575 |     |      |
| tct | tac | atg | agt | gcc | ctc | ttt | ttc | gcc | ctc | att | ata | ctt | ctt | gtt | gac | 1776 |
| Ser | Tyr | Met | Ser | Ala | Leu | Phe | Phe | Ala | Leu | Ile | Ile | Leu | Leu | Val | Asp |      |
|     |     |     | 580 |     |     |     |     | 585 |     |     |     |     | 590 |     |     |      |
| gga | ttc | cca | gag | ttg | tct | atg | acg | gct | caa | cgt | cta | gcc | gtg | ttt | tat | 1824 |
| Gly | Phe | Pro | Glu | Leu | Ser | Met | Thr | Ala | Gln | Arg | Leu | Ala | Val | Phe | Tyr |      |
| 595 |     |     |     |     |     | 600 |     |     |     |     | 605 |     |     |     |     |      |
| aag | cag | aag | cag | ttg | tgt | ttc | tat | cct | gca | tgg | gcg | tat | gca | atc | cct | 1872 |
| Lys | Gln | Lys | Gln | Leu | Cys | Phe | Tyr | Pro | Ala | Trp | Ala | Tyr | Ala | Ile | Pro |      |
|     | 610 |     |     |     |     | 615 |     |     |     |     | 620 |     |     |     |     |      |
| gca | aca | gtg | tta | aag | gtc | cct | ctc | tcg | ttc | ttt | gaa | tct | ctc | gtt | tgg | 1920 |
| Ala | Thr | Val | Leu | Lys | Val | Pro | Leu | Ser | Phe | Phe | Glu | Ser | Leu | Val | Trp |      |
| 625 |     |     |     |     | 630 |     |     |     |     | 635 |     |     |     |     | 640 |      |
| acc | tgc | ctc | tca | tac | tat | gtc | att | gga | tac | acc | cct | gaa | gca | tcc | agg | 1968 |
| Thr | Cys | Leu | Ser | Tyr | Tyr | Val | Ile | Gly | Tyr | Thr | Pro | Glu | Ala | Ser | Arg |      |
|     |     |     |     | 645 |     |     |     |     | 650 |     |     |     |     | 655 |     |      |
| ttc | ttc | aag | cag | ttc | att | cta | ctc | ttt | gct | gtt | cac | ttc | acc | tcg | ata | 2016 |
| Phe | Phe | Lys | Gln | Phe | Ile | Leu | Leu | Phe | Ala | Val | His | Phe | Thr | Ser | Ile |      |
|     |     |     | 660 |     |     |     |     | 665 |     |     |     |     | 670 |     |     |      |
| tcc | atg | ttc | cgg | tgt | cta | gct | gca | atc | ttc | cag | aca | gta | gtt | gct | tca | 2064 |
| Ser | Met | Phe | Arg | Cys | Leu | Ala | Ala | Ile | Phe | Gln | Thr | Val | Val | Ala | Ser |      |
| 675 |     |     |     |     |     | 680 |     |     |     |     | 685 |     |     |     |     |      |
| atc | aca | gct | ggc | agt | ttt | ggt | ata | tta | ttc | aca | ttt | gtc | ttt | gcc | ggt | 2112 |
| Ile | Thr | Ala | Gly | Ser | Phe | Gly | Ile | Leu | Phe | Thr | Phe | Val | Phe | Ala | Gly |      |
|     | 690 |     |     |     |     | 695 |     |     |     |     | 700 |     |     |     |     |      |
| ttc | gtc | att | cca | cca | cct | tct | atg | cca | gca | tgg | ctc | aag | tgg | ggt | ttc | 2160 |
| Phe | Val | Ile | Pro | Pro | Pro | Ser | Met | Pro | Ala | Trp | Leu | Lys | Trp | Gly | Phe |      |
| 705 |     |     |     |     | 710 |     |     |     |     | 715 |     |     |     |     | 720 |      |
| tgg | gca | aat | cct | ttg | agt | tac | ggt | gag | att | ggg | tta | tca | gta | aac | gag | 2208 |
| Trp | Ala | Asn | Pro | Leu | Ser | Tyr | Gly | Glu | Ile | Gly | Leu | Ser | Val | Asn | Glu |      |
|     |     |     |     | 725 |     |     |     |     | 730 |     |     |     |     | 735 |     |      |
| ttt | ctt | gct | cca | agg | tgg | aat | cag | atg | caa | ccc | aat | aat | ttt | acc | tta | 2256 |
| Phe | Leu | Ala | Pro | Arg | Trp | Asn | Gln | Met | Gln | Pro | Asn | Asn | Phe | Thr | Leu |      |
|     |     |     | 740 |     |     |     |     | 745 |     |     |     |     | 750 |     |     |      |
| gga | cga | acc | ata | ctc | caa | acc | cgt | gga | atg | gac | tac | aac | ggt | tac | atg | 2304 |
| Gly | Arg | Thr | Ile | Leu | Gln | Thr | Arg | Gly | Met | Asp | Tyr | Asn | Gly | Tyr | Met |      |
| 755 |     |     |     |     |     | 760 |     |     |     |     | 765 |     |     |     |     |      |
| tac | tgg | gta | tca | tta | tgt | gcc | ttg | ttg | ggt | ttc | act | gtg | ctc | ttc | aac | 2352 |

|  |  |
|---|---|
| Tyr Trp Val Ser Leu Cys Ala Leu Leu Gly Phe Thr Val Leu Phe Asn<br>770                  775                  780 |  |
| atc att ttc act ctg gct cta acg ttc ttg aaa tca ccc aca tca tct<br>Ile Ile Phe Thr Leu Ala Leu Thr Phe Leu Lys Ser Pro Thr Ser Ser<br>785                  790                  795                  800 | 2400 |
| cga gcc atg att tcg caa gac aaa ctc tct gag ctg caa gga aca gaa<br>Arg Ala Met Ile Ser Gln Asp Lys Leu Ser Glu Leu Gln Gly Thr Glu<br>                  805                  810                  815 | 2448 |
| aag tca aca gaa gat tct tct gtc agg aaa aag acc aca gac tcc cct<br>Lys Ser Thr Glu Asp Ser Ser Val Arg Lys Lys Thr Thr Asp Ser Pro<br>        820                  825                  830 | 2496 |
| gta aag acc gaa gaa gaa gac aaa atg gtc tta cca ttc aag cct ctc<br>Val Lys Thr Glu Glu Glu Asp Lys Met Val Leu Pro Phe Lys Pro Leu<br>              835                  840                  845 | 2544 |
| act gta aca ttt caa gac ttg aac tat ttc gtt gac atg cca gtg gag<br>Thr Val Thr Phe Gln Asp Leu Asn Tyr Phe Val Asp Met Pro Val Glu<br>850                  855                  860 | 2592 |
| atg aga gac caa gga tat gat cag aag aaa cta caa ctt ctc tca gat<br>Met Arg Asp Gln Gly Tyr Asp Gln Lys Lys Leu Gln Leu Leu Ser Asp<br>865                  870                  875                  880 | 2640 |
| atc aca gga gct ttc cgt ccc gga atc cta acg gca cta atg gga gtg<br>Ile Thr Gly Ala Phe Arg Pro Gly Ile Leu Thr Ala Leu Met Gly Val<br>                  885                  890                  895 | 2688 |
| agt gga gct gga aaa acc act ctt ctc gac gtt cta gcc gga agg aaa<br>Ser Gly Ala Gly Lys Thr Thr Leu Leu Asp Val Leu Ala Gly Arg Lys<br>        900                  905                  910 | 2736 |
| aca agc gga tac atc gaa gga gac att aga atc agt ggc ttc cct aaa<br>Thr Ser Gly Tyr Ile Glu Gly Asp Ile Arg Ile Ser Gly Phe Pro Lys<br>              915                  920                  925 | 2784 |
| gtc caa gaa aca ttc gct aga gtc tca ggc tac tgt gaa caa aca gat<br>Val Gln Glu Thr Phe Ala Arg Val Ser Gly Tyr Cys Glu Gln Thr Asp<br>930                  935                  940 | 2832 |
| att cac tca cca aac atc act gta gaa gaa tcc gta atc tac tcg gct<br>Ile His Ser Pro Asn Ile Thr Val Glu Glu Ser Val Ile Tyr Ser Ala<br>945                  950                  955                  960 | 2880 |
| tgg ctt cgt cta gct cct gag atc gat gcc aca aca aaa acc aaa ttc<br>Trp Leu Arg Leu Ala Pro Glu Ile Asp Ala Thr Thr Lys Thr Lys Phe<br>                  965                  970                  975 | 2928 |
| gtg aag caa gtg ctt gag acg atc gaa tta gat gag att aaa gat tca<br>Val Lys Gln Val Leu Glu Thr Ile Glu Leu Asp Glu Ile Lys Asp Ser<br>        980                  985                  990 | 2976 |
| ttg gtg gga gtc acc gga gtt agt gga tta tcg acg gag caa agg aag<br>Leu Val Gly Val Thr Gly Val Ser Gly Leu Ser Thr Glu Gln Arg Lys<br>              995                  1000                1005 | 3024 |
| aga ttg acg att gcg gtg gag ttg gtg gcg aat ccg tcg att ata<br>Arg Leu Thr Ile Ala Val Glu Leu Val Ala Asn Pro Ser Ile Ile<br>1010                  1015                1020 | 3069 |
| ttt atg gat gag cca acg acg ggg cta gac gca aga gca gct gcc<br>Phe Met Asp Glu Pro Thr Thr Gly Leu Asp Ala Arg Ala Ala Ala<br>1025                  1030                1035 | 3114 |
| att gtt atg aga gct gtg aag aac gtc gct gat act gga cga acc<br>Ile Val Met Arg Ala Val Lys Asn Val Ala Asp Thr Gly Arg Thr<br>1040                  1045                1050 | 3159 |
| atc gtc tgt act att cat cag cct agt atc gac att ttt gaa gcc<br>Ile Val Cys Thr Ile His Gln Pro Ser Ile Asp Ile Phe Glu Ala<br>1055                  1060                1065 | 3204 |
| ttc gac gag ctg gtg ctt ctt aaa aga ggt ggt cgc atg atc tac<br>Phe Asp Glu Leu Val Leu Leu Lys Arg Gly Gly Arg Met Ile Tyr<br>1070                  1075                1080 | 3249 |

-continued

| | |
|---|---|
| aca gga cca tta ggc caa cat tca cgt cac att atc gag tat ttt<br>Thr Gly Pro Leu Gly Gln His Ser Arg His Ile Ile Glu Tyr Phe<br>     1085                     1090                    1095 | 3294 |
| gag agt gtt cct gaa att cct aaa ata aaa gac aac cac aat cca<br>Glu Ser Val Pro Glu Ile Pro Lys Ile Lys Asp Asn His Asn Pro<br>     1100                     1105                    1110 | 3339 |
| gca aca tgg atg ctt gat gtt agt tca cag tcg gta gaa att gaa<br>Ala Thr Trp Met Leu Asp Val Ser Ser Gln Ser Val Glu Ile Glu<br>     1115                     1120                    1125 | 3384 |
| ctt ggt gtc gat ttc gca aaa atc tac cat gac tct gct ctt tac<br>Leu Gly Val Asp Phe Ala Lys Ile Tyr His Asp Ser Ala Leu Tyr<br>     1130                     1135                    1140 | 3429 |
| aag cga aac tca gag ctt gtg aaa cag ttg agc cag cca gat tca<br>Lys Arg Asn Ser Glu Leu Val Lys Gln Leu Ser Gln Pro Asp Ser<br>     1145                     1150                    1155 | 3474 |
| gga tca agt gat ata cag ttt aag aga acc ttt gca caa agc tgg<br>Gly Ser Ser Asp Ile Gln Phe Lys Arg Thr Phe Ala Gln Ser Trp<br>     1160                     1165                    1170 | 3519 |
| tgg gga caa ttc aaa tct att cta tgg aaa atg aac ttg tct tat<br>Trp Gly Gln Phe Lys Ser Ile Leu Trp Lys Met Asn Leu Ser Tyr<br>     1175                     1180                    1185 | 3564 |
| tgg aga agc cct tct tat aac cta atg cgt atg atg cac act tta<br>Trp Arg Ser Pro Ser Tyr Asn Leu Met Arg Met Met His Thr Leu<br>     1190                     1195                    1200 | 3609 |
| gtc tct tct ttg atc ttc ggc gca ctt ttc tgg aaa caa ggc caa<br>Val Ser Ser Leu Ile Phe Gly Ala Leu Phe Trp Lys Gln Gly Gln<br>     1205                     1210                    1215 | 3654 |
| aat cta gat act caa cag agt atg ttc aca gta ttt gga gcg atc<br>Asn Leu Asp Thr Gln Gln Ser Met Phe Thr Val Phe Gly Ala Ile<br>     1220                     1225                    1230 | 3699 |
| tac ggt ttg gta ctc ttc tta ggg ata aac aat tgt gca tca gct<br>Tyr Gly Leu Val Leu Phe Leu Gly Ile Asn Asn Cys Ala Ser Ala<br>     1235                     1240                    1245 | 3744 |
| ctt caa tat ttc gaa aca gag aga aat gtt atg tac cgg gaa aga<br>Leu Gln Tyr Phe Glu Thr Glu Arg Asn Val Met Tyr Arg Glu Arg<br>     1250                     1255                    1260 | 3789 |
| ttc gca ggg atg tac tca gcg act gct tat gca ttg ggt caa gtg<br>Phe Ala Gly Met Tyr Ser Ala Thr Ala Tyr Ala Leu Gly Gln Val<br>     1265                     1270                    1275 | 3834 |
| gtg act gag ata cct tat ata ttc ata caa gct gcc gag ttt gtg<br>Val Thr Glu Ile Pro Tyr Ile Phe Ile Gln Ala Ala Glu Phe Val<br>     1280                     1285                    1290 | 3879 |
| atc gta aca tat cca atg atc ggt ttc tat cct tca gcc tac aaa<br>Ile Val Thr Tyr Pro Met Ile Gly Phe Tyr Pro Ser Ala Tyr Lys<br>     1295                     1300                    1305 | 3924 |
| gtc ttt tgg tca ctc tac tct atg ttt tgc tca cta ctc act ttc<br>Val Phe Trp Ser Leu Tyr Ser Met Phe Cys Ser Leu Leu Thr Phe<br>     1310                     1315                    1320 | 3969 |
| aac tac ctt gcg atg ttc ctc gtc tcc atc acg cca aac ttc atg<br>Asn Tyr Leu Ala Met Phe Leu Val Ser Ile Thr Pro Asn Phe Met<br>     1325                     1330                    1335 | 4014 |
| gtt gcc gcg att ctt caa tcg ctc ttt tat gtt ggt ttc aac ctt<br>Val Ala Ala Ile Leu Gln Ser Leu Phe Tyr Val Gly Phe Asn Leu<br>     1340                     1345                    1350 | 4059 |
| ttt tcg ggg ttt ttg atc ccc caa acg caa gta cca ggg tgg tgg<br>Phe Ser Gly Phe Leu Ile Pro Gln Thr Gln Val Pro Gly Trp Trp<br>     1355                     1360                    1365 | 4104 |
| att tgg tta tat tat cta aca cca acg tct tgg aca ctc aac ggg<br>Ile Trp Leu Tyr Tyr Leu Thr Pro Thr Ser Trp Thr Leu Asn Gly<br>     1370                     1375                    1380 | 4149 |

-continued

```
ttt atc tcg tcc caa tac ggc gat att cat gaa gag atc aat gtc      4194
Phe Ile Ser Ser Gln Tyr Gly Asp Ile His Glu Glu Ile Asn Val
    1385            1390                1395 ttt gga caa tcc acg acg gtt gca aga ttc ttg aaa gac tat ttt      4239
Phe Gly Gln Ser Thr Thr Val Ala Arg Phe Leu Lys Asp Tyr Phe
1400            1405                1410 gga ttt cat cat gac ctt ttg gcg gtt acc gcg gtt gtt caa atc      4284
Gly Phe His His Asp Leu Leu Ala Val Thr Ala Val Val Gln Ile
    1415            1420                1425 gct ttt ccc att gcc tta gct tct atg ttt gca ttc ttc gtg ggc      4329
Ala Phe Pro Ile Ala Leu Ala Ser Met Phe Ala Phe Phe Val Gly
1430            1435                1440 aaa ctc aac ttc caa cga aga tga                                  4353
Lys Leu Asn Phe Gln Arg Arg
    1445            1450
```

<210> SEQ ID NO 6
<211> LENGTH: 1450
<212> TYPE: PRT
<213> ORGANISM: Arabidopsis thaliana

<400> SEQUENCE: 6

```
Met Ala His Met Val Gly Ala Asp Asp Ile Glu Ser Leu Arg Val Glu
1               5                   10                  15

Leu Ala Glu Ile Gly Arg Ser Ile Arg Ser Ser Phe Arg Arg His Thr
            20                  25                  30

Ser Ser Phe Arg Ser Ser Ser Ile Tyr Glu Val Glu Asn Asp Gly
        35                  40                  45

Asp Val Asn Asp His Asp Ala Glu Tyr Ala Leu Gln Trp Ala Glu Ile
    50                  55                  60

Glu Arg Leu Pro Thr Val Lys Arg Met Arg Ser Thr Leu Leu Asp Asp
65                  70                  75                  80

Gly Asp Glu Ser Met Thr Glu Lys Gly Arg Arg Val Val Asp Val Thr
                85                  90                  95

Lys Leu Gly Ala Val Glu Arg His Leu Met Ile Glu Lys Leu Ile Lys
            100                 105                 110

His Ile Glu Asn Asp Asn Leu Lys Leu Leu Lys Lys Ile Arg Arg Arg
        115                 120                 125

Ile Asp Arg Val Gly Met Glu Leu Pro Thr Ile Glu Val Arg Tyr Glu
    130                 135                 140

Ser Leu Lys Val Val Ala Glu Cys Glu Val Val Glu Gly Lys Ala Leu
145                 150                 155                 160

Pro Thr Leu Trp Asn Thr Ala Lys Arg Val Leu Ser Glu Leu Val Lys
                165                 170                 175

Leu Thr Gly Ala Lys Thr His Glu Ala Lys Ile Asn Ile Asn Asp
            180                 185                 190

Val Asn Gly Ile Ile Lys Pro Gly Arg Leu Thr Leu Leu Gly Pro
        195                 200                 205

Pro Ser Cys Gly Lys Thr Thr Leu Leu Lys Ala Leu Ser Gly Asn Leu
    210                 215                 220

Glu Asn Asn Leu Lys Cys Ser Gly Glu Ile Ser Tyr Asn Gly His Arg
225                 230                 235                 240

Leu Asp Glu Phe Val Pro Gln Lys Thr Ser Ala Tyr Ile Ser Gln Tyr
                245                 250                 255

Asp Leu His Ile Ala Glu Met Thr Val Arg Glu Thr Val Asp Phe Ser
            260                 265                 270
```

-continued

```
Ala Arg Cys Gln Gly Val Gly Ser Arg Thr Asp Ile Met Met Glu Val
        275                 280                 285
Ser Lys Arg Glu Lys Glu Lys Gly Ile Ile Pro Asp Thr Glu Val Asp
    290                 295                 300
Ala Tyr Met Lys Ala Ile Ser Val Glu Gly Leu Gln Arg Ser Leu Gln
305                 310                 315                 320
Thr Asp Tyr Ile Leu Lys Ile Leu Gly Leu Asp Ile Cys Ala Glu Ile
                325                 330                 335
Leu Ile Gly Asp Val Met Arg Arg Gly Ile Ser Gly Gly Gln Lys Lys
            340                 345                 350
Arg Leu Thr Thr Ala Glu Met Ile Val Gly Pro Thr Lys Ala Leu Phe
        355                 360                 365
Met Asp Glu Ile Thr Asn Gly Leu Asp Ser Ser Thr Ala Phe Gln Ile
    370                 375                 380
Val Lys Ser Leu Gln Gln Phe Ala His Ile Ser Ser Ala Thr Val Leu
385                 390                 395                 400
Val Ser Leu Leu Gln Pro Ala Pro Glu Ser Tyr Asp Leu Phe Asp Asp
                405                 410                 415
Ile Met Leu Met Ala Lys Gly Arg Ile Val Tyr His Gly Pro Arg Gly
            420                 425                 430
Glu Val Leu Asn Phe Phe Glu Asp Cys Gly Phe Arg Cys Pro Glu Arg
        435                 440                 445
Lys Gly Val Ala Asp Phe Leu Gln Glu Val Ile Ser Lys Lys Asp Gln
    450                 455                 460
Ala Gln Tyr Trp Trp His Glu Asp Leu Pro Tyr Ser Phe Val Ser Val
465                 470                 475                 480
Glu Met Leu Ser Lys Lys Phe Lys Asp Leu Ser Ile Gly Lys Lys Ile
                485                 490                 495
Glu Asp Thr Leu Ser Lys Pro Tyr Asp Arg Ser Lys Ser His Lys Asp
            500                 505                 510
Ala Leu Ser Phe Ser Val Tyr Ser Leu Pro Asn Trp Glu Leu Phe Ile
        515                 520                 525
Ala Cys Ile Ser Arg Glu Tyr Leu Leu Met Lys Arg Asn Tyr Phe Val
    530                 535                 540
Tyr Ile Phe Lys Thr Ala Gln Leu Val Met Ala Ala Phe Ile Thr Met
545                 550                 555                 560
Thr Val Phe Ile Arg Thr Arg Met Gly Ile Asp Ile His Gly Asn
                565                 570                 575
Ser Tyr Met Ser Ala Leu Phe Phe Ala Leu Ile Ile Leu Leu Val Asp
            580                 585                 590
Gly Phe Pro Glu Leu Ser Met Thr Ala Gln Arg Leu Ala Val Phe Tyr
        595                 600                 605
Lys Gln Lys Gln Leu Cys Phe Tyr Pro Ala Trp Ala Tyr Ala Ile Pro
    610                 615                 620
Ala Thr Val Leu Lys Val Pro Leu Ser Phe Glu Ser Leu Val Trp
625                 630                 635                 640
Thr Cys Leu Ser Tyr Tyr Val Ile Gly Tyr Thr Pro Glu Ala Ser Arg
                645                 650                 655
Phe Phe Lys Gln Phe Ile Leu Leu Phe Ala Val His Phe Thr Ser Ile
            660                 665                 670
Ser Met Phe Arg Cys Leu Ala Ala Ile Phe Gln Thr Val Val Ala Ser
        675                 680                 685
```

-continued

```
Ile Thr Ala Gly Ser Phe Gly Ile Leu Phe Thr Phe Val Phe Ala Gly
690                 695                 700
Phe Val Ile Pro Pro Ser Met Pro Ala Trp Leu Lys Trp Gly Phe
705                 710                 715                 720
Trp Ala Asn Pro Leu Ser Tyr Gly Glu Ile Gly Leu Ser Val Asn Glu
                725                 730                 735
Phe Leu Ala Pro Arg Trp Asn Gln Met Gln Pro Asn Asn Phe Thr Leu
                740                 745                 750
Gly Arg Thr Ile Leu Gln Thr Arg Gly Met Asp Tyr Asn Gly Tyr Met
                755                 760                 765
Tyr Trp Val Ser Leu Cys Ala Leu Leu Gly Phe Thr Val Leu Phe Asn
770                 775                 780
Ile Ile Phe Thr Leu Ala Leu Thr Phe Leu Lys Ser Pro Thr Ser Ser
785                 790                 795                 800
Arg Ala Met Ile Ser Gln Asp Lys Leu Ser Glu Leu Gln Gly Thr Glu
                805                 810                 815
Lys Ser Thr Glu Asp Ser Ser Val Arg Lys Lys Thr Thr Asp Ser Pro
                820                 825                 830
Val Lys Thr Glu Glu Asp Lys Met Val Leu Pro Phe Lys Pro Leu
                835                 840                 845
Thr Val Thr Phe Gln Asp Leu Asn Tyr Phe Val Asp Met Pro Val Glu
850                 855                 860
Met Arg Asp Gln Gly Tyr Asp Gln Lys Lys Leu Gln Leu Leu Ser Asp
865                 870                 875                 880
Ile Thr Gly Ala Phe Arg Pro Gly Ile Leu Thr Ala Leu Met Gly Val
                885                 890                 895
Ser Gly Ala Gly Lys Thr Thr Leu Leu Asp Val Leu Ala Gly Arg Lys
                900                 905                 910
Thr Ser Gly Tyr Ile Glu Gly Asp Ile Arg Ile Ser Gly Phe Pro Lys
                915                 920                 925
Val Gln Glu Thr Phe Ala Arg Val Ser Gly Tyr Cys Glu Gln Thr Asp
                930                 935                 940
Ile His Ser Pro Asn Ile Thr Val Glu Glu Ser Val Ile Tyr Ser Ala
945                 950                 955                 960
Trp Leu Arg Leu Ala Pro Glu Ile Asp Ala Thr Thr Lys Thr Lys Phe
                965                 970                 975
Val Lys Gln Val Leu Glu Thr Ile Glu Leu Asp Glu Ile Lys Asp Ser
                980                 985                 990
Leu Val Gly Val Thr Gly Val Ser Gly Leu Ser Thr Glu Gln Arg Lys
                995                 1000                1005
Arg Leu Thr Ile Ala Val Glu Leu Val Ala Asn Pro Ser Ile Ile
                1010                1015                1020
Phe Met Asp Glu Pro Thr Thr Gly Leu Asp Ala Arg Ala Ala Ala
                1025                1030                1035
Ile Val Met Arg Ala Val Lys Asn Val Ala Asp Thr Gly Arg Thr
                1040                1045                1050
Ile Val Cys Thr Ile His Gln Pro Ser Ile Asp Ile Phe Glu Ala
                1055                1060                1065
Phe Asp Glu Leu Val Leu Leu Lys Arg Gly Gly Arg Met Ile Tyr
                1070                1075                1080
Thr Gly Pro Leu Gly Gln His Ser Arg His Ile Ile Glu Tyr Phe
                1085                1090                1095
Glu Ser Val Pro Glu Ile Pro Lys Ile Lys Asp Asn His Asn Pro
```

Ala Thr Trp Met Leu Asp Val Ser Ser Gln Ser Val Glu Ile Glu
1115                 1120                 1125

Leu Gly Val Asp Phe Ala Lys Ile Tyr His Asp Ser Ala Leu Tyr
1130                 1135                 1140

Lys Arg Asn Ser Glu Leu Val Lys Gln Leu Ser Gln Pro Asp Ser
1145                 1150                 1155

Gly Ser Ser Asp Ile Gln Phe Lys Arg Thr Phe Ala Gln Ser Trp
1160                 1165                 1170

Trp Gly Gln Phe Lys Ser Ile Leu Trp Lys Met Asn Leu Ser Tyr
1175                 1180                 1185

Trp Arg Ser Pro Ser Tyr Asn Leu Met Arg Met Met His Thr Leu
1190                 1195                 1200

Val Ser Ser Leu Ile Phe Gly Ala Leu Phe Trp Lys Gln Gly Gln
1205                 1210                 1215

Asn Leu Asp Thr Gln Gln Ser Met Phe Thr Val Phe Gly Ala Ile
1220                 1225                 1230

Tyr Gly Leu Val Leu Phe Leu Gly Ile Asn Asn Cys Ala Ser Ala
1235                 1240                 1245

Leu Gln Tyr Phe Glu Thr Glu Arg Asn Val Met Tyr Arg Glu Arg
1250                 1255                 1260

Phe Ala Gly Met Tyr Ser Ala Thr Ala Tyr Ala Leu Gly Gln Val
1265                 1270                 1275

Val Thr Glu Ile Pro Tyr Ile Phe Ile Gln Ala Ala Glu Phe Val
1280                 1285                 1290

Ile Val Thr Tyr Pro Met Ile Gly Phe Tyr Pro Ser Ala Tyr Lys
1295                 1300                 1305

Val Phe Trp Ser Leu Tyr Ser Met Phe Cys Ser Leu Leu Thr Phe
1310                 1315                 1320

Asn Tyr Leu Ala Met Phe Leu Val Ser Ile Thr Pro Asn Phe Met
1325                 1330                 1335

Val Ala Ala Ile Leu Gln Ser Leu Phe Tyr Val Gly Phe Asn Leu
1340                 1345                 1350

Phe Ser Gly Phe Leu Ile Pro Gln Thr Gln Val Pro Gly Trp Trp
1355                 1360                 1365

Ile Trp Leu Tyr Tyr Leu Thr Pro Thr Ser Trp Thr Leu Asn Gly
1370                 1375                 1380

Phe Ile Ser Ser Gln Tyr Gly Asp Ile His Glu Glu Ile Asn Val
1385                 1390                 1395

Phe Gly Gln Ser Thr Thr Val Ala Arg Phe Leu Lys Asp Tyr Phe
1400                 1405                 1410

Gly Phe His His Asp Leu Leu Ala Val Thr Ala Val Val Gln Ile
1415                 1420                 1425

Ala Phe Pro Ile Ala Leu Ala Ser Met Phe Ala Phe Phe Val Gly
1430                 1435                 1440

Lys Leu Asn Phe Gln Arg Arg
1445                 1450

<210> SEQ ID NO 7
<211> LENGTH: 1446
<212> TYPE: DNA
<213> ORGANISM: Arabidopsis thaliana
<220> FEATURE:
<221> NAME/KEY: CDS
<222> LOCATION: (1)..(1446)

<400> SEQUENCE: 7

```
atg ggg aag caa gaa gat gca gag ctc gtc atc ata cct ttc cct ttc      48
Met Gly Lys Gln Glu Asp Ala Glu Leu Val Ile Ile Pro Phe Pro Phe
 1               5                  10                  15 tcc gga cac att ctc gca aca atc gaa ctc gcc aaa cgt ctc ata agt      96
Ser Gly His Ile Leu Ala Thr Ile Glu Leu Ala Lys Arg Leu Ile Ser
             20                  25                  30 caa gac aat cct cgg atc cac acc atc acc atc ctc tat tgg gga tta    144
Gln Asp Asn Pro Arg Ile His Thr Ile Thr Ile Leu Tyr Trp Gly Leu
         35                  40                  45 cct ttt att cct caa gct gac aca atc gct ttc ctc cga tcc cta gtc    192
Pro Phe Ile Pro Gln Ala Asp Thr Ile Ala Phe Leu Arg Ser Leu Val
     50                  55                  60 aaa aat gag cct cgt atc cgt ctc gtt acg ttg ccc gaa gtc caa gac    240
Lys Asn Glu Pro Arg Ile Arg Leu Val Thr Leu Pro Glu Val Gln Asp
 65                  70                  75                  80 cct cca cca atg gaa ctc ttt gtg gaa ttt gcc gaa tct tac att ctt    288
Pro Pro Pro Met Glu Leu Phe Val Glu Phe Ala Glu Ser Tyr Ile Leu
                 85                  90                  95 gaa tac gtc aag aaa atg gtt ccc atc atc aga gaa gct ctc tcc act    336
Glu Tyr Val Lys Lys Met Val Pro Ile Ile Arg Glu Ala Leu Ser Thr
            100                 105                 110 ctc ttg tct tcc cgc gat gaa tcg ggt tca gtt cgt gtg gct gga ttg    384
Leu Leu Ser Ser Arg Asp Glu Ser Gly Ser Val Arg Val Ala Gly Leu
        115                 120                 125 gtt ctt gac ttc ttc tgc gtc cct atg atc gat gta gga aac gag ttt    432
Val Leu Asp Phe Phe Cys Val Pro Met Ile Asp Val Gly Asn Glu Phe
    130                 135                 140 aat ctc cct tct tac att ttc ttg acg tgt agc gca ggg ttc ttg ggt    480
Asn Leu Pro Ser Tyr Ile Phe Leu Thr Cys Ser Ala Gly Phe Leu Gly
145                 150                 155                 160 atg atg aag tat ctt cca gag aga cac cgc gaa atc aaa tcg gaa ttc    528
Met Met Lys Tyr Leu Pro Glu Arg His Arg Glu Ile Lys Ser Glu Phe
                165                 170                 175 aac cgg agc ttc aac gag gag ttg aat ctc att cct ggt tat gtc aac    576
Asn Arg Ser Phe Asn Glu Glu Leu Asn Leu Ile Pro Gly Tyr Val Asn
            180                 185                 190 tct gtt cct act aag gtt ttg ccg tca ggt cta ttc atg aaa gag acc    624
Ser Val Pro Thr Lys Val Leu Pro Ser Gly Leu Phe Met Lys Glu Thr
        195                 200                 205 tac gag cct tgg gtc gaa cta gca gag agg ttt cct gaa gct aag ggt    672
Tyr Glu Pro Trp Val Glu Leu Ala Glu Arg Phe Pro Glu Ala Lys Gly
    210                 215                 220 att ttg gtt aat tca tac aca gct ctc gag cca aac ggt ttt aaa tat    720
Ile Leu Val Asn Ser Tyr Thr Ala Leu Glu Pro Asn Gly Phe Lys Tyr
225                 230                 235                 240 ttc gat cgt tgt ccg gat aac tac cca acc att tac cca atc ggg ccg    768
Phe Asp Arg Cys Pro Asp Asn Tyr Pro Thr Ile Tyr Pro Ile Gly Pro
                245                 250                 255 ata tta tgc tcc aac gac cgt ccg aat ttg gac tca tcg gaa cga gat    816
Ile Leu Cys Ser Asn Asp Arg Pro Asn Leu Asp Ser Ser Glu Arg Asp
            260                 265                 270 cgg atc ata act tgg cta gat gac caa ccc gag tca tcg gtc gtg ttc    864
Arg Ile Ile Thr Trp Leu Asp Asp Gln Pro Glu Ser Ser Val Val Phe
        275                 280                 285 ctc tgt ttc ggg agc ttg aag aat ctc agc gct act cag atc aac gag    912
Leu Cys Phe Gly Ser Leu Lys Asn Leu Ser Ala Thr Gln Ile Asn Glu
    290                 295                 300
```

```
ata gct caa gcc tta gag atc gtt gac tgc aaa ttc atc tgg tcg ttt    960
Ile Ala Gln Ala Leu Glu Ile Val Asp Cys Lys Phe Ile Trp Ser Phe
305                 310                 315                 320 cga acc aac ccg aag gag tac gcg agc cct tac gag gct cta cca cac   1008
Arg Thr Asn Pro Lys Glu Tyr Ala Ser Pro Tyr Glu Ala Leu Pro His
            325                 330                 335 ggg ttc atg gac cgg gtc atg gat caa ggc att gtt tgt ggt tgg gct   1056
Gly Phe Met Asp Arg Val Met Asp Gln Gly Ile Val Cys Gly Trp Ala
        340                 345                 350 cct caa gtt gaa atc cta gcc cat aaa gct gtg gga gga ttc gta tct   1104
Pro Gln Val Glu Ile Leu Ala His Lys Ala Val Gly Gly Phe Val Ser
    355                 360                 365 cat tgt ggt tgg aac tcg ata ttg gag agt ttg ggt ttc ggc gtt cca   1152
His Cys Gly Trp Asn Ser Ile Leu Glu Ser Leu Gly Phe Gly Val Pro
370                 375                 380 atc gcc acg tgg ccg atg tac gcg gaa caa caa cta aac gcg ttc acg   1200
Ile Ala Thr Trp Pro Met Tyr Ala Glu Gln Gln Leu Asn Ala Phe Thr
385                 390                 395                 400 atg gtg aag gag ctt ggt tta gcc ttg gag atg cgg ttg gat tac gtg   1248
Met Val Lys Glu Leu Gly Leu Ala Leu Glu Met Arg Leu Asp Tyr Val
            405                 410                 415 tcg gaa gat gga gat ata gtg aaa gct gat gag atc gca gga acc gtt   1296
Ser Glu Asp Gly Asp Ile Val Lys Ala Asp Glu Ile Ala Gly Thr Val
        420                 425                 430 aga tct tta atg gac ggt gtg gat gtg ccg aag agt aaa gtg aag gag   1344
Arg Ser Leu Met Asp Gly Val Asp Val Pro Lys Ser Lys Val Lys Glu
    435                 440                 445 att gct gag gcg gga aaa gaa gct gtg gac ggt gga tct tcg ttt ctt   1392
Ile Ala Glu Ala Gly Lys Glu Ala Val Asp Gly Gly Ser Ser Phe Leu
450                 455                 460 gcg gtt aaa aga ttc atc ggt gac ttg atc gac ggc gtt tct ata agt   1440
Ala Val Lys Arg Phe Ile Gly Asp Leu Ile Asp Gly Val Ser Ile Ser
465                 470                 475                 480 aag tag                                                           1446
Lys

<210> SEQ ID NO 8
<211> LENGTH: 481
<212> TYPE: PRT
<213> ORGANISM: Arabidopsis thaliana

<400> SEQUENCE: 8

Met Gly Lys Gln Glu Asp Ala Glu Leu Val Ile Ile Pro Phe Pro Phe
1               5                   10                  15

Ser Gly His Ile Leu Ala Thr Ile Glu Leu Ala Lys Arg Leu Ile Ser
            20                  25                  30

Gln Asp Asn Pro Arg Ile His Thr Ile Thr Ile Leu Tyr Trp Gly Leu
        35                  40                  45

Pro Phe Ile Pro Gln Ala Asp Thr Ile Ala Phe Leu Arg Ser Leu Val
    50                  55                  60

Lys Asn Glu Pro Arg Ile Arg Leu Val Thr Leu Pro Glu Val Gln Asp
65                  70                  75                  80

Pro Pro Pro Met Glu Leu Phe Val Glu Phe Ala Glu Ser Tyr Ile Leu
                85                  90                  95

Glu Tyr Val Lys Lys Met Val Pro Ile Ile Arg Glu Ala Leu Ser Thr
            100                 105                 110

Leu Leu Ser Ser Arg Asp Glu Ser Gly Ser Val Arg Val Ala Gly Leu
        115                 120                 125
```

| | | | | | | | | | | | |
|---|---|---|---|---|---|---|---|---|---|---|---|
|Val|Leu|Asp|Phe|Phe|Cys|Val|Pro|Met|Ile|Asp|Val|Gly|Asn|Glu|Phe|
| |130| | | | |135| | | |140| | | | | |

Val Leu Asp Phe Phe Cys Val Pro Met Ile Asp Val Gly Asn Glu Phe
    130                 135             140

Asn Leu Pro Ser Tyr Ile Phe Leu Thr Cys Ser Ala Gly Phe Leu Gly
145                 150                 155                 160

Met Met Lys Tyr Leu Pro Glu Arg His Arg Glu Ile Lys Ser Glu Phe
            165                 170                 175

Asn Arg Ser Phe Asn Glu Glu Leu Asn Leu Ile Pro Gly Tyr Val Asn
            180                 185                 190

Ser Val Pro Thr Lys Val Leu Pro Ser Gly Leu Phe Met Lys Glu Thr
        195                 200                 205

Tyr Glu Pro Trp Val Glu Leu Ala Glu Arg Phe Pro Glu Ala Lys Gly
    210                 215                 220

Ile Leu Val Asn Ser Tyr Thr Ala Leu Glu Pro Asn Gly Phe Lys Tyr
225                 230                 235                 240

Phe Asp Arg Cys Pro Asp Asn Tyr Pro Thr Ile Tyr Pro Ile Gly Pro
                245                 250                 255

Ile Leu Cys Ser Asn Asp Arg Pro Asn Leu Asp Ser Ser Glu Arg Asp
            260                 265                 270

Arg Ile Ile Thr Trp Leu Asp Asp Gln Pro Glu Ser Ser Val Val Phe
        275                 280                 285

Leu Cys Phe Gly Ser Leu Lys Asn Leu Ser Ala Thr Gln Ile Asn Glu
    290                 295                 300

Ile Ala Gln Ala Leu Glu Ile Val Asp Cys Lys Phe Ile Trp Ser Phe
305                 310                 315                 320

Arg Thr Asn Pro Lys Glu Tyr Ala Ser Pro Tyr Glu Ala Leu Pro His
                325                 330                 335

Gly Phe Met Asp Arg Val Met Asp Gln Gly Ile Val Cys Gly Trp Ala
            340                 345                 350

Pro Gln Val Glu Ile Leu Ala His Lys Ala Val Gly Phe Gly Val Ser
        355                 360                 365

His Cys Gly Trp Asn Ser Ile Leu Glu Ser Leu Gly Phe Gly Val Pro
    370                 375                 380

Ile Ala Thr Trp Pro Met Tyr Ala Glu Gln Gln Leu Asn Ala Phe Thr
385                 390                 395                 400

Met Val Lys Glu Leu Gly Leu Ala Leu Glu Met Arg Leu Asp Tyr Val
                405                 410                 415

Ser Glu Asp Gly Asp Ile Val Lys Ala Asp Glu Ile Ala Gly Thr Val
            420                 425                 430

Arg Ser Leu Met Asp Gly Val Asp Val Pro Lys Ser Lys Val Lys Glu
        435                 440                 445

Ile Ala Glu Ala Gly Lys Glu Ala Val Asp Gly Gly Ser Ser Phe Leu
450                 455                 460

Ala Val Lys Arg Phe Ile Gly Asp Leu Ile Asp Gly Val Ser Ile Ser
465                 470                 475                 480

Lys

<210> SEQ ID NO 9
<211> LENGTH: 1086
<212> TYPE: DNA
<213> ORGANISM: Brassica rapa
<220> FEATURE:
<221> NAME/KEY: CDS
<222> LOCATION: (1)..(1086)

<400> SEQUENCE: 9

| | | |
|---|---|---|
| atg gct cca aca ctc tct acc tta cag ttc gca gat cca gct gaa gta<br>Met Ala Pro Thr Leu Ser Thr Leu Gln Phe Ala Asp Pro Ala Glu Val<br>1                   5                        10                   15 | | 48 |
| acc gag ttc gtg gtc aac aaa gga aac ggc gta aag ggt tta tca gaa<br>Thr Glu Phe Val Val Asn Lys Gly Asn Gly Val Lys Gly Leu Ser Glu<br>              20                        25                       30 | | 96 |
| aca ggg atc aaa gct ctt ccc gac caa tac att caa cca ttc gaa gag<br>Thr Gly Ile Lys Ala Leu Pro Asp Gln Tyr Ile Gln Pro Phe Glu Glu<br>           35                       40                       45 | | 144 |
| cgt ctc atc aac aag ttc gtc aac gaa aca gac gag gcc att ccc gtc<br>Arg Leu Ile Asn Lys Phe Val Asn Glu Thr Asp Glu Ala Ile Pro Val<br>    50                        55                       60 | | 192 |
| atc gac atg tcc tac ccc gaa gag gac aaa gtc gct gaa gct gta tgt<br>Ile Asp Met Ser Tyr Pro Glu Glu Asp Lys Val Ala Glu Ala Val Cys<br>65                     70                        75                   80 | | 240 |
| gac gct gct gag aga tgg ggt ttc ttt caa gtg atc aac cat gga gtt<br>Asp Ala Ala Glu Arg Trp Gly Phe Phe Gln Val Ile Asn His Gly Val<br>                  85                       90                       95 | | 288 |
| cct ctt gaa gtt ctt gac aac gtg aag gct gcg act cat agg ttc ttt<br>Pro Leu Glu Val Leu Asp Asn Val Lys Ala Ala Thr His Arg Phe Phe<br>                100                      105                    110 | | 336 |
| aat ctc cct gtt gag gag aag agt agg ttc aca agg gag aac tcg ttg<br>Asn Leu Pro Val Glu Glu Lys Ser Arg Phe Thr Arg Glu Asn Ser Leu<br>       115                      120                    125 | | 384 |
| tcg acg aat gta agg ttt gga acg agt ttt agt cct cgt gca gag aaa<br>Ser Thr Asn Val Arg Phe Gly Thr Ser Phe Ser Pro Arg Ala Glu Lys<br>130                      135                    140 | | 432 |
| gct ctt gag tgg aaa gat tat ctc agt ctc ttc ttt gtt tct gaa act<br>Ala Leu Glu Trp Lys Asp Tyr Leu Ser Leu Phe Phe Val Ser Glu Thr<br>145                     150                      155                  160 | | 480 |
| gaa gct gaa cag tac tgg cct aat gct tgc aag aac gaa gct cta gag<br>Glu Ala Glu Gln Tyr Trp Pro Asn Ala Cys Lys Asn Glu Ala Leu Glu<br>                  165                      170                    175 | | 528 |
| tac atg aac aag tcc aag aca atg gtg agg aag ctt tta gag tat tta<br>Tyr Met Asn Lys Ser Lys Thr Met Val Arg Lys Leu Leu Glu Tyr Leu<br>       180                      185                    190 | | 576 |
| ggg aag aat ctc aac gtg aag gag cta gac gag acc aaa gaa tca ctc<br>Gly Lys Asn Leu Asn Val Lys Glu Leu Asp Glu Thr Lys Glu Ser Leu<br>195                      200                    205 | | 624 |
| ttc atg ggt tca att cga atc aac ctc aac tac tat ccc atc tgt cct<br>Phe Met Gly Ser Ile Arg Ile Asn Leu Asn Tyr Tyr Pro Ile Cys Pro<br>210                     215                      220 | | 672 |
| agt ccc gac cta acc gtt ggc gtt ggt cga cac tca gat gtc tct tcc<br>Ser Pro Asp Leu Thr Val Gly Val Gly Arg His Ser Asp Val Ser Ser<br>225                     230                      235                  240 | | 720 |
| ctc acc att ctc tta caa gac cag atc ggt ggc ctc cac gtg cgt tct<br>Leu Thr Ile Leu Leu Gln Asp Gln Ile Gly Gly Leu His Val Arg Ser<br>                  245                      250                    255 | | 768 |
| cta acg tca ggg aac tgg gtt cac gtg cca ccg gtt cct gga tct ttc<br>Leu Thr Ser Gly Asn Trp Val His Val Pro Pro Val Pro Gly Ser Phe<br>       260                      265                    270 | | 816 |
| gtg atc aac atc gga gac gcc atg cag atc ttg agc aat ggt cgt tac<br>Val Ile Asn Ile Gly Asp Ala Met Gln Ile Leu Ser Asn Gly Arg Tyr<br>275                      280                    285 | | 864 |
| aag agc gtg gag cat cgt gtc tta gcc aac ggt agc aac aac aga atc<br>Lys Ser Val Glu His Arg Val Leu Ala Asn Gly Ser Asn Asn Arg Ile<br>290                     295                    300 | | 912 |
| tct gtt cct atc ttc gtg aat cca aaa cca gag tct gtg att ggt cct<br>Ser Val Pro Ile Phe Val Asn Pro Lys Pro Glu Ser Val Ile Gly Pro<br>305                     310                      315                  320 | | 960 |

```
ctt act gag gtg gtc tca aat gga gag gaa ccc gtt tat aga gac gtt    1008
Leu Thr Glu Val Val Ser Asn Gly Glu Glu Pro Val Tyr Arg Asp Val
            325                 330                 335 gtg tac tct gat tac gtc aga tac ttt ttc aag aag gcg cac gac gga    1056
Val Tyr Ser Asp Tyr Val Arg Tyr Phe Phe Lys Lys Ala His Asp Gly
        340                 345                 350 aag aaa acc atc gat ttc gcg aag att tga                            1086
Lys Lys Thr Ile Asp Phe Ala Lys Ile
        355                 360

<210> SEQ ID NO 10
<211> LENGTH: 361
<212> TYPE: PRT
<213> ORGANISM: Brassica rapa

<400> SEQUENCE: 10

Met Ala Pro Thr Leu Ser Thr Leu Gln Phe Ala Asp Pro Ala Glu Val
1               5                   10                  15

Thr Glu Phe Val Val Asn Lys Gly Asn Gly Val Lys Gly Leu Ser Glu
            20                  25                  30

Thr Gly Ile Lys Ala Leu Pro Asp Gln Tyr Ile Gln Pro Phe Glu Glu
        35                  40                  45

Arg Leu Ile Asn Lys Phe Val Asn Glu Thr Asp Glu Ala Ile Pro Val
    50                  55                  60

Ile Asp Met Ser Tyr Pro Glu Glu Asp Lys Val Ala Glu Ala Val Cys
65                  70                  75                  80

Asp Ala Ala Glu Arg Trp Gly Phe Phe Gln Val Ile Asn His Gly Val
                85                  90                  95

Pro Leu Glu Val Leu Asp Asn Val Lys Ala Ala Thr His Arg Phe Phe
            100                 105                 110

Asn Leu Pro Val Glu Glu Lys Ser Arg Phe Thr Arg Glu Asn Ser Leu
        115                 120                 125

Ser Thr Asn Val Arg Phe Gly Thr Ser Phe Ser Pro Arg Ala Glu Lys
    130                 135                 140

Ala Leu Glu Trp Lys Asp Tyr Leu Ser Leu Phe Phe Val Ser Glu Thr
145                 150                 155                 160

Glu Ala Glu Gln Tyr Trp Pro Asn Ala Cys Lys Asn Glu Ala Leu Glu
                165                 170                 175

Tyr Met Asn Lys Ser Lys Thr Met Val Arg Lys Leu Leu Glu Tyr Leu
            180                 185                 190

Gly Lys Asn Leu Asn Val Lys Glu Leu Asp Glu Thr Lys Glu Ser Leu
        195                 200                 205

Phe Met Gly Ser Ile Arg Ile Asn Leu Asn Tyr Tyr Pro Ile Cys Pro
    210                 215                 220

Ser Pro Asp Leu Thr Val Gly Val Gly Arg His Ser Asp Val Ser Ser
225                 230                 235                 240

Leu Thr Ile Leu Leu Gln Asp Gln Ile Gly Gly Leu His Val Arg Ser
                245                 250                 255

Leu Thr Ser Gly Asn Trp Val His Val Pro Pro Val Pro Gly Ser Phe
            260                 265                 270

Val Ile Asn Ile Gly Asp Ala Met Gln Ile Leu Ser Asn Gly Arg Tyr
        275                 280                 285

Lys Ser Val Glu His Arg Val Leu Ala Asn Gly Ser Asn Asn Arg Ile
    290                 295                 300

Ser Val Pro Ile Phe Val Asn Pro Lys Pro Glu Ser Val Ile Gly Pro
```

```
                305                 310                 315                 320
Leu Thr Glu Val Val Ser Asn Gly Glu Glu Pro Val Tyr Arg Asp Val
                    325                 330                 335
Val Tyr Ser Asp Tyr Val Arg Tyr Phe Phe Lys Lys Ala His Asp Gly
                340                 345                 350
Lys Lys Thr Ile Asp Phe Ala Lys Ile
            355                 360

<210> SEQ ID NO 11
<211> LENGTH: 1086
<212> TYPE: DNA
<213> ORGANISM: Brassica rapa
<220> FEATURE:
<221> NAME/KEY: CDS
<222> LOCATION: (1)..(1086)

<400> SEQUENCE: 11 atg gct cca aca gtc tct aca acc caa ttc tcg gac cca gct gaa gta        48
Met Ala Pro Thr Val Ser Thr Thr Gln Phe Ser Asp Pro Ala Glu Val
1               5                   10                  15 acc gag ttc gtt gtc aac caa gga aac ggc gta aag ggt ttg tca gaa        96
Thr Glu Phe Val Val Asn Gln Gly Asn Gly Val Lys Gly Leu Ser Glu
                20                  25                  30 aca gga ata aaa gct ctt cca gat caa tac att caa cca ttc gaa gaa       144
Thr Gly Ile Lys Ala Leu Pro Asp Gln Tyr Ile Gln Pro Phe Glu Glu
            35                  40                  45 cgt ctc atc aac aat ttc gtc aac gag aca gac gaa gcc att cct gtc       192
Arg Leu Ile Asn Asn Phe Val Asn Glu Thr Asp Glu Ala Ile Pro Val
        50                  55                  60 atc gac atg tcg tac ccc gac gag agc aaa gtg gct aaa gct atc tgt       240
Ile Asp Met Ser Tyr Pro Asp Glu Ser Lys Val Ala Lys Ala Ile Cys
65                  70                  75                  80 gac gct gct gag aaa tgg ggt ttc ttt caa gtg atc aac cat gga gtt       288
Asp Ala Ala Glu Lys Trp Gly Phe Phe Gln Val Ile Asn His Gly Val
                85                  90                  95 cct ttg gaa gtt ctt gac aac gtg aag gcc gct act cac aga ttc ttc       336
Pro Leu Glu Val Leu Asp Asn Val Lys Ala Ala Thr His Arg Phe Phe
                100                 105                 110 aat ctt cct gta gaa gag aag agc aaa tac aca aag gag aat tct ctg       384
Asn Leu Pro Val Glu Glu Lys Ser Lys Tyr Thr Lys Glu Asn Ser Leu
            115                 120                 125 tcg acc aat gtt agg ttc ggt acg agt ttc agt cct cgt gca gag aag       432
Ser Thr Asn Val Arg Phe Gly Thr Ser Phe Ser Pro Arg Ala Glu Lys
        130                 135                 140 gct ttg gag tgg aaa gat tat ctc agt ctc ttc ttt gtc tct gaa act       480
Ala Leu Glu Trp Lys Asp Tyr Leu Ser Leu Phe Phe Val Ser Glu Thr
145                 150                 155                 160 gaa gca tca cag ttt tgg cct gat gtt tgc aag aat gaa gct cta gac       528
Glu Ala Ser Gln Phe Trp Pro Asp Val Cys Lys Asn Glu Ala Leu Asp
                165                 170                 175 tac atg aac aag tcc aag aca atg gtg agg aag ctt cta gag tat ttg       576
Tyr Met Asn Lys Ser Lys Thr Met Val Arg Lys Leu Leu Glu Tyr Leu
                180                 185                 190 ggg aag aac ctc aat gtg aaa gag cta gac gag acc aaa gag tca ctc       624
Gly Lys Asn Leu Asn Val Lys Glu Leu Asp Glu Thr Lys Glu Ser Leu
            195                 200                 205 ttc atg ggt tcg att cga gtc aac ctc aac tac tat ccc atc tgt cct       672
Phe Met Gly Ser Ile Arg Val Asn Leu Asn Tyr Tyr Pro Ile Cys Pro
        210                 215                 220 aac cct gac cta acc gtt ggc gtt ggc cgc cac tct gac gtc tct tcc       720
```

```
Asn Pro Asp Leu Thr Val Gly Val Gly Arg His Ser Asp Val Ser Ser
225                 230                 235                 240 ctc acc att gtc tta caa gac cag atc gat ggt ctc cac gtg cgt tct      768
Leu Thr Ile Val Leu Gln Asp Gln Ile Asp Gly Leu His Val Arg Ser
                    245                 250                 255 ctg gtg tca ggg aac tgg gtt cac gtg cca ccg gtt ccc gga tct ttc      816
Leu Val Ser Gly Asn Trp Val His Val Pro Pro Val Pro Gly Ser Phe
                260                 265                 270 gtg atc aac atc gga gac acc atg cag atc ttg agc aat ggt cgt tac      864
Val Ile Asn Ile Gly Asp Thr Met Gln Ile Leu Ser Asn Gly Arg Tyr
            275                 280                 285 aag agc gtg gag cct cgt gtc tta gct aac ggt agc aac aac aga atc      912
Lys Ser Val Glu Pro Arg Val Leu Ala Asn Gly Ser Asn Asn Arg Ile
        290                 295                 300 tcg gta cct atc ttt gtg aat cca aaa cca gag tca gtg att ggt cct      960
Ser Val Pro Ile Phe Val Asn Pro Lys Pro Glu Ser Val Ile Gly Pro
305                 310                 315                 320 ctt ctc gag gtg ata gca aat gga gag gaa ccg atc gat aga gac gtc     1008
Leu Leu Glu Val Ile Ala Asn Gly Glu Glu Pro Ile Asp Arg Asp Val
                    325                 330                 335 gtg tac tct gat tac gtt agg tac ttc ttc aag aag gca cat gat gga     1056
Val Tyr Ser Asp Tyr Val Arg Tyr Phe Phe Lys Lys Ala His Asp Gly
                340                 345                 350 aag aag acc gtt gat ttt gcc aag ata tga                             1086
Lys Lys Thr Val Asp Phe Ala Lys Ile
            355                 360

<210> SEQ ID NO 12
<211> LENGTH: 361
<212> TYPE: PRT
<213> ORGANISM: Brassica rapa

<400> SEQUENCE: 12

Met Ala Pro Thr Val Ser Thr Thr Gln Phe Ser Asp Pro Ala Glu Val
1               5                   10                  15

Thr Glu Phe Val Val Asn Gln Gly Asn Gly Val Lys Gly Leu Ser Glu
            20                  25                  30

Thr Gly Ile Lys Ala Leu Pro Asp Gln Tyr Ile Gln Pro Phe Glu Glu
        35                  40                  45

Arg Leu Ile Asn Asn Phe Val Asn Glu Thr Asp Glu Ala Ile Pro Val
    50                  55                  60

Ile Asp Met Ser Tyr Pro Asp Glu Ser Lys Val Ala Lys Ala Ile Cys
65                  70                  75                  80

Asp Ala Ala Glu Lys Trp Gly Phe Phe Gln Val Ile Asn His Gly Val
                85                  90                  95

Pro Leu Glu Val Leu Asp Asn Val Lys Ala Ala Thr His Arg Phe Phe
            100                 105                 110

Asn Leu Pro Val Glu Glu Lys Ser Lys Tyr Thr Lys Glu Asn Ser Leu
        115                 120                 125

Ser Thr Asn Val Arg Phe Gly Thr Ser Phe Ser Pro Arg Ala Glu Lys
    130                 135                 140

Ala Leu Glu Trp Lys Asp Tyr Leu Ser Leu Phe Phe Val Ser Glu Thr
145                 150                 155                 160

Glu Ala Ser Gln Phe Trp Pro Asp Val Cys Lys Asn Glu Ala Leu Asp
                165                 170                 175

Tyr Met Asn Lys Ser Lys Thr Met Val Arg Lys Leu Leu Glu Tyr Leu
            180                 185                 190
```

```
Gly Lys Asn Leu Asn Val Lys Glu Leu Asp Glu Thr Lys Glu Ser Leu
            195                 200                 205

Phe Met Gly Ser Ile Arg Val Asn Leu Asn Tyr Tyr Pro Ile Cys Pro
    210                 215                 220

Asn Pro Asp Leu Thr Val Gly Val Gly Arg His Ser Asp Val Ser Ser
225                 230                 235                 240

Leu Thr Ile Val Leu Gln Asp Gln Ile Asp Gly Leu His Val Arg Ser
                245                 250                 255

Leu Val Ser Gly Asn Trp Val His Val Pro Val Pro Gly Ser Phe
            260                 265                 270

Val Ile Asn Ile Gly Asp Thr Met Gln Ile Leu Ser Asn Gly Arg Tyr
    275                 280                 285

Lys Ser Val Glu Pro Arg Val Leu Ala Asn Gly Ser Asn Asn Arg Ile
290                 295                 300

Ser Val Pro Ile Phe Val Asn Pro Lys Pro Glu Ser Val Ile Gly Pro
305                 310                 315                 320

Leu Leu Glu Val Ile Ala Asn Gly Glu Glu Pro Ile Asp Arg Asp Val
                325                 330                 335

Val Tyr Ser Asp Tyr Val Arg Tyr Phe Phe Lys Lys Ala His Asp Gly
                340                 345                 350

Lys Lys Thr Val Asp Phe Ala Lys Ile
            355                 360

<210> SEQ ID NO 13
<211> LENGTH: 1086
<212> TYPE: DNA
<213> ORGANISM: Brassica rapa
<220> FEATURE:
<221> NAME/KEY: CDS
<222> LOCATION: (1)..(1086)

<400> SEQUENCE: 13 atg gct cca act ctc tct acc gct aac ttc gca gac cca gct gaa gta      48
Met Ala Pro Thr Leu Ser Thr Ala Asn Phe Ala Asp Pro Ala Glu Val
1               5                   10                  15 acc gag ttc gtg gtc aac aaa ggc aat ggc gta aag ggt ttg tca gaa      96
Thr Glu Phe Val Val Asn Lys Gly Asn Gly Val Lys Gly Leu Ser Glu
            20                  25                  30 aca gga atc aaa gct ctt ccg gac caa tac att caa cca ttt gaa gag     144
Thr Gly Ile Lys Ala Leu Pro Asp Gln Tyr Ile Gln Pro Phe Glu Glu
        35                  40                  45 cgt ctc atc aac aag ttc gtc aac gag aca gac gaa gct att cca gtc     192
Arg Leu Ile Asn Lys Phe Val Asn Glu Thr Asp Glu Ala Ile Pro Val
    50                  55                  60 atc gac atg tcg gac cct gat gag aac aaa gtc gct gaa gct atc tgt     240
Ile Asp Met Ser Asp Pro Asp Glu Asn Lys Val Ala Glu Ala Ile Cys
65                  70                  75                  80 gac gct gct gag aaa tgg ggt ttc ttt cag gtg atc aac cat gga gtt     288
Asp Ala Ala Glu Lys Trp Gly Phe Phe Gln Val Ile Asn His Gly Val
                85                  90                  95 cct ttg gat gtt ctt gac aac gtg aag gct gcg act cac agg ttc ttt     336
Pro Leu Asp Val Leu Asp Asn Val Lys Ala Ala Thr His Arg Phe Phe
            100                 105                 110 aat ctt cct gtt gag gag aag agc agg ttc aca aag gag aat tct ctg     384
Asn Leu Pro Val Glu Glu Lys Ser Arg Phe Thr Lys Glu Asn Ser Leu
        115                 120                 125 acg acc aat gtt agg ttc ggt act agt ttc agt cct cgt gct gag aag     432
Thr Thr Asn Val Arg Phe Gly Thr Ser Phe Ser Pro Arg Ala Glu Lys
    130                 135                 140
```

```
gct ctc gag tgg aaa gat tat ctc agt ctc ttc ttt gtg tcc gaa gcc      480
Ala Leu Glu Trp Lys Asp Tyr Leu Ser Leu Phe Phe Val Ser Glu Ala
145                 150                 155                 160 gaa gct gaa cag ttt tgg cct gat gtt tgc aag aat gaa gct cta gag      528
Glu Ala Glu Gln Phe Trp Pro Asp Val Cys Lys Asn Glu Ala Leu Glu
                165                 170                 175 tac atg aac aag tcc aag aca atg gtg cgg aag ctt cta gag tat tta      576
Tyr Met Asn Lys Ser Lys Thr Met Val Arg Lys Leu Leu Glu Tyr Leu
            180                 185                 190 gga aaa aat ctc aac gtg aaa gag cta gac gag acc aaa gaa tca ctc      624
Gly Lys Asn Leu Asn Val Lys Glu Leu Asp Glu Thr Lys Glu Ser Leu
        195                 200                 205 ttc atg ggc tca atc cga gtc aac ctc aac tac tat ccc atc tgt cct      672
Phe Met Gly Ser Ile Arg Val Asn Leu Asn Tyr Tyr Pro Ile Cys Pro
    210                 215                 220 aac cct gac cta acc gtt ggc gtt ggt cgt cac tca gac gtc tct tcc      720
Asn Pro Asp Leu Thr Val Gly Val Gly Arg His Ser Asp Val Ser Ser
225                 230                 235                 240 ctc acc att ctc tta caa gac caa atc ggt ggc ctc cac gtg cgt tct      768
Leu Thr Ile Leu Leu Gln Asp Gln Ile Gly Gly Leu His Val Arg Ser
                245                 250                 255 cta tct tca ggg aac tgg gtt cac gtg cca ccg gtt cct gga tcc ttt      816
Leu Ser Ser Gly Asn Trp Val His Val Pro Pro Val Pro Gly Ser Phe
            260                 265                 270 gtc atc aac ata gga gac gcc atg cag atc ttg agc aac ggt cgt tac      864
Val Ile Asn Ile Gly Asp Ala Met Gln Ile Leu Ser Asn Gly Arg Tyr
        275                 280                 285 aag agc gtg gag cat cgt gtc tta gct aac ggt agt aac aac aga atc      912
Lys Ser Val Glu His Arg Val Leu Ala Asn Gly Ser Asn Asn Arg Ile
    290                 295                 300 tct gtt cct atc ttt gtg aat cca aaa cca gag tca gtg att ggt cct      960
Ser Val Pro Ile Phe Val Asn Pro Lys Pro Glu Ser Val Ile Gly Pro
305                 310                 315                 320 ctc cct gag gtg gtc gca aat ggt gag gaa ccg att tat aaa gac gtt     1008
Leu Pro Glu Val Val Ala Asn Gly Glu Glu Pro Ile Tyr Lys Asp Val
                325                 330                 335 gtg tac tct gat tac gtc agg tac ttc ttc aag aag gca cat gat gga     1056
Val Tyr Ser Asp Tyr Val Arg Tyr Phe Phe Lys Lys Ala His Asp Gly
            340                 345                 350 aag aaa acc gtt gac ttc gcc aag ata tga                             1086
Lys Lys Thr Val Asp Phe Ala Lys Ile
        355                 360

<210> SEQ ID NO 14
<211> LENGTH: 361
<212> TYPE: PRT
<213> ORGANISM: Brassica rapa

<400> SEQUENCE: 14

Met Ala Pro Thr Leu Ser Thr Ala Asn Phe Ala Asp Pro Ala Glu Val
1               5                   10                  15

Thr Glu Phe Val Val Asn Lys Gly Asn Gly Val Lys Gly Leu Ser Glu
                20                  25                  30

Thr Gly Ile Lys Ala Leu Pro Asp Gln Tyr Ile Gln Pro Phe Glu Glu
            35                  40                  45

Arg Leu Ile Asn Lys Phe Val Asn Glu Thr Asp Glu Ala Ile Pro Val
        50                  55                  60

Ile Asp Met Ser Asp Pro Asp Glu Asn Lys Val Ala Glu Ala Ile Cys
65                  70                  75                  80
```

```
Asp Ala Ala Glu Lys Trp Gly Phe Phe Gln Val Ile Asn His Gly Val
                85                  90                  95

Pro Leu Asp Val Leu Asp Asn Val Lys Ala Ala Thr His Arg Phe Phe
            100                 105                 110

Asn Leu Pro Val Glu Glu Lys Ser Arg Phe Thr Lys Glu Asn Ser Leu
        115                 120                 125

Thr Thr Asn Val Arg Phe Gly Thr Ser Phe Ser Pro Arg Ala Glu Lys
    130                 135                 140

Ala Leu Glu Trp Lys Asp Tyr Leu Ser Leu Phe Phe Val Ser Glu Ala
145                 150                 155                 160

Glu Ala Glu Gln Phe Trp Pro Asp Val Cys Lys Asn Glu Ala Leu Glu
                165                 170                 175

Tyr Met Asn Lys Ser Lys Thr Met Val Arg Lys Leu Leu Glu Tyr Leu
            180                 185                 190

Gly Lys Asn Leu Asn Val Lys Glu Leu Asp Glu Thr Lys Glu Ser Leu
        195                 200                 205

Phe Met Gly Ser Ile Arg Val Asn Leu Asn Tyr Tyr Pro Ile Cys Pro
    210                 215                 220

Asn Pro Asp Leu Thr Val Gly Val Gly Arg His Ser Asp Val Ser Ser
225                 230                 235                 240

Leu Thr Ile Leu Leu Gln Asp Gln Ile Gly Gly Leu His Val Arg Ser
                245                 250                 255

Leu Ser Ser Gly Asn Trp Val His Val Pro Val Pro Gly Ser Phe
            260                 265                 270

Val Ile Asn Ile Gly Asp Ala Met Gln Ile Leu Ser Asn Gly Arg Tyr
        275                 280                 285

Lys Ser Val Glu His Arg Val Leu Ala Asn Gly Ser Asn Asn Arg Ile
    290                 295                 300

Ser Val Pro Ile Phe Val Asn Pro Lys Pro Glu Ser Val Ile Gly Pro
305                 310                 315                 320

Leu Pro Glu Val Val Ala Asn Gly Glu Glu Pro Ile Tyr Lys Asp Val
                325                 330                 335

Val Tyr Ser Asp Tyr Val Arg Tyr Phe Phe Lys Lys Ala His Asp Gly
            340                 345                 350

Lys Lys Thr Val Asp Phe Ala Lys Ile
        355                 360

<210> SEQ ID NO 15
<211> LENGTH: 1086
<212> TYPE: DNA
<213> ORGANISM: Arabidopsis thaliana
<220> FEATURE:
<221> NAME/KEY: CDS
<222> LOCATION: (1)..(1086)

<400> SEQUENCE: 15 atg aat caa aca ctc gct gcc caa ttc tta acc cga gac caa gtc acc      48
Met Asn Gln Thr Leu Ala Ala Gln Phe Leu Thr Arg Asp Gln Val Thr
1               5                   10                  15 aac ttt gtt gta cac gaa ggt aac ggt gtt aaa ggc ttg tct gag acc      96
Asn Phe Val Val His Glu Gly Asn Gly Val Lys Gly Leu Ser Glu Thr
            20                  25                  30 gga atc aaa gtt ctt cct gac caa tac att cag cca ttc gaa gag aga     144
Gly Ile Lys Val Leu Pro Asp Gln Tyr Ile Gln Pro Phe Glu Glu Arg
        35                  40                  45 ctg atc aac ttc cac gta aaa gag gat tca gac gaa tcc ata ccc gtg     192
```

```
Leu Ile Asn Phe His Val Lys Glu Asp Ser Asp Glu Ser Ile Pro Val
    50              55                  60 atc gac ata tca aat tta gac gag aag agt gtc tcc aag gcc gta tgt      240
Ile Asp Ile Ser Asn Leu Asp Glu Lys Ser Val Ser Lys Ala Val Cys
65              70                  75                  80 gat gct gca gaa gaa tgg ggt ttc ttt cag gtg atc aac cat ggc gtg      288
Asp Ala Ala Glu Glu Trp Gly Phe Phe Gln Val Ile Asn His Gly Val
                    85                  90                  95 tca atg gaa gtt ctt gag aat atg aaa aca gct act cac aga ttc ttc      336
Ser Met Glu Val Leu Glu Asn Met Lys Thr Ala Thr His Arg Phe Phe
            100                 105                 110 ggt tta ccg gta gaa gag aaa aga aag ttc tca aga gag aag tct ttg      384
Gly Leu Pro Val Glu Glu Lys Arg Lys Phe Ser Arg Glu Lys Ser Leu
        115                 120                 125 tca acg aat gtg aga ttc ggg acg agt ttt agt cct cat gct gag aaa      432
Ser Thr Asn Val Arg Phe Gly Thr Ser Phe Ser Pro His Ala Glu Lys
    130                 135                 140 gct ctc gag tgg aaa gat tat ctg agc ctc ttt ttt gtc tct gaa gct      480
Ala Leu Glu Trp Lys Asp Tyr Leu Ser Leu Phe Phe Val Ser Glu Ala
145                 150                 155                 160 gaa gca tca caa ctc tgg cct gac tct tgc agg agt gaa acg cta gaa      528
Glu Ala Ser Gln Leu Trp Pro Asp Ser Cys Arg Ser Glu Thr Leu Glu
                165                 170                 175 tac atg aac gag aca aaa cct cta gtg aag aaa ctc tta cgg ttt cta      576
Tyr Met Asn Glu Thr Lys Pro Leu Val Lys Lys Leu Leu Arg Phe Leu
            180                 185                 190 ggc gag aat ctg aac gtg aaa gag cta gac aag acc aaa gag tca ttc      624
Gly Glu Asn Leu Asn Val Lys Glu Leu Asp Lys Thr Lys Glu Ser Phe
        195                 200                 205 ttc atg ggt tca aca cgt atc aac ctc aac tat tac cct att tgt ccc      672
Phe Met Gly Ser Thr Arg Ile Asn Leu Asn Tyr Tyr Pro Ile Cys Pro
    210                 215                 220 aat cca gaa ctc acg gtt gga gtc gga cgt cac tct gat gtt tcc tca      720
Asn Pro Glu Leu Thr Val Gly Val Gly Arg His Ser Asp Val Ser Ser
225                 230                 235                 240 ctc aca atc ctc tta caa gac gag atc ggt ggt ctc cac gtt cgt tct      768
Leu Thr Ile Leu Leu Gln Asp Glu Ile Gly Gly Leu His Val Arg Ser
                245                 250                 255 ctc acc acg ggg aga tgg gtt cac gtg cct cca atc tcc gga tct tta      816
Leu Thr Thr Gly Arg Trp Val His Val Pro Pro Ile Ser Gly Ser Leu
            260                 265                 270 gtc att aac att gga gac gct atg caa atc atg agt aat ggt cgt tac      864
Val Ile Asn Ile Gly Asp Ala Met Gln Ile Met Ser Asn Gly Arg Tyr
        275                 280                 285 aag agt gtt gag cat cgt gtc tta gct aac ggt tct tat aac aga atc      912
Lys Ser Val Glu His Arg Val Leu Ala Asn Gly Ser Tyr Asn Arg Ile
    290                 295                 300 tct gtt cct att ttc gtg agc ccg aaa cca gag tct gtg atc ggt cct      960
Ser Val Pro Ile Phe Val Ser Pro Lys Pro Glu Ser Val Ile Gly Pro
305                 310                 315                 320 ctt ctt gaa gtg atc gaa aat gga gag aaa ccg gtt tat aaa gat att     1008
Leu Leu Glu Val Ile Glu Asn Gly Glu Lys Pro Val Tyr Lys Asp Ile
                325                 330                 335 ctt tat acc gat tac gtg aaa cat ttc ttc aga aaa gct cat gat ggg     1056
Leu Tyr Thr Asp Tyr Val Lys His Phe Phe Arg Lys Ala His Asp Gly
            340                 345                 350 aag aaa acc atc gat ttt gcc aac att tga                             1086
Lys Lys Thr Ile Asp Phe Ala Asn Ile
        355                 360
```

```
<210> SEQ ID NO 16
<211> LENGTH: 361
<212> TYPE: PRT
<213> ORGANISM: Arabidopsis thaliana

<400> SEQUENCE: 16

Met Asn Gln Thr Leu Ala Ala Gln Phe Leu Thr Arg Asp Gln Val Thr
1               5                   10                  15

Asn Phe Val Val His Glu Gly Asn Gly Val Lys Gly Leu Ser Glu Thr
            20                  25                  30

Gly Ile Lys Val Leu Pro Asp Gln Tyr Ile Gln Pro Phe Glu Glu Arg
        35                  40                  45

Leu Ile Asn Phe His Val Lys Glu Asp Ser Asp Glu Ser Ile Pro Val
    50                  55                  60

Ile Asp Ile Ser Asn Leu Asp Glu Lys Ser Val Ser Lys Ala Val Cys
65                  70                  75                  80

Asp Ala Ala Glu Glu Trp Gly Phe Phe Gln Val Ile Asn His Gly Val
                85                  90                  95

Ser Met Glu Val Leu Glu Asn Met Lys Thr Ala Thr His Arg Phe Phe
            100                 105                 110

Gly Leu Pro Val Glu Glu Lys Arg Lys Phe Ser Arg Glu Lys Ser Leu
        115                 120                 125

Ser Thr Asn Val Arg Phe Gly Thr Ser Phe Ser Pro His Ala Glu Lys
    130                 135                 140

Ala Leu Glu Trp Lys Asp Tyr Leu Ser Leu Phe Phe Val Ser Glu Ala
145                 150                 155                 160

Glu Ala Ser Gln Leu Trp Pro Asp Ser Cys Arg Ser Glu Thr Leu Glu
                165                 170                 175

Tyr Met Asn Glu Thr Lys Pro Leu Val Lys Lys Leu Leu Arg Phe Leu
            180                 185                 190

Gly Glu Asn Leu Asn Val Lys Glu Leu Asp Lys Thr Lys Glu Ser Phe
        195                 200                 205

Phe Met Gly Ser Thr Arg Ile Asn Leu Asn Tyr Tyr Pro Ile Cys Pro
    210                 215                 220

Asn Pro Glu Leu Thr Val Gly Val Gly Arg His Ser Asp Val Ser Ser
225                 230                 235                 240

Leu Thr Ile Leu Leu Gln Asp Glu Ile Gly Gly Leu His Val Arg Ser
                245                 250                 255

Leu Thr Thr Gly Arg Trp Val His Val Pro Pro Ile Ser Gly Ser Leu
            260                 265                 270

Val Ile Asn Ile Gly Asp Ala Met Gln Ile Met Ser Asn Gly Arg Tyr
        275                 280                 285

Lys Ser Val Glu His Arg Val Leu Ala Asn Gly Ser Tyr Asn Arg Ile
    290                 295                 300

Ser Val Pro Ile Phe Val Ser Pro Lys Pro Glu Ser Val Ile Gly Pro
305                 310                 315                 320

Leu Leu Glu Val Ile Glu Asn Gly Glu Lys Pro Val Tyr Lys Asp Ile
                325                 330                 335

Leu Tyr Thr Asp Tyr Val Lys His Phe Phe Arg Lys Ala His Asp Gly
            340                 345                 350

Lys Lys Thr Ile Asp Phe Ala Asn Ile
        355                 360

<210> SEQ ID NO 17
```

```
<211> LENGTH: 1086
<212> TYPE: DNA
<213> ORGANISM: Arabidopsis lyrata
<220> FEATURE:
<221> NAME/KEY: misc_feature
<223> OTHER INFORMATION: subsp. lyrata
<220> FEATURE:
<221> NAME/KEY: CDS
<222> LOCATION: (1)..(1086)

<400> SEQUENCE: 17
```

| | | | | | | | | | | | | | | | | |
|---|---|---|---|---|---|---|---|---|---|---|---|---|---|---|---|---|
| atg | gct | cca | aca | ctc | tca | aca | acc | caa | ttc | tca | aac | cca | gct | gaa | gta | 48 |
| Met | Ala | Pro | Thr | Leu | Ser | Thr | Thr | Gln | Phe | Ser | Asn | Pro | Ala | Glu | Val | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| acc | gac | ttc | gta | gtc | cac | aaa | gga | aat | ggt | gta | aag | ggt | tta | tca | gaa | 96 |
| Thr | Asp | Phe | Val | Val | His | Lys | Gly | Asn | Gly | Val | Lys | Gly | Leu | Ser | Glu | |
| | | | 20 | | | | | 25 | | | | | 30 | | | |

| | | | | | | | | | | | | | | | | |
|---|---|---|---|---|---|---|---|---|---|---|---|---|---|---|---|---|
| aca | gga | atc | aaa | gct | ctt | cca | gat | caa | tac | atc | cag | cca | ttt | gaa | gaa | 144 |
| Thr | Gly | Ile | Lys | Ala | Leu | Pro | Asp | Gln | Tyr | Ile | Gln | Pro | Phe | Glu | Glu | |
| | | 35 | | | | | 40 | | | | | 45 | | | | |

| | | | | | | | | | | | | | | | | |
|---|---|---|---|---|---|---|---|---|---|---|---|---|---|---|---|---|
| cga | ctc | atc | aac | aaa | ttc | gtc | aac | gaa | aca | gac | gaa | gcc | att | ccg | gtg | 192 |
| Arg | Leu | Ile | Asn | Lys | Phe | Val | Asn | Glu | Thr | Asp | Glu | Ala | Ile | Pro | Val | |
| 50 | | | | | 55 | | | | | 60 | | | | | | |

| | | | | | | | | | | | | | | | | |
|---|---|---|---|---|---|---|---|---|---|---|---|---|---|---|---|---|
| atc | gat | atg | tcg | aac | cct | gac | gag | aac | aga | gtc | gct | gaa | gct | gtc | tgt | 240 |
| Ile | Asp | Met | Ser | Asn | Pro | Asp | Glu | Asn | Arg | Val | Ala | Glu | Ala | Val | Cys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gat | gct | gct | gag | aaa | tgg | ggt | ttc | ttt | caa | gtg | atc | aac | cat | gga | gtc | 288 |
| Asp | Ala | Ala | Glu | Lys | Trp | Gly | Phe | Phe | Gln | Val | Ile | Asn | His | Gly | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| cct | ttg | gaa | gtt | ctt | gac | gat | gtt | aag | gcg | gcg | act | cac | aga | ttc | ttc | 336 |
| Pro | Leu | Glu | Val | Leu | Asp | Asp | Val | Lys | Ala | Ala | Thr | His | Arg | Phe | Phe | |
| | | | 100 | | | | | 105 | | | | | 110 | | | |

| | | | | | | | | | | | | | | | | |
|---|---|---|---|---|---|---|---|---|---|---|---|---|---|---|---|---|
| aat | ctc | cct | gtt | gaa | gag | aag | tgc | aaa | ttc | act | aaa | gag | aat | tct | ctg | 384 |
| Asn | Leu | Pro | Val | Glu | Glu | Lys | Cys | Lys | Phe | Thr | Lys | Glu | Asn | Ser | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| tcg | acg | act | gtt | agg | ttt | ggg | acg | agt | ttt | agt | cct | ctt | gca | gag | caa | 432 |
| Ser | Thr | Thr | Val | Arg | Phe | Gly | Thr | Ser | Phe | Ser | Pro | Leu | Ala | Glu | Gln | |
| 130 | | | | | 135 | | | | | 140 | | | | | | |

| | | | | | | | | | | | | | | | | |
|---|---|---|---|---|---|---|---|---|---|---|---|---|---|---|---|---|
| gct | ctc | gag | tgg | aaa | gat | tat | ctc | agt | ctc | ttc | ttt | gtc | tct | gaa | gct | 480 |
| Ala | Leu | Glu | Trp | Lys | Asp | Tyr | Leu | Ser | Leu | Phe | Phe | Val | Ser | Glu | Ala | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gaa | gct | gaa | cag | ttc | tgg | cct | gat | atc | tgc | agg | aat | gaa | acg | tta | gag | 528 |
| Glu | Ala | Glu | Gln | Phe | Trp | Pro | Asp | Ile | Cys | Arg | Asn | Glu | Thr | Leu | Glu | |
| | | | | 165 | | | | | 170 | | | | | 175 | | |

| | | | | | | | | | | | | | | | | |
|---|---|---|---|---|---|---|---|---|---|---|---|---|---|---|---|---|
| tac | att | gac | aag | tca | aag | aag | atg | gtg | agg | aag | ctt | cta | gag | tat | ttg | 576 |
| Tyr | Ile | Asp | Lys | Ser | Lys | Lys | Met | Val | Arg | Lys | Leu | Leu | Glu | Tyr | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| ggg | aag | aat | ctc | aac | gtg | aag | gag | cta | gac | gag | acg | aaa | gaa | tca | ctc | 624 |
| Gly | Lys | Asn | Leu | Asn | Val | Lys | Glu | Leu | Asp | Glu | Thr | Lys | Glu | Ser | Leu | |
| | | 195 | | | | | 200 | | | | | 205 | | | | |

| | | | | | | | | | | | | | | | | |
|---|---|---|---|---|---|---|---|---|---|---|---|---|---|---|---|---|
| ttt | atg | ggt | tcg | att | cga | gtc | aac | ctc | aac | tac | tat | ccg | att | tgt | cct | 672 |
| Phe | Met | Gly | Ser | Ile | Arg | Val | Asn | Leu | Asn | Tyr | Tyr | Pro | Ile | Cys | Pro | |
| 210 | | | | | 215 | | | | | 220 | | | | | | |

| | | | | | | | | | | | | | | | | |
|---|---|---|---|---|---|---|---|---|---|---|---|---|---|---|---|---|
| aac | ccg | gac | cta | acc | gtt | ggt | gtt | ggt | cgc | cac | tca | gac | gtc | tct | tct | 720 |
| Asn | Pro | Asp | Leu | Thr | Val | Gly | Val | Gly | Arg | His | Ser | Asp | Val | Ser | Ser | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ctc | acc | atc | ctc | tta | caa | gac | cag | atc | ggt | ggt | cta | cac | gtg | cgt | tct | 768 |
| Leu | Thr | Ile | Leu | Leu | Gln | Asp | Gln | Ile | Gly | Gly | Leu | His | Val | Arg | Ser | |
| | | | | 245 | | | | | 250 | | | | | 255 | | |

| | | | | | | | | | | | | | | | | |
|---|---|---|---|---|---|---|---|---|---|---|---|---|---|---|---|---|
| ctg | gca | tca | ggg | aac | tgg | gtt | cac | gtg | cca | ccg | gtt | ccc | ggg | tct | ttt | 816 |
| Leu | Ala | Ser | Gly | Asn | Trp | Val | His | Val | Pro | Pro | Val | Pro | Gly | Ser | Phe | |
| | | | 260 | | | | | 265 | | | | | 270 | | | |

```
gtg atc aac atc gga gat gcg atg cag atc ttg agc aat ggt cgg tac        864
Val Ile Asn Ile Gly Asp Ala Met Gln Ile Leu Ser Asn Gly Arg Tyr
            275                 280                 285 aag agc gtg gag cat cgt gtc tta gcc aac ggt aac aat aac aga atc        912
Lys Ser Val Glu His Arg Val Leu Ala Asn Gly Asn Asn Asn Arg Ile
        290                 295                 300 tct gtt cct atc ttt gtg aat cca aaa cca gag tca gtg att ggt cct        960
Ser Val Pro Ile Phe Val Asn Pro Lys Pro Glu Ser Val Ile Gly Pro
305                 310                 315                 320 cta cct gag gtg att gca aac gga gag gaa ccg att tac aga gac gtc       1008
Leu Pro Glu Val Ile Ala Asn Gly Glu Glu Pro Ile Tyr Arg Asp Val
                325                 330                 335 ctg tac tct gat tac gtc aag tat ttc ttc agg aag gca cac gat gga       1056
Leu Tyr Ser Asp Tyr Val Lys Tyr Phe Phe Arg Lys Ala His Asp Gly
            340                 345                 350 aag aaa acc gtc gat tac gcc aag atc tga                               1086
Lys Lys Thr Val Asp Tyr Ala Lys Ile
        355                 360

<210> SEQ ID NO 18
<211> LENGTH: 361
<212> TYPE: PRT
<213> ORGANISM: Arabidopsis lyrata

<400> SEQUENCE: 18

Met Ala Pro Thr Leu Ser Thr Thr Gln Phe Ser Asn Pro Ala Glu Val
1               5                   10                  15

Thr Asp Phe Val Val His Lys Gly Asn Gly Val Lys Gly Leu Ser Glu
            20                  25                  30

Thr Gly Ile Lys Ala Leu Pro Asp Gln Tyr Ile Gln Pro Phe Glu Glu
        35                  40                  45

Arg Leu Ile Asn Lys Phe Val Asn Glu Thr Asp Glu Ala Ile Pro Val
    50                  55                  60

Ile Asp Met Ser Asn Pro Asp Glu Asn Arg Val Ala Glu Ala Val Cys
65                  70                  75                  80

Asp Ala Ala Glu Lys Trp Gly Phe Phe Gln Val Ile Asn His Gly Val
                85                  90                  95

Pro Leu Glu Val Leu Asp Val Lys Ala Ala Thr His Arg Phe Phe
            100                 105                 110

Asn Leu Pro Val Glu Glu Lys Cys Lys Phe Thr Lys Glu Asn Ser Leu
        115                 120                 125

Ser Thr Thr Val Arg Phe Gly Thr Ser Phe Ser Pro Leu Ala Glu Gln
    130                 135                 140

Ala Leu Glu Trp Lys Asp Tyr Leu Ser Leu Phe Phe Val Ser Glu Ala
145                 150                 155                 160

Glu Ala Glu Gln Phe Trp Pro Asp Ile Cys Arg Asn Glu Thr Leu Glu
                165                 170                 175

Tyr Ile Asp Lys Ser Lys Lys Met Val Arg Lys Leu Leu Glu Tyr Leu
            180                 185                 190

Gly Lys Asn Leu Asn Val Lys Glu Leu Asp Glu Thr Lys Glu Ser Leu
        195                 200                 205

Phe Met Gly Ser Ile Arg Val Asn Leu Asn Tyr Tyr Pro Ile Cys Pro
    210                 215                 220

Asn Pro Asp Leu Thr Val Gly Val Gly Arg His Ser Asp Val Ser Ser
225                 230                 235                 240

Leu Thr Ile Leu Leu Gln Asp Gln Ile Gly Gly Leu His Val Arg Ser
```

```
                        245                 250                 255
Leu Ala Ser Gly Asn Trp Val His Val Pro Pro Val Pro Gly Ser Phe
            260                 265                 270

Val Ile Asn Ile Gly Asp Ala Met Gln Ile Leu Ser Asn Gly Arg Tyr
            275                 280                 285

Lys Ser Val Glu His Arg Val Leu Ala Asn Gly Asn Asn Arg Ile
            290                 295                 300

Ser Val Pro Ile Phe Val Asn Pro Lys Pro Glu Ser Val Ile Gly Pro
305                 310                 315                 320

Leu Pro Glu Val Ile Ala Asn Gly Glu Glu Pro Ile Tyr Arg Asp Val
                325                 330                 335

Leu Tyr Ser Asp Tyr Val Lys Tyr Phe Phe Arg Lys Ala His Asp Gly
            340                 345                 350

Lys Lys Thr Val Asp Tyr Ala Lys Ile
            355                 360

<210> SEQ ID NO 19
<211> LENGTH: 1086
<212> TYPE: DNA
<213> ORGANISM: Arabidopsis lyrata
<220> FEATURE:
<221> NAME/KEY: misc_feature
<223> OTHER INFORMATION: subsp. lyrata
<220> FEATURE:
<221> NAME/KEY: CDS
<222> LOCATION: (1)..(1086)

<400> SEQUENCE: 19
```

| atg gct cca aca ctc tca aca acc caa ttc tca aac cca gct gaa gta | 48 |
|---|---|
| Met Ala Pro Thr Leu Ser Thr Thr Gln Phe Ser Asn Pro Ala Glu Val | |
| 1               5                   10                  15     | |

| acc gac ttc gta gtt cac aaa gga aat ggt gta aag ggt tta tca gaa | 96 |
|---|---|
| Thr Asp Phe Val Val His Lys Gly Asn Gly Val Lys Gly Leu Ser Glu | |
|                 20                  25                  30     | |

| act gga atc aaa gct ctt cca gat caa tac atc cag cca ctt gaa gaa | 144 |
|---|---|
| Thr Gly Ile Lys Ala Leu Pro Asp Gln Tyr Ile Gln Pro Leu Glu Glu | |
|             35                  40                  45         | |

| cga ctc atc aac aaa ttc gtc aac gaa aca gat gaa gcc att ccg gtg | 192 |
|---|---|
| Arg Leu Ile Asn Lys Phe Val Asn Glu Thr Asp Glu Ala Ile Pro Val | |
|         50                  55                  60             | |

| atc gat atg tcg agc cct gac gag aac aga gtc gct gaa gct gtc tgt | 240 |
|---|---|
| Ile Asp Met Ser Ser Pro Asp Glu Asn Arg Val Ala Glu Ala Val Cys | |
| 65                  70                  75                  80 | |

| gat gct gct gag aaa tgg ggt ttc ttt caa gtt atc aat cat gga gtc | 288 |
|---|---|
| Asp Ala Ala Glu Lys Trp Gly Phe Phe Gln Val Ile Asn His Gly Val | |
|                 85                  90                  95     | |

| cct ttg gaa gtt ctt gac gac gtg aag gct gcg act cac aga ttc ttc | 336 |
|---|---|
| Pro Leu Glu Val Leu Asp Asp Val Lys Ala Ala Thr His Arg Phe Phe | |
|             100                 105                 110        | |

| aat ctc cct gtt gaa gag aag tgc aaa ttc act aaa gag aat tct ctg | 384 |
|---|---|
| Asn Leu Pro Val Glu Glu Lys Cys Lys Phe Thr Lys Glu Asn Ser Leu | |
|         115                 120                 125            | |

| tcg acg aat gtt agg ttt ggg acg agt ttt agt ccc ctt gca gag aaa | 432 |
|---|---|
| Ser Thr Asn Val Arg Phe Gly Thr Ser Phe Ser Pro Leu Ala Glu Lys | |
|     130                 135                 140                | |

| tct ctc gag tgg aaa gat tat ctc agt ctc ttt gtc tct gaa gct | 480 |
|---|---|
| Ser Leu Glu Trp Lys Asp Tyr Leu Ser Leu Phe Val Ser Glu Ala | |
| 145                 150                 155                 160 | |

| gaa gct gaa cag ttc tgg cct gat atc tgc agg aat gaa aca tta gag | 528 |
|---|---|
| Glu Ala Glu Gln Phe Trp Pro Asp Ile Cys Arg Asn Glu Thr Leu Glu | |

```
                165                 170                 175
tac atg aac aag tca aag aag atg gtg agg aag ctt cta gag tat ttg    576
Tyr Met Asn Lys Ser Lys Lys Met Val Arg Lys Leu Leu Glu Tyr Leu
        180                 185                 190 ggg aag aat ctc aat gtt aaa gag ctc gac gag acg aaa gaa tca ctc    624
Gly Lys Asn Leu Asn Val Lys Glu Leu Asp Glu Thr Lys Glu Ser Leu
        195                 200                 205 ttt atg ggt tcg att cga gtc aac ctc aac tac tat ccg atc tgc cct    672
Phe Met Gly Ser Ile Arg Val Asn Leu Asn Tyr Tyr Pro Ile Cys Pro
    210                 215                 220 aac ccg gac cta acc gtc ggt gtt ggt cgc cac tca gac gtc tct tct    720
Asn Pro Asp Leu Thr Val Gly Val Gly Arg His Ser Asp Val Ser Ser
225                 230                 235                 240 ctc act att ctc tta caa gat cag atc ggc ggt cta cac gtg cgt tct    768
Leu Thr Ile Leu Leu Gln Asp Gln Ile Gly Gly Leu His Val Arg Ser
                245                 250                 255 ctg gcg tca ggg aac tgg gtt cac gtg cca ccg gtt ccc gga tct ttt    816
Leu Ala Ser Gly Asn Trp Val His Val Pro Pro Val Pro Gly Ser Phe
            260                 265                 270 gtg atc aac atc gga gat gcg atg cag atc ttg agc aat ggt cgg tac    864
Val Ile Asn Ile Gly Asp Ala Met Gln Ile Leu Ser Asn Gly Arg Tyr
        275                 280                 285 aag agc gtg gag cat cgt gtc tta gcc aat ggc aac aat aac aga atc    912
Lys Ser Val Glu His Arg Val Leu Ala Asn Gly Asn Asn Asn Arg Ile
    290                 295                 300 tct gtt cct atc ttt gtg aat cca aaa cca gag tca gtg att ggt cct    960
Ser Val Pro Ile Phe Val Asn Pro Lys Pro Glu Ser Val Ile Gly Pro
305                 310                 315                 320 cta cct gag gtg att gca aat gga gag gaa ccg att tac aga gac gtc   1008
Leu Pro Glu Val Ile Ala Asn Gly Glu Glu Pro Ile Tyr Arg Asp Val
                325                 330                 335 ctg tac tct gat tac gtc agg tat ttc ttc agg aag gca cac gac gga   1056
Leu Tyr Ser Asp Tyr Val Arg Tyr Phe Phe Arg Lys Ala His Asp Gly
            340                 345                 350 aag aaa acc gtc gat tac gcc aag atc tga                           1086
Lys Lys Thr Val Asp Tyr Ala Lys Ile
        355                 360
```

<210> SEQ ID NO 20
<211> LENGTH: 361
<212> TYPE: PRT
<213> ORGANISM: Arabidopsis lyrata

<400> SEQUENCE: 20

```
Met Ala Pro Thr Leu Ser Thr Thr Gln Phe Ser Asn Pro Ala Glu Val
1               5                   10                  15

Thr Asp Phe Val Val His Lys Gly Asn Gly Val Lys Gly Leu Ser Glu
            20                  25                  30

Thr Gly Ile Lys Ala Leu Pro Asp Gln Tyr Ile Gln Pro Leu Glu Glu
        35                  40                  45

Arg Leu Ile Asn Lys Phe Val Asn Glu Thr Asp Glu Ala Ile Pro Val
    50                  55                  60

Ile Asp Met Ser Ser Pro Asp Glu Asn Arg Val Ala Glu Ala Val Cys
65                  70                  75                  80

Asp Ala Ala Glu Lys Trp Gly Phe Phe Gln Val Ile Asn His Gly Val
                85                  90                  95

Pro Leu Glu Val Leu Asp Asp Val Lys Ala Ala Thr His Arg Phe Phe
            100                 105                 110
```

```
Asn Leu Pro Val Glu Glu Lys Cys Lys Phe Thr Lys Glu Asn Ser Leu
            115                 120                 125

Ser Thr Asn Val Arg Phe Gly Thr Ser Phe Ser Pro Leu Ala Glu Lys
        130                 135                 140

Ser Leu Glu Trp Lys Asp Tyr Leu Ser Leu Phe Phe Val Ser Glu Ala
145                 150                 155                 160

Glu Ala Glu Gln Phe Trp Pro Asp Ile Cys Arg Asn Glu Thr Leu Glu
                165                 170                 175

Tyr Met Asn Lys Ser Lys Lys Met Val Arg Lys Leu Leu Glu Tyr Leu
                180                 185                 190

Gly Lys Asn Leu Asn Val Lys Glu Leu Asp Glu Thr Lys Glu Ser Leu
        195                 200                 205

Phe Met Gly Ser Ile Arg Val Asn Leu Asn Tyr Tyr Pro Ile Cys Pro
210                 215                 220

Asn Pro Asp Leu Thr Val Gly Val Gly Arg His Ser Asp Val Ser Ser
225                 230                 235                 240

Leu Thr Ile Leu Leu Gln Asp Gln Ile Gly Gly Leu His Val Arg Ser
                245                 250                 255

Leu Ala Ser Gly Asn Trp Val His Val Pro Pro Val Pro Gly Ser Phe
                260                 265                 270

Val Ile Asn Ile Gly Asp Ala Met Gln Ile Leu Ser Asn Gly Arg Tyr
        275                 280                 285

Lys Ser Val Glu His Arg Val Leu Ala Asn Gly Asn Asn Arg Ile
290                 295                 300

Ser Val Pro Ile Phe Val Asn Pro Lys Pro Glu Ser Val Ile Gly Pro
305                 310                 315                 320

Leu Pro Glu Val Ile Ala Asn Gly Glu Glu Pro Ile Tyr Arg Asp Val
                325                 330                 335

Leu Tyr Ser Asp Tyr Val Arg Tyr Phe Phe Arg Lys Ala His Asp Gly
                340                 345                 350

Lys Lys Thr Val Asp Tyr Ala Lys Ile
            355                 360

<210> SEQ ID NO 21
<211> LENGTH: 1086
<212> TYPE: DNA
<213> ORGANISM: Capsella rubella
<220> FEATURE:
<221> NAME/KEY: CDS
<222> LOCATION: (1)..(1086)

<400> SEQUENCE: 21 atg gct cct act ctc tcc aca gct cag ttc tca acc cca gct gaa gta       48
Met Ala Pro Thr Leu Ser Thr Ala Gln Phe Ser Thr Pro Ala Glu Val
1               5                   10                  15 acc gac ttc gta gtc cac aga gga aac ggt gta aag ggt ttg tca gaa       96
Thr Asp Phe Val Val His Arg Gly Asn Gly Val Lys Gly Leu Ser Glu
                20                  25                  30 aca ggg atc aaa gct ctt cca gac caa tac att cag cca ctt gaa gag      144
Thr Gly Ile Lys Ala Leu Pro Asp Gln Tyr Ile Gln Pro Leu Glu Glu
            35                  40                  45 cgg ctc atc aac aaa ttc gtc aac gaa aca gac gaa gcc att ccg gtg      192
Arg Leu Ile Asn Lys Phe Val Asn Glu Thr Asp Glu Ala Ile Pro Val
        50                  55                  60 atc gac atg tcc aac cct gat gag aaa aaa gtc gct gaa gct gtc tgt      240
Ile Asp Met Ser Asn Pro Asp Glu Lys Lys Val Ala Glu Ala Val Cys
65                  70                  75                  80
```

```
gat gct gct gag aaa tgg ggt ttc ttc cag gtg gtc aat cat gga gtt        288
Asp Ala Ala Glu Lys Trp Gly Phe Phe Gln Val Val Asn His Gly Val
            85                  90                  95 cct ttg gag gtt ctt gat aac gtc aag gcc gcg act cac aga ttc ttt        336
Pro Leu Glu Val Leu Asp Asn Val Lys Ala Ala Thr His Arg Phe Phe
                100                 105                 110 aat ctc cct gtg gag gag aag agc aag ttc act aag gag aac tct ttg        384
Asn Leu Pro Val Glu Glu Lys Ser Lys Phe Thr Lys Glu Asn Ser Leu
            115                 120                 125 tcg gct act gtt agg ttt ggt acg agt ttt agt cct ctt gca gag aaa        432
Ser Ala Thr Val Arg Phe Gly Thr Ser Phe Ser Pro Leu Ala Glu Lys
        130                 135                 140 gct ctt gag tgg aaa gat tat ctt agt ctc ttc ttc gtc tct gac gct        480
Ala Leu Glu Trp Lys Asp Tyr Leu Ser Leu Phe Phe Val Ser Asp Ala
145                 150                 155                 160 gaa gct gaa cag ttc tgg cct gat gct tgc agg aat gaa acg tta gag        528
Glu Ala Glu Gln Phe Trp Pro Asp Ala Cys Arg Asn Glu Thr Leu Glu
                165                 170                 175 tac ata gac aag tca aag aag atg gtg agg aag ctt tta gag tat ttg        576
Tyr Ile Asp Lys Ser Lys Lys Met Val Arg Lys Leu Leu Glu Tyr Leu
            180                 185                 190 ggg aag aat ctc aac gtt aaa gag ctc gac gag acg aaa gaa tca ctc        624
Gly Lys Asn Leu Asn Val Lys Glu Leu Asp Glu Thr Lys Glu Ser Leu
        195                 200                 205 ttc atg ggt tcg att cga gtc aac ctc aac tac tac ccc atc tgc cct        672
Phe Met Gly Ser Ile Arg Val Asn Leu Asn Tyr Tyr Pro Ile Cys Pro
    210                 215                 220 aac ccg gac cta acc gtc ggt gtt ggt cgc cac tca gac gtc tct tct        720
Asn Pro Asp Leu Thr Val Gly Val Gly Arg His Ser Asp Val Ser Ser
225                 230                 235                 240 ctc acc atc ctc tta caa gac cag atc ggt ggt cta cac gtg cgt tct        768
Leu Thr Ile Leu Leu Gln Asp Gln Ile Gly Gly Leu His Val Arg Ser
                245                 250                 255 ctg gcg tca ggg aac tgg gtt cac gtg cca ccg gtt cct gga tct ttt        816
Leu Ala Ser Gly Asn Trp Val His Val Pro Pro Val Pro Gly Ser Phe
            260                 265                 270 gtg atc aac atc gga gat gcg atg cag atc ttg agc aat ggt ctg tac        864
Val Ile Asn Ile Gly Asp Ala Met Gln Ile Leu Ser Asn Gly Leu Tyr
        275                 280                 285 aag agc gtg gag cat cgt gtc tta gcc aat ggt agc aat aac aga atc        912
Lys Ser Val Glu His Arg Val Leu Ala Asn Gly Ser Asn Asn Arg Ile
    290                 295                 300 tct gtt cct atc ttt gtg aat cca aaa cca gag tcc gtg att ggt cct        960
Ser Val Pro Ile Phe Val Asn Pro Lys Pro Glu Ser Val Ile Gly Pro
305                 310                 315                 320 cta cct gag gtc att gca aaa gga gag gag ccg att tac aga gac gtc       1008
Leu Pro Glu Val Ile Ala Lys Gly Glu Glu Pro Ile Tyr Arg Asp Val
                325                 330                 335 gtc tac tct gac tac gtc aag tat ttc ttc agg aag gca cac gac gga       1056
Val Tyr Ser Asp Tyr Val Lys Tyr Phe Phe Arg Lys Ala His Asp Gly
            340                 345                 350 aag aaa acc gtt gat ttc gcc aag ata tga                               1086
Lys Lys Thr Val Asp Phe Ala Lys Ile
        355                 360

<210> SEQ ID NO 22
<211> LENGTH: 361
<212> TYPE: PRT
<213> ORGANISM: Capsella rubella

<400> SEQUENCE: 22
```

```
Met Ala Pro Thr Leu Ser Thr Ala Gln Phe Ser Thr Pro Ala Glu Val
1               5                   10                  15

Thr Asp Phe Val Val His Arg Gly Asn Gly Val Lys Gly Leu Ser Glu
            20                  25                  30

Thr Gly Ile Lys Ala Leu Pro Asp Gln Tyr Ile Gln Pro Leu Glu Glu
        35                  40                  45

Arg Leu Ile Asn Lys Phe Val Asn Glu Thr Asp Glu Ala Ile Pro Val
50                  55                  60

Ile Asp Met Ser Asn Pro Asp Glu Lys Lys Val Ala Glu Ala Val Cys
65                  70                  75                  80

Asp Ala Ala Glu Lys Trp Gly Phe Phe Gln Val Asn His Gly Val
                85                  90                  95

Pro Leu Glu Val Leu Asp Asn Val Lys Ala Ala Thr His Arg Phe Phe
                100                 105                 110

Asn Leu Pro Val Glu Glu Lys Ser Lys Phe Thr Lys Glu Asn Ser Leu
            115                 120                 125

Ser Ala Thr Val Arg Phe Gly Thr Ser Phe Ser Pro Leu Ala Glu Lys
130                 135                 140

Ala Leu Glu Trp Lys Asp Tyr Leu Ser Leu Phe Phe Val Ser Asp Ala
145                 150                 155                 160

Glu Ala Glu Gln Phe Trp Pro Asp Ala Cys Arg Asn Glu Thr Leu Glu
                165                 170                 175

Tyr Ile Asp Lys Ser Lys Lys Met Val Arg Lys Leu Leu Glu Tyr Leu
            180                 185                 190

Gly Lys Asn Leu Asn Val Lys Glu Leu Asp Glu Thr Lys Glu Ser Leu
        195                 200                 205

Phe Met Gly Ser Ile Arg Val Asn Leu Asn Tyr Tyr Pro Ile Cys Pro
210                 215                 220

Asn Pro Asp Leu Thr Val Gly Val Gly Arg His Ser Asp Val Ser Ser
225                 230                 235                 240

Leu Thr Ile Leu Leu Gln Asp Gln Ile Gly Gly Leu His Val Arg Ser
                245                 250                 255

Leu Ala Ser Gly Asn Trp Val His Val Pro Pro Val Pro Gly Ser Phe
            260                 265                 270

Val Ile Asn Ile Gly Asp Ala Met Gln Ile Leu Ser Asn Gly Leu Tyr
        275                 280                 285

Lys Ser Val Glu His Arg Val Leu Ala Asn Gly Ser Asn Asn Arg Ile
290                 295                 300

Ser Val Pro Ile Phe Val Asn Pro Lys Pro Glu Ser Val Ile Gly Pro
305                 310                 315                 320

Leu Pro Glu Val Ile Ala Lys Gly Glu Glu Pro Ile Tyr Arg Asp Val
                325                 330                 335

Val Tyr Ser Asp Tyr Val Lys Tyr Phe Phe Arg Lys Ala His Asp Gly
            340                 345                 350

Lys Lys Thr Val Asp Phe Ala Lys Ile
        355                 360

<210> SEQ ID NO 23
<211> LENGTH: 747
<212> TYPE: DNA
<213> ORGANISM: Linum usitatissimum
<220> FEATURE:
<221> NAME/KEY: CDS
<222> LOCATION: (1)..(747)
```

```
<400> SEQUENCE: 23 atg gcg gaa gag cag aag cag agc agc agc gag aat gtc agc cgg cac        48
Met Ala Glu Glu Gln Lys Gln Ser Ser Ser Glu Asn Val Ser Arg His
1               5                   10                  15 cag gaa gtc ggc cac aag agc ctc ctc cag agc gac gcc ctt tac cag        96
Gln Glu Val Gly His Lys Ser Leu Leu Gln Ser Asp Ala Leu Tyr Gln
            20                  25                  30 tat att ctt gag acg agt gtt tat cct aga gag cca gag tcc atg aag       144
Tyr Ile Leu Glu Thr Ser Val Tyr Pro Arg Glu Pro Glu Ser Met Lys
        35                  40                  45 gag ctc aga gaa gtc aca gcc aaa cac ccc tgg aac ata atg acg acg       192
Glu Leu Arg Glu Val Thr Ala Lys His Pro Trp Asn Ile Met Thr Thr
50                  55                  60 tcg gcc gac gaa gga cag ttc ctg aac atg ctg ttg aag ctc atc aac       240
Ser Ala Asp Glu Gly Gln Phe Leu Asn Met Leu Leu Lys Leu Ile Asn
65                  70                  75                  80 gcc aag aac acc atg gag atc ggc gtc tac acc ggt tac tcc ctc ctc       288
Ala Lys Asn Thr Met Glu Ile Gly Val Tyr Thr Gly Tyr Ser Leu Leu
                85                  90                  95 gcc acc gcc cta gct atc ccc gac gac ggc aag atc ttg gcc atg gac       336
Ala Thr Ala Leu Ala Ile Pro Asp Asp Gly Lys Ile Leu Ala Met Asp
            100                 105                 110 atc aac cgg gag aac tac gag atc gga ctt ccg atc atc gag aag gcc       384
Ile Asn Arg Glu Asn Tyr Glu Ile Gly Leu Pro Ile Ile Glu Lys Ala
        115                 120                 125 ggc ctc gct cac aag atc gag ttc cgt gaa ggc cct gcg ttg ccg gcg       432
Gly Leu Ala His Lys Ile Glu Phe Arg Glu Gly Pro Ala Leu Pro Ala
    130                 135                 140 ctc gac ctg atg gtt gaa gac aaa tcg ttg cac gga acc tac gac ttc       480
Leu Asp Leu Met Val Glu Asp Lys Ser Leu His Gly Thr Tyr Asp Phe
145                 150                 155                 160 ata ttc gtg gac gcg gac aag gac aac tac atc aac tat cac aag agg       528
Ile Phe Val Asp Ala Asp Lys Asp Asn Tyr Ile Asn Tyr His Lys Arg
                165                 170                 175 ttg atc gac ctg gtg aaa atc ggg gga gtg atc ggg tat gac aac acc       576
Leu Ile Asp Leu Val Lys Ile Gly Gly Val Ile Gly Tyr Asp Asn Thr
            180                 185                 190 cta tgg aac gga tcg gtg gtc gcg cct ccc gac gct ccg ttg agg aag       624
Leu Trp Asn Gly Ser Val Val Ala Pro Pro Asp Ala Pro Leu Arg Lys
        195                 200                 205 tac gtt agg tac tac agg gat ttc gtg ctc gag ctc aac aag gcg ctc       672
Tyr Val Arg Tyr Tyr Arg Asp Phe Val Leu Glu Leu Asn Lys Ala Leu
    210                 215                 220 gcc gcg gac ccc agg atc gag att tgc atg ctc ccc gtc ggt gat gga       720
Ala Ala Asp Pro Arg Ile Glu Ile Cys Met Leu Pro Val Gly Asp Gly
225                 230                 235                 240 atc act ctc tgc cgt cgg atc agt tga                                   747
Ile Thr Leu Cys Arg Arg Ile Ser
                245

<210> SEQ ID NO 24
<211> LENGTH: 248
<212> TYPE: PRT
<213> ORGANISM: Linum usitatissimum

<400> SEQUENCE: 24

Met Ala Glu Glu Gln Lys Gln Ser Ser Ser Glu Asn Val Ser Arg His
1               5                   10                  15

Gln Glu Val Gly His Lys Ser Leu Leu Gln Ser Asp Ala Leu Tyr Gln
            20                  25                  30
```

```
Tyr Ile Leu Glu Thr Ser Val Tyr Pro Arg Glu Pro Glu Ser Met Lys
             35                  40                  45

Glu Leu Arg Glu Val Thr Ala Lys His Pro Trp Asn Ile Met Thr Thr
 50                  55                  60

Ser Ala Asp Glu Gly Gln Phe Leu Asn Met Leu Leu Lys Leu Ile Asn
 65                      70                  75                  80

Ala Lys Asn Thr Met Glu Ile Gly Val Tyr Thr Gly Tyr Ser Leu Leu
                     85                  90                  95

Ala Thr Ala Leu Ala Ile Pro Asp Asp Gly Lys Ile Leu Ala Met Asp
                 100                 105                 110

Ile Asn Arg Glu Asn Tyr Glu Ile Gly Leu Pro Ile Ile Glu Lys Ala
                 115                 120                 125

Gly Leu Ala His Lys Ile Glu Phe Arg Glu Gly Pro Ala Leu Pro Ala
         130                 135                 140

Leu Asp Leu Met Val Glu Asp Lys Ser Leu His Gly Thr Tyr Asp Phe
145                 150                 155                 160

Ile Phe Val Asp Ala Asp Lys Asp Asn Tyr Ile Asn Tyr His Lys Arg
                 165                 170                 175

Leu Ile Asp Leu Val Lys Ile Gly Gly Val Ile Gly Tyr Asp Asn Thr
             180                 185                 190

Leu Trp Asn Gly Ser Val Val Ala Pro Pro Asp Ala Pro Leu Arg Lys
         195                 200                 205

Tyr Val Arg Tyr Tyr Arg Asp Phe Val Leu Glu Leu Asn Lys Ala Leu
    210                 215                 220

Ala Ala Asp Pro Arg Ile Glu Ile Cys Met Leu Pro Val Gly Asp Gly
225                 230                 235                 240

Ile Thr Leu Cys Arg Arg Ile Ser
                 245

<210> SEQ ID NO 25
<211> LENGTH: 729
<212> TYPE: DNA
<213> ORGANISM: Vitis vinifera
<220> FEATURE:
<221> NAME/KEY: CDS
<222> LOCATION: (1)..(729)

<400> SEQUENCE: 25 atg gcc acg aag caa gaa gct ggg agg cac cag gag gtt ggc cac aag    48
Met Ala Thr Lys Gln Glu Ala Gly Arg His Gln Glu Val Gly His Lys
 1               5                  10                  15 agc ctt ttg cag agt gat gct ctt tat cag tat ata ctt gaa acc agt    96
Ser Leu Leu Gln Ser Asp Ala Leu Tyr Gln Tyr Ile Leu Glu Thr Ser
             20                  25                  30 gtg tac cca aga gag ccc gaa tcc atg aag gag ctc aga gag ttg act   144
Val Tyr Pro Arg Glu Pro Glu Ser Met Lys Glu Leu Arg Glu Leu Thr
         35                  40                  45 gcc cag cat cca tgg aac atc atg act acg tct gct gat gaa ggg cag   192
Ala Gln His Pro Trp Asn Ile Met Thr Thr Ser Ala Asp Glu Gly Gln
 50                  55                  60 ttc ttg aac atg ctt ctc aag ctc atc aat gcc aag aac acc atg gag   240
Phe Leu Asn Met Leu Leu Lys Leu Ile Asn Ala Lys Asn Thr Met Glu
 65                  70                  75                  80 ata ggc gtc tac act ggc tac tct ctt ctg gcc aca gcc ctt gct ctc   288
Ile Gly Val Tyr Thr Gly Tyr Ser Leu Leu Ala Thr Ala Leu Ala Leu
                 85                  90                  95 ccc gat gac gga aag atc ctg gct atg gac atc aac aaa gaa aat tac   336
```

```
Pro Asp Asp Gly Lys Ile Leu Ala Met Asp Ile Asn Lys Glu Asn Tyr
            100                 105                 110 gag ctg ggc ctg cca gta att caa aag gca ggg gtt gcc cac aag att    384
Glu Leu Gly Leu Pro Val Ile Gln Lys Ala Gly Val Ala His Lys Ile
            115                 120                 125 gac ttc aaa gaa ggc cct gct ttg cct gtt ctt gat cag atg atc gaa    432
Asp Phe Lys Glu Gly Pro Ala Leu Pro Val Leu Asp Gln Met Ile Glu
130                 135                 140 gat ggg aag tat cac ggg tcg ttc gac ttc ata ttc gtg gac gca gac    480
Asp Gly Lys Tyr His Gly Ser Phe Asp Phe Ile Phe Val Asp Ala Asp
145                 150                 155                 160 aag gac aat tat ctg aac tac cac aag aga ttg atc gat ttg gtg aag    528
Lys Asp Asn Tyr Leu Asn Tyr His Lys Arg Leu Ile Asp Leu Val Lys
                165                 170                 175 gtg ggg gga atc atc ggc tac gac aac acc ctc tgg aac ggg tcg gtg    576
Val Gly Gly Ile Ile Gly Tyr Asp Asn Thr Leu Trp Asn Gly Ser Val
            180                 185                 190 gtg gcg cca ccc gat gct ccg ctg cgg aag tac gtg agg tac tac aga    624
Val Ala Pro Pro Asp Ala Pro Leu Arg Lys Tyr Val Arg Tyr Tyr Arg
        195                 200                 205 gac ttc gtg ttg gag ctg aac aag gct ctt gct gct gac cca aga atc    672
Asp Phe Val Leu Glu Leu Asn Lys Ala Leu Ala Ala Asp Pro Arg Ile
210                 215                 220 gag atc tgt atg ctt ccg gtt ggt gac ggg atc acc ctt tgc cgt cgg    720
Glu Ile Cys Met Leu Pro Val Gly Asp Gly Ile Thr Leu Cys Arg Arg
225                 230                 235                 240 cta agc tga                                                         729
Leu Ser

<210> SEQ ID NO 26
<211> LENGTH: 242
<212> TYPE: PRT
<213> ORGANISM: Vitis vinifera

<400> SEQUENCE: 26

Met Ala Thr Lys Gln Glu Ala Gly Arg His Gln Val Gly His Lys
1               5                   10                  15

Ser Leu Leu Gln Ser Asp Ala Leu Tyr Gln Tyr Ile Leu Glu Thr Ser
            20                  25                  30

Val Tyr Pro Arg Glu Pro Glu Ser Met Lys Glu Leu Arg Glu Leu Thr
        35                  40                  45

Ala Gln His Pro Trp Asn Ile Met Thr Thr Ser Ala Asp Glu Gly Gln
    50                  55                  60

Phe Leu Asn Met Leu Leu Lys Leu Ile Asn Ala Lys Asn Thr Met Glu
65                  70                  75                  80

Ile Gly Val Tyr Thr Gly Tyr Ser Leu Leu Ala Thr Ala Leu Ala Leu
                85                  90                  95

Pro Asp Asp Gly Lys Ile Leu Ala Met Asp Ile Asn Lys Glu Asn Tyr
            100                 105                 110

Glu Leu Gly Leu Pro Val Ile Gln Lys Ala Gly Val Ala His Lys Ile
        115                 120                 125

Asp Phe Lys Glu Gly Pro Ala Leu Pro Val Leu Asp Gln Met Ile Glu
130                 135                 140

Asp Gly Lys Tyr His Gly Ser Phe Asp Phe Ile Phe Val Asp Ala Asp
145                 150                 155                 160

Lys Asp Asn Tyr Leu Asn Tyr His Lys Arg Leu Ile Asp Leu Val Lys
                165                 170                 175
```

```
Val Gly Gly Ile Ile Gly Tyr Asp Asn Thr Leu Trp Asn Gly Ser Val
            180                 185                 190

Val Ala Pro Pro Asp Ala Pro Leu Arg Lys Tyr Val Arg Tyr Tyr Arg
        195                 200                 205

Asp Phe Val Leu Glu Leu Asn Lys Ala Leu Ala Asp Pro Arg Ile
    210                 215                 220

Glu Ile Cys Met Leu Pro Val Gly Asp Gly Ile Thr Leu Cys Arg Arg
225                 230                 235                 240

Leu Ser

<210> SEQ ID NO 27
<211> LENGTH: 978
<212> TYPE: DNA
<213> ORGANISM: Solanum lycopersicum
<220> FEATURE:
<221> NAME/KEY: CDS
<222> LOCATION: (23)..(751)

<400> SEQUENCE: 27
ctgtttcaga gtcaaaaaag ca atg gca acc aac gga gaa aat gga aga cat         52
                         Met Ala Thr Asn Gly Glu Asn Gly Arg His
                          1               5                  10 caa gaa gtt gga cac aag agt cta ttg caa agt gat gcc ctt tat cag         100
Gln Glu Val Gly His Lys Ser Leu Leu Gln Ser Asp Ala Leu Tyr Gln
             15                  20                  25 tat att ctt gaa acc agt gtg tac cca aga gag cct gaa gcc atg aaa         148
Tyr Ile Leu Glu Thr Ser Val Tyr Pro Arg Glu Pro Glu Ala Met Lys
         30                  35                  40 gag cta aga gag att act gca aaa cac cct tgg aac ctt atg acc act         196
Glu Leu Arg Glu Ile Thr Ala Lys His Pro Trp Asn Leu Met Thr Thr
     45                  50                  55 tct gct gac gaa ggg cag ttc ttg aat atg ctt ctc aaa ctc atc aat         244
Ser Ala Asp Glu Gly Gln Phe Leu Asn Met Leu Leu Lys Leu Ile Asn
 60                  65                  70 gcc aaa aac aca atg gaa att ggg gtt ttt act ggt tac tct ctg ctt         292
Ala Lys Asn Thr Met Glu Ile Gly Val Phe Thr Gly Tyr Ser Leu Leu
 75                  80                  85                  90 gct act gcc atg gct ctt cct gat gat ggc aag att cta gcc atg gat         340
Ala Thr Ala Met Ala Leu Pro Asp Asp Gly Lys Ile Leu Ala Met Asp
                 95                 100                 105 atc aac cgc gat aac tat gag att gga ctt cca gta att gaa aag gct         388
Ile Asn Arg Asp Asn Tyr Glu Ile Gly Leu Pro Val Ile Glu Lys Ala
            110                 115                 120 ggt cta gcg cac aaa att gaa ttc aga gaa ggc cct gca cta cct gtt         436
Gly Leu Ala His Lys Ile Glu Phe Arg Glu Gly Pro Ala Leu Pro Val
        125                 130                 135 ctt gac caa atg att gaa gac ggc caa tac cat gga tca tat gat ttc         484
Leu Asp Gln Met Ile Glu Asp Gly Gln Tyr His Gly Ser Tyr Asp Phe
    140                 145                 150 ata ttt gtg gat gct gac aag gac aat tac ttg aac tat cac aag aga         532
Ile Phe Val Asp Ala Asp Lys Asp Asn Tyr Leu Asn Tyr His Lys Arg
155                 160                 165                 170 tta atc gac ttg gtc aag att ggt gga tta att ggc tat gac aac acc         580
Leu Ile Asp Leu Val Lys Ile Gly Gly Leu Ile Gly Tyr Asp Asn Thr
                175                 180                 185 cta tgg aat gga tca gta gtt gca cca cct gat gca ccc ctc agg aaa         628
Leu Trp Asn Gly Ser Val Val Ala Pro Pro Asp Ala Pro Leu Arg Lys
            190                 195                 200 tat gtt agg tat tac agg gat ttc gta ttg gaa ctt aac aag gcg ttg         676
Tyr Val Arg Tyr Tyr Arg Asp Phe Val Leu Glu Leu Asn Lys Ala Leu
```

```
gct gct gat ccc aga atc gaa att tgc cag ctt cct gtt ggt gat ggc    724
Ala Ala Asp Pro Arg Ile Glu Ile Cys Gln Leu Pro Val Gly Asp Gly
    220                 225                 230 atc act ctt tgc cgt cgc atc agt taa aatattcgta tagtactatt          771
Ile Thr Leu Cys Arg Arg Ile Ser
235                 240 ggtggcaatc aacaactcat gagtcatgac gatagaggat ttatcatttt tgaaatcccc   831
tgttttactc attcgtttaa ttttatcatt ttagttcgta ttatggcaaa agattgcatt   891
gtctatgtta ccaaatgctt atttcacaat gtatttgatg aataaaaaaa gaaagaaatt   951
caagttgaaa aaaaaaaaaa aaaaaaa                                      978
```

<210> SEQ ID NO 28
<211> LENGTH: 242
<212> TYPE: PRT
<213> ORGANISM: Solanum lycopersicum

<400> SEQUENCE: 28

```
Met Ala Thr Asn Gly Glu Asn Gly Arg His Gln Glu Val Gly His Lys
1               5                   10                  15

Ser Leu Leu Gln Ser Asp Ala Leu Tyr Gln Tyr Ile Leu Glu Thr Ser
                20                  25                  30

Val Tyr Pro Arg Glu Pro Glu Ala Met Lys Glu Leu Arg Glu Ile Thr
            35                  40                  45

Ala Lys His Pro Trp Asn Leu Met Thr Thr Ser Ala Asp Glu Gly Gln
        50                  55                  60

Phe Leu Asn Met Leu Leu Lys Leu Ile Asn Ala Lys Asn Thr Met Glu
65                  70                  75                  80

Ile Gly Val Phe Thr Gly Tyr Ser Leu Leu Ala Thr Ala Met Ala Leu
                85                  90                  95

Pro Asp Asp Gly Lys Ile Leu Ala Met Asp Ile Asn Arg Asp Asn Tyr
            100                 105                 110

Glu Ile Gly Leu Pro Val Ile Glu Lys Ala Gly Leu Ala His Lys Ile
        115                 120                 125

Glu Phe Arg Glu Gly Pro Ala Leu Pro Val Leu Asp Gln Met Ile Glu
    130                 135                 140

Asp Gly Gln Tyr His Gly Ser Tyr Asp Phe Ile Phe Val Asp Ala Asp
145                 150                 155                 160

Lys Asp Asn Tyr Leu Asn Tyr His Lys Arg Leu Ile Asp Leu Val Lys
                165                 170                 175

Ile Gly Gly Leu Ile Gly Tyr Asp Asn Thr Leu Trp Asn Gly Ser Val
            180                 185                 190

Val Ala Pro Pro Asp Ala Pro Leu Arg Lys Tyr Val Arg Tyr Tyr Arg
        195                 200                 205

Asp Phe Val Leu Glu Leu Asn Lys Ala Leu Ala Ala Asp Pro Arg Ile
    210                 215                 220

Glu Ile Cys Gln Leu Pro Val Gly Asp Gly Ile Thr Leu Cys Arg Arg
225                 230                 235                 240

Ile Ser
```

<210> SEQ ID NO 29
<211> LENGTH: 744
<212> TYPE: DNA
<213> ORGANISM: Cicer arietinum
<220> FEATURE:

```
<221> NAME/KEY: CDS
<222> LOCATION: (1)..(744)

<400> SEQUENCE: 29 atg gca acc aac gag gat caa aag caa act gaa tct gga agg cat caa      48
Met Ala Thr Asn Glu Asp Gln Lys Gln Thr Glu Ser Gly Arg His Gln
1               5                   10                  15 gag gtt ggt cac aaa agc ctt ctg caa agt gat gct ctt tac cag tat      96
Glu Val Gly His Lys Ser Leu Leu Gln Ser Asp Ala Leu Tyr Gln Tyr
                20                  25                  30 att cta gag aca agc gtg ttc cca aga gaa cat gaa gcc atg aaa gag     144
Ile Leu Glu Thr Ser Val Phe Pro Arg Glu His Glu Ala Met Lys Glu
            35                  40                  45 ttg aga gag gtc aca gca aaa cat cca tgg aac atc atg aca acc tct     192
Leu Arg Glu Val Thr Ala Lys His Pro Trp Asn Ile Met Thr Thr Ser
50                  55                  60 gca gac gag gga caa ttt ttg aac atg ctc ctt aaa ctt atc aat gcc     240
Ala Asp Glu Gly Gln Phe Leu Asn Met Leu Leu Lys Leu Ile Asn Ala
65                  70                  75                  80 aag aat acc atg gaa att ggt gtc tac act ggc tac tcc ctt ctt gcc     288
Lys Asn Thr Met Glu Ile Gly Val Tyr Thr Gly Tyr Ser Leu Leu Ala
                85                  90                  95 act gcc ctt gct ctt cct gaa gat gga aag att ttg gcc atg gac att     336
Thr Ala Leu Ala Leu Pro Glu Asp Gly Lys Ile Leu Ala Met Asp Ile
            100                 105                 110 aac aag gaa aat tac gaa ttg ggt ctg ccc gta att aaa aaa gct ggt     384
Asn Lys Glu Asn Tyr Glu Leu Gly Leu Pro Val Ile Lys Lys Ala Gly
        115                 120                 125 gtt gcc cac aaa att gat ttc aga gaa ggc cct gct ctt ccg gtt ctt     432
Val Ala His Lys Ile Asp Phe Arg Glu Gly Pro Ala Leu Pro Val Leu
130                 135                 140 gat gaa atg gtt aaa gat gaa aag aat cat ggg agc tac gat ttc atc     480
Asp Glu Met Val Lys Asp Glu Lys Asn His Gly Ser Tyr Asp Phe Ile
145                 150                 155                 160 ttc gtg gat gcg gac aaa gac aat tac atc aac tac cat aag agg tta     528
Phe Val Asp Ala Asp Lys Asp Asn Tyr Ile Asn Tyr His Lys Arg Leu
                165                 170                 175 att gaa ctt gtt aaa gtg gga ggt gtg atc ggg tac gac aac acc ttg     576
Ile Glu Leu Val Lys Val Gly Gly Val Ile Gly Tyr Asp Asn Thr Leu
            180                 185                 190 tgg aat gga tct gta gtg gca cct cct gat gct cct ctc agg aaa tat     624
Trp Asn Gly Ser Val Val Ala Pro Pro Asp Ala Pro Leu Arg Lys Tyr
        195                 200                 205 gtt agg tat tac agg gat ttc gtg ttg gaa ctt aac aag gct ttg gct     672
Val Arg Tyr Tyr Arg Asp Phe Val Leu Glu Leu Asn Lys Ala Leu Ala
    210                 215                 220 gtc gac cct agg att gaa atc tgt atg ctt cct gtt ggt gat gga atc     720
Val Asp Pro Arg Ile Glu Ile Cys Met Leu Pro Val Gly Asp Gly Ile
225                 230                 235                 240 act atc tgc cgt cgg atc aag taa                                     744
Thr Ile Cys Arg Arg Ile Lys
                245

<210> SEQ ID NO 30
<211> LENGTH: 247
<212> TYPE: PRT
<213> ORGANISM: Cicer arietinum

<400> SEQUENCE: 30

Met Ala Thr Asn Glu Asp Gln Lys Gln Thr Glu Ser Gly Arg His Gln
1               5                   10                  15
```

```
Glu Val Gly His Lys Ser Leu Leu Gln Ser Asp Ala Leu Tyr Gln Tyr
         20                  25                  30

Ile Leu Glu Thr Ser Val Phe Pro Arg Glu His Glu Ala Met Lys Glu
         35                  40                  45

Leu Arg Glu Val Thr Ala Lys His Pro Trp Asn Ile Met Thr Thr Ser
 50                  55                  60

Ala Asp Glu Gly Gln Phe Leu Asn Met Leu Leu Lys Leu Ile Asn Ala
 65                  70                  75                  80

Lys Asn Thr Met Glu Ile Gly Val Tyr Thr Gly Tyr Ser Leu Leu Ala
                 85                  90                  95

Thr Ala Leu Ala Leu Pro Glu Asp Gly Lys Ile Leu Ala Met Asp Ile
                100                 105                 110

Asn Lys Glu Asn Tyr Glu Leu Gly Leu Pro Val Ile Lys Lys Ala Gly
                115                 120                 125

Val Ala His Lys Ile Asp Phe Arg Glu Gly Pro Ala Leu Pro Val Leu
         130                 135                 140

Asp Glu Met Val Lys Asp Glu Lys Asn His Gly Ser Tyr Asp Phe Ile
145                 150                 155                 160

Phe Val Asp Ala Asp Lys Asp Asn Tyr Ile Asn Tyr His Lys Arg Leu
                165                 170                 175

Ile Glu Leu Val Lys Val Gly Gly Val Ile Gly Tyr Asp Asn Thr Leu
                180                 185                 190

Trp Asn Gly Ser Val Val Ala Pro Pro Asp Ala Pro Leu Arg Lys Tyr
                195                 200                 205

Val Arg Tyr Tyr Arg Asp Phe Val Leu Glu Leu Asn Lys Ala Leu Ala
         210                 215                 220

Val Asp Pro Arg Ile Glu Ile Cys Met Leu Pro Val Gly Asp Gly Ile
225                 230                 235                 240

Thr Ile Cys Arg Arg Ile Lys
                245
```

<210> SEQ ID NO 31
<211> LENGTH: 744
<212> TYPE: DNA
<213> ORGANISM: Coffea canephora
<220> FEATURE:
<221> NAME/KEY: CDS
<222> LOCATION: (1)..(744)

<400> SEQUENCE: 31

```
atg gcc cag aat gga gaa gga aag gat agc caa aat ctc agg cat caa      48
Met Ala Gln Asn Gly Glu Gly Lys Asp Ser Gln Asn Leu Arg His Gln
 1               5                  10                  15 gaa gta ggc cac aaa agc ctt ctg caa agt gat gca ctc tac cag tac      96
Glu Val Gly His Lys Ser Leu Leu Gln Ser Asp Ala Leu Tyr Gln Tyr
             20                  25                  30 atc ctg gaa acc agc gtg tat cca aga gag cca gag ccc atg aaa gag     144
Ile Leu Glu Thr Ser Val Tyr Pro Arg Glu Pro Glu Pro Met Lys Glu
         35                  40                  45 ctg aga gaa ctg aca gca aag cat cca tgg aat att atg act aca tct     192
Leu Arg Glu Leu Thr Ala Lys His Pro Trp Asn Ile Met Thr Thr Ser
 50                  55                  60 gct gat gaa ggg cag ttc ttg aac atg att atc aag ttg atc aat gcc     240
Ala Asp Glu Gly Gln Phe Leu Asn Met Ile Ile Lys Leu Ile Asn Ala
65                  70                  75                  80 aag aaa acc atg gag att gga gtt tac act ggt tac tcg ctt ctg gct     288
Lys Lys Thr Met Glu Ile Gly Val Tyr Thr Gly Tyr Ser Leu Leu Ala
                 85                  90                  95
```

```
aca gct ctc gct ctt cca gaa gat ggg aag ata ttg gcc atg gat att    336
Thr Ala Leu Ala Leu Pro Glu Asp Gly Lys Ile Leu Ala Met Asp Ile
            100                 105                 110 aac aga gaa aac tac gaa ttg ggt ctg ccc gtg atc gaa agg gct ggt    384
Asn Arg Glu Asn Tyr Glu Leu Gly Leu Pro Val Ile Glu Arg Ala Gly
                115                 120                 125 gtg tcc cat aaa att gac ttc aga gaa ggc cct gct ttg cca gtg ctt    432
Val Ser His Lys Ile Asp Phe Arg Glu Gly Pro Ala Leu Pro Val Leu
        130                 135                 140 gat gag ttg att gaa gat gac aag aac cat gga agt ttt gat ttc atc    480
Asp Glu Leu Ile Glu Asp Asp Lys Asn His Gly Ser Phe Asp Phe Ile
145                 150                 155                 160 ttc gtg gat gct gac aag gac aac tat ctc aac tac cac aag agg ata    528
Phe Val Asp Ala Asp Lys Asp Asn Tyr Leu Asn Tyr His Lys Arg Ile
                165                 170                 175 atc gag ttg gtc aag gtt ggg gga atg att ggg tac gac aac acc cta    576
Ile Glu Leu Val Lys Val Gly Gly Met Ile Gly Tyr Asp Asn Thr Leu
            180                 185                 190 tgg aac ggc tcc gtg gtg gcc cca cca gat gct cca atg agg aag tac    624
Trp Asn Gly Ser Val Val Ala Pro Pro Asp Ala Pro Met Arg Lys Tyr
        195                 200                 205 gtg agg tac tac agg gac ttc gtc ttg gag ctc aac aaa gcc ctg gcc    672
Val Arg Tyr Tyr Arg Asp Phe Val Leu Glu Leu Asn Lys Ala Leu Ala
210                 215                 220 gct gat ccc agg atc gag atc tgc atg ctc ccc gtt ggc gac ggt atc    720
Ala Asp Pro Arg Ile Glu Ile Cys Met Leu Pro Val Gly Asp Gly Ile
225                 230                 235                 240 acc ctg tgc cgc cgc gtc agc taa                                    744
Thr Leu Cys Arg Arg Val Ser
                245

<210> SEQ ID NO 32
<211> LENGTH: 247
<212> TYPE: PRT
<213> ORGANISM: Coffea canephora

<400> SEQUENCE: 32

Met Ala Gln Asn Gly Glu Gly Lys Asp Ser Gln Asn Leu Arg His Gln
1               5                   10                  15

Glu Val Gly His Lys Ser Leu Leu Gln Ser Asp Ala Leu Tyr Gln Tyr
            20                  25                  30

Ile Leu Glu Thr Ser Val Tyr Pro Arg Glu Pro Glu Pro Met Lys Glu
        35                  40                  45

Leu Arg Glu Leu Thr Ala Lys His Pro Trp Asn Ile Met Thr Thr Ser
    50                  55                  60

Ala Asp Glu Gly Gln Phe Leu Asn Met Ile Ile Lys Leu Ile Asn Ala
65                  70                  75                  80

Lys Lys Thr Met Glu Ile Gly Val Tyr Thr Gly Tyr Ser Leu Leu Ala
                85                  90                  95

Thr Ala Leu Ala Leu Pro Glu Asp Gly Lys Ile Leu Ala Met Asp Ile
            100                 105                 110

Asn Arg Glu Asn Tyr Glu Leu Gly Leu Pro Val Ile Glu Arg Ala Gly
        115                 120                 125

Val Ser His Lys Ile Asp Phe Arg Glu Gly Pro Ala Leu Pro Val Leu
    130                 135                 140

Asp Glu Leu Ile Glu Asp Asp Lys Asn His Gly Ser Phe Asp Phe Ile
145                 150                 155                 160
```

```
Phe Val Asp Ala Asp Lys Asp Asn Tyr Leu Asn Tyr His Lys Arg Ile
                165                 170                 175

Ile Glu Leu Val Lys Val Gly Gly Met Ile Gly Tyr Asp Asn Thr Leu
            180                 185                 190

Trp Asn Gly Ser Val Val Ala Pro Pro Asp Ala Pro Met Arg Lys Tyr
        195                 200                 205

Val Arg Tyr Tyr Arg Asp Phe Val Leu Glu Leu Asn Lys Ala Leu Ala
    210                 215                 220

Ala Asp Pro Arg Ile Glu Ile Cys Met Leu Pro Val Gly Asp Gly Ile
225                 230                 235                 240

Thr Leu Cys Arg Arg Val Ser
                245

<210> SEQ ID NO 33
<211> LENGTH: 780
<212> TYPE: DNA
<213> ORGANISM: Bambusa oldhamii
<220> FEATURE:
<221> NAME/KEY: CDS
<222> LOCATION: (1)..(780)

<400> SEQUENCE: 33 atg gcc acc gcg acc gcc gat gcg acg acg gcg acc aag gag caa acc      48
Met Ala Thr Ala Thr Ala Asp Ala Thr Thr Ala Thr Lys Glu Gln Thr
1               5                   10                  15 agc ggc ggc ggc ggc gag cag aag acg cgc cac tcc gag gtc ggg cac      96
Ser Gly Gly Gly Gly Glu Gln Lys Thr Arg His Ser Glu Val Gly His
                20                  25                  30 aag agc ctg ctc cag agc gac gcg ctc tac cag tac ata ctg gag acg     144
Lys Ser Leu Leu Gln Ser Asp Ala Leu Tyr Gln Tyr Ile Leu Glu Thr
            35                  40                  45 agc gtg tac ccg cgc gag cac gag tgc atg aag gag ctc cgc gag gtc     192
Ser Val Tyr Pro Arg Glu His Glu Cys Met Lys Glu Leu Arg Glu Val
        50                  55                  60 acc gcc aag cac cca tgg aac ctg atg acg acg tcg gcg gac gag ggg     240
Thr Ala Lys His Pro Trp Asn Leu Met Thr Thr Ser Ala Asp Glu Gly
65                  70                  75                  80 cag ttc ctg aac atg ctg ctc aag ctc atc ggc gcc aag aag acc atg     288
Gln Phe Leu Asn Met Leu Leu Lys Leu Ile Gly Ala Lys Lys Thr Met
                85                  90                  95 gag atc ggc gtc tac acc ggc tac tcc ctc ctc gcc acc gcg ctc gcc     336
Glu Ile Gly Val Tyr Thr Gly Tyr Ser Leu Leu Ala Thr Ala Leu Ala
                100                 105                 110 atc ccc gag gac ggc acg atc ttg gcc atg gac atc aac cgc gag aac     384
Ile Pro Glu Asp Gly Thr Ile Leu Ala Met Asp Ile Asn Arg Glu Asn
            115                 120                 125 tac gag ctc ggc ctg ccc tgc atc gag aag gcc ggc gtc gcc cac aag     432
Tyr Glu Leu Gly Leu Pro Cys Ile Glu Lys Ala Gly Val Ala His Lys
        130                 135                 140 atc gac ttc cgc gag ggc ccc gcc ctc ccc gtc ctc gac cag ctc ctc     480
Ile Asp Phe Arg Glu Gly Pro Ala Leu Pro Val Leu Asp Gln Leu Leu
145                 150                 155                 160 gag gac gag gcc aac cac ggc tcg ttc gac ttc gtc ttc gtc gac gcc     528
Glu Asp Glu Ala Asn His Gly Ser Phe Asp Phe Val Phe Val Asp Ala
                165                 170                 175 gac aag gac aac tac ctc aac tac cac gac cgc ctg atg aag ctg gtc     576
Asp Lys Asp Asn Tyr Leu Asn Tyr His Asp Arg Leu Met Lys Leu Val
                180                 185                 190 aag gtc ggc ggc ctc gtt ggc tac gac aac acg ctc tgg aac ggc tcc     624
```

| | | | | | | | | | | | | |
|---|---|---|---|---|---|---|---|---|---|---|---|---|
|Lys|Val|Gly|Gly|Leu|Val|Gly|Tyr|Asp|Asn|Thr|Leu|Trp|Asn|Gly|Ser|
| | |195| | | |200| | | |205| | | | | |

```
gtc gtg ctc ccc gcc gac gcg ccc atg cgc aag tac atc cgc tac tac     672
Val Val Leu Pro Ala Asp Ala Pro Met Arg Lys Tyr Ile Arg Tyr Tyr
    210             215             220 cgc gac ttc gtg ctc gag ctc aac aag gcc ctc gcc gcc gac gag cgc     720
Arg Asp Phe Val Leu Glu Leu Asn Lys Ala Leu Ala Ala Asp Glu Arg
225             230             235             240 gtc gag atc tgc cag ctc ccc gtc ggc gac ggc atc acc ctc tgc cgc     768
Val Glu Ile Cys Gln Leu Pro Val Gly Asp Gly Ile Thr Leu Cys Arg
            245             250             255 cgc gcc aag tga                                                     780
Arg Ala Lys
```

<210> SEQ ID NO 34
<211> LENGTH: 259
<212> TYPE: PRT
<213> ORGANISM: Bambusa oldhamii

<400> SEQUENCE: 34

Met Ala Thr Ala Thr Ala Asp Ala Thr Thr Ala Thr Lys Glu Gln Thr
1               5                   10                  15

Ser Gly Gly Gly Glu Gln Lys Thr Arg His Ser Glu Val Gly His
            20                  25                  30

Lys Ser Leu Leu Gln Ser Asp Ala Leu Tyr Gln Tyr Ile Leu Glu Thr
        35                  40                  45

Ser Val Tyr Pro Arg Glu His Glu Cys Met Lys Glu Leu Arg Glu Val
    50                  55                  60

Thr Ala Lys His Pro Trp Asn Leu Met Thr Thr Ser Ala Asp Glu Gly
65                  70                  75                  80

Gln Phe Leu Asn Met Leu Leu Lys Leu Ile Gly Ala Lys Lys Thr Met
                85                  90                  95

Glu Ile Gly Val Tyr Thr Gly Tyr Ser Leu Leu Ala Thr Ala Leu Ala
            100                 105                 110

Ile Pro Glu Asp Gly Thr Ile Leu Ala Met Asp Ile Asn Arg Glu Asn
        115                 120                 125

Tyr Glu Leu Gly Leu Pro Cys Ile Glu Lys Ala Gly Val Ala His Lys
    130                 135                 140

Ile Asp Phe Arg Glu Gly Pro Ala Leu Pro Val Leu Asp Gln Leu Leu
145                 150                 155                 160

Glu Asp Glu Ala Asn His Gly Ser Phe Asp Phe Val Phe Val Asp Ala
                165                 170                 175

Asp Lys Asp Asn Tyr Leu Asn Tyr His Asp Arg Leu Met Lys Leu Val
            180                 185                 190

Lys Val Gly Gly Leu Val Gly Tyr Asp Asn Thr Leu Trp Asn Gly Ser
        195                 200                 205

Val Val Leu Pro Ala Asp Ala Pro Met Arg Lys Tyr Ile Arg Tyr Tyr
    210                 215                 220

Arg Asp Phe Val Leu Glu Leu Asn Lys Ala Leu Ala Ala Asp Glu Arg
225                 230                 235                 240

Val Glu Ile Cys Gln Leu Pro Val Gly Asp Gly Ile Thr Leu Cys Arg
                245                 250                 255

Arg Ala Lys

<210> SEQ ID NO 35
<211> LENGTH: 744

```
<212> TYPE: DNA
<213> ORGANISM: Eucalyptus camaldulensis
<220> FEATURE:
<221> NAME/KEY: CDS
<222> LOCATION: (1)..(744)

<400> SEQUENCE: 35 atg gca gcc aac gca gag cct cag cag acc caa cca gcg aag cat tcg      48
Met Ala Ala Asn Ala Glu Pro Gln Gln Thr Gln Pro Ala Lys His Ser
1               5                   10                  15 gaa gtc ggc cac aag agc ctc ttg cag agc gat gct ctc tac cag tac      96
Glu Val Gly His Lys Ser Leu Leu Gln Ser Asp Ala Leu Tyr Gln Tyr
                20                  25                  30 ata ttg gag acc agc gtc tac cca aga gag cca gag tcc atg aag gag     144
Ile Leu Glu Thr Ser Val Tyr Pro Arg Glu Pro Glu Ser Met Lys Glu
            35                  40                  45 ctc agg gaa ata aca gcc aaa cat cca tgg aac ctg atg acc aca tcg     192
Leu Arg Glu Ile Thr Ala Lys His Pro Trp Asn Leu Met Thr Thr Ser
        50                  55                  60 gct gat gaa ggg cag ttc ctg aac atg ctc ctc aag ctc atc aac gcc     240
Ala Asp Glu Gly Gln Phe Leu Asn Met Leu Leu Lys Leu Ile Asn Ala
65                  70                  75                  80 aag aac acc atg gag atc ggt gtc tac acc ggc tac tct ctc ctc gcc     288
Lys Asn Thr Met Glu Ile Gly Val Tyr Thr Gly Tyr Ser Leu Leu Ala
                85                  90                  95 acc gcc ctt gct ctt cct gat gac gga aag atc ttg gcc atg gac atc     336
Thr Ala Leu Ala Leu Pro Asp Asp Gly Lys Ile Leu Ala Met Asp Ile
            100                 105                 110 aat agg gag aac ttc gag atc ggg ctg ccc gtc atc cag aag gcc ggc     384
Asn Arg Glu Asn Phe Glu Ile Gly Leu Pro Val Ile Gln Lys Ala Gly
        115                 120                 125 ctt gcc cac aag atc gat ttc aga gaa ggc cct gcc ctg ccg ctc ctt     432
Leu Ala His Lys Ile Asp Phe Arg Glu Gly Pro Ala Leu Pro Leu Leu
    130                 135                 140 gat cag ctc gtg caa gat gag aag aac cat gga acg tac gac ttc ata     480
Asp Gln Leu Val Gln Asp Glu Lys Asn His Gly Thr Tyr Asp Phe Ile
145                 150                 155                 160 ttc gtg gat gcc gac aag gac aac tac atc aac tac cac aag agg ctg     528
Phe Val Asp Ala Asp Lys Asp Asn Tyr Ile Asn Tyr His Lys Arg Leu
                165                 170                 175 atc gac ctg gtc aag gtt ggc ggc ctg atc gga tac gac aac acc ctg     576
Ile Asp Leu Val Lys Val Gly Gly Leu Ile Gly Tyr Asp Asn Thr Leu
            180                 185                 190 tgg aac ggc tcc gtg gtc gcg ccc gcc gac gcg ccc ctc cgc aag tac     624
Trp Asn Gly Ser Val Val Ala Pro Ala Asp Ala Pro Leu Arg Lys Tyr
        195                 200                 205 gtg cgg tac tac cgg gac ttc gtg ctg gag ctc aac aag gcc ctc gcc     672
Val Arg Tyr Tyr Arg Asp Phe Val Leu Glu Leu Asn Lys Ala Leu Ala
    210                 215                 220 gtg gac ccg agg atc gag atc tgc atg ctt ccc gtc ggg gat ggt atc     720
Val Asp Pro Arg Ile Glu Ile Cys Met Leu Pro Val Gly Asp Gly Ile
225                 230                 235                 240 acc ctg tgc cgc cgg gtc agc tga                                     744
Thr Leu Cys Arg Arg Val Ser
                245

<210> SEQ ID NO 36
<211> LENGTH: 247
<212> TYPE: PRT
<213> ORGANISM: Eucalyptus camaldulensis

<400> SEQUENCE: 36
```

```
Met Ala Ala Asn Ala Glu Pro Gln Gln Thr Gln Pro Ala Lys His Ser
1               5                   10                  15

Glu Val Gly His Lys Ser Leu Leu Gln Ser Asp Ala Leu Tyr Gln Tyr
            20                  25                  30

Ile Leu Glu Thr Ser Val Tyr Pro Arg Glu Pro Glu Ser Met Lys Glu
        35                  40                  45

Leu Arg Glu Ile Thr Ala Lys His Pro Trp Asn Leu Met Thr Thr Ser
    50                  55                  60

Ala Asp Glu Gly Gln Phe Leu Asn Met Leu Leu Lys Leu Ile Asn Ala
65              70                  75                  80

Lys Asn Thr Met Glu Ile Gly Val Tyr Thr Gly Tyr Ser Leu Leu Ala
                85                  90                  95

Thr Ala Leu Ala Leu Pro Asp Asp Gly Lys Ile Leu Ala Met Asp Ile
            100                 105                 110

Asn Arg Glu Asn Phe Glu Ile Gly Leu Pro Val Ile Gln Lys Ala Gly
        115                 120                 125

Leu Ala His Lys Ile Asp Phe Arg Glu Gly Pro Ala Leu Pro Leu Leu
    130                 135                 140

Asp Gln Leu Val Gln Asp Glu Lys Asn His Gly Thr Tyr Asp Phe Ile
145                 150                 155                 160

Phe Val Asp Ala Asp Lys Asp Asn Tyr Ile Asn Tyr His Lys Arg Leu
                165                 170                 175

Ile Asp Leu Val Lys Val Gly Gly Leu Ile Gly Tyr Asp Asn Thr Leu
            180                 185                 190

Trp Asn Gly Ser Val Val Ala Pro Ala Asp Ala Pro Leu Arg Lys Tyr
        195                 200                 205

Val Arg Tyr Tyr Arg Asp Phe Val Leu Glu Leu Asn Lys Ala Leu Ala
    210                 215                 220

Val Asp Pro Arg Ile Glu Ile Cys Met Leu Pro Val Gly Asp Gly Ile
225                 230                 235                 240

Thr Leu Cys Arg Arg Val Ser
                245
```

```
<210> SEQ ID NO 37
<211> LENGTH: 753
<212> TYPE: DNA
<213> ORGANISM: Gossypium hirsutum
<220> FEATURE:
<221> NAME/KEY: CDS
<222> LOCATION: (1)..(753)

<400> SEQUENCE: 37
```

```
atg gca acc aac aaa aca gaa gag cag cag cag caa tct cag gcg ggt      48
Met Ala Thr Asn Lys Thr Glu Glu Gln Gln Gln Gln Ser Gln Ala Gly
1               5                   10                  15 agg cac caa gaa gtt ggc cat aag agc ctt tta caa agc gat gct ctt      96
Arg His Gln Glu Val Gly His Lys Ser Leu Leu Gln Ser Asp Ala Leu
            20                  25                  30 tac cag tat atc ctg gag aca agt gta tat ccc agg gag cct gaa ccc     144
Tyr Gln Tyr Ile Leu Glu Thr Ser Val Tyr Pro Arg Glu Pro Glu Pro
        35                  40                  45 atg aaa gag ctc aga gag ata aca gcc aag cat cca tgg aac ctt atg     192
Met Lys Glu Leu Arg Glu Ile Thr Ala Lys His Pro Trp Asn Leu Met
    50                  55                  60 aca aca tca gct gat gaa ggc caa ttc ttg aac atg ctt ctt aag ttg     240
Thr Thr Ser Ala Asp Glu Gly Gln Phe Leu Asn Met Leu Leu Lys Leu
65              70                  75                  80
```

```
atc aat gcc aag aac acc atg gag att ggt gtt tac act ggc tac tct    288
Ile Asn Ala Lys Asn Thr Met Glu Ile Gly Val Tyr Thr Gly Tyr Ser
                85                  90                  95 ctt tta gcc acg gcc ctt gct ctc ccc gat gat ggg aag atc ttc gcc    336
Leu Leu Ala Thr Ala Leu Ala Leu Pro Asp Asp Gly Lys Ile Phe Ala
            100                 105                 110 atg gat att aac aga gaa aac tac gag ttg ggt cta cct gta atc caa    384
Met Asp Ile Asn Arg Glu Asn Tyr Glu Leu Gly Leu Pro Val Ile Gln
        115                 120                 125 aaa gct ggt gtt gct cac aaa att gat ttc aaa gaa ggg cct gca atg    432
Lys Ala Gly Val Ala His Lys Ile Asp Phe Lys Glu Gly Pro Ala Met
    130                 135                 140 cca gtt ctt gat gaa ctt gtc caa gat gaa aag aat cac gga tcc ttt    480
Pro Val Leu Asp Glu Leu Val Gln Asp Glu Lys Asn His Gly Ser Phe
145                 150                 155                 160 gac ttc ata ttc gtg gat gct gat aag gac aac tac tta aac tac cat    528
Asp Phe Ile Phe Val Asp Ala Asp Lys Asp Asn Tyr Leu Asn Tyr His
                165                 170                 175 aag agg ttg att gag ttg gtg aaa gtg gga ggt tta atc ggc tac gac    576
Lys Arg Leu Ile Glu Leu Val Lys Val Gly Gly Leu Ile Gly Tyr Asp
            180                 185                 190 aac acc cta tgg aac ggc tcg gtg gtg gcg ccg cct gat gct ccg ctc    624
Asn Thr Leu Trp Asn Gly Ser Val Val Ala Pro Pro Asp Ala Pro Leu
        195                 200                 205 agg aag tac gtc agg tat tat aga gac ttt gtt ttg gaa ctc aac aag    672
Arg Lys Tyr Val Arg Tyr Tyr Arg Asp Phe Val Leu Glu Leu Asn Lys
    210                 215                 220 gct ctt gct gtt gac cct agg att gag atc tgc atg ctc cct gtt ggt    720
Ala Leu Ala Val Asp Pro Arg Ile Glu Ile Cys Met Leu Pro Val Gly
225                 230                 235                 240 gat gga atc acc ctt tgc cgt cgc ctc aaa tga                        753
Asp Gly Ile Thr Leu Cys Arg Arg Leu Lys
                245                 250

<210> SEQ ID NO 38
<211> LENGTH: 250
<212> TYPE: PRT
<213> ORGANISM: Gossypium hirsutum

<400> SEQUENCE: 38

Met Ala Thr Asn Lys Thr Glu Glu Gln Gln Gln Ser Gln Ala Gly
1               5                   10                  15

Arg His Gln Glu Val Gly His Lys Ser Leu Leu Gln Ser Asp Ala Leu
            20                  25                  30

Tyr Gln Tyr Ile Leu Glu Thr Ser Val Tyr Pro Arg Glu Pro Glu Pro
        35                  40                  45

Met Lys Glu Leu Arg Glu Ile Thr Ala Lys His Pro Trp Asn Leu Met
    50                  55                  60

Thr Thr Ser Ala Asp Glu Gly Gln Phe Leu Asn Met Leu Leu Lys Leu
65                  70                  75                  80

Ile Asn Ala Lys Asn Thr Met Glu Ile Gly Val Tyr Thr Gly Tyr Ser
                85                  90                  95

Leu Leu Ala Thr Ala Leu Ala Leu Pro Asp Asp Gly Lys Ile Phe Ala
            100                 105                 110

Met Asp Ile Asn Arg Glu Asn Tyr Glu Leu Gly Leu Pro Val Ile Gln
        115                 120                 125

Lys Ala Gly Val Ala His Lys Ile Asp Phe Lys Glu Gly Pro Ala Met
    130                 135                 140
```

```
Pro Val Leu Asp Glu Leu Val Gln Asp Glu Lys Asn His Gly Ser Phe
145                 150                 155                 160

Asp Phe Ile Phe Val Asp Ala Asp Lys Asp Asn Tyr Leu Asn Tyr His
            165                 170                 175

Lys Arg Leu Ile Glu Leu Val Lys Val Gly Gly Leu Ile Gly Tyr Asp
        180                 185                 190

Asn Thr Leu Trp Asn Gly Ser Val Val Ala Pro Pro Asp Ala Pro Leu
    195                 200                 205

Arg Lys Tyr Val Arg Tyr Arg Asp Phe Val Leu Glu Leu Asn Lys
210                 215                 220

Ala Leu Ala Val Asp Pro Arg Ile Glu Ile Cys Met Leu Pro Val Gly
225                 230                 235                 240

Asp Gly Ile Thr Leu Cys Arg Arg Leu Lys
            245                 250

<210> SEQ ID NO 39
<211> LENGTH: 744
<212> TYPE: DNA
<213> ORGANISM: Eucalyptus globulus
<220> FEATURE:
<221> NAME/KEY: misc_feature
<223> OTHER INFORMATION: subsp. globulus
<220> FEATURE:
<221> NAME/KEY: CDS
<222> LOCATION: (1)..(744)
<220> FEATURE:
<221> NAME/KEY: misc_feature
<222> LOCATION: (12)..(12)
<223> OTHER INFORMATION: s is g or c

<400> SEQUENCE: 39 atg gcc acc gcs gga gag gag agc cag acc caa gcc ggg agg cac cag      48
Met Ala Thr Ala Gly Glu Glu Ser Gln Thr Gln Ala Gly Arg His Gln
1               5                   10                  15 gag gtt ggc cac aag tct ctc cat att cag agt gat gct ctt tac caa      96
Glu Val Gly His Lys Ser Leu His Ile Gln Ser Asp Ala Leu Tyr Gln
            20                  25                  30 tat att ttg gag acc agc gtg tac cca aga gag cct gag ccc atg aag     144
Tyr Ile Leu Glu Thr Ser Val Tyr Pro Arg Glu Pro Glu Pro Met Lys
        35                  40                  45 gag ctc agg gaa ata aca gca aaa cat cca tgg aac ata atg aca aca     192
Glu Leu Arg Glu Ile Thr Ala Lys His Pro Trp Asn Ile Met Thr Thr
    50                  55                  60 tca gca gac gaa ggg cag ttc ttg aac atg ctt ctc aag ctc atc aac     240
Ser Ala Asp Glu Gly Gln Phe Leu Asn Met Leu Leu Lys Leu Ile Asn
65                  70                  75                  80 gcc aag aac acc atg gag att ggt gtc ttc act ggc tac tct ctc ctt     288
Ala Lys Asn Thr Met Glu Ile Gly Val Phe Thr Gly Tyr Ser Leu Leu
                85                  90                  95 gcc acc gct ctt gct ctt cct gat gac gga aag att ttg gct atg gac     336
Ala Thr Ala Leu Ala Leu Pro Asp Asp Gly Lys Ile Leu Ala Met Asp
            100                 105                 110 att aac aga gag aac tat gaa ctt ggc ctg ccg gtc atc caa aaa gcc     384
Ile Asn Arg Glu Asn Tyr Glu Leu Gly Leu Pro Val Ile Gln Lys Ala
        115                 120                 125 ggt gtt gcc gac aag att gac ttc aga gaa ggc cct gct ttg cct att     432
Gly Val Ala Asp Lys Ile Asp Phe Arg Glu Gly Pro Ala Leu Pro Ile
    130                 135                 140 ctt gat cag ttg atc gaa gat ggg aag caa ggg tcg ttc gac ttc ata     480
Leu Asp Gln Leu Ile Glu Asp Gly Lys Gln Gly Ser Phe Asp Phe Ile
145                 150                 155                 160
```

```
ttc gtg gac gcg gac aag gac aat tac ctc aac tac cac aag agg ctg      528
Phe Val Asp Ala Asp Lys Asp Asn Tyr Leu Asn Tyr His Lys Arg Leu
                165                 170                 175 atc gag ctt gtc aag gtt gga ggc ctc att ggc tac gac aac acc cta      576
Ile Glu Leu Val Lys Val Gly Gly Leu Ile Gly Tyr Asp Asn Thr Leu
            180                 185                 190 tgg aac ggc tcc gtg gtt gcg ccg ccg gac gcc ccg ctc agg aag tat      624
Trp Asn Gly Ser Val Val Ala Pro Pro Asp Ala Pro Leu Arg Lys Tyr
        195                 200                 205 gtg agg tac tac agg gat ttt gtg ctg gag ctc aac aag gct ctt gcc      672
Val Arg Tyr Tyr Arg Asp Phe Val Leu Glu Leu Asn Lys Ala Leu Ala
    210                 215                 220 gct gat cct agg att gag atc tgc atg ctc ccc gtg ggt gat ggc atc      720
Ala Asp Pro Arg Ile Glu Ile Cys Met Leu Pro Val Gly Asp Gly Ile
225                 230                 235                 240 act ctc tgc cgt cgg atc agc tga                                      744
Thr Leu Cys Arg Arg Ile Ser
                245

<210> SEQ ID NO 40
<211> LENGTH: 247
<212> TYPE: PRT
<213> ORGANISM: Eucalyptus globulus

<400> SEQUENCE: 40

Met Ala Thr Ala Gly Glu Glu Ser Gln Thr Gln Ala Gly Arg His Gln
1               5                   10                  15

Glu Val Gly His Lys Ser Leu His Ile Gln Ser Asp Ala Leu Tyr Gln
            20                  25                  30

Tyr Ile Leu Glu Thr Ser Val Tyr Pro Arg Glu Pro Glu Pro Met Lys
        35                  40                  45

Glu Leu Arg Glu Ile Thr Ala Lys His Pro Trp Asn Ile Met Thr Thr
    50                  55                  60

Ser Ala Asp Glu Gly Gln Phe Leu Asn Met Leu Leu Lys Leu Ile Asn
65                  70                  75                  80

Ala Lys Asn Thr Met Glu Ile Gly Val Phe Thr Gly Tyr Ser Leu Leu
                85                  90                  95

Ala Thr Ala Leu Ala Leu Pro Asp Asp Gly Lys Ile Leu Ala Met Asp
            100                 105                 110

Ile Asn Arg Glu Asn Tyr Glu Leu Gly Leu Pro Val Ile Gln Lys Ala
        115                 120                 125

Gly Val Ala Asp Lys Ile Asp Phe Arg Glu Gly Pro Ala Leu Pro Ile
    130                 135                 140

Leu Asp Gln Leu Ile Glu Asp Gly Lys Gln Gly Ser Phe Asp Phe Ile
145                 150                 155                 160

Phe Val Asp Ala Asp Lys Asp Asn Tyr Leu Asn Tyr His Lys Arg Leu
                165                 170                 175

Ile Glu Leu Val Lys Val Gly Gly Leu Ile Gly Tyr Asp Asn Thr Leu
            180                 185                 190

Trp Asn Gly Ser Val Val Ala Pro Pro Asp Ala Pro Leu Arg Lys Tyr
        195                 200                 205

Val Arg Tyr Tyr Arg Asp Phe Val Leu Glu Leu Asn Lys Ala Leu Ala
    210                 215                 220

Ala Asp Pro Arg Ile Glu Ile Cys Met Leu Pro Val Gly Asp Gly Ile
225                 230                 235                 240

Thr Leu Cys Arg Arg Ile Ser
```

<210> SEQ ID NO 41
<211> LENGTH: 768
<212> TYPE: DNA
<213> ORGANISM: Cunninghamia lanceolata
<220> FEATURE:
<221> NAME/KEY: CDS
<222> LOCATION: (1)..(768)

<400> SEQUENCE: 41

| | | | | | | | | | | | | | | | | |
|---|---|---|---|---|---|---|---|---|---|---|---|---|---|---|---|---|
| atg | gca | agt | aca | aat | gta | cag | aat | ggt | gca | gat | gca | tcc | aag | gat | tcg | 48 |
| Met | Ala | Ser | Thr | Asn | Val | Gln | Asn | Gly | Ala | Asp | Ala | Ser | Lys | Asp | Ser | |
| 1 | | | | 5 | | | | | 10 | | | | | 15 | | |
| act | aag | cag | gtt | agc | cgt | cac | cag | gaa | gta | ggc | cac | aag | agc | ctt | ctt | 96 |
| Thr | Lys | Gln | Val | Ser | Arg | His | Gln | Glu | Val | Gly | His | Lys | Ser | Leu | Leu | |
| | | | 20 | | | | | 25 | | | | | 30 | | | |
| cag | agc | gat | gcc | ctt | tat | cag | tat | ata | ttg | gaa | aca | agt | gta | tat | ccc | 144 |
| Gln | Ser | Asp | Ala | Leu | Tyr | Gln | Tyr | Ile | Leu | Glu | Thr | Ser | Val | Tyr | Pro | |
| | | 35 | | | | | 40 | | | | | 45 | | | | |
| cgt | gag | cct | gag | tca | atg | agg | gag | ctc | aga | gaa | ata | act | gcc | aag | cat | 192 |
| Arg | Glu | Pro | Glu | Ser | Met | Arg | Glu | Leu | Arg | Glu | Ile | Thr | Ala | Lys | His | |
| | 50 | | | | | 55 | | | | | 60 | | | | | |
| cca | tgg | aat | ctg | atg | act | act | tcg | gct | gat | gag | ggc | caa | ttt | tta | aat | 240 |
| Pro | Trp | Asn | Leu | Met | Thr | Thr | Ser | Ala | Asp | Glu | Gly | Gln | Phe | Leu | Asn | |
| 65 | | | | | 70 | | | | | 75 | | | | | 80 | |
| ctg | ttg | ttg | aag | ctg | ata | aat | gcc | aag | aac | acc | atg | gag | att | ggt | gtg | 288 |
| Leu | Leu | Leu | Lys | Leu | Ile | Asn | Ala | Lys | Asn | Thr | Met | Glu | Ile | Gly | Val | |
| | | | | 85 | | | | | 90 | | | | | 95 | | |
| tat | act | ggt | tac | tcg | ctt | ctc | agc | act | gct | ctt | gcc | ctg | cct | gat | gat | 336 |
| Tyr | Thr | Gly | Tyr | Ser | Leu | Leu | Ser | Thr | Ala | Leu | Ala | Leu | Pro | Asp | Asp | |
| | | | | 100 | | | | | 105 | | | | | 110 | | |
| gga | aag | ata | ata | gca | atg | gac | att | aac | agg | gag | aac | tat | gag | ttg | ggg | 384 |
| Gly | Lys | Ile | Ile | Ala | Met | Asp | Ile | Asn | Arg | Glu | Asn | Tyr | Glu | Leu | Gly | |
| | | | 115 | | | | | 120 | | | | | 125 | | | |
| ctg | cct | gta | att | caa | aaa | gca | ggg | gtt | gcc | cac | aaa | att | gac | ttc | aga | 432 |
| Leu | Pro | Val | Ile | Gln | Lys | Ala | Gly | Val | Ala | His | Lys | Ile | Asp | Phe | Arg | |
| | 130 | | | | | 135 | | | | | 140 | | | | | |
| gag | ggc | cct | gcc | ctg | cca | gtt | ctt | gat | caa | atg | ttg | gaa | aat | aag | gaa | 480 |
| Glu | Gly | Pro | Ala | Leu | Pro | Val | Leu | Asp | Gln | Met | Leu | Glu | Asn | Lys | Glu | |
| 145 | | | | | 150 | | | | | 155 | | | | | 160 | |
| atg | cat | ggc | tcc | ttc | gat | ttc | ata | ttt | gtg | gac | gca | gac | aaa | gac | aat | 528 |
| Met | His | Gly | Ser | Phe | Asp | Phe | Ile | Phe | Val | Asp | Ala | Asp | Lys | Asp | Asn | |
| | | | | 165 | | | | | 170 | | | | | 175 | | |
| tat | ctg | aat | tac | cac | aag | cgg | ctg | att | gat | ctg | gtt | aag | att | ggg | gga | 576 |
| Tyr | Leu | Asn | Tyr | His | Lys | Arg | Leu | Ile | Asp | Leu | Val | Lys | Ile | Gly | Gly | |
| | | | | 180 | | | | | 185 | | | | | 190 | | |
| gtg | atc | ggc | tat | gac | aat | act | ctg | tgg | aat | gga | tca | gtg | gtg | gct | cca | 624 |
| Val | Ile | Gly | Tyr | Asp | Asn | Thr | Leu | Trp | Asn | Gly | Ser | Val | Val | Ala | Pro | |
| | | | 195 | | | | | 200 | | | | | 205 | | | |
| ccc | gat | gcc | ccg | cta | agg | aaa | tat | gtg | aga | tat | tac | aga | gat | ttt | gta | 672 |
| Pro | Asp | Ala | Pro | Leu | Arg | Lys | Tyr | Val | Arg | Tyr | Tyr | Arg | Asp | Phe | Val | |
| | 210 | | | | | 215 | | | | | 220 | | | | | |
| att | gaa | ctg | aac | aag | gcc | ctg | gct | gca | gac | cct | cgt | att | gaa | atc | agc | 720 |
| Ile | Glu | Leu | Asn | Lys | Ala | Leu | Ala | Ala | Asp | Pro | Arg | Ile | Glu | Ile | Ser | |
| 225 | | | | | 230 | | | | | 235 | | | | | 240 | |
| caa | att | cca | gta | gga | gat | ggc | atc | act | ctt | tgc | agg | agg | gtt | tct | taa | 768 |
| Gln | Ile | Pro | Val | Gly | Asp | Gly | Ile | Thr | Leu | Cys | Arg | Arg | Val | Ser | | |
| | | | | 245 | | | | | 250 | | | | | 255 | | |

<210> SEQ ID NO 42

```
<211> LENGTH: 255
<212> TYPE: PRT
<213> ORGANISM: Cunninghamia lanceolata

<400> SEQUENCE: 42

Met Ala Ser Thr Asn Val Gln Asn Gly Ala Asp Ala Ser Lys Asp Ser
1               5                   10                  15

Thr Lys Gln Val Ser Arg His Gln Glu Val Gly His Lys Ser Leu Leu
            20                  25                  30

Gln Ser Asp Ala Leu Tyr Gln Tyr Ile Leu Glu Thr Ser Val Tyr Pro
        35                  40                  45

Arg Glu Pro Glu Ser Met Arg Glu Leu Arg Glu Ile Thr Ala Lys His
    50                  55                  60

Pro Trp Asn Leu Met Thr Thr Ser Ala Asp Glu Gly Gln Phe Leu Asn
65                  70                  75                  80

Leu Leu Leu Lys Leu Ile Asn Ala Lys Asn Thr Met Glu Ile Gly Val
                85                  90                  95

Tyr Thr Gly Tyr Ser Leu Leu Ser Thr Ala Leu Ala Leu Pro Asp Asp
            100                 105                 110

Gly Lys Ile Ile Ala Met Asp Ile Asn Arg Glu Asn Tyr Glu Leu Gly
        115                 120                 125

Leu Pro Val Ile Gln Lys Ala Gly Val Ala His Lys Ile Asp Phe Arg
    130                 135                 140

Glu Gly Pro Ala Leu Pro Val Leu Asp Gln Met Leu Glu Asn Lys Glu
145                 150                 155                 160

Met His Gly Ser Phe Asp Phe Ile Phe Val Asp Ala Asp Lys Asp Asn
                165                 170                 175

Tyr Leu Asn Tyr His Lys Arg Leu Ile Asp Leu Val Lys Ile Gly Gly
            180                 185                 190

Val Ile Gly Tyr Asp Asn Thr Leu Trp Asn Gly Ser Val Val Ala Pro
        195                 200                 205

Pro Asp Ala Pro Leu Arg Lys Tyr Val Arg Tyr Arg Asp Phe Val
    210                 215                 220

Ile Glu Leu Asn Lys Ala Leu Ala Ala Asp Pro Arg Ile Glu Ile Ser
225                 230                 235                 240

Gln Ile Pro Val Gly Asp Gly Ile Thr Leu Cys Arg Arg Val Ser
                245                 250                 255

<210> SEQ ID NO 43
<211> LENGTH: 777
<212> TYPE: DNA
<213> ORGANISM: Panicum virgatum
<220> FEATURE:
<221> NAME/KEY: CDS
<222> LOCATION: (1)..(777)

<400> SEQUENCE: 43 atg gcc agc acg gcg gcc gag gcg gcg aag gcg gcg gag cag ccg gcc      48
Met Ala Ser Thr Ala Ala Glu Ala Ala Lys Ala Ala Glu Gln Pro Ala
1               5                   10                  15 aac ggc aac ggc gag cag aag acg cgc cac tcc gag gtc ggc cac aag      96
Asn Gly Asn Gly Glu Gln Lys Thr Arg His Ser Glu Val Gly His Lys
            20                  25                  30 agc ctg ctc aag agc gac gac ctc tac cag tac atc ctg gac acg agc     144
Ser Leu Leu Lys Ser Asp Asp Leu Tyr Gln Tyr Ile Leu Asp Thr Ser
        35                  40                  45 gtg tac ccg cgg gag ccc gag agc atg aag gag ctc cgc gag atc acc     192
Val Tyr Pro Arg Glu Pro Glu Ser Met Lys Glu Leu Arg Glu Ile Thr
```

```
gcc aag cac ccg tgg aac ctg atg acg acg tcg gcg gac gag ggg cag      240
Ala Lys His Pro Trp Asn Leu Met Thr Thr Ser Ala Asp Glu Gly Gln
65                  70                  75                  80 ttc ctc aac atg ctc atc aag ctc atc ggc gcc aag aag acc atg gag      288
Phe Leu Asn Met Leu Ile Lys Leu Ile Gly Ala Lys Lys Thr Met Glu
                85                  90                  95 atc ggc gtc tac acc ggc tac tcc ctc ctc gcc acc gcc ctc gcg ctc      336
Ile Gly Val Tyr Thr Gly Tyr Ser Leu Leu Ala Thr Ala Leu Ala Leu
            100                 105                 110 ccc gag gac ggc acg atc ttg gcc atg gac atc aac cgc gag aac tac      384
Pro Glu Asp Gly Thr Ile Leu Ala Met Asp Ile Asn Arg Glu Asn Tyr
        115                 120                 125 gag ctc ggc ctg ccc tgc atc gag aag gcc ggc gtc gcc cac aag atc      432
Glu Leu Gly Leu Pro Cys Ile Glu Lys Ala Gly Val Ala His Lys Ile
130                 135                 140 gac ttc cgc gag ggc ccc gcg ctc ccc gtc ctc gac gac ctc atc gcc      480
Asp Phe Arg Glu Gly Pro Ala Leu Pro Val Leu Asp Asp Leu Ile Ala
145                 150                 155                 160 gac gag aag aac cac ggc acc ttc gac ttc gcc ttc gtg gac gcc gac      528
Asp Glu Lys Asn His Gly Thr Phe Asp Phe Ala Phe Val Asp Ala Asp
                165                 170                 175 aag gac aac tac ctc aac tac cac gag cgg ctg ctc aag ctc gtg aag      576
Lys Asp Asn Tyr Leu Asn Tyr His Glu Arg Leu Leu Lys Leu Val Lys
            180                 185                 190 ctc ggc ggc ctc atc ggc tac gac aac acg ctg tgg aac ggc tcc gtc      624
Leu Gly Gly Leu Ile Gly Tyr Asp Asn Thr Leu Trp Asn Gly Ser Val
        195                 200                 205 gtg ctc ccc gac gac gcg ccc atg cgc aag tac atc cgc tac tac cgc      672
Val Leu Pro Asp Asp Ala Pro Met Arg Lys Tyr Ile Arg Tyr Tyr Arg
210                 215                 220 gac ttc gtg ctc gtg ctc aac aag gcg ctc gcc gcc gac gag cgc gtc      720
Asp Phe Val Leu Val Leu Asn Lys Ala Leu Ala Ala Asp Glu Arg Val
225                 230                 235                 240 gag atc tgc cag ctc ccc gtc ggc gac ggc gtc acc ctc tgc cgc cgc      768
Glu Ile Cys Gln Leu Pro Val Gly Asp Gly Val Thr Leu Cys Arg Arg
                245                 250                 255 gtc aag tga                                                          777
Val Lys <210> SEQ ID NO 44
<211> LENGTH: 258
<212> TYPE: PRT
<213> ORGANISM: Panicum virgatum

<400> SEQUENCE: 44

Met Ala Ser Thr Ala Ala Glu Ala Ala Lys Ala Glu Gln Pro Ala
1               5                   10                  15

Asn Gly Asn Gly Glu Gln Lys Thr Arg His Ser Glu Val Gly His Lys
            20                  25                  30

Ser Leu Leu Lys Ser Asp Asp Leu Tyr Gln Tyr Ile Leu Asp Thr Ser
        35                  40                  45

Val Tyr Pro Arg Glu Pro Glu Ser Met Lys Glu Leu Arg Glu Ile Thr
    50                  55                  60

Ala Lys His Pro Trp Asn Leu Met Thr Thr Ser Ala Asp Glu Gly Gln
65                  70                  75                  80

Phe Leu Asn Met Leu Ile Lys Leu Ile Gly Ala Lys Lys Thr Met Glu
                85                  90                  95
```

```
Ile Gly Val Tyr Thr Gly Tyr Ser Leu Leu Ala Thr Ala Leu Ala Leu
            100                 105                 110

Pro Glu Asp Gly Thr Ile Leu Ala Met Asp Ile Asn Arg Glu Asn Tyr
            115                 120                 125

Glu Leu Gly Leu Pro Cys Ile Glu Lys Ala Gly Val Ala His Lys Ile
            130                 135                 140

Asp Phe Arg Glu Gly Pro Ala Leu Pro Val Leu Asp Asp Leu Ile Ala
145                 150                 155                 160

Asp Glu Lys Asn His Gly Thr Phe Asp Phe Ala Phe Val Asp Ala Asp
                165                 170                 175

Lys Asp Asn Tyr Leu Asn Tyr His Glu Arg Leu Leu Lys Leu Val Lys
            180                 185                 190

Leu Gly Gly Leu Ile Gly Tyr Asp Asn Thr Leu Trp Asn Gly Ser Val
            195                 200                 205

Val Leu Pro Asp Asp Ala Pro Met Arg Lys Tyr Ile Arg Tyr Tyr Arg
            210                 215                 220

Asp Phe Val Leu Val Leu Asn Lys Ala Leu Ala Ala Asp Glu Arg Val
225                 230                 235                 240

Glu Ile Cys Gln Leu Pro Val Gly Asp Gly Val Thr Leu Cys Arg Arg
            245                 250                 255

Val Lys

<210> SEQ ID NO 45
<211> LENGTH: 738
<212> TYPE: DNA
<213> ORGANISM: Camellia sinensis
<220> FEATURE:
<221> NAME/KEY: CDS
<222> LOCATION: (1)..(738)

<400> SEQUENCE: 45 atg gca aca aac gga gaa gga gaa cag aat ctc agg cac caa gag gtc      48
Met Ala Thr Asn Gly Glu Gly Glu Gln Asn Leu Arg His Gln Glu Val
1               5                   10                  15 ggc cac aag agt ctt tta cag agc gat gct ctc tac cag tat ata ctt      96
Gly His Lys Ser Leu Leu Gln Ser Asp Ala Leu Tyr Gln Tyr Ile Leu
            20                  25                  30 gag acc agt gtt tac cca aga gag cca gag gcg atg aag gag ctc aga     144
Glu Thr Ser Val Tyr Pro Arg Glu Pro Glu Ala Met Lys Glu Leu Arg
        35                  40                  45 gag gtc act gca aaa cat cca tgg aac atc atg act acc tct gcc gac     192
Glu Val Thr Ala Lys His Pro Trp Asn Ile Met Thr Thr Ser Ala Asp
    50                  55                  60 gaa ggt cag ttc ttg aac atg ctt ttg aag ctt atc aac gcc aag aac     240
Glu Gly Gln Phe Leu Asn Met Leu Leu Lys Leu Ile Asn Ala Lys Asn
65                  70                  75                  80 acg atg gaa atc ggt gtt tac act ggt tac tct ctt cta gcc acc gcc     288
Thr Met Glu Ile Gly Val Tyr Thr Gly Tyr Ser Leu Leu Ala Thr Ala
                85                  90                  95 ctt gct ctc ccc gat gat ggg aag att ttg gca atg gac att aac aga     336
Leu Ala Leu Pro Asp Asp Gly Lys Ile Leu Ala Met Asp Ile Asn Arg
            100                 105                 110 gat aac ttc gaa atc ggt ctg ccg ata att gaa aag gcc ggc gtc gct     384
Asp Asn Phe Glu Ile Gly Leu Pro Ile Ile Glu Lys Ala Gly Val Ala
        115                 120                 125 cac aaa atc gac ttc aga gaa ggc ccc gct ctg cct gct ctc gat aaa     432
His Lys Ile Asp Phe Arg Glu Gly Pro Ala Leu Pro Ala Leu Asp Lys
    130                 135                 140
```

```
atg atc gaa gat gga aag cat cat ggg tcg ttt gat ttc att ttc gtg      480
Met Ile Glu Asp Gly Lys His His Gly Ser Phe Asp Phe Ile Phe Val
145                 150                 155                 160 gac gct gac aag gac aac tac aac aac tac cac aag agg ctg att gat      528
Asp Ala Asp Lys Asp Asn Tyr Asn Asn Tyr His Lys Arg Leu Ile Asp
                165                 170                 175 ctg gtg aag gtt ggg gga ctg atc ggc tac gat aac acc ctc tgg aac      576
Leu Val Lys Val Gly Gly Leu Ile Gly Tyr Asp Asn Thr Leu Trp Asn
            180                 185                 190 ggc tct gtg gtg gcg cct ccg gac gct ccg atg agg aag tac gta agg      624
Gly Ser Val Val Ala Pro Pro Asp Ala Pro Met Arg Lys Tyr Val Arg
        195                 200                 205 tac tac aga gac ttc gtc ctg gag ctc aac aag gca ctc gcc gcc gat      672
Tyr Tyr Arg Asp Phe Val Leu Glu Leu Asn Lys Ala Leu Ala Ala Asp
    210                 215                 220 ccc cgc atc gag atc tgc atg ctt ccc gtc ggc gat ggc att acc ctg      720
Pro Arg Ile Glu Ile Cys Met Leu Pro Val Gly Asp Gly Ile Thr Leu
225                 230                 235                 240 tgc cgg cgt gtc tgc tga                                              738
Cys Arg Arg Val Cys
                245

<210> SEQ ID NO 46
<211> LENGTH: 245
<212> TYPE: PRT
<213> ORGANISM: Camellia sinensis

<400> SEQUENCE: 46

Met Ala Thr Asn Gly Glu Gly Glu Gln Asn Leu Arg His Gln Glu Val
1               5                   10                  15

Gly His Lys Ser Leu Leu Gln Ser Asp Ala Leu Tyr Gln Tyr Ile Leu
            20                  25                  30

Glu Thr Ser Val Tyr Pro Arg Glu Pro Glu Ala Met Lys Glu Leu Arg
        35                  40                  45

Glu Val Thr Ala Lys His Pro Trp Asn Ile Met Thr Thr Ser Ala Asp
    50                  55                  60

Glu Gly Gln Phe Leu Asn Met Leu Leu Lys Leu Ile Asn Ala Lys Asn
65                  70                  75                  80

Thr Met Glu Ile Gly Val Tyr Thr Gly Tyr Ser Leu Leu Ala Thr Ala
                85                  90                  95

Leu Ala Leu Pro Asp Asp Gly Lys Ile Leu Ala Met Asp Ile Asn Arg
            100                 105                 110

Asp Asn Phe Glu Ile Gly Leu Pro Ile Ile Glu Lys Ala Gly Val Ala
        115                 120                 125

His Lys Ile Asp Phe Arg Glu Gly Pro Ala Leu Pro Ala Leu Asp Lys
    130                 135                 140

Met Ile Glu Asp Gly Lys His His Gly Ser Phe Asp Phe Ile Phe Val
145                 150                 155                 160

Asp Ala Asp Lys Asp Asn Tyr Asn Asn Tyr His Lys Arg Leu Ile Asp
                165                 170                 175

Leu Val Lys Val Gly Gly Leu Ile Gly Tyr Asp Asn Thr Leu Trp Asn
            180                 185                 190

Gly Ser Val Val Ala Pro Pro Asp Ala Pro Met Arg Lys Tyr Val Arg
        195                 200                 205

Tyr Tyr Arg Asp Phe Val Leu Glu Leu Asn Lys Ala Leu Ala Ala Asp
    210                 215                 220

Pro Arg Ile Glu Ile Cys Met Leu Pro Val Gly Asp Gly Ile Thr Leu
```

Cys Arg Arg Val Cys
              245

<210> SEQ ID NO 47
<211> LENGTH: 801
<212> TYPE: DNA
<213> ORGANISM: Zea mays
<220> FEATURE:
<221> NAME/KEY: CDS
<222> LOCATION: (1)..(801)

<400> SEQUENCE: 47

```
atg gcc acc acg gcg acc gag gcg acc aag acg act gca ccg gcg cgg      48
Met Ala Thr Thr Ala Thr Glu Ala Thr Lys Thr Thr Ala Pro Ala Arg
1               5                   10                  15 gag cag cag gcc aac ggc aac ggc aac ggc aac ggc gag cag aag acg      96
Glu Gln Gln Ala Asn Gly Asn Gly Asn Gly Asn Gly Glu Gln Lys Thr
            20                  25                  30 cgc cac tcc gag gtc ggc cac aag agc ctg ctc aag agc gac gac ctc     144
Arg His Ser Glu Val Gly His Lys Ser Leu Leu Lys Ser Asp Asp Leu
        35                  40                  45 tac cag tac atc ctg gac acg agc gtg tac ccg cgg gag ccg gag agc     192
Tyr Gln Tyr Ile Leu Asp Thr Ser Val Tyr Pro Arg Glu Pro Glu Ser
50                  55                  60 atg aag gag ctg cgc gag atc acc gcc aag cac cca tgg aac ctg atg     240
Met Lys Glu Leu Arg Glu Ile Thr Ala Lys His Pro Trp Asn Leu Met
65                  70                  75                  80 acc acc tcc gcc gac gag ggc cag ttc ctc aac atg ctc atc aag ctc     288
Thr Thr Ser Ala Asp Glu Gly Gln Phe Leu Asn Met Leu Ile Lys Leu
                85                  90                  95 atc ggc gcc aag aag acc atg gag atc ggc gtc tac acc ggc tac tcg     336
Ile Gly Ala Lys Lys Thr Met Glu Ile Gly Val Tyr Thr Gly Tyr Ser
            100                 105                 110 ctc ctc gcc acc gcg ctc gca ctc ccg gag gac ggc acg atc ttg gcc     384
Leu Leu Ala Thr Ala Leu Ala Leu Pro Glu Asp Gly Thr Ile Leu Ala
        115                 120                 125 atg gac atc aac cgc gag aac tac gag cta ggc ctt ccc tgc atc aac     432
Met Asp Ile Asn Arg Glu Asn Tyr Glu Leu Gly Leu Pro Cys Ile Asn
130                 135                 140 aag gcc ggc gtg ggc cac aag atc gac ttc cgc gag ggc ccc gcg ctc     480
Lys Ala Gly Val Gly His Lys Ile Asp Phe Arg Glu Gly Pro Ala Leu
145                 150                 155                 160 ccc gtc ctg gac gac ctc gtg gcg gac aag gag cag cac ggg tcg ttc     528
Pro Val Leu Asp Asp Leu Val Ala Asp Lys Glu Gln His Gly Ser Phe
                165                 170                 175 gac ttc gcc ttc gtg gac gcc gac aag gac aac tac ctc agc tac cac     576
Asp Phe Ala Phe Val Asp Ala Asp Lys Asp Asn Tyr Leu Ser Tyr His
            180                 185                 190 gag cgg ctc ctg aag ctg gtg agg ccc ggc ggc ctc atc ggc tac gac     624
Glu Arg Leu Leu Lys Leu Val Arg Pro Gly Gly Leu Ile Gly Tyr Asp
        195                 200                 205 aac acg ctg tgg aac ggc tcc gtc gtg ctc ccc gac gac gcg ccc atg     672
Asn Thr Leu Trp Asn Gly Ser Val Val Leu Pro Asp Asp Ala Pro Met
210                 215                 220 cgc aag tac atc cgc ttc tac cgc gac ttc gtc ctc gcc ctc aac agc     720
Arg Lys Tyr Ile Arg Phe Tyr Arg Asp Phe Val Leu Ala Leu Asn Ser
225                 230                 235                 240 gcg ctc gcc gcc gac gac cgc gtc gag atc tgc cag ctc ccc gtc ggc     768
Ala Leu Ala Ala Asp Asp Arg Val Glu Ile Cys Gln Leu Pro Val Gly
                245                 250                 255
```

```
gac ggc gtc acg ctc tgc cgc cgc gtc aag tga                         801
Asp Gly Val Thr Leu Cys Arg Arg Val Lys
            260                 265

<210> SEQ ID NO 48
<211> LENGTH: 266
<212> TYPE: PRT
<213> ORGANISM: Zea mays

<400> SEQUENCE: 48

Met Ala Thr Thr Ala Thr Glu Ala Thr Lys Thr Thr Ala Pro Ala Arg
1               5                   10                  15

Glu Gln Gln Ala Asn Gly Asn Gly Asn Gly Asn Gly Glu Gln Lys Thr
            20                  25                  30

Arg His Ser Glu Val Gly His Lys Ser Leu Leu Lys Ser Asp Asp Leu
        35                  40                  45

Tyr Gln Tyr Ile Leu Asp Thr Ser Val Tyr Pro Arg Glu Pro Glu Ser
    50                  55                  60

Met Lys Glu Leu Arg Glu Ile Thr Ala Lys His Pro Trp Asn Leu Met
65                  70                  75                  80

Thr Thr Ser Ala Asp Glu Gly Gln Phe Leu Asn Met Leu Ile Lys Leu
                85                  90                  95

Ile Gly Ala Lys Lys Thr Met Glu Ile Gly Val Tyr Thr Gly Tyr Ser
            100                 105                 110

Leu Leu Ala Thr Ala Leu Ala Leu Pro Glu Asp Gly Thr Ile Leu Ala
        115                 120                 125

Met Asp Ile Asn Arg Glu Asn Tyr Glu Leu Gly Leu Pro Cys Ile Asn
    130                 135                 140

Lys Ala Gly Val Gly His Lys Ile Asp Phe Arg Glu Gly Pro Ala Leu
145                 150                 155                 160

Pro Val Leu Asp Asp Leu Val Ala Asp Lys Glu Gln His Gly Ser Phe
                165                 170                 175

Asp Phe Ala Phe Val Asp Ala Asp Lys Asp Asn Tyr Leu Ser Tyr His
            180                 185                 190

Glu Arg Leu Leu Lys Leu Val Arg Pro Gly Gly Leu Ile Gly Tyr Asp
        195                 200                 205

Asn Thr Leu Trp Asn Gly Ser Val Val Leu Pro Asp Asp Ala Pro Met
    210                 215                 220

Arg Lys Tyr Ile Arg Phe Tyr Arg Asp Phe Val Leu Ala Leu Asn Ser
225                 230                 235                 240

Ala Leu Ala Ala Asp Asp Arg Val Glu Ile Cys Gln Leu Pro Val Gly
                245                 250                 255

Asp Gly Val Thr Leu Cys Arg Arg Val Lys
            260                 265

<210> SEQ ID NO 49
<211> LENGTH: 4431
<212> TYPE: DNA
<213> ORGANISM: Brassica rapa
<220> FEATURE:
<221> NAME/KEY: CDS
<222> LOCATION: (1)..(4431)

<400> SEQUENCE: 49 atg gct aat atg gct gga gca gac gag att gag tcg ttg aga gtg gag    48
Met Ala Asn Met Ala Gly Ala Asp Glu Ile Glu Ser Leu Arg Val Glu
1               5                   10                  15
```

```
                                                              -continued ctt gca gag att gga aga agc atc aga tca tcg ttc cat aga cac acc        96
Leu Ala Glu Ile Gly Arg Ser Ile Arg Ser Ser Phe His Arg His Thr
            20                  25                  30 tcg agt ttc aga agc ggc tct tca agg tat gaa cct gat cat gat ggt       144
Ser Ser Phe Arg Ser Gly Ser Ser Arg Tyr Glu Pro Asp His Asp Gly
        35                  40                  45 gag ggc aat aat acg aat gca gag tat gct ctg caa tgg gct gag atc       192
Glu Gly Asn Asn Thr Asn Ala Glu Tyr Ala Leu Gln Trp Ala Glu Ile
    50                  55                  60 gag aga ttg cca acc gtc aaa cgc atg aga tcc tct ctc ctt gat gat       240
Glu Arg Leu Pro Thr Val Lys Arg Met Arg Ser Ser Leu Leu Asp Asp
65                  70                  75                  80 ggt gat gag tcc atg gcc gag aaa ggt aaa aga gtc gtt gat gtc acg       288
Gly Asp Glu Ser Met Ala Glu Lys Gly Lys Arg Val Val Asp Val Thr
                85                  90                  95 aag ctt gga gcc atg gaa cgt cat ctg atg att gag aaa ctc atc aaa       336
Lys Leu Gly Ala Met Glu Arg His Leu Met Ile Glu Lys Leu Ile Lys
            100                 105                 110 cac att gag aat gat aat ctc aag ttg ctc aag aaa atc agg aga aga       384
His Ile Glu Asn Asp Asn Leu Lys Leu Leu Lys Lys Ile Arg Arg Arg
        115                 120                 125 ata gac aga gtt gga atg gag tta ccg acc ata gaa gtg agg tat gag       432
Ile Asp Arg Val Gly Met Glu Leu Pro Thr Ile Glu Val Arg Tyr Glu
    130                 135                 140 ggt tta aaa gtg gag gca gag tgc gag att gtt gaa ggg aag gca ctt       480
Gly Leu Lys Val Glu Ala Glu Cys Glu Ile Val Glu Gly Lys Ala Leu
145                 150                 155                 160 cca aca ctg tgg aac act gct aag cgt gtt ttg tct gaa ctg gtg aag       528
Pro Thr Leu Trp Asn Thr Ala Lys Arg Val Leu Ser Glu Leu Val Lys
                165                 170                 175 ctc act ggt gca aaa aca cga gaa gcc aag ata agc att ctt aat gat       576
Leu Thr Gly Ala Lys Thr Arg Glu Ala Lys Ile Ser Ile Leu Asn Asp
            180                 185                 190 gtt aat ggc att ata aaa cca gga agg tta aca ctg ttg ctt ggt cct       624
Val Asn Gly Ile Ile Lys Pro Gly Arg Leu Thr Leu Leu Leu Gly Pro
        195                 200                 205 cct gga tgt gga aaa acg act ttg tta aag gcc tta tca gga aac tta       672
Pro Gly Cys Gly Lys Thr Thr Leu Leu Lys Ala Leu Ser Gly Asn Leu
    210                 215                 220 gaa aac aat cta aag tgt tca ggt gaa atc tcc tac aat ggg cat aga       720
Glu Asn Asn Leu Lys Cys Ser Gly Glu Ile Ser Tyr Asn Gly His Arg
225                 230                 235                 240 ctt gac gag ttt gtt cct cag aaa aca tcc gcg tac ata agc caa tat       768
Leu Asp Glu Phe Val Pro Gln Lys Thr Ser Ala Tyr Ile Ser Gln Tyr
                245                 250                 255 gat ctg cac att gct gag atg aca gtg agg gag aca gtc gac ttc tca       816
Asp Leu His Ile Ala Glu Met Thr Val Arg Glu Thr Val Asp Phe Ser
            260                 265                 270 gct cgt tgt cag ggt gtt gga agc cga aca gaa att atg atg gaa gtt       864
Ala Arg Cys Gln Gly Val Gly Ser Arg Thr Glu Ile Met Met Glu Val
        275                 280                 285 agt aaa aga gaa aag gaa gca gga atc att cct gac aca gaa gtg gat       912
Ser Lys Arg Glu Lys Glu Ala Gly Ile Ile Pro Asp Thr Glu Val Asp
    290                 295                 300 gct tac atg aaa gca ata tct gtt gaa gga ctt gaa aga agt ctg caa       960
Ala Tyr Met Lys Ala Ile Ser Val Glu Gly Leu Glu Arg Ser Leu Gln
305                 310                 315                 320 aca gat tac atc ttg aag att ctt gga ctc gac att tgc gca gaa aca      1008
Thr Asp Tyr Ile Leu Lys Ile Leu Gly Leu Asp Ile Cys Ala Glu Thr
                325                 330                 335
```

```
ttg att gga gat gtg atg agg aga ggc ata tca ggg ggc caa aag aaa    1056
Leu Ile Gly Asp Val Met Arg Arg Gly Ile Ser Gly Gly Gln Lys Lys
            340                 345                 350 cgt ctt acc aca gcc gag atg atc gtt ggt cca aca aag gca ctg ttt    1104
Arg Leu Thr Thr Ala Glu Met Ile Val Gly Pro Thr Lys Ala Leu Phe
        355                 360                 365 atg gat gaa ata aca aac ggc tta gac agt tcc acg gct ttt cag att    1152
Met Asp Glu Ile Thr Asn Gly Leu Asp Ser Ser Thr Ala Phe Gln Ile
    370                 375                 380 gtt aaa tct ctt cag cag ctg gct cac ata tca aac gct act gtt gtt    1200
Val Lys Ser Leu Gln Gln Leu Ala His Ile Ser Asn Ala Thr Val Val
385                 390                 395                 400 gtt tcg ctt ctt caa cct gct cca gag tcc ttt gac ctc ttt gat gac    1248
Val Ser Leu Leu Gln Pro Ala Pro Glu Ser Phe Asp Leu Phe Asp Asp
                405                 410                 415 gtt atg ctg atg gcc aag ggg aaa ata gtg tat cat ggc cca cgc ggt    1296
Val Met Leu Met Ala Lys Gly Lys Ile Val Tyr His Gly Pro Arg Gly
            420                 425                 430 gag gtc ctg aac ttc ttt gag gag tgt gga ttc caa tgc cct gaa agg    1344
Glu Val Leu Asn Phe Phe Glu Glu Cys Gly Phe Gln Cys Pro Glu Arg
        435                 440                 445 aaa ggt gtt gca gac tat ctc cag gag gtt ata tca aga aaa gac caa    1392
Lys Gly Val Ala Asp Tyr Leu Gln Glu Val Ile Ser Arg Lys Asp Gln
    450                 455                 460 gca caa tac tgg cgg cat gag gat gta cct tat agc ttt gtc tcg gta    1440
Ala Gln Tyr Trp Arg His Glu Asp Val Pro Tyr Ser Phe Val Ser Val
465                 470                 475                 480 gac atg ttg tcg aag aaa ttc aag gac ttc agc atc ggg aag aag att    1488
Asp Met Leu Ser Lys Lys Phe Lys Asp Phe Ser Ile Gly Lys Lys Ile
                485                 490                 495 gag gac gct cta tct aag cca tat gat aga tca aaa agc cat aag gat    1536
Glu Asp Ala Leu Ser Lys Pro Tyr Asp Arg Ser Lys Ser His Lys Asp
            500                 505                 510 gct ctt tcc ttc agc gtg tac tct cta cca aac tgg gag atg ttc ata    1584
Ala Leu Ser Phe Ser Val Tyr Ser Leu Pro Asn Trp Glu Met Phe Ile
        515                 520                 525 gct tgc ata tca aga gag tat ctt ctc atg aag aga aac tat ttc gtc    1632
Ala Cys Ile Ser Arg Glu Tyr Leu Leu Met Lys Arg Asn Tyr Phe Val
    530                 535                 540 tat ata ttc aag acg ggt cag ctt gtg atg gca gca ttc atc act atg    1680
Tyr Ile Phe Lys Thr Gly Gln Leu Val Met Ala Ala Phe Ile Thr Met
545                 550                 555                 560 act gtg ttt atc cga aca cgg atg ggt att gat atc ctt cat gga aac    1728
Thr Val Phe Ile Arg Thr Arg Met Gly Ile Asp Ile Leu His Gly Asn
                565                 570                 575 tct tac atg agt gcc ctc ttc ttc gcc gtc atc att ctt ctt gtt gat    1776
Ser Tyr Met Ser Ala Leu Phe Phe Ala Val Ile Ile Leu Leu Val Asp
            580                 585                 590 gga ttc cct gag ttg gct atg acg gct caa cgc tta gcg gtg ttt tac    1824
Gly Phe Pro Glu Leu Ala Met Thr Ala Gln Arg Leu Ala Val Phe Tyr
        595                 600                 605 aaa cag aag cag ttg tgt ttc tat cca gca tgg gct tat gca atc cct    1872
Lys Gln Lys Gln Leu Cys Phe Tyr Pro Ala Trp Ala Tyr Ala Ile Pro
    610                 615                 620 gca acg gtg tta aag gtc cca ctg tca tta ctg gaa tct ttc gtt tgg    1920
Ala Thr Val Leu Lys Val Pro Leu Ser Leu Leu Glu Ser Phe Val Trp
625                 630                 635                 640 acc ggc ctg aca tac tat gtc att ggg tac acc cct gaa gct tcc agg    1968
Thr Gly Leu Thr Tyr Tyr Val Ile Gly Tyr Thr Pro Glu Ala Ser Arg
```

-continued

```
                645                 650                 655
ttc ttc aag cag ttc att cta ctg ttt ctt gtt cac ttc act tcg ata    2016
Phe Phe Lys Gln Phe Ile Leu Leu Phe Leu Val His Phe Thr Ser Ile
        660                 665                 670 tcc atg ttt cgg tgc ctc gct gca atc ttc cag aca gta gtt gct tca    2064
Ser Met Phe Arg Cys Leu Ala Ala Ile Phe Gln Thr Val Val Ala Ser
            675                 680                 685 gtc aca gct ggc agt ttt ggt ata tta atc aca ttt gtc ttt gcc ggt    2112
Val Thr Ala Gly Ser Phe Gly Ile Leu Ile Thr Phe Val Phe Ala Gly
690                 695                 700 ttt gtc att cca cca cct tct atg cct gca tgg ctc aag tgg ggt ttc    2160
Phe Val Ile Pro Pro Pro Ser Met Pro Ala Trp Leu Lys Trp Gly Phe
705                 710                 715                 720 tgg gcg aat cct ttg agt tac agt gag att ggg cta tcg gta aat gag    2208
Trp Ala Asn Pro Leu Ser Tyr Ser Glu Ile Gly Leu Ser Val Asn Glu
                725                 730                 735 ttt ctt gct cca agg tgg aac cag ata caa cca agt act aat ctt acc    2256
Phe Leu Ala Pro Arg Trp Asn Gln Ile Gln Pro Ser Thr Asn Leu Thr
                740                 745                 750 tta ggt aga acc ata ctc gaa agc cgt gga ctg aac tac gat ggt tat    2304
Leu Gly Arg Thr Ile Leu Glu Ser Arg Gly Leu Asn Tyr Asp Gly Tyr
            755                 760                 765 atg tat tgg gta tca ctc tgt gcc ttg gtg ggt ttc act gtg ctc ttc    2352
Met Tyr Trp Val Ser Leu Cys Ala Leu Val Gly Phe Thr Val Leu Phe
770                 775                 780 aac aca att ttc act ctg gcg ctg act ttc ctg aaa tca cca aca tca    2400
Asn Thr Ile Phe Thr Leu Ala Leu Thr Phe Leu Lys Ser Pro Thr Ser
785                 790                 795                 800 tca cga gcc atg atc tca caa gaa aaa ctc tct gag ctg caa gga aca    2448
Ser Arg Ala Met Ile Ser Gln Glu Lys Leu Ser Glu Leu Gln Gly Thr
                805                 810                 815 gaa gat aca aca gac tac tct tcc atc aag aaa aag acc aca gat tcc    2496
Glu Asp Thr Thr Asp Tyr Ser Ser Ile Lys Lys Lys Thr Thr Asp Ser
                820                 825                 830 cct gta aaa aca gaa ggc aag atg gtg tta cct ttc aag ccc ctc act    2544
Pro Val Lys Thr Glu Gly Lys Met Val Leu Pro Phe Lys Pro Leu Thr
            835                 840                 845 gta aca ttt caa gaa cta aac tac ttc gtt gac act cca gtg gag atg    2592
Val Thr Phe Gln Glu Leu Asn Tyr Phe Val Asp Thr Pro Val Glu Met
850                 855                 860 aga gag caa gga tat gct aac aag aag ctg caa cta ctc aca gac atc    2640
Arg Glu Gln Gly Tyr Ala Asn Lys Lys Leu Gln Leu Leu Thr Asp Ile
865                 870                 875                 880 acc gga gct ttc cgt ccg gga atc cta acg gcg tta atg gga gtg agc    2688
Thr Gly Ala Phe Arg Pro Gly Ile Leu Thr Ala Leu Met Gly Val Ser
                885                 890                 895 gga gcc gga aag acc aca ctc ctc gac gtc cta gcc gga aga aaa acg    2736
Gly Ala Gly Lys Thr Thr Leu Leu Asp Val Leu Ala Gly Arg Lys Thr
                900                 905                 910 agc gga tac ata gaa ggc gac atc aga atc agc ggc ttc cct aaa gtc    2784
Ser Gly Tyr Ile Glu Gly Asp Ile Arg Ile Ser Gly Phe Pro Lys Val
            915                 920                 925 caa gaa acg ttc gcc aga gtc tca ggc tac tgc gaa caa aca gat att    2832
Gln Glu Thr Phe Ala Arg Val Ser Gly Tyr Cys Glu Gln Thr Asp Ile
930                 935                 940 cac tca cca aac atc acc gtc gaa gaa tcc gtc atc tac tcc gct tgg    2880
His Ser Pro Asn Ile Thr Val Glu Glu Ser Val Ile Tyr Ser Ala Trp
945                 950                 955                 960 ctc cgt ctc gct cct gag atc gag tcc gca acc aaa acc gta cgc atc    2928
```

-continued

```
                    Leu Arg Leu Ala Pro Glu Ile Glu Ser Ala Thr Lys Thr Val Arg Ile
                                    965                 970                 975 tcc tcc ttc ttc ttc ttc ttc ctt ctt ctt ccc cgc gca aat tcg aca        2976
Ser Ser Phe Phe Phe Phe Phe Leu Leu Leu Pro Arg Ala Asn Ser Thr
            980                 985                 990 cca atc tca acc caa tct tta cag gaa ttc gtg agg caa gtg ctg gag        3024
Pro Ile Ser Thr Gln Ser Leu Gln Glu Phe Val Arg Gln Val Leu Glu
            995                 1000                1005 acg atc gag tta gac gag atc aag gat gcg ttg gtg gga gtc gcc            3069
Thr Ile Glu Leu Asp Glu Ile Lys Asp Ala Leu Val Gly Val Ala
    1010                1015                1020 gga gag agc gga tta tcg acg gag cag agg aaa cgg ctt acg atc            3114
Gly Glu Ser Gly Leu Ser Thr Glu Gln Arg Lys Arg Leu Thr Ile
    1025                1030                1035 gcg gtg gag ttg gtg gcg aat ccg tcg atc atc ttc atg gac gag            3159
Ala Val Glu Leu Val Ala Asn Pro Ser Ile Ile Phe Met Asp Glu
    1040                1045                1050 cct acg acg gga ttg gat gca aga gca gcc gcc att gtt atg aga            3204
Pro Thr Thr Gly Leu Asp Ala Arg Ala Ala Ala Ile Val Met Arg
    1055                1060                1065 gct gtg aag aac gta gct gac act gga cga acc atc gtc tgc act            3249
Ala Val Lys Asn Val Ala Asp Thr Gly Arg Thr Ile Val Cys Thr
    1070                1075                1080 att cat cag cct agc ata gat att ttc gaa gct ttc gac gag ttg            3294
Ile His Gln Pro Ser Ile Asp Ile Phe Glu Ala Phe Asp Glu Leu
    1085                1090                1095 gtc ctt ctc aaa aga ggt ggt cgc atg atc tac aca gga cca cta            3339
Val Leu Leu Lys Arg Gly Gly Arg Met Ile Tyr Thr Gly Pro Leu
    1100                1105                1110 ggc cta aac tca tgt cat att att gag tat ttt gag aat gtt ccc            3384
Gly Leu Asn Ser Cys His Ile Ile Glu Tyr Phe Glu Asn Val Pro
    1115                1120                1125 gga gtt cct aaa ata aga gac aac cac aat cct gca aca tgg atg            3429
Gly Val Pro Lys Ile Arg Asp Asn His Asn Pro Ala Thr Trp Met
    1130                1135                1140 ctt gat gtt agt tca caa tct gcg gaa gtt gaa ctt ggt gtc gat            3474
Leu Asp Val Ser Ser Gln Ser Ala Glu Val Glu Leu Gly Val Asp
    1145                1150                1155 ttc gct aaa atc tac cac gaa tcc cct ctt ttc aag agc aac tca            3519
Phe Ala Lys Ile Tyr His Glu Ser Pro Leu Phe Lys Ser Asn Ser
    1160                1165                1170 gag ctt gtg aaa cag ttg agc caa cca gat tca ggg tca agt gat            3564
Glu Leu Val Lys Gln Leu Ser Gln Pro Asp Ser Gly Ser Ser Asp
    1175                1180                1185 tta cag ttt aaa aga act tat gca cag agc tgg tat gga caa ttc            3609
Leu Gln Phe Lys Arg Thr Tyr Ala Gln Ser Trp Tyr Gly Gln Phe
    1190                1195                1200 aaa tcc att ttg tgg aag atg aac ttg tct tac tgg agg aac cct            3654
Lys Ser Ile Leu Trp Lys Met Asn Leu Ser Tyr Trp Arg Asn Pro
    1205                1210                1215 tct tat aac cta atg cgt ttg att cac aca tta atc tct tct ttg            3699
Ser Tyr Asn Leu Met Arg Leu Ile His Thr Leu Ile Ser Ser Leu
    1220                1225                1230 atc ttc ggc gca ctc ttt tgg aaa caa ggc cag aaa ata gat act            3744
Ile Phe Gly Ala Leu Phe Trp Lys Gln Gly Gln Lys Ile Asp Thr
    1235                1240                1245 caa caa agt gtg ttc act gta gtt gga gcg atc tat ggg gct gtg            3789
Gln Gln Ser Val Phe Thr Val Val Gly Ala Ile Tyr Gly Ala Val
    1250                1255                1260
```

| | | | | | | | | | | | | |
|---|---|---|---|---|---|---|---|---|---|---|---|---|
| ctt | ttc | tta | ggg | att | aac | aat | tgt | gca | tca | gct | ctt | cgg aat tta | 3834 |
| Leu | Phe | Leu | Gly | Ile | Asn | Asn | Cys | Ala | Ser | Ala | Leu | Arg Asn Leu |
| | 1265 | | | | 1270 | | | | | 1275 | | |

| gaa | aca | gaa | cgt | aat | gtt | atg | tac | cgt | gaa | aga | ttt | gca gga atg | 3879 |
|---|---|---|---|---|---|---|---|---|---|---|---|---|---|
| Glu | Thr | Glu | Arg | Asn | Val | Met | Tyr | Arg | Glu | Arg | Phe | Ala Gly Met |
| | 1280 | | | | 1285 | | | | | 1290 | | |

| tac | tca | gca | aca | gct | tat | gca | tta | ggt | caa | gtt | gtg | act gag ata | 3924 |
|---|---|---|---|---|---|---|---|---|---|---|---|---|---|
| Tyr | Ser | Ala | Thr | Ala | Tyr | Ala | Leu | Gly | Gln | Val | Val | Thr Glu Ile |
| | 1295 | | | | 1300 | | | | | 1305 | | |

| cct | tac | ttg | ttc | ata | caa | gca | gcc | gag | ttt | gtg | atc | ata aca tat | 3969 |
|---|---|---|---|---|---|---|---|---|---|---|---|---|---|
| Pro | Tyr | Leu | Phe | Ile | Gln | Ala | Ala | Glu | Phe | Val | Ile | Ile Thr Tyr |
| | 1310 | | | | 1315 | | | | | 1320 | | |

| cct | atg | atc | ggt | ttc | tat | cct | tcg | acc | tac | aaa | gtc | ttt tgg gca | 4014 |
|---|---|---|---|---|---|---|---|---|---|---|---|---|---|
| Pro | Met | Ile | Gly | Phe | Tyr | Pro | Ser | Thr | Tyr | Lys | Val | Phe Trp Ala |
| | 1325 | | | | 1330 | | | | | 1335 | | |

| ctc | tac | tct | atg | ttc | act | tca | ctt | ctc | act | tac | aac | tat ctc gca | 4059 |
|---|---|---|---|---|---|---|---|---|---|---|---|---|---|
| Leu | Tyr | Ser | Met | Phe | Thr | Ser | Leu | Leu | Thr | Tyr | Asn | Tyr Leu Ala |
| | 1340 | | | | 1345 | | | | | 1350 | | |

| atg | ttc | ctc | atc | tcc | atc | aca | cca | aac | ttc | atg | gtt | gcc tcg att | 4104 |
|---|---|---|---|---|---|---|---|---|---|---|---|---|---|
| Met | Phe | Leu | Ile | Ser | Ile | Thr | Pro | Asn | Phe | Met | Val | Ala Ser Ile |
| | 1355 | | | | 1360 | | | | | 1365 | | |

| ctt | cag | tcc | atc | ttc | ttt | gtt | aac | ttt | aac | ctc | ttt | tcc ggg ttc | 4149 |
|---|---|---|---|---|---|---|---|---|---|---|---|---|---|
| Leu | Gln | Ser | Ile | Phe | Phe | Val | Asn | Phe | Asn | Leu | Phe | Ser Gly Phe |
| | 1370 | | | | 1375 | | | | | 1380 | | |

| ttg | att | cct | gaa | acg | caa | gtt | cca | agg | tgg | tgg | att | tgg tta tat | 4194 |
|---|---|---|---|---|---|---|---|---|---|---|---|---|---|
| Leu | Ile | Pro | Glu | Thr | Gln | Val | Pro | Arg | Trp | Trp | Ile | Trp Leu Tyr |
| | 1385 | | | | 1390 | | | | | 1395 | | |

| tat | ata | aca | cca | acg | tca | tgg | aca | ctc | aac | ggg | ttt | ttc tcg gct | 4239 |
|---|---|---|---|---|---|---|---|---|---|---|---|---|---|
| Tyr | Ile | Thr | Pro | Thr | Ser | Trp | Thr | Leu | Asn | Gly | Phe | Phe Ser Ala |
| | 1400 | | | | 1405 | | | | | 1410 | | |

| cag | tat | gaa | aat | att | cat | gag | gag | atc | att | gtc | ttt | gga gaa tcc | 4284 |
|---|---|---|---|---|---|---|---|---|---|---|---|---|---|
| Gln | Tyr | Glu | Asn | Ile | His | Glu | Glu | Ile | Ile | Val | Phe | Gly Glu Ser |
| | 1415 | | | | 1420 | | | | | 1425 | | |

| acg | acg | gct | tca | aaa | ttc | tta | gaa | gac | tat | ttt | gga | ttc cat cat | 4329 |
|---|---|---|---|---|---|---|---|---|---|---|---|---|---|
| Thr | Thr | Ala | Ser | Lys | Phe | Leu | Glu | Asp | Tyr | Phe | Gly | Phe His His |
| | 1430 | | | | 1435 | | | | | 1440 | | |

| gac | cgt | ttg | gca | gtt | aca | gca | gtt | gtt | caa | atc | gct | ttt cct att | 4374 |
|---|---|---|---|---|---|---|---|---|---|---|---|---|---|
| Asp | Arg | Leu | Ala | Val | Thr | Ala | Val | Val | Gln | Ile | Ala | Phe Pro Ile |
| | 1445 | | | | 1450 | | | | | 1455 | | |

| gca | ttg | gct | ttg | atg | ttt | gca | ttc | ttt | gtt | ggc | aaa | ctc aat ttc | 4419 |
|---|---|---|---|---|---|---|---|---|---|---|---|---|---|
| Ala | Leu | Ala | Leu | Met | Phe | Ala | Phe | Phe | Val | Gly | Lys | Leu Asn Phe |
| | 1460 | | | | 1465 | | | | | 1470 | | |

| caa | aga | aga | tga | | | | | | | | | | 4431 |
|---|---|---|---|---|---|---|---|---|---|---|---|---|---|
| Gln | Arg | Arg | | | | | | | | | | |
| | 1475 | | | | | | | | | | | |

<210> SEQ ID NO 50
<211> LENGTH: 1476
<212> TYPE: PRT
<213> ORGANISM: Brassica rapa

<400> SEQUENCE: 50

Met Ala Asn Met Ala Gly Ala Asp Glu Ile Glu Ser Leu Arg Val Glu
1               5                   10                  15

Leu Ala Glu Ile Gly Arg Ser Ile Arg Ser Ser Phe His Arg His Thr
            20                  25                  30

Ser Ser Phe Arg Ser Gly Ser Ser Arg Tyr Glu Pro Asp His Asp Gly
        35                  40                  45

Glu Gly Asn Asn Thr Asn Ala Glu Tyr Ala Leu Gln Trp Ala Glu Ile
    50                  55                  60

```
Glu Arg Leu Pro Thr Val Lys Arg Met Arg Ser Ser Leu Leu Asp Asp
65                  70                  75                  80

Gly Asp Glu Ser Met Ala Glu Lys Gly Lys Arg Val Val Asp Val Thr
                85                  90                  95

Lys Leu Gly Ala Met Glu Arg His Leu Met Ile Glu Lys Leu Ile Lys
                100                 105                 110

His Ile Glu Asn Asp Asn Leu Lys Leu Leu Lys Lys Ile Arg Arg Arg
                115                 120                 125

Ile Asp Arg Val Gly Met Glu Leu Pro Thr Ile Glu Val Arg Tyr Glu
130                 135                 140

Gly Leu Lys Val Glu Ala Glu Cys Glu Ile Val Glu Gly Lys Ala Leu
145                 150                 155                 160

Pro Thr Leu Trp Asn Thr Ala Lys Arg Val Leu Ser Glu Leu Val Lys
                165                 170                 175

Leu Thr Gly Ala Lys Thr Arg Glu Ala Lys Ile Ser Ile Leu Asn Asp
                180                 185                 190

Val Asn Gly Ile Ile Lys Pro Gly Arg Leu Thr Leu Leu Gly Pro
                195                 200                 205

Pro Gly Cys Gly Lys Thr Thr Leu Leu Lys Ala Leu Ser Gly Asn Leu
210                 215                 220

Glu Asn Asn Leu Lys Cys Ser Gly Glu Ile Ser Tyr Asn Gly His Arg
225                 230                 235                 240

Leu Asp Glu Phe Val Pro Gln Lys Thr Ser Ala Tyr Ile Ser Gln Tyr
                245                 250                 255

Asp Leu His Ile Ala Glu Met Thr Val Arg Glu Thr Val Asp Phe Ser
                260                 265                 270

Ala Arg Cys Gln Gly Val Gly Ser Arg Thr Glu Ile Met Met Glu Val
                275                 280                 285

Ser Lys Arg Glu Lys Glu Ala Gly Ile Ile Pro Asp Thr Glu Val Asp
290                 295                 300

Ala Tyr Met Lys Ala Ile Ser Val Glu Gly Leu Glu Arg Ser Leu Gln
305                 310                 315                 320

Thr Asp Tyr Ile Leu Lys Ile Leu Gly Leu Asp Ile Cys Ala Glu Thr
                325                 330                 335

Leu Ile Gly Asp Val Met Arg Arg Gly Ile Ser Gly Gly Gln Lys Lys
                340                 345                 350

Arg Leu Thr Thr Ala Glu Met Ile Val Gly Pro Thr Lys Ala Leu Phe
                355                 360                 365

Met Asp Glu Ile Thr Asn Gly Leu Asp Ser Ser Thr Ala Phe Gln Ile
                370                 375                 380

Val Lys Ser Leu Gln Gln Leu Ala His Ile Ser Asn Ala Thr Val Val
385                 390                 395                 400

Val Ser Leu Leu Gln Pro Ala Pro Glu Ser Phe Asp Leu Phe Asp Asp
                405                 410                 415

Val Met Leu Met Ala Lys Gly Lys Ile Val Tyr His Gly Pro Arg Gly
                420                 425                 430

Glu Val Leu Asn Phe Phe Glu Glu Cys Gly Phe Gln Cys Pro Glu Arg
                435                 440                 445

Lys Gly Val Ala Asp Tyr Leu Gln Glu Val Ile Ser Arg Lys Asp Gln
                450                 455                 460

Ala Gln Tyr Trp Arg His Glu Asp Val Pro Tyr Ser Phe Val Ser Val
465                 470                 475                 480
```

```
Asp Met Leu Ser Lys Lys Phe Lys Asp Phe Ser Ile Gly Lys Lys Ile
            485                 490                 495
Glu Asp Ala Leu Ser Lys Pro Tyr Asp Arg Ser Lys Ser His Lys Asp
        500                 505                 510
Ala Leu Ser Phe Ser Val Tyr Ser Leu Pro Asn Trp Glu Met Phe Ile
    515                 520                 525
Ala Cys Ile Ser Arg Glu Tyr Leu Leu Met Lys Arg Asn Tyr Phe Val
530                 535                 540
Tyr Ile Phe Lys Thr Gly Gln Leu Val Met Ala Ala Phe Ile Thr Met
545                 550                 555                 560
Thr Val Phe Ile Arg Thr Arg Met Gly Ile Asp Ile Leu His Gly Asn
                565                 570                 575
Ser Tyr Met Ser Ala Leu Phe Phe Ala Val Ile Ile Leu Leu Val Asp
            580                 585                 590
Gly Phe Pro Glu Leu Ala Met Thr Ala Gln Arg Leu Ala Val Phe Tyr
        595                 600                 605
Lys Gln Lys Gln Leu Cys Phe Tyr Pro Ala Trp Ala Tyr Ala Ile Pro
    610                 615                 620
Ala Thr Val Leu Lys Val Pro Leu Ser Leu Leu Glu Ser Phe Val Trp
625                 630                 635                 640
Thr Gly Leu Thr Tyr Tyr Val Ile Gly Tyr Thr Pro Glu Ala Ser Arg
                645                 650                 655
Phe Phe Lys Gln Phe Ile Leu Leu Phe Leu Val His Phe Thr Ser Ile
            660                 665                 670
Ser Met Phe Arg Cys Leu Ala Ala Ile Phe Gln Thr Val Val Ala Ser
        675                 680                 685
Val Thr Ala Gly Ser Phe Gly Ile Leu Ile Thr Phe Val Phe Ala Gly
    690                 695                 700
Phe Val Ile Pro Pro Ser Met Pro Ala Trp Leu Lys Trp Gly Phe
705                 710                 715                 720
Trp Ala Asn Pro Leu Ser Tyr Ser Glu Ile Gly Leu Ser Val Asn Glu
                725                 730                 735
Phe Leu Ala Pro Arg Trp Asn Gln Ile Gln Pro Ser Thr Asn Leu Thr
            740                 745                 750
Leu Gly Arg Thr Ile Leu Glu Ser Arg Gly Leu Asn Tyr Asp Gly Tyr
        755                 760                 765
Met Tyr Trp Val Ser Leu Cys Ala Leu Val Gly Phe Thr Val Leu Phe
    770                 775                 780
Asn Thr Ile Phe Thr Leu Ala Leu Thr Phe Leu Lys Ser Pro Thr Ser
785                 790                 795                 800
Ser Arg Ala Met Ile Ser Gln Glu Lys Leu Ser Glu Leu Gln Gly Thr
                805                 810                 815
Glu Asp Thr Thr Asp Tyr Ser Ser Ile Lys Lys Thr Thr Asp Ser
            820                 825                 830
Pro Val Lys Thr Glu Gly Lys Met Val Leu Pro Phe Lys Pro Leu Thr
        835                 840                 845
Val Thr Phe Gln Glu Leu Asn Tyr Phe Val Asp Thr Pro Val Glu Met
    850                 855                 860
Arg Glu Gln Gly Tyr Ala Asn Lys Lys Leu Gln Leu Leu Thr Asp Ile
865                 870                 875                 880
Thr Gly Ala Phe Arg Pro Gly Ile Leu Thr Ala Leu Met Gly Val Ser
                885                 890                 895
Gly Ala Gly Lys Thr Thr Leu Leu Asp Val Leu Ala Gly Arg Lys Thr
```

```
               900             905             910
Ser Gly Tyr Ile Glu Gly Asp Ile Arg Ile Ser Gly Phe Pro Lys Val
            915             920             925

Gln Glu Thr Phe Ala Arg Val Ser Gly Tyr Cys Glu Gln Thr Asp Ile
        930             935             940

His Ser Pro Asn Ile Thr Val Glu Glu Ser Val Ile Tyr Ser Ala Trp
945             950             955             960

Leu Arg Leu Ala Pro Glu Ile Glu Ser Ala Thr Lys Thr Val Arg Ile
            965             970             975

Ser Ser Phe Phe Phe Phe Phe Leu Leu Leu Pro Arg Ala Asn Ser Thr
        980             985             990

Pro Ile Ser Thr Gln Ser Leu Gln Glu Phe Val Arg Gln Val Leu Glu
        995             1000            1005

Thr Ile Glu Leu Asp Glu Ile Lys Asp Ala Leu Val Gly Val Ala
     1010            1015            1020

Gly Glu Ser Gly Leu Ser Thr Glu Gln Arg Lys Arg Leu Thr Ile
     1025            1030            1035

Ala Val Glu Leu Val Ala Asn Pro Ser Ile Ile Phe Met Asp Glu
     1040            1045            1050

Pro Thr Thr Gly Leu Asp Ala Arg Ala Ala Ala Ile Val Met Arg
     1055            1060            1065

Ala Val Lys Asn Val Ala Asp Thr Gly Arg Thr Ile Val Cys Thr
     1070            1075            1080

Ile His Gln Pro Ser Ile Asp Ile Phe Glu Ala Phe Asp Glu Leu
     1085            1090            1095

Val Leu Leu Lys Arg Gly Gly Arg Met Ile Tyr Thr Gly Pro Leu
     1100            1105            1110

Gly Leu Asn Ser Cys His Ile Ile Glu Tyr Phe Glu Asn Val Pro
     1115            1120            1125

Gly Val Pro Lys Ile Arg Asp Asn His Asn Pro Ala Thr Trp Met
     1130            1135            1140

Leu Asp Val Ser Ser Gln Ser Ala Glu Val Glu Leu Gly Val Asp
     1145            1150            1155

Phe Ala Lys Ile Tyr His Glu Ser Pro Leu Phe Lys Ser Asn Ser
     1160            1165            1170

Glu Leu Val Lys Gln Leu Ser Gln Pro Asp Ser Gly Ser Ser Asp
     1175            1180            1185

Leu Gln Phe Lys Arg Thr Tyr Ala Gln Ser Trp Tyr Gly Gln Phe
     1190            1195            1200

Lys Ser Ile Leu Trp Lys Met Asn Leu Ser Tyr Trp Arg Asn Pro
     1205            1210            1215

Ser Tyr Asn Leu Met Arg Leu Ile His Thr Leu Ile Ser Ser Leu
     1220            1225            1230

Ile Phe Gly Ala Leu Phe Trp Lys Gln Gly Gln Lys Ile Asp Thr
     1235            1240            1245

Gln Gln Ser Val Phe Thr Val Val Gly Ala Ile Tyr Gly Ala Val
     1250            1255            1260

Leu Phe Leu Gly Ile Asn Asn Cys Ala Ser Ala Leu Arg Asn Leu
     1265            1270            1275

Glu Thr Glu Arg Asn Val Met Tyr Arg Glu Arg Phe Ala Gly Met
     1280            1285            1290

Tyr Ser Ala Thr Ala Tyr Ala Leu Gly Gln Val Val Thr Glu Ile
     1295            1300            1305
```

```
Pro Tyr Leu Phe Ile Gln Ala  Ala Glu Phe Val Ile  Ile Thr Tyr
    1310            1315              1320

Pro Met Ile Gly Phe Tyr Pro  Ser Thr Tyr Lys Val  Phe Trp Ala
    1325            1330              1335

Leu Tyr Ser Met Phe Thr Ser  Leu Leu Thr Tyr Asn  Tyr Leu Ala
    1340            1345              1350

Met Phe Leu Ile Ser Ile Thr  Pro Asn Phe Met Val  Ala Ser Ile
    1355            1360              1365

Leu Gln Ser Ile Phe Phe Val  Asn Phe Asn Leu Phe  Ser Gly Phe
    1370            1375              1380

Leu Ile Pro Glu Thr Gln Val  Pro Arg Trp Trp Ile  Trp Leu Tyr
    1385            1390              1395

Tyr Ile Thr Pro Thr Ser Trp  Thr Leu Asn Gly Phe  Phe Ser Ala
    1400            1405              1410

Gln Tyr Glu Asn Ile His Glu  Glu Ile Ile Val Phe  Gly Glu Ser
    1415            1420              1425

Thr Thr Ala Ser Lys Phe Leu  Glu Asp Tyr Phe Gly  Phe His His
    1430            1435              1440

Asp Arg Leu Ala Val Thr Ala  Val Val Gln Ile Ala  Phe Pro Ile
    1445            1450              1455

Ala Leu Ala Leu Met Phe Ala  Phe Phe Val Gly Lys  Leu Asn Phe
    1460            1465              1470

Gln Arg Arg
    1475

<210> SEQ ID NO 51
<211> LENGTH: 4353
<212> TYPE: DNA
<213> ORGANISM: Arabidopsis lyrata
<220> FEATURE:
<221> NAME/KEY: misc_feature
<223> OTHER INFORMATION: subsp. lyrata
<220> FEATURE:
<221> NAME/KEY: CDS
<222> LOCATION: (1)..(4353)

<400> SEQUENCE: 51 atg gct cat atg gtt gga gca gac gag att gag tcg ttg aga gtg gag      48
Met Ala His Met Val Gly Ala Asp Glu Ile Glu Ser Leu Arg Val Glu
1               5                   10                  15 ctt gca gag att gga aga agc atc aga tca tcg ttc cgg aga cac act      96
Leu Ala Glu Ile Gly Arg Ser Ile Arg Ser Ser Phe Arg Arg His Thr
            20                  25                  30 tcg agt ttc aga agc agc tct tca aga tat gaa ctt gaa aat gat ggt     144
Ser Ser Phe Arg Ser Ser Ser Ser Arg Tyr Glu Leu Glu Asn Asp Gly
        35                  40                  45 gat gtt att gat cat gat gca gag tat gct ctg caa tgg gct gag att     192
Asp Val Ile Asp His Asp Ala Glu Tyr Ala Leu Gln Trp Ala Glu Ile
    50                  55                  60 gag aga tta cca act gtc aaa cga atg aga tcg act ctc ctt gat gat     240
Glu Arg Leu Pro Thr Val Lys Arg Met Arg Ser Thr Leu Leu Asp Asp
65                  70                  75                  80 ggc gat gag tcc atg tcc gag aaa gga aga agg gtc gtt gat gtc aca     288
Gly Asp Glu Ser Met Ser Glu Lys Gly Arg Arg Val Val Asp Val Thr
                85                  90                  95 aag ctt gga gcc atg gaa cgt cat ctg atg att gag aaa ctc atc aaa     336
Lys Leu Gly Ala Met Glu Arg His Leu Met Ile Glu Lys Leu Ile Lys
            100                 105                 110
```

```
cac att gag aat gat aat ctc aaa ttg ctc aag aaa atc agg aaa aga        384
His Ile Glu Asn Asp Asn Leu Lys Leu Leu Lys Lys Ile Arg Lys Arg
            115                 120                 125 ata gac aga gtc ggg atg gag tta ccg acc ata gaa gtg agg tac gag        432
Ile Asp Arg Val Gly Met Glu Leu Pro Thr Ile Glu Val Arg Tyr Glu
        130                 135                 140 agt tta aaa gtg gag gcc gag tgc gag att gtt gaa ggg aag gca ctt        480
Ser Leu Lys Val Glu Ala Glu Cys Glu Ile Val Glu Gly Lys Ala Leu
145                 150                 155                 160 cca aca ctg tgg aac act gct aag cgc gtt tta tct gaa ctg gtg aag        528
Pro Thr Leu Trp Asn Thr Ala Lys Arg Val Leu Ser Glu Leu Val Lys
                165                 170                 175 ctc act ggt gca aaa aca cac gaa gcg aag ata aac att att aat gat        576
Leu Thr Gly Ala Lys Thr His Glu Ala Lys Ile Asn Ile Ile Asn Asp
            180                 185                 190 gtt aat ggc gtt ata aag ccg gga agg tta aca ctg ttg ctt ggt cct        624
Val Asn Gly Val Ile Lys Pro Gly Arg Leu Thr Leu Leu Leu Gly Pro
        195                 200                 205 cct gga tgt gga aaa aca act ttg tta aag gcc ttg tct gga aat tta        672
Pro Gly Cys Gly Lys Thr Thr Leu Leu Lys Ala Leu Ser Gly Asn Leu
210                 215                 220 gaa aac aat cta aag tgt tca ggt gaa ata tct tac aat gga cac aga        720
Glu Asn Asn Leu Lys Cys Ser Gly Glu Ile Ser Tyr Asn Gly His Arg
225                 230                 235                 240 ctg gac gag ttt gtt cct cag aaa act tcg gcg tac ata agt caa tat        768
Leu Asp Glu Phe Val Pro Gln Lys Thr Ser Ala Tyr Ile Ser Gln Tyr
                245                 250                 255 gat ctg cac att gca gag atg aca gtg aga gag aca gtt gat ttc tca        816
Asp Leu His Ile Ala Glu Met Thr Val Arg Glu Thr Val Asp Phe Ser
            260                 265                 270 gct cgt tgt cag gga gtt ggt agc cga aca gat ata atg atg gaa gtc        864
Ala Arg Cys Gln Gly Val Gly Ser Arg Thr Asp Ile Met Met Glu Val
        275                 280                 285 agt aaa aga gaa aag gaa aaa gga atc att cct gac aca gaa gtg gat        912
Ser Lys Arg Glu Lys Glu Lys Gly Ile Ile Pro Asp Thr Glu Val Asp
290                 295                 300 gct tac atg aaa gca att tct gtt gaa gga ctc caa aga aat ctg caa        960
Ala Tyr Met Lys Ala Ile Ser Val Glu Gly Leu Gln Arg Asn Leu Gln
305                 310                 315                 320 aca gat tac atc ttg aag att ctc gga ctt gat att tgt gca gaa aca       1008
Thr Asp Tyr Ile Leu Lys Ile Leu Gly Leu Asp Ile Cys Ala Glu Thr
                325                 330                 335 ttg att gga gat gtg atg agg aga ggt ata tca gga ggt caa aag aag       1056
Leu Ile Gly Asp Val Met Arg Arg Gly Ile Ser Gly Gly Gln Lys Lys
            340                 345                 350 cgt ctt acc aca gct gag atg att gtt ggc ccg aca aag gct ctg ttt       1104
Arg Leu Thr Thr Ala Glu Met Ile Val Gly Pro Thr Lys Ala Leu Phe
        355                 360                 365 atg gat gaa ata aca aat ggc tta gac agt tcc aca gct ttt cag att       1152
Met Asp Glu Ile Thr Asn Gly Leu Asp Ser Ser Thr Ala Phe Gln Ile
370                 375                 380 gtc aaa tct ctt cag cag ttt gct cac ata tca agc gct act gtg ctt       1200
Val Lys Ser Leu Gln Gln Phe Ala His Ile Ser Ser Ala Thr Val Leu
385                 390                 395                 400 gtt tcg ctt ctt caa ccc gcc cca gag tcc ttt gac ctc ttt gat gac       1248
Val Ser Leu Leu Gln Pro Ala Pro Glu Ser Phe Asp Leu Phe Asp Asp
                405                 410                 415 ata atg ctg atg gcc aaa gga aga atc atg tat cat ggt cca cgc ggt       1296
Ile Met Leu Met Ala Lys Gly Arg Ile Met Tyr His Gly Pro Arg Gly
            420                 425                 430
```

```
gag gtc ctc aac ttc ttt gag gat tgt gga ttc cga tgc cct gaa agg      1344
Glu Val Leu Asn Phe Phe Glu Asp Cys Gly Phe Arg Cys Pro Glu Arg
        435                 440                 445 aaa ggt gtc gca gac ttt ctc cag gag gtt ata tcc aaa aaa gac caa      1392
Lys Gly Val Ala Asp Phe Leu Gln Glu Val Ile Ser Lys Lys Asp Gln
450                 455                 460 gca caa tac tgg cgg cac gag gat tta cct tat agt ttt gtc tcg gta      1440
Ala Gln Tyr Trp Arg His Glu Asp Leu Pro Tyr Ser Phe Val Ser Val
465                 470                 475                 480 gat atg ttg tca aag aag ttc aag gag ttg agt att gga aaa aag atg      1488
Asp Met Leu Ser Lys Lys Phe Lys Glu Leu Ser Ile Gly Lys Lys Met
        485                 490                 495 gaa cac act ctg tca aag cca tat gat aga tcc aaa agc cat aag gat      1536
Glu His Thr Leu Ser Lys Pro Tyr Asp Arg Ser Lys Ser His Lys Asp
        500                 505                 510 gct ttg tcc ttc agt gtg tat tct ctt cca aac tgg gag ctg ttc ata      1584
Ala Leu Ser Phe Ser Val Tyr Ser Leu Pro Asn Trp Glu Leu Phe Ile
        515                 520                 525 gca tgc ata tca aga gaa tat ctt ctc atg aag aga aac tat ttc gtc      1632
Ala Cys Ile Ser Arg Glu Tyr Leu Leu Met Lys Arg Asn Tyr Phe Val
        530                 535                 540 tat att ttc aag aca tct cag ctt gtt atg gcc gca ttt atc act atg      1680
Tyr Ile Phe Lys Thr Ser Gln Leu Val Met Ala Ala Phe Ile Thr Met
545                 550                 555                 560 act gtg tat atc cga aca cgg atg ggt att gat atc att cat gga aat      1728
Thr Val Tyr Ile Arg Thr Arg Met Gly Ile Asp Ile Ile His Gly Asn
                565                 570                 575 tct tac atg agt gcc ctc ttt ttc gcc ctc att ata ctt ctt gtt gac      1776
Ser Tyr Met Ser Ala Leu Phe Phe Ala Leu Ile Ile Leu Leu Val Asp
        580                 585                 590 gga ttc cca gag ttg tct atg acg gct caa cgc cta gcc gtg ttt tac      1824
Gly Phe Pro Glu Leu Ser Met Thr Ala Gln Arg Leu Ala Val Phe Tyr
        595                 600                 605 aag cag aag cag ttg tgt ttc tat cct gca tgg gcg tat gca atc cct      1872
Lys Gln Lys Gln Leu Cys Phe Tyr Pro Ala Trp Ala Tyr Ala Ile Pro
        610                 615                 620 gca aca gtg tta aag gtc cct ctc tcg ttc ttt gaa tct ctc gtt tgg      1920
Ala Thr Val Leu Lys Val Pro Leu Ser Phe Phe Glu Ser Leu Val Trp
625                 630                 635                 640 acc ggc ctc aca tac tat gtc att gga tac acc cct gaa gca tcc agg      1968
Thr Gly Leu Thr Tyr Tyr Val Ile Gly Tyr Thr Pro Glu Ala Ser Arg
                645                 650                 655 ttt ttc aag cag ttc att cta ctc ttt gct gtc cac ttc acc tcg ata      2016
Phe Phe Lys Gln Phe Ile Leu Leu Phe Ala Val His Phe Thr Ser Ile
                660                 665                 670 tcc atg ttc cgg tgt cta gct gca atc ttc cag aca gta gtt gct tca      2064
Ser Met Phe Arg Cys Leu Ala Ala Ile Phe Gln Thr Val Val Ala Ser
        675                 680                 685 atc acc gct ggc agt ttt ggt ata tta ttc aca ttt gtc ttt gcc ggt      2112
Ile Thr Ala Gly Ser Phe Gly Ile Leu Phe Thr Phe Val Phe Ala Gly
        690                 695                 700 ttc gtc att cca cca cct tct atg cca gca tgg ctt aag tgg ggt ttc      2160
Phe Val Ile Pro Pro Pro Ser Met Pro Ala Trp Leu Lys Trp Gly Phe
705                 710                 715                 720 tgg gta aat cct ttg agt tac ggt gag att ggg cta tcg gta aac gag      2208
Trp Val Asn Pro Leu Ser Tyr Gly Glu Ile Gly Leu Ser Val Asn Glu
                725                 730                 735 ttt ctt gct cca agg tgg aat cag atg caa ccc aat aat gtt acc tta      2256
Phe Leu Ala Pro Arg Trp Asn Gln Met Gln Pro Asn Asn Val Thr Leu
```

```
              740                 745                 750
gga cga acc ata ctc caa acc cgt gga atg gac tac gat ggt tac atg      2304
Gly Arg Thr Ile Leu Gln Thr Arg Gly Met Asp Tyr Asp Gly Tyr Met
        755                 760                 765 tac tgg gta tca ttg tat gcc ttg ttg ggt ttc act gtg ctc ttc aac      2352
Tyr Trp Val Ser Leu Tyr Ala Leu Leu Gly Phe Thr Val Leu Phe Asn
770                 775                 780 atc att ttc act ctg gct cta acg ttc ttg aaa tca ccc aca tca tct      2400
Ile Ile Phe Thr Leu Ala Leu Thr Phe Leu Lys Ser Pro Thr Ser Ser
785                 790                 795                 800 cga gcc atg att tcg caa gac aaa ctc tca gag ctg caa gga aca gaa      2448
Arg Ala Met Ile Ser Gln Asp Lys Leu Ser Glu Leu Gln Gly Thr Glu
            805                 810                 815 aat tca aca gac gac tct tct gtc aag aaa aag acc aca gat tcc cct      2496
Asn Ser Thr Asp Asp Ser Ser Val Lys Lys Lys Thr Thr Asp Ser Pro
                820                 825                 830 gta aag acg gaa gaa gaa ggc aat atg gtc tta cca ttc aag cct ctc      2544
Val Lys Thr Glu Glu Glu Gly Asn Met Val Leu Pro Phe Lys Pro Leu
                    835                 840                 845 act gta aca ttt caa gac ttg aag tat ttc gtt gac atg ccc gtg gag      2592
Thr Val Thr Phe Gln Asp Leu Lys Tyr Phe Val Asp Met Pro Val Glu
850                 855                 860 atg aga gac caa gga tat gat cag aag aaa cta caa ctt ctc tca gat      2640
Met Arg Asp Gln Gly Tyr Asp Gln Lys Lys Leu Gln Leu Leu Ser Asp
865                 870                 875                 880 atc aca gga gct ttc cgt ccc gga att cta acg gca tta atg gga gtg      2688
Ile Thr Gly Ala Phe Arg Pro Gly Ile Leu Thr Ala Leu Met Gly Val
                885                 890                 895 agt gga gcc gga aaa aca act ctc ctc gac gtt tta gcc gga aga aaa      2736
Ser Gly Ala Gly Lys Thr Thr Leu Leu Asp Val Leu Ala Gly Arg Lys
                    900                 905                 910 acc agc gga tac atc gaa gga gac atc aga atc agt ggc ttc cct aaa      2784
Thr Ser Gly Tyr Ile Glu Gly Asp Ile Arg Ile Ser Gly Phe Pro Lys
                915                 920                 925 atc caa gaa aca ttc gct aga gtc tca ggg tac tgt gaa caa aca gat      2832
Ile Gln Glu Thr Phe Ala Arg Val Ser Gly Tyr Cys Glu Gln Thr Asp
930                 935                 940 att cac tca cca aac atc acc gtc gaa gaa tcc gta atc tac tcc gct      2880
Ile His Ser Pro Asn Ile Thr Val Glu Glu Ser Val Ile Tyr Ser Ala
945                 950                 955                 960 tgg ctt cgt cta gct cct gag atc gat tcc gca acc aaa acc aaa ttt      2928
Trp Leu Arg Leu Ala Pro Glu Ile Asp Ser Ala Thr Lys Thr Lys Phe
                965                 970                 975 gtg aag caa gtg ctt gag acg atc gaa tta gat gaa atc aaa gat tca      2976
Val Lys Gln Val Leu Glu Thr Ile Glu Leu Asp Glu Ile Lys Asp Ser
                    980                 985                 990 ttg gtg gga gtc acc gga gtg agt gga tta tcg acg gag cag agg aag      3024
Leu Val Gly Val Thr Gly Val Ser Gly Leu Ser Thr Glu Gln Arg Lys
                995                 1000                1005 aga ttg acg att gcg gtg gaa ttg gtg gcg aat ccg tcg att ata           3069
Arg Leu Thr Ile Ala Val Glu Leu Val Ala Asn Pro Ser Ile Ile
        1010                1015                1020 ttc atg gac gag cca acg acg ggg cta gac gca aga gca gcc gcc           3114
Phe Met Asp Glu Pro Thr Thr Gly Leu Asp Ala Arg Ala Ala Ala
        1025                1030                1035 att gtt atg aga gct gtg aag aac gtt gct gat act gga cga acc           3159
Ile Val Met Arg Ala Val Lys Asn Val Ala Asp Thr Gly Arg Thr
        1040                1045                1050 atc gtc tgc act att cat cag cct agt atc gac att ttt gaa gcc           3204
```

```
      Ile Val Cys Thr Ile His Gln Pro Ser Ile Asp Ile Phe Glu Ala
          1055            1060            1065 ttc gac gag ttg gtg ctt ctt aaa aga ggt ggt cgc atg att tac      3249
Phe Asp Glu Leu Val Leu Leu Lys Arg Gly Gly Arg Met Ile Tyr
    1070            1075            1080 aca gga cca ttg ggt caa cat tca cgt cat att att gag tat ttt      3294
Thr Gly Pro Leu Gly Gln His Ser Arg His Ile Ile Glu Tyr Phe
    1085            1090            1095 gag agt gtt cct gaa att cct aaa ata aaa gac aac cat aat cca      3339
Glu Ser Val Pro Glu Ile Pro Lys Ile Lys Asp Asn His Asn Pro
    1100            1105            1110 gca aca tgg atg ctt gat gtt agt tca caa tct gta gaa gtt gaa      3384
Ala Thr Trp Met Leu Asp Val Ser Ser Gln Ser Val Glu Val Glu
    1115            1120            1125 ctt ggc gtc gat ttt gct aaa atc tac cat gac tct gct ctt tac      3429
Leu Gly Val Asp Phe Ala Lys Ile Tyr His Asp Ser Ala Leu Tyr
    1130            1135            1140 aag aga aac gca gag ctt gtg aaa cag ttg agc caa cca gat tca      3474
Lys Arg Asn Ala Glu Leu Val Lys Gln Leu Ser Gln Pro Asp Ser
    1145            1150            1155 gga tca agt gat ata cag ttt aag aga act ttt gca caa agt tgg      3519
Gly Ser Ser Asp Ile Gln Phe Lys Arg Thr Phe Ala Gln Ser Trp
    1160            1165            1170 tgg gga caa ttc aga tct att cta tgg aaa atg aac ttg tct tat      3564
Trp Gly Gln Phe Arg Ser Ile Leu Trp Lys Met Asn Leu Ser Tyr
    1175            1180            1185 tgg aga agc cct tct tat aac cta atg cgt atg att cac aca tta      3609
Trp Arg Ser Pro Ser Tyr Asn Leu Met Arg Met Ile His Thr Leu
    1190            1195            1200 gtc tct tct ttg atc ttc ggc tca ctt ttc tgg aaa caa ggc cag      3654
Val Ser Ser Leu Ile Phe Gly Ser Leu Phe Trp Lys Gln Gly Gln
    1205            1210            1215 aat ata gat act caa cag ggt atg ttc act gtg ttt gga gcg atc      3699
Asn Ile Asp Thr Gln Gln Gly Met Phe Thr Val Phe Gly Ala Ile
    1220            1225            1230 tat ggt ttg gtg ctc ttc tta ggg ata aac aat tgt tca tca gct      3744
Tyr Gly Leu Val Leu Phe Leu Gly Ile Asn Asn Cys Ser Ser Ala
    1235            1240            1245 att caa tat ata gaa aca gag cga aat gtt atg tac cgc gaa aga      3789
Ile Gln Tyr Ile Glu Thr Glu Arg Asn Val Met Tyr Arg Glu Arg
    1250            1255            1260 ttc gca gga atg tac tca gcg act gct tac gca ttg ggt caa gtg      3834
Phe Ala Gly Met Tyr Ser Ala Thr Ala Tyr Ala Leu Gly Gln Val
    1265            1270            1275 gtg act gag ata cct tat ata ttc ata caa gcc gcc gag ttt gtg      3879
Val Thr Glu Ile Pro Tyr Ile Phe Ile Gln Ala Ala Glu Phe Val
    1280            1285            1290 atc ata aca tat cca atg atc ggt ttc tat cct tca acc tac aaa      3924
Ile Ile Thr Tyr Pro Met Ile Gly Phe Tyr Pro Ser Thr Tyr Lys
    1295            1300            1305 gtc ttc tgg tca ctc tac tct atg ttt tgc tca ctc ctc act ttt      3969
Val Phe Trp Ser Leu Tyr Ser Met Phe Cys Ser Leu Leu Thr Phe
    1310            1315            1320 aac tac ctt gcg atg ttc ctc gtc tcc atc acg cca aac ttc atg      4014
Asn Tyr Leu Ala Met Phe Leu Val Ser Ile Thr Pro Asn Phe Met
    1325            1330            1335 gtt gcc gcg att ctt caa tcg ctc ttc tat gtt aat ttc aac ctt      4059
Val Ala Ala Ile Leu Gln Ser Leu Phe Tyr Val Asn Phe Asn Leu
    1340            1345            1350
```

| | | | | | | | | | | | |
|---|---|---|---|---|---|---|---|---|---|---|---|
| ttt | tcc | ggg | ttt | ttg | atc | ccc | caa | acg | caa | gtt | cca | ggg | tgg | tgg | | 4104 |
| Phe | Ser | Gly | Phe | Leu | Ile | Pro | Gln | Thr | Gln | Val | Pro | Gly | Trp | Trp | | |
| | 1355 | | | | 1360 | | | | | 1365 | | | | | | |
| att | tgg | tta | tat | tat | cta | aca | cca | acg | tct | tgg | aca | ctg | aac | gga | | 4149 |
| Ile | Trp | Leu | Tyr | Tyr | Leu | Thr | Pro | Thr | Ser | Trp | Thr | Leu | Asn | Gly | | |
| | 1370 | | | | 1375 | | | | | 1380 | | | | | | |
| ttt | ttc | tcg | tcc | caa | tac | ggt | gat | att | gac | gaa | aag | atc | aat | gtc | | 4194 |
| Phe | Phe | Ser | Ser | Gln | Tyr | Gly | Asp | Ile | Asp | Glu | Lys | Ile | Asn | Val | | |
| | 1385 | | | | 1390 | | | | | 1395 | | | | | | |
| ttt | gga | gaa | tcc | acg | acg | gtt | gca | aga | ttc | ttg | aaa | gac | tat | ttt | | 4239 |
| Phe | Gly | Glu | Ser | Thr | Thr | Val | Ala | Arg | Phe | Leu | Lys | Asp | Tyr | Phe | | |
| | 1400 | | | | 1405 | | | | | 1410 | | | | | | |
| gga | ttt | cat | cat | gac | cgt | ttg | gcg | gtt | acg | gcg | gtt | gtt | caa | atc | | 4284 |
| Gly | Phe | His | His | Asp | Arg | Leu | Ala | Val | Thr | Ala | Val | Val | Gln | Ile | | |
| | 1415 | | | | 1420 | | | | | 1425 | | | | | | |
| gct | ttt | ccc | att | gcg | tta | gct | tct | atg | ttt | gca | ttc | ttc | gtg | ggc | | 4329 |
| Ala | Phe | Pro | Ile | Ala | Leu | Ala | Ser | Met | Phe | Ala | Phe | Phe | Val | Gly | | |
| | 1430 | | | | 1435 | | | | | 1440 | | | | | | |
| aaa | ctc | aac | ttc | caa | cga | aga | tga | | | | | | | | | 4353 |
| Lys | Leu | Asn | Phe | Gln | Arg | Arg | | | | | | | | | | |
| | 1445 | | | | 1450 | | | | | | | | | | | |

<210> SEQ ID NO 52
<211> LENGTH: 1450
<212> TYPE: PRT
<213> ORGANISM: Arabidopsis lyrata

<400> SEQUENCE: 52

Met Ala His Met Val Gly Ala Asp Glu Ile Glu Ser Leu Arg Val Glu
1               5                   10                  15

Leu Ala Glu Ile Gly Arg Ser Ile Arg Ser Ser Phe Arg Arg His Thr
            20                  25                  30

Ser Ser Phe Arg Ser Ser Ser Arg Tyr Glu Leu Glu Asn Asp Gly
        35                  40                  45

Asp Val Ile Asp His Asp Ala Glu Tyr Ala Leu Gln Trp Ala Glu Ile
    50                  55                  60

Glu Arg Leu Pro Thr Val Lys Arg Met Arg Ser Thr Leu Leu Asp Asp
65                  70                  75                  80

Gly Asp Glu Ser Met Ser Glu Lys Gly Arg Arg Val Val Asp Val Thr
                85                  90                  95

Lys Leu Gly Ala Met Glu Arg His Leu Met Ile Glu Lys Leu Ile Lys
            100                 105                 110

His Ile Glu Asn Asp Asn Leu Lys Leu Leu Lys Lys Ile Arg Lys Arg
        115                 120                 125

Ile Asp Arg Val Gly Met Glu Leu Pro Thr Ile Glu Val Arg Tyr Glu
    130                 135                 140

Ser Leu Lys Val Glu Ala Glu Cys Glu Ile Val Glu Gly Lys Ala Leu
145                 150                 155                 160

Pro Thr Leu Trp Asn Thr Ala Lys Arg Val Leu Ser Glu Leu Val Lys
                165                 170                 175

Leu Thr Gly Ala Lys Thr His Glu Ala Lys Ile Asn Ile Asn Asp
            180                 185                 190

Val Asn Gly Val Ile Lys Pro Gly Arg Leu Thr Leu Leu Gly Pro
        195                 200                 205

Pro Gly Cys Gly Lys Thr Thr Leu Leu Lys Ala Leu Ser Gly Asn Leu
    210                 215                 220

Glu Asn Asn Leu Lys Cys Ser Gly Glu Ile Ser Tyr Asn Gly His Arg

```
            225                 230                 235                 240

Leu Asp Glu Phe Val Pro Gln Lys Thr Ser Ala Tyr Ile Ser Gln Tyr
                    245                 250                 255

Asp Leu His Ile Ala Glu Met Thr Val Arg Glu Thr Val Asp Phe Ser
                260                 265                 270

Ala Arg Cys Gln Gly Val Gly Ser Arg Thr Asp Ile Met Met Glu Val
            275                 280                 285

Ser Lys Arg Glu Lys Glu Lys Gly Ile Ile Pro Asp Thr Glu Val Asp
        290                 295                 300

Ala Tyr Met Lys Ala Ile Ser Val Glu Gly Leu Gln Arg Asn Leu Gln
305                 310                 315                 320

Thr Asp Tyr Ile Leu Lys Ile Leu Gly Leu Asp Ile Cys Ala Glu Thr
                    325                 330                 335

Leu Ile Gly Asp Val Met Arg Arg Gly Ile Ser Gly Gln Lys Lys
                340                 345                 350

Arg Leu Thr Thr Ala Glu Met Ile Val Gly Pro Thr Lys Ala Leu Phe
                355                 360                 365

Met Asp Glu Ile Thr Asn Gly Leu Asp Ser Ser Thr Ala Phe Gln Ile
370                 375                 380

Val Lys Ser Leu Gln Gln Phe Ala His Ile Ser Ser Ala Thr Val Leu
385                 390                 395                 400

Val Ser Leu Leu Gln Pro Ala Pro Glu Ser Phe Asp Leu Phe Asp Asp
                405                 410                 415

Ile Met Leu Met Ala Lys Gly Arg Ile Met Tyr His Gly Pro Arg Gly
                420                 425                 430

Glu Val Leu Asn Phe Phe Glu Asp Cys Gly Phe Arg Cys Pro Glu Arg
                435                 440                 445

Lys Gly Val Ala Asp Phe Leu Gln Glu Val Ile Ser Lys Lys Asp Gln
            450                 455                 460

Ala Gln Tyr Trp Arg His Glu Asp Leu Pro Tyr Ser Phe Val Ser Val
465                 470                 475                 480

Asp Met Leu Ser Lys Lys Phe Lys Glu Leu Ser Ile Gly Lys Lys Met
                485                 490                 495

Glu His Thr Leu Ser Lys Pro Tyr Asp Arg Ser Lys Ser His Lys Asp
                500                 505                 510

Ala Leu Ser Phe Ser Val Tyr Ser Leu Pro Asn Trp Glu Leu Phe Ile
            515                 520                 525

Ala Cys Ile Ser Arg Glu Tyr Leu Leu Met Lys Arg Asn Tyr Phe Val
            530                 535                 540

Tyr Ile Phe Lys Thr Ser Gln Leu Val Met Ala Ala Phe Ile Thr Met
545                 550                 555                 560

Thr Val Tyr Ile Arg Thr Arg Met Gly Ile Asp Ile His Gly Asn
                565                 570                 575

Ser Tyr Met Ser Ala Leu Phe Phe Ala Leu Ile Ile Leu Leu Val Asp
                580                 585                 590

Gly Phe Pro Glu Leu Ser Met Thr Ala Gln Arg Leu Ala Val Phe Tyr
            595                 600                 605

Lys Gln Lys Gln Leu Cys Phe Tyr Pro Ala Trp Ala Tyr Ala Ile Pro
            610                 615                 620

Ala Thr Val Leu Lys Val Pro Leu Ser Phe Phe Glu Ser Leu Val Trp
625                 630                 635                 640

Thr Gly Leu Thr Tyr Tyr Val Ile Gly Tyr Thr Pro Glu Ala Ser Arg
                645                 650                 655
```

```
Phe Phe Lys Gln Phe Ile Leu Leu Phe Ala Val His Phe Thr Ser Ile
            660                 665                 670

Ser Met Phe Arg Cys Leu Ala Ala Ile Phe Gln Thr Val Val Ala Ser
            675                 680                 685

Ile Thr Ala Gly Ser Phe Gly Ile Leu Phe Thr Phe Val Phe Ala Gly
            690                 695                 700

Phe Val Ile Pro Pro Ser Met Pro Ala Trp Leu Lys Trp Gly Phe
705                 710                 715                 720

Trp Val Asn Pro Leu Ser Tyr Gly Glu Ile Gly Leu Ser Val Asn Glu
                725                 730                 735

Phe Leu Ala Pro Arg Trp Asn Gln Met Gln Pro Asn Asn Val Thr Leu
            740                 745                 750

Gly Arg Thr Ile Leu Gln Thr Arg Gly Met Asp Tyr Asp Gly Tyr Met
            755                 760                 765

Tyr Trp Val Ser Leu Tyr Ala Leu Leu Gly Phe Thr Val Leu Phe Asn
            770                 775                 780

Ile Ile Phe Thr Leu Ala Leu Thr Phe Leu Lys Ser Pro Thr Ser Ser
785                 790                 795                 800

Arg Ala Met Ile Ser Gln Asp Lys Leu Ser Glu Leu Gln Gly Thr Glu
            805                 810                 815

Asn Ser Thr Asp Asp Ser Ser Val Lys Lys Thr Thr Asp Ser Pro
            820                 825                 830

Val Lys Thr Glu Glu Glu Gly Asn Met Val Leu Pro Phe Lys Pro Leu
            835                 840                 845

Thr Val Thr Phe Gln Asp Leu Lys Tyr Phe Val Asp Met Pro Val Glu
            850                 855                 860

Met Arg Asp Gln Gly Tyr Asp Gln Lys Lys Leu Gln Leu Leu Ser Asp
865                 870                 875                 880

Ile Thr Gly Ala Phe Arg Pro Gly Ile Leu Thr Ala Leu Met Gly Val
            885                 890                 895

Ser Gly Ala Gly Lys Thr Thr Leu Leu Asp Val Leu Ala Gly Arg Lys
            900                 905                 910

Thr Ser Gly Tyr Ile Glu Gly Asp Ile Arg Ile Ser Gly Phe Pro Lys
            915                 920                 925

Ile Gln Glu Thr Phe Ala Arg Val Ser Gly Tyr Cys Glu Gln Thr Asp
            930                 935                 940

Ile His Ser Pro Asn Ile Thr Val Glu Glu Ser Val Ile Tyr Ser Ala
945                 950                 955                 960

Trp Leu Arg Leu Ala Pro Glu Ile Asp Ser Ala Thr Lys Thr Lys Phe
            965                 970                 975

Val Lys Gln Val Leu Glu Thr Ile Glu Leu Asp Glu Ile Lys Asp Ser
            980                 985                 990

Leu Val Gly Val Thr Gly Val Ser  Gly Leu Ser Thr Glu  Gln Arg Lys
            995                 1000                1005

Arg Leu  Thr Ile Ala Val Glu  Leu Val Ala Asn Pro  Ser Ile Ile
    1010                1015                1020

Phe Met  Asp Glu Pro Thr Thr  Gly Leu Asp Ala Arg  Ala Ala Ala
    1025                1030                1035

Ile Val  Met Arg Ala Val Lys  Asn Val Ala Asp Thr  Gly Arg Thr
    1040                1045                1050

Ile Val  Cys Thr Ile His Gln  Pro Ser Ile Asp Ile  Phe Glu Ala
    1055                1060                1065
```

```
Phe Asp Glu Leu Val Leu Leu Lys Arg Gly Gly Arg Met Ile Tyr
1070                1075                1080

Thr Gly Pro Leu Gly Gln His Ser Arg His Ile Ile Glu Tyr Phe
1085                1090                1095

Glu Ser Val Pro Glu Ile Pro Lys Ile Lys Asp Asn His Asn Pro
1100                1105                1110

Ala Thr Trp Met Leu Asp Val Ser Ser Gln Ser Val Glu Val Glu
1115                1120                1125

Leu Gly Val Asp Phe Ala Lys Ile Tyr His Asp Ser Ala Leu Tyr
1130                1135                1140

Lys Arg Asn Ala Glu Leu Val Lys Gln Leu Ser Gln Pro Asp Ser
1145                1150                1155

Gly Ser Ser Asp Ile Gln Phe Lys Arg Thr Phe Ala Gln Ser Trp
1160                1165                1170

Trp Gly Gln Phe Arg Ser Ile Leu Trp Lys Met Asn Leu Ser Tyr
1175                1180                1185

Trp Arg Ser Pro Ser Tyr Asn Leu Met Arg Met Ile His Thr Leu
1190                1195                1200

Val Ser Ser Leu Ile Phe Gly Ser Leu Phe Trp Lys Gln Gly Gln
1205                1210                1215

Asn Ile Asp Thr Gln Gln Gly Met Phe Thr Val Phe Gly Ala Ile
1220                1225                1230

Tyr Gly Leu Val Leu Phe Leu Gly Ile Asn Asn Cys Ser Ser Ala
1235                1240                1245

Ile Gln Tyr Ile Glu Thr Glu Arg Asn Val Met Tyr Arg Glu Arg
1250                1255                1260

Phe Ala Gly Met Tyr Ser Ala Thr Ala Tyr Ala Leu Gly Gln Val
1265                1270                1275

Val Thr Glu Ile Pro Tyr Ile Phe Ile Gln Ala Ala Glu Phe Val
1280                1285                1290

Ile Ile Thr Tyr Pro Met Ile Gly Phe Tyr Pro Ser Thr Tyr Lys
1295                1300                1305

Val Phe Trp Ser Leu Tyr Ser Met Phe Cys Ser Leu Leu Thr Phe
1310                1315                1320

Asn Tyr Leu Ala Met Phe Leu Val Ser Ile Thr Pro Asn Phe Met
1325                1330                1335

Val Ala Ala Ile Leu Gln Ser Leu Phe Tyr Val Asn Phe Asn Leu
1340                1345                1350

Phe Ser Gly Phe Leu Ile Pro Gln Thr Gln Val Pro Gly Trp Trp
1355                1360                1365

Ile Trp Leu Tyr Tyr Leu Thr Pro Thr Ser Trp Thr Leu Asn Gly
1370                1375                1380

Phe Phe Ser Ser Gln Tyr Gly Asp Ile Asp Glu Lys Ile Asn Val
1385                1390                1395

Phe Gly Glu Ser Thr Thr Val Ala Arg Phe Leu Lys Asp Tyr Phe
1400                1405                1410

Gly Phe His His Asp Arg Leu Ala Val Thr Ala Val Val Gln Ile
1415                1420                1425

Ala Phe Pro Ile Ala Leu Ala Ser Met Phe Ala Phe Phe Val Gly
1430                1435                1440

Lys Leu Asn Phe Gln Arg Arg
1445                1450
```

```
<210> SEQ ID NO 53
<211> LENGTH: 4347
<212> TYPE: DNA
<213> ORGANISM: Capsella rubella
<220> FEATURE:
<221> NAME/KEY: CDS
<222> LOCATION: (1)..(4347)

<400> SEQUENCE: 53
```

| | | | | | | | | | | | | | | | | |
|---|---|---|---|---|---|---|---|---|---|---|---|---|---|---|---|---|
| atg | gct | cac | atg | gtt | gga | cca | gac | gag | att | gag | tcc | ttg | aga | gtg | gag | 48 |
| Met | Ala | His | Met | Val | Gly | Pro | Asp | Glu | Ile | Glu | Ser | Leu | Arg | Val | Glu | |
| 1 | | | | 5 | | | | | 10 | | | | | 15 | | |
| ctt | gca | gag | att | gga | aga | agc | atc | aga | tca | tct | ttc | cgg | aga | cac | act | 96 |
| Leu | Ala | Glu | Ile | Gly | Arg | Ser | Ile | Arg | Ser | Ser | Phe | Arg | Arg | His | Thr | |
| | | | 20 | | | | | 25 | | | | | 30 | | | |
| tct | agt | ttc | aga | agc | agc | tct | tca | atc | tat | gaa | gct | gat | aat | gac | ggt | 144 |
| Ser | Ser | Phe | Arg | Ser | Ser | Ser | Ser | Ile | Tyr | Glu | Ala | Asp | Asn | Asp | Gly | |
| | 35 | | | | | 40 | | | | | 45 | | | | | |
| gat | gtt | aat | gat | gat | cat | cat | gat | gca | gag | tat | gct | ctg | caa | tgg | gct | 192 |
| Asp | Val | Asn | Asp | Asp | His | His | Asp | Ala | Glu | Tyr | Ala | Leu | Gln | Trp | Ala | |
| 50 | | | | | 55 | | | | | 60 | | | | | | |
| aag | att | gag | aga | tta | cca | act | gcc | aaa | cgc | atg | aga | tcg | act | ctc | ctc | 240 |
| Lys | Ile | Glu | Arg | Leu | Pro | Thr | Ala | Lys | Arg | Met | Arg | Ser | Thr | Leu | Leu | |
| 65 | | | | | 70 | | | | | 75 | | | | | 80 | |
| gat | gaa | tcc | atc | acc | gag | aat | gga | aaa | aga | gtc | gtt | gat | gtc | tca | aag | 288 |
| Asp | Glu | Ser | Ile | Thr | Glu | Asn | Gly | Lys | Arg | Val | Val | Asp | Val | Ser | Lys | |
| | | | | 85 | | | | | 90 | | | | | 95 | | |
| ctt | gga | gcc | acc | gaa | cgt | cat | ctg | atg | att | gag | gga | ctt | atc | aaa | cac | 336 |
| Leu | Gly | Ala | Thr | Glu | Arg | His | Leu | Met | Ile | Glu | Gly | Leu | Ile | Lys | His | |
| | | | 100 | | | | | 105 | | | | | 110 | | | |
| att | gag | aat | gat | aat | ctc | aag | ttg | ctc | aag | aaa | atc | aga | aga | aga | ata | 384 |
| Ile | Glu | Asn | Asp | Asn | Leu | Lys | Leu | Leu | Lys | Lys | Ile | Arg | Arg | Arg | Ile | |
| | | 115 | | | | | 120 | | | | | 125 | | | | |
| gac | agg | gtg | ggg | atg | gag | tta | ccg | acc | ata | gaa | gtg | agg | tac | acg | agt | 432 |
| Asp | Arg | Val | Gly | Met | Glu | Leu | Pro | Thr | Ile | Glu | Val | Arg | Tyr | Thr | Ser | |
| 130 | | | | | 135 | | | | | 140 | | | | | | |
| tta | aaa | gta | gag | gcc | gag | tgc | gag | att | gtt | gaa | ggg | aag | gca | ctt | cca | 480 |
| Leu | Lys | Val | Glu | Ala | Glu | Cys | Glu | Ile | Val | Glu | Gly | Lys | Ala | Leu | Pro | |
| 145 | | | | | 150 | | | | | 155 | | | | | 160 | |
| aca | ctg | tgg | aac | act | gcc | aag | cgc | att | ttc | tct | gaa | ctg | gtg | aag | ctc | 528 |
| Thr | Leu | Trp | Asn | Thr | Ala | Lys | Arg | Ile | Phe | Ser | Glu | Leu | Val | Lys | Leu | |
| | | | | 165 | | | | | 170 | | | | | 175 | | |
| act | ggt | gca | aaa | gca | cac | gaa | gcc | aat | ata | agc | att | ctt | aat | gat | gtt | 576 |
| Thr | Gly | Ala | Lys | Ala | His | Glu | Ala | Asn | Ile | Ser | Ile | Leu | Asn | Asp | Val | |
| | | | 180 | | | | | 185 | | | | | 190 | | | |
| aat | ggc | att | ata | aag | ccc | gga | agg | tta | aca | ctg | ttg | ctt | ggt | cct | cct | 624 |
| Asn | Gly | Ile | Ile | Lys | Pro | Gly | Arg | Leu | Thr | Leu | Leu | Leu | Gly | Pro | Pro | |
| | | 195 | | | | | 200 | | | | | 205 | | | | |
| gga | tgc | ggt | aaa | aca | act | atg | tta | aag | gcc | ttg | tct | gga | aat | tta | gaa | 672 |
| Gly | Cys | Gly | Lys | Thr | Thr | Met | Leu | Lys | Ala | Leu | Ser | Gly | Asn | Leu | Glu | |
| 210 | | | | | 215 | | | | | 220 | | | | | | |
| aac | aat | cta | aag | tgt | tca | ggt | gaa | atc | tct | tac | aat | gga | cac | aga | cta | 720 |
| Asn | Asn | Leu | Lys | Cys | Ser | Gly | Glu | Ile | Ser | Tyr | Asn | Gly | His | Arg | Leu | |
| 225 | | | | | 230 | | | | | 235 | | | | | 240 | |
| gac | gag | ttc | gtt | cct | cag | aaa | acc | tcg | gca | tat | ata | agt | caa | tat | gac | 768 |
| Asp | Glu | Phe | Val | Pro | Gln | Lys | Thr | Ser | Ala | Tyr | Ile | Ser | Gln | Tyr | Asp | |
| | | | | 245 | | | | | 250 | | | | | 255 | | |
| ctg | cat | att | gcg | gag | atg | acg | gtg | agg | gag | act | gtt | gac | ttc | tca | gct | 816 |
| Leu | His | Ile | Ala | Glu | Met | Thr | Val | Arg | Glu | Thr | Val | Asp | Phe | Ser | Ala | |
| | | | 260 | | | | | 265 | | | | | 270 | | | |
| cgt | tgt | cag | ggc | gtt | ggt | agc | cga | aca | gat | att | atg | atg | gaa | gtc | agt | 864 |
| | | | | | | | | | | | | | | | | |

-continued

```
                    Arg Cys Gln Gly Val Gly Ser Arg Thr Asp Ile Met Met Glu Val Ser
                            275                 280                 285 aaa cga gaa aag gaa aaa gga atc att cct gac aca gaa gtg gat gct       912
Lys Arg Glu Lys Glu Lys Gly Ile Ile Pro Asp Thr Glu Val Asp Ala
    290                 295                 300 tac atg aaa gca att tct gtt gaa gga ctc aaa aga agt ctg caa aca       960
Tyr Met Lys Ala Ile Ser Val Glu Gly Leu Lys Arg Ser Leu Gln Thr
305                 310                 315                 320 gat tac atc ttg aag att ctc gga cta gac att tgt gca gaa aca ctg      1008
Asp Tyr Ile Leu Lys Ile Leu Gly Leu Asp Ile Cys Ala Glu Thr Leu
                325                 330                 335 att gga gat gtg atg agg aga ggt ata tca gga ggc caa aag aag cgt      1056
Ile Gly Asp Val Met Arg Arg Gly Ile Ser Gly Gly Gln Lys Lys Arg
            340                 345                 350 ctt acg aca gcc gag atg att gtt ggc ccg aca aag gct ctg ttt atg      1104
Leu Thr Thr Ala Glu Met Ile Val Gly Pro Thr Lys Ala Leu Phe Met
        355                 360                 365 gat gaa ata aca aat ggc tta gac agt tcc aca gct ttt cag att gtc      1152
Asp Glu Ile Thr Asn Gly Leu Asp Ser Ser Thr Ala Phe Gln Ile Val
370                 375                 380 aaa tct ctt cag caa ttt gct cac ata tca agt gct act gtg ctt gtt      1200
Lys Ser Leu Gln Gln Phe Ala His Ile Ser Ser Ala Thr Val Leu Val
385                 390                 395                 400 tcg ctt ctt caa ccg gcc cca gaa tct ttc gat ctc ttt gat gac gtt      1248
Ser Leu Leu Gln Pro Ala Pro Glu Ser Phe Asp Leu Phe Asp Asp Val
                405                 410                 415 atg ctg atg gcc aaa gga aga att gtg tat cat ggt cca cgc ggc gaa      1296
Met Leu Met Ala Lys Gly Arg Ile Val Tyr His Gly Pro Arg Gly Glu
            420                 425                 430 gtc ctg aaa ttc ttt gag gat tgt gga ttc caa tgc cct gaa agg aaa      1344
Val Leu Lys Phe Phe Glu Asp Cys Gly Phe Gln Cys Pro Glu Arg Lys
        435                 440                 445 ggt gtt gca gac ttt ctc cag gag gtt ata tcc aaa aaa gac caa gca      1392
Gly Val Ala Asp Phe Leu Gln Glu Val Ile Ser Lys Lys Asp Gln Ala
450                 455                 460 caa tac tgg cgg cac gag gat tta cct tat agt ttt gtc tcg gtg gaa      1440
Gln Tyr Trp Arg His Glu Asp Leu Pro Tyr Ser Phe Val Ser Val Glu
465                 470                 475                 480 atg ttg tca aag aag ttc aag gac ttg agt att gga aaa aag att gag      1488
Met Leu Ser Lys Lys Phe Lys Asp Leu Ser Ile Gly Lys Lys Ile Glu
                485                 490                 495 gaa aca ctt tct aag ccg tat gat aga tcc aaa agc cat aag gat gcc      1536
Glu Thr Leu Ser Lys Pro Tyr Asp Arg Ser Lys Ser His Lys Asp Ala
            500                 505                 510 tta tcc ttc agt gtg tat tca ctt cca aac tgg gag ttg ttc atc gca      1584
Leu Ser Phe Ser Val Tyr Ser Leu Pro Asn Trp Glu Leu Phe Ile Ala
        515                 520                 525 tgc ata tca aga gag tat ctt ctc atg aag aga aac tat ttc gtc tat      1632
Cys Ile Ser Arg Glu Tyr Leu Leu Met Lys Arg Asn Tyr Phe Val Tyr
530                 535                 540 att ttc aag aca tct cag ctt gtt atg gct gca ttc atc act atg act      1680
Ile Phe Lys Thr Ser Gln Leu Val Met Ala Ala Phe Ile Thr Met Thr
545                 550                 555                 560 gtg tat atc cga aca cgg atg ggt att gat atc att cat ggg aat tct      1728
Val Tyr Ile Arg Thr Arg Met Gly Ile Asp Ile Ile His Gly Asn Ser
                565                 570                 575 tac atg agt gcc ctc ttt ttt gcc ctc gtt ata ctt ctt gtt gac gga      1776
Tyr Met Ser Ala Leu Phe Phe Ala Leu Val Ile Leu Leu Val Asp Gly
            580                 585                 590
```

-continued

| | |
|---|---|
| ttc cct gag ttg tct atg acg gct caa cgc cta gcc gtg ttt tac aag<br>Phe Pro Glu Leu Ser Met Thr Ala Gln Arg Leu Ala Val Phe Tyr Lys<br>595                        600                    605 | 1824 |
| cag aag cag ttg tgt ttc tat cct gca tgg gcg tat gca atc cct gca<br>Gln Lys Gln Leu Cys Phe Tyr Pro Ala Trp Ala Tyr Ala Ile Pro Ala<br>610                        615                    620 | 1872 |
| aca gtg cta aag gtc cct ctc tcg ttc ttc gaa tct tta gtt tgg acc<br>Thr Val Leu Lys Val Pro Leu Ser Phe Phe Glu Ser Leu Val Trp Thr<br>625                        630                    635                    640 | 1920 |
| ggc ctc aca tac tat gtc att gga tac acc cct gaa gcc tcc agg ttc<br>Gly Leu Thr Tyr Tyr Val Ile Gly Tyr Thr Pro Glu Ala Ser Arg Phe<br>                    645                    650                    655 | 1968 |
| ttc aag cag ttc att cta ctg ttt gct gtt cac ttc acc tcg ata tcc<br>Phe Lys Gln Phe Ile Leu Leu Phe Ala Val His Phe Thr Ser Ile Ser<br>                    660                    665                    670 | 2016 |
| atg ttt cgg tgt cta gct gca atc ttc cag aca gta gtt gct tca atc<br>Met Phe Arg Cys Leu Ala Ala Ile Phe Gln Thr Val Val Ala Ser Ile<br>          675                    680                    685 | 2064 |
| aca gct ggc agt ttt ggt ata tta ttc aca ttt gtc ttt gct ggt ttt<br>Thr Ala Gly Ser Phe Gly Ile Leu Phe Thr Phe Val Phe Ala Gly Phe<br>690                        695                    700 | 2112 |
| gtc att cca cca aca tca atg cca gca tgg ctc aag tgg ggt ttc tgg<br>Val Ile Pro Pro Thr Ser Met Pro Ala Trp Leu Lys Trp Gly Phe Trp<br>705                        710                    715                    720 | 2160 |
| gca aat cct ttg agt tac ggt gag att ggg cta tcg gta aac gag ttc<br>Ala Asn Pro Leu Ser Tyr Gly Glu Ile Gly Leu Ser Val Asn Glu Phe<br>                    725                    730                    735 | 2208 |
| ctt gcc ccc agg tgg aat cag atg caa ccc aat aat gtt acc tta ggg<br>Leu Ala Pro Arg Trp Asn Gln Met Gln Pro Asn Asn Val Thr Leu Gly<br>          740                    745                    750 | 2256 |
| cga acc ata ctc caa acc cgt gga atg gac tac gat ggt tac atg tac<br>Arg Thr Ile Leu Gln Thr Arg Gly Met Asp Tyr Asp Gly Tyr Met Tyr<br>755                        760                    765 | 2304 |
| tgg gta tca tta tgt gcc ttg ttg gga ttc act gtg ctc ttt aac atc<br>Trp Val Ser Leu Cys Ala Leu Leu Gly Phe Thr Val Leu Phe Asn Ile<br>770                        775                    780 | 2352 |
| att ttc acc ctg gca ctg act ttc ttg aaa tca ccc aca tca tct aaa<br>Ile Phe Thr Leu Ala Leu Thr Phe Leu Lys Ser Pro Thr Ser Ser Lys<br>785                        790                    795                    800 | 2400 |
| gct atg att tcg caa gaa aaa ctc ttt gag ctg caa gga aaa gaa gct<br>Ala Met Ile Ser Gln Glu Lys Leu Phe Glu Leu Gln Gly Lys Glu Ala<br>          805                    810                    815 | 2448 |
| tca aca ggc gac act tca gtc aag aac aag act aca ggt tcc cct gta<br>Ser Thr Gly Asp Thr Ser Val Lys Asn Lys Thr Thr Gly Ser Pro Val<br>820                        825                    830 | 2496 |
| aac aca gaa gaa ggc aag atg gtc tta cct ttc aag ccc ctc aca gta<br>Asn Thr Glu Glu Gly Lys Met Val Leu Pro Phe Lys Pro Leu Thr Val<br>835                        840                    845 | 2544 |
| aca ttt caa gat ttg aac tat ttc gtt gac atg ccc gtg gag atg aga<br>Thr Phe Gln Asp Leu Asn Tyr Phe Val Asp Met Pro Val Glu Met Arg<br>850                        855                    860 | 2592 |
| gac caa gga tat gac cag aag aaa cta caa ctt cta tca aat atc acc<br>Asp Gln Gly Tyr Asp Gln Lys Lys Leu Gln Leu Leu Ser Asn Ile Thr<br>865                        870                    875                    880 | 2640 |
| gga gct ttc cgc cct gga atc cta acg gct ttg atg gga gtg agt gga<br>Gly Ala Phe Arg Pro Gly Ile Leu Thr Ala Leu Met Gly Val Ser Gly<br>                    885                    890                    895 | 2688 |
| gcc gga aaa acc aca ctc ctc gat gtt cta gcc gga aga aaa aca agt<br>Ala Gly Lys Thr Thr Leu Leu Asp Val Leu Ala Gly Arg Lys Thr Ser<br>          900                    905                    910 | 2736 |

```
gga tac atc gaa gga gac atc aga atc agt ggt ttc cct aaa gtt cag    2784
Gly Tyr Ile Glu Gly Asp Ile Arg Ile Ser Gly Phe Pro Lys Val Gln
            915                 920                 925 gaa acg ttc gct aga gtc tca ggc tac tgc gaa caa aca gat atc cac    2832
Glu Thr Phe Ala Arg Val Ser Gly Tyr Cys Glu Gln Thr Asp Ile His
        930                 935                 940 tca cca aac atc acc gtc ggt gaa tct gtg att tac tca gct tgg ctt    2880
Ser Pro Asn Ile Thr Val Gly Glu Ser Val Ile Tyr Ser Ala Trp Leu
945                 950                 955                 960 cgt ctt gct cct gag atc gat tcc gca acc aaa acc caa ttc gtg aaa    2928
Arg Leu Ala Pro Glu Ile Asp Ser Ala Thr Lys Thr Gln Phe Val Lys
                965                 970                 975 caa gtg ctc gag acg atc gaa tta gat gaa atc aaa gac gca ttg gtg    2976
Gln Val Leu Glu Thr Ile Glu Leu Asp Glu Ile Lys Asp Ala Leu Val
            980                 985                 990 gga gtc gcc gga gtg agc ggg ttg tcg acg gag cag agg aag aga ctg    3024
Gly Val Ala Gly Val Ser Gly Leu Ser Thr Glu Gln Arg Lys Arg Leu
        995                 1000                1005 acg att gcg gtg gag ttg gtg gcg aat ccg tcg atc atc ttc atg        3069
Thr Ile Ala Val Glu Leu Val Ala Asn Pro Ser Ile Ile Phe Met
    1010                1015                1020 gac gag ccc acg acg ggg cta gac gca aga gca gcc gcc att gtt        3114
Asp Glu Pro Thr Thr Gly Leu Asp Ala Arg Ala Ala Ala Ile Val
1025                1030                1035 atg aga gct gtg aag aac gtc gct gat act gga cga acc atc gtc        3159
Met Arg Ala Val Lys Asn Val Ala Asp Thr Gly Arg Thr Ile Val
    1040                1045                1050 tgt act att cat cag cct agt atc gac att ttc gaa gct ttc gac        3204
Cys Thr Ile His Gln Pro Ser Ile Asp Ile Phe Glu Ala Phe Asp
    1055                1060                1065 gag ttg gtg ctt ctt aaa aga ggt ggt cgc atg atc tac aca gga        3249
Glu Leu Val Leu Leu Lys Arg Gly Gly Arg Met Ile Tyr Thr Gly
    1070                1075                1080 cca tta ggc cta cat tca tgt cac att atc gag tat ttt gag agt        3294
Pro Leu Gly Leu His Ser Cys His Ile Ile Glu Tyr Phe Glu Ser
1085                1090                1095 gtt cct gaa att cct aaa ata aga gac aac cac aat cca gca aca        3339
Val Pro Glu Ile Pro Lys Ile Arg Asp Asn His Asn Pro Ala Thr
    1100                1105                1110 tgg atg ctt gat gtt agt tca caa tct gta gaa gtt gaa ctt ggc        3384
Trp Met Leu Asp Val Ser Ser Gln Ser Val Glu Val Glu Leu Gly
    1115                1120                1125 gtc gat ttc gca aat atc tac cat gag tct gct ctt tac aag aga        3429
Val Asp Phe Ala Asn Ile Tyr His Glu Ser Ala Leu Tyr Lys Arg
1130                1135                1140 aac tca gag ctt gtt aaa cag tta agc caa cca gat gca gaa tca        3474
Asn Ser Glu Leu Val Lys Gln Leu Ser Gln Pro Asp Ala Glu Ser
1145                1150                1155 agt gat ata cag ttt aag aga act ttt gca caa agt tgg tgg ggg        3519
Ser Asp Ile Gln Phe Lys Arg Thr Phe Ala Gln Ser Trp Trp Gly
    1160                1165                1170 caa ttc aaa tct att cta tgg aaa atg agt ttg tca tat tgg aga        3564
Gln Phe Lys Ser Ile Leu Trp Lys Met Ser Leu Ser Tyr Trp Arg
    1175                1180                1185 agc cct tct tat aac ctt atg cgt atg att cac act ttg atc tct        3609
Ser Pro Ser Tyr Asn Leu Met Arg Met Ile His Thr Leu Ile Ser
    1190                1195                1200 tct ttg atc ttt ggc gca ctc ttc tgg aaa caa ggc caa aaa ata        3654
Ser Leu Ile Phe Gly Ala Leu Phe Trp Lys Gln Gly Gln Lys Ile
```

| | | | | | | | | | | | |
|---|---|---|---|---|---|---|---|---|---|---|---|
| | 1205 | | | 1210 | | | | 1215 | | | |
| gat | act | caa | cag | agt | ttg | ttc | acc | gta | ttt | gga | gcc | atc | tac | ggt | 3699 |
| Asp | Thr | Gln | Gln | Ser | Leu | Phe | Thr | Val | Phe | Gly | Ala | Ile | Tyr | Gly | |
| | 1220 | | | | 1225 | | | | 1230 | | | | | | |
| ttg | gta | ctc | ttc | tta | ggg | ata | aac | aac | tgt | tca | tca | gct | ctt | cag | 3744 |
| Leu | Val | Leu | Phe | Leu | Gly | Ile | Asn | Asn | Cys | Ser | Ser | Ala | Leu | Gln | |
| | 1235 | | | | 1240 | | | | 1245 | | | | | | |
| tat | ttt | gaa | acg | gag | aga | aat | gta | atg | tat | cga | gaa | aga | ttc | gca | 3789 |
| Tyr | Phe | Glu | Thr | Glu | Arg | Asn | Val | Met | Tyr | Arg | Glu | Arg | Phe | Ala | |
| | 1250 | | | | 1255 | | | | 1260 | | | | | | |
| ggg | atg | tac | tca | gcg | aca | gct | tac | gcg | ttg | agt | caa | gtg | gtg | aca | 3834 |
| Gly | Met | Tyr | Ser | Ala | Thr | Ala | Tyr | Ala | Leu | Ser | Gln | Val | Val | Thr | |
| | 1265 | | | | 1270 | | | | 1275 | | | | | | |
| gag | ata | cct | tat | ata | ttc | ata | caa | gct | gcg | gag | ttt | gtg | atc | ata | 3879 |
| Glu | Ile | Pro | Tyr | Ile | Phe | Ile | Gln | Ala | Ala | Glu | Phe | Val | Ile | Ile | |
| | 1280 | | | | 1285 | | | | 1290 | | | | | | |
| aca | tat | cca | atg | atc | ggt | ttc | tat | cct | tcg | acc | tac | aaa | gtc | ttt | 3924 |
| Thr | Tyr | Pro | Met | Ile | Gly | Phe | Tyr | Pro | Ser | Thr | Tyr | Lys | Val | Phe | |
| | 1295 | | | | 1300 | | | | 1305 | | | | | | |
| tgg | tca | ctc | tac | tct | atg | ttt | tgc | tca | ctt | ctc | act | ttc | aac | tac | 3969 |
| Trp | Ser | Leu | Tyr | Ser | Met | Phe | Cys | Ser | Leu | Leu | Thr | Phe | Asn | Tyr | |
| | 1310 | | | | 1315 | | | | 1320 | | | | | | |
| ctt | gcc | atg | ttc | ctc | gta | tcc | atc | acg | cca | aac | ttc | atg | gtt | gcc | 4014 |
| Leu | Ala | Met | Phe | Leu | Val | Ser | Ile | Thr | Pro | Asn | Phe | Met | Val | Ala | |
| | 1325 | | | | 1330 | | | | 1335 | | | | | | |
| gcg | att | ctt | cag | tcg | ctt | ttc | tat | gtt | aat | ttc | aac | ctc | ttc | tcc | 4059 |
| Ala | Ile | Leu | Gln | Ser | Leu | Phe | Tyr | Val | Asn | Phe | Asn | Leu | Phe | Ser | |
| | 1340 | | | | 1345 | | | | 1350 | | | | | | |
| ggg | ttt | ttg | atc | ccc | caa | acg | caa | gtt | cca | ggg | tgg | tgg | att | tgg | 4104 |
| Gly | Phe | Leu | Ile | Pro | Gln | Thr | Gln | Val | Pro | Gly | Trp | Trp | Ile | Trp | |
| | 1355 | | | | 1360 | | | | 1365 | | | | | | |
| tta | tat | tat | cta | aca | cca | acg | tca | tgg | aca | ctc | aac | ggg | ttc | atc | 4149 |
| Leu | Tyr | Tyr | Leu | Thr | Pro | Thr | Ser | Trp | Thr | Leu | Asn | Gly | Phe | Ile | |
| | 1370 | | | | 1375 | | | | 1380 | | | | | | |
| tcg | tct | cag | tac | gga | gat | att | cat | gac | gag | atc | aat | gtc | ttt | gga | 4194 |
| Ser | Ser | Gln | Tyr | Gly | Asp | Ile | His | Asp | Glu | Ile | Asn | Val | Phe | Gly | |
| | 1385 | | | | 1390 | | | | 1395 | | | | | | |
| gaa | aca | acg | act | gtt | gca | gca | ttc | ttg | aaa | gac | tat | ttt | gga | ttt | 4239 |
| Glu | Thr | Thr | Thr | Val | Ala | Ala | Phe | Leu | Lys | Asp | Tyr | Phe | Gly | Phe | |
| | 1400 | | | | 1405 | | | | 1410 | | | | | | |
| cac | cat | gaa | cgt | ttg | gcg | att | acg | gcg | gtt | gtt | caa | atc | gct | ttt | 4284 |
| His | His | Glu | Arg | Leu | Ala | Ile | Thr | Ala | Val | Val | Gln | Ile | Ala | Phe | |
| | 1415 | | | | 1420 | | | | 1425 | | | | | | |
| cca | att | gcg | ttt | gcg | tct | atg | ttt | gcc | ttc | ttc | gtg | ggc | aaa | ctc | 4329 |
| Pro | Ile | Ala | Phe | Ala | Ser | Met | Phe | Ala | Phe | Phe | Val | Gly | Lys | Leu | |
| | 1430 | | | | 1435 | | | | 1440 | | | | | | |
| aac | ttc | caa | cga | cga | tga | | | | | | | | | | 4347 |
| Asn | Phe | Gln | Arg | Arg | | | | | | | | | | | |
| | 1445 | | | | | | | | | | | | | | |

<210> SEQ ID NO 54
<211> LENGTH: 1448
<212> TYPE: PRT
<213> ORGANISM: Capsella rubella

<400> SEQUENCE: 54

Met Ala His Met Val Gly Pro Asp Glu Ile Glu Ser Leu Arg Val Glu
1               5                   10                  15

Leu Ala Glu Ile Gly Arg Ser Ile Arg Ser Ser Phe Arg Arg His Thr
            20                  25                  30

```
Ser Ser Phe Arg Ser Ser Ser Ile Tyr Glu Ala Asp Asn Asp Gly
        35                  40                  45

Asp Val Asn Asp Asp His His Asp Ala Glu Tyr Ala Leu Gln Trp Ala
50                      55                  60

Lys Ile Glu Arg Leu Pro Thr Ala Lys Arg Met Arg Ser Thr Leu Leu
65                  70                  75                  80

Asp Glu Ser Ile Thr Glu Asn Gly Lys Arg Val Val Asp Val Ser Lys
                85                  90                  95

Leu Gly Ala Thr Glu Arg His Leu Met Ile Glu Gly Leu Ile Lys His
            100                 105                 110

Ile Glu Asn Asp Asn Leu Lys Leu Leu Lys Lys Ile Arg Arg Arg Ile
            115                 120                 125

Asp Arg Val Gly Met Glu Leu Pro Thr Ile Glu Val Arg Tyr Thr Ser
        130                 135                 140

Leu Lys Val Glu Ala Glu Cys Glu Ile Val Glu Gly Lys Ala Leu Pro
145                 150                 155                 160

Thr Leu Trp Asn Thr Ala Lys Arg Ile Phe Ser Glu Leu Val Lys Leu
                165                 170                 175

Thr Gly Ala Lys Ala His Glu Ala Asn Ile Ser Ile Leu Asn Asp Val
            180                 185                 190

Asn Gly Ile Ile Lys Pro Gly Arg Leu Thr Leu Leu Leu Gly Pro Pro
            195                 200                 205

Gly Cys Gly Lys Thr Thr Met Leu Lys Ala Leu Ser Gly Asn Leu Glu
        210                 215                 220

Asn Asn Leu Lys Cys Ser Gly Glu Ile Ser Tyr Asn Gly His Arg Leu
225                 230                 235                 240

Asp Glu Phe Val Pro Gln Lys Thr Ser Ala Tyr Ile Ser Gln Tyr Asp
                245                 250                 255

Leu His Ile Ala Glu Met Thr Val Arg Glu Thr Val Asp Phe Ser Ala
            260                 265                 270

Arg Cys Gln Gly Val Gly Ser Arg Thr Asp Ile Met Met Glu Val Ser
        275                 280                 285

Lys Arg Glu Lys Glu Lys Gly Ile Ile Pro Asp Thr Glu Val Asp Ala
290                 295                 300

Tyr Met Lys Ala Ile Ser Val Glu Gly Leu Lys Arg Ser Leu Gln Thr
305                 310                 315                 320

Asp Tyr Ile Leu Lys Ile Leu Gly Leu Asp Ile Cys Ala Glu Thr Leu
                325                 330                 335

Ile Gly Asp Val Met Arg Arg Gly Ile Ser Gly Gly Gln Lys Lys Arg
            340                 345                 350

Leu Thr Thr Ala Glu Met Ile Val Gly Pro Thr Lys Ala Leu Phe Met
        355                 360                 365

Asp Glu Ile Thr Asn Gly Leu Asp Ser Ser Thr Ala Phe Gln Ile Val
        370                 375                 380

Lys Ser Leu Gln Gln Phe Ala His Ile Ser Ser Ala Thr Val Leu Val
385                 390                 395                 400

Ser Leu Leu Gln Pro Ala Pro Glu Ser Phe Asp Leu Phe Asp Asp Val
                405                 410                 415

Met Leu Met Ala Lys Gly Arg Ile Val Tyr His Gly Pro Arg Gly Glu
            420                 425                 430

Val Leu Lys Phe Phe Glu Asp Cys Gly Phe Gln Cys Pro Glu Arg Lys
        435                 440                 445
```

-continued

```
Gly Val Ala Asp Phe Leu Gln Glu Val Ile Ser Lys Lys Asp Gln Ala
        450                 455                 460

Gln Tyr Trp Arg His Glu Asp Leu Pro Tyr Ser Phe Val Ser Val Glu
465                 470                 475                 480

Met Leu Ser Lys Lys Phe Lys Asp Leu Ser Ile Gly Lys Lys Ile Glu
                485                 490                 495

Glu Thr Leu Ser Lys Pro Tyr Asp Arg Ser Lys Ser His Lys Asp Ala
                500                 505                 510

Leu Ser Phe Ser Val Tyr Ser Leu Pro Asn Trp Glu Leu Phe Ile Ala
            515                 520                 525

Cys Ile Ser Arg Glu Tyr Leu Leu Met Lys Arg Asn Tyr Phe Val Tyr
530                 535                 540

Ile Phe Lys Thr Ser Gln Leu Val Met Ala Ala Phe Ile Thr Met Thr
545                 550                 555                 560

Val Tyr Ile Arg Thr Arg Met Gly Ile Asp Ile Ile His Gly Asn Ser
                565                 570                 575

Tyr Met Ser Ala Leu Phe Phe Ala Leu Val Ile Leu Leu Val Asp Gly
            580                 585                 590

Phe Pro Glu Leu Ser Met Thr Ala Gln Arg Leu Ala Val Phe Tyr Lys
            595                 600                 605

Gln Lys Gln Leu Cys Phe Tyr Pro Ala Trp Ala Tyr Ala Ile Pro Ala
610                 615                 620

Thr Val Leu Lys Val Pro Leu Ser Phe Phe Glu Ser Leu Val Trp Thr
625                 630                 635                 640

Gly Leu Thr Tyr Tyr Val Ile Gly Tyr Thr Pro Glu Ala Ser Arg Phe
                645                 650                 655

Phe Lys Gln Phe Ile Leu Leu Phe Ala Val His Phe Thr Ser Ile Ser
                660                 665                 670

Met Phe Arg Cys Leu Ala Ala Ile Phe Gln Thr Val Val Ala Ser Ile
            675                 680                 685

Thr Ala Gly Ser Phe Gly Ile Leu Phe Thr Phe Val Phe Ala Gly Phe
            690                 695                 700

Val Ile Pro Pro Thr Ser Met Pro Ala Trp Leu Lys Trp Gly Phe Trp
705                 710                 715                 720

Ala Asn Pro Leu Ser Tyr Gly Glu Ile Gly Leu Ser Val Asn Glu Phe
                725                 730                 735

Leu Ala Pro Arg Trp Asn Gln Met Gln Pro Asn Asn Val Thr Leu Gly
                740                 745                 750

Arg Thr Ile Leu Gln Thr Arg Gly Met Asp Tyr Asp Gly Tyr Met Tyr
            755                 760                 765

Trp Val Ser Leu Cys Ala Leu Leu Gly Phe Thr Val Leu Phe Asn Ile
770                 775                 780

Ile Phe Thr Leu Ala Leu Thr Phe Leu Lys Ser Pro Thr Ser Ser Lys
785                 790                 795                 800

Ala Met Ile Ser Gln Glu Lys Leu Phe Glu Leu Gln Gly Lys Glu Ala
                805                 810                 815

Ser Thr Gly Asp Thr Ser Val Lys Asn Lys Thr Thr Gly Ser Pro Val
                820                 825                 830

Asn Thr Glu Glu Gly Lys Met Val Leu Pro Phe Lys Pro Leu Thr Val
            835                 840                 845

Thr Phe Gln Asp Leu Asn Tyr Phe Val Asp Met Pro Val Glu Met Arg
850                 855                 860

Asp Gln Gly Tyr Asp Gln Lys Lys Leu Gln Leu Leu Ser Asn Ile Thr
```

-continued

```
865                 870                 875                 880
Gly Ala Phe Arg Pro Gly Ile Leu Thr Ala Leu Met Gly Val Ser Gly
                885                 890                 895
Ala Gly Lys Thr Thr Leu Leu Asp Val Leu Ala Gly Arg Lys Thr Ser
                900                 905                 910
Gly Tyr Ile Glu Gly Asp Ile Arg Ile Ser Gly Phe Pro Lys Val Gln
                915                 920                 925
Glu Thr Phe Ala Arg Val Ser Gly Tyr Cys Glu Gln Thr Asp Ile His
            930                 935                 940
Ser Pro Asn Ile Thr Val Gly Glu Ser Val Ile Tyr Ser Ala Trp Leu
945                 950                 955                 960
Arg Leu Ala Pro Glu Ile Asp Ser Ala Thr Lys Thr Gln Phe Val Lys
                965                 970                 975
Gln Val Leu Glu Thr Ile Glu Leu Asp Glu Ile Lys Asp Ala Leu Val
                980                 985                 990
Gly Val Ala Gly Val Ser Gly Leu  Ser Thr Glu Gln Arg  Lys Arg Leu
                995                 1000                1005
Thr Ile  Ala Val Glu Leu Val  Ala Asn Pro Ser Ile  Ile Phe Met
    1010                1015                1020
Asp Glu  Pro Thr Thr Gly Leu  Asp Ala Arg Ala Ala  Ala Ile Val
    1025                1030                1035
Met Arg  Ala Val Lys Asn Val  Ala Asp Thr Gly Arg  Thr Ile Val
    1040                1045                1050
Cys Thr  Ile His Gln Pro Ser  Ile Asp Ile Phe Glu  Ala Phe Asp
    1055                1060                1065
Glu Leu  Val Leu Leu Lys Arg  Gly Gly Arg Met Ile  Tyr Thr Gly
    1070                1075                1080
Pro Leu  Gly Leu His Ser Cys  His Ile Ile Glu Tyr  Phe Glu Ser
    1085                1090                1095
Val Pro  Glu Ile Pro Lys Ile  Arg Asp Asn His Asn  Pro Ala Thr
    1100                1105                1110
Trp Met  Leu Asp Val Ser Ser  Gln Ser Val Glu Val  Glu Leu Gly
    1115                1120                1125
Val Asp  Phe Ala Asn Ile Tyr  His Glu Ser Ala Leu  Tyr Lys Arg
    1130                1135                1140
Asn Ser  Glu Leu Val Lys Gln  Leu Ser Gln Pro Asp  Ala Glu Ser
    1145                1150                1155
Ser Asp  Ile Gln Phe Lys Arg  Thr Phe Ala Gln Ser  Trp Trp Gly
    1160                1165                1170
Gln Phe  Lys Ser Ile Leu Trp  Lys Met Ser Leu Ser  Tyr Trp Arg
    1175                1180                1185
Ser Pro  Ser Tyr Asn Leu Met  Arg Met Ile His Thr  Leu Ile Ser
    1190                1195                1200
Ser Leu  Ile Phe Gly Ala Leu  Phe Trp Lys Gln Gly  Gln Lys Ile
    1205                1210                1215
Asp Thr  Gln Gln Ser Leu Phe  Thr Val Phe Gly Ala  Ile Tyr Gly
    1220                1225                1230
Leu Val  Leu Phe Leu Gly Ile  Asn Asn Cys Ser Ser  Ala Leu Gln
    1235                1240                1245
Tyr Phe  Glu Thr Glu Arg Asn  Val Met Tyr Arg Glu  Arg Phe Ala
    1250                1255                1260
Gly Met  Tyr Ser Ala Thr Ala  Tyr Ala Leu Ser Gln  Val Val Thr
    1265                1270                1275
```

```
Glu Ile Pro Tyr Ile Phe Gln Ala Ala Glu Phe Val Ile Ile
    1280            1285                1290

Thr Tyr Pro Met Ile Gly Phe Tyr Pro Ser Thr Tyr Lys Val Phe
    1295            1300                1305

Trp Ser Leu Tyr Ser Met Phe Cys Ser Leu Leu Thr Phe Asn Tyr
    1310            1315                1320

Leu Ala Met Phe Leu Val Ser Ile Thr Pro Asn Phe Met Val Ala
    1325            1330                1335

Ala Ile Leu Gln Ser Leu Phe Tyr Val Asn Phe Asn Leu Phe Ser
    1340            1345                1350

Gly Phe Leu Ile Pro Gln Thr Gln Val Pro Gly Trp Trp Ile Trp
    1355            1360                1365

Leu Tyr Tyr Leu Thr Pro Thr Ser Trp Thr Leu Asn Gly Phe Ile
    1370            1375                1380

Ser Ser Gln Tyr Gly Asp Ile His Asp Glu Ile Asn Val Phe Gly
    1385            1390                1395

Glu Thr Thr Thr Val Ala Ala Phe Leu Lys Asp Tyr Phe Gly Phe
    1400            1405                1410

His His Glu Arg Leu Ala Ile Thr Ala Val Val Gln Ile Ala Phe
    1415            1420                1425

Pro Ile Ala Phe Ala Ser Met Phe Ala Phe Phe Val Gly Lys Leu
    1430            1435                1440

Asn Phe Gln Arg Arg
    1445

<210> SEQ ID NO 55
<211> LENGTH: 1658
<212> TYPE: DNA
<213> ORGANISM: Arabidopsis thaliana
<220> FEATURE:
<221> NAME/KEY: CDS
<222> LOCATION: (38)..(1462)

<400> SEQUENCE: 55
gactactaag ttgatctaga aaaaaatcgc cggaaga atg gcg aag cag caa gaa      55
                                        Met Ala Lys Gln Gln Glu
                                          1               5 gca gag ctc atc ttc atc cca ttt cca atc ccc gga cac att ctc gcc     103
Ala Glu Leu Ile Phe Ile Pro Phe Pro Ile Pro Gly His Ile Leu Ala
         10                  15                  20 aca atc gaa ctc gcg aaa cgt ctc atc agt cac caa cct agt cgg atc     151
Thr Ile Glu Leu Ala Lys Arg Leu Ile Ser His Gln Pro Ser Arg Ile
     25                  30                  35 cac acc atc acc atc ctc cat tgg agc tta cct ttt ctt cct caa tct     199
His Thr Ile Thr Ile Leu His Trp Ser Leu Pro Phe Leu Pro Gln Ser
 40                  45                  50 gac act atc gcc ttc ctc aaa tcc cta atc gaa aca gag tct cgt atc     247
Asp Thr Ile Ala Phe Leu Lys Ser Leu Ile Glu Thr Glu Ser Arg Ile
55                   60                  65                  70 cgt ctc att acc tta ccc gat gtc caa aac cct cca cca atg gag cta     295
Arg Leu Ile Thr Leu Pro Asp Val Gln Asn Pro Pro Pro Met Glu Leu
                 75                  80                  85 ttt gtg aaa gct tcc gaa tct tac att ctt gaa tac gtc aag aaa atg     343
Phe Val Lys Ala Ser Glu Ser Tyr Ile Leu Glu Tyr Val Lys Lys Met
             90                  95                 100 gtt cct ttg gtc aga aac gct ctc tcc act ctc ttg tct tct cgt gat     391
Val Pro Leu Val Arg Asn Ala Leu Ser Thr Leu Leu Ser Ser Arg Asp
        105                 110                 115
```

```
gaa tcg gat tca gtt cat gtc gcc gga tta gtt ctt gat ttc ttc tgt      439
Glu Ser Asp Ser Val His Val Ala Gly Leu Val Leu Asp Phe Phe Cys
        120             125             130 gtc cct ttg atc gat gtc gga aac gag ttt aat ctc cct tct tac atc      487
Val Pro Leu Ile Asp Val Gly Asn Glu Phe Asn Leu Pro Ser Tyr Ile
135             140             145             150 ttc ttg acg tgt agc gca agt ttc ttg ggt atg atg aag tat ctt ctg      535
Phe Leu Thr Cys Ser Ala Ser Phe Leu Gly Met Met Lys Tyr Leu Leu
                155             160             165 gag aga aac cgc gaa acc aaa ccg gaa ctt aac cgg agc tct gac gag      583
Glu Arg Asn Arg Glu Thr Lys Pro Glu Leu Asn Arg Ser Ser Asp Glu
        170             175             180 gaa aca ata tca gtt cct ggt ttt gtt aac tcc gtt ccg gtt aaa gtt      631
Glu Thr Ile Ser Val Pro Gly Phe Val Asn Ser Val Pro Val Lys Val
            185             190             195 ttg cca ccg ggt ttg ttc acg act gag tct tac gaa gct tgg gtc gaa      679
Leu Pro Pro Gly Leu Phe Thr Thr Glu Ser Tyr Glu Ala Trp Val Glu
        200             205             210 atg gcg gaa agg ttc cct gaa gcc aag ggt att ttg gtc aat tca ttt      727
Met Ala Glu Arg Phe Pro Glu Ala Lys Gly Ile Leu Val Asn Ser Phe
215             220             225             230 gaa tct cta gaa cgt aac gct ttt gat tat ttc gat cgt cgt ccg gat      775
Glu Ser Leu Glu Arg Asn Ala Phe Asp Tyr Phe Asp Arg Arg Pro Asp
                235             240             245 aat tac cca ccc gtt tac cca atc ggg cca att cta tgc tcc aac gat      823
Asn Tyr Pro Pro Val Tyr Pro Ile Gly Pro Ile Leu Cys Ser Asn Asp
        250             255             260 cgt ccg aat ttg gat tta tcg gaa cga gac cgg atc ttg aaa tgg ctc      871
Arg Pro Asn Leu Asp Leu Ser Glu Arg Asp Arg Ile Leu Lys Trp Leu
            265             270             275 gat gac caa ccc gag tca tct gtt gtg ttt ctc tgc ttc ggg agc ttg      919
Asp Asp Gln Pro Glu Ser Ser Val Val Phe Leu Cys Phe Gly Ser Leu
        280             285             290 aag agt ctc gct gcg tct cag att aaa gag atc gct caa gcc tta gag      967
Lys Ser Leu Ala Ala Ser Gln Ile Lys Glu Ile Ala Gln Ala Leu Glu
295             300             305             310 ctc gtc gga atc aga ttc ctc tgg tcg att cga acg gac ccg aag gag     1015
Leu Val Gly Ile Arg Phe Leu Trp Ser Ile Arg Thr Asp Pro Lys Glu
                315             320             325 tac gcg agc ccg aac gag att tta ccg gac ggg ttt atg aac cga gtc     1063
Tyr Ala Ser Pro Asn Glu Ile Leu Pro Asp Gly Phe Met Asn Arg Val
        330             335             340 atg ggt ttg ggc ctt gtt tgt ggt tgg gct cct caa gtt gaa att ctg     1111
Met Gly Leu Gly Leu Val Cys Gly Trp Ala Pro Gln Val Glu Ile Leu
            345             350             355 gcc cat aaa gca att gga ggg ttc gtg tca cac tgc ggt tgg aac tcg     1159
Ala His Lys Ala Ile Gly Gly Phe Val Ser His Cys Gly Trp Asn Ser
        360             365             370 ata ttg gag agt ttg cgt ttc gga gtt cca att gcc acg tgg cca atg     1207
Ile Leu Glu Ser Leu Arg Phe Gly Val Pro Ile Ala Thr Trp Pro Met
375             380             385             390 tac gcg gaa caa caa cta aac gcg ttc acg att gtg aag gag ctt ggt     1255
Tyr Ala Glu Gln Gln Leu Asn Ala Phe Thr Ile Val Lys Glu Leu Gly
                395             400             405 ttg gcg ttg gag atg cgg ttg gat tac gtg tcg gaa tat gga gaa atc     1303
Leu Ala Leu Glu Met Arg Leu Asp Tyr Val Ser Glu Tyr Gly Glu Ile
        410             415             420 gtg aaa gct gat gaa atc gca gga gcc gta cga tct ttg atg gac ggt     1351
Val Lys Ala Asp Glu Ile Ala Gly Ala Val Arg Ser Leu Met Asp Gly
```

-continued

```
                425                 430                 435
gag gat gtg ccg agg agg aaa ctg aag gag att gcg gag gcg gga aaa    1399
Glu Asp Val Pro Arg Arg Lys Leu Lys Glu Ile Ala Glu Ala Gly Lys
440                 445                 450 gag gct gtg atg gac ggt gga tct tcg ttt gtt gcg gtt aaa aga ttc    1447
Glu Ala Val Met Asp Gly Gly Ser Ser Phe Val Ala Val Lys Arg Phe
455                 460                 465                 470 ata gat ggg ctt tga tcggtgatgg gttttaaagt tttacacca tgcaaacgtt    1502
Ile Asp Gly Leu gtcgttttat gtaatttaag cttgctttga gtgagtctct aatggctttg agctttatcc    1562
aactctataa aagtcctcct tttgatagta tgcatgatct tttgtgttta ctcatttgtt    1622
atatatctaa atagctcatt ttgcattttg ttttat                              1658
```

<210> SEQ ID NO 56
<211> LENGTH: 474
<212> TYPE: PRT
<213> ORGANISM: Arabidopsis thaliana

<400> SEQUENCE: 56

```
Met Ala Lys Gln Gln Glu Ala Glu Leu Ile Phe Ile Pro Phe Pro Ile
1               5                   10                  15

Pro Gly His Ile Leu Ala Thr Ile Glu Leu Ala Lys Arg Leu Ile Ser
                20                  25                  30

His Gln Pro Ser Arg Ile His Thr Ile Thr Ile Leu His Trp Ser Leu
            35                  40                  45

Pro Phe Leu Pro Gln Ser Asp Thr Ile Ala Phe Leu Lys Ser Leu Ile
        50                  55                  60

Glu Thr Glu Ser Arg Ile Arg Leu Ile Thr Leu Pro Asp Val Gln Asn
65                  70                  75                  80

Pro Pro Pro Met Glu Leu Phe Val Lys Ala Ser Glu Ser Tyr Ile Leu
                85                  90                  95

Glu Tyr Val Lys Lys Met Val Pro Leu Val Arg Asn Ala Leu Ser Thr
                100                 105                 110

Leu Leu Ser Ser Arg Asp Glu Ser Asp Ser Val His Val Ala Gly Leu
            115                 120                 125

Val Leu Asp Phe Phe Cys Val Pro Leu Ile Asp Val Gly Asn Glu Phe
        130                 135                 140

Asn Leu Pro Ser Tyr Ile Phe Leu Thr Cys Ser Ala Ser Phe Leu Gly
145                 150                 155                 160

Met Met Lys Tyr Leu Leu Glu Arg Asn Arg Glu Thr Lys Pro Glu Leu
                165                 170                 175

Asn Arg Ser Ser Asp Glu Glu Thr Ile Ser Val Pro Gly Phe Val Asn
            180                 185                 190

Ser Val Pro Val Lys Val Leu Pro Gly Leu Phe Thr Thr Glu Ser
        195                 200                 205

Tyr Glu Ala Trp Val Glu Met Ala Glu Arg Phe Pro Glu Ala Lys Gly
    210                 215                 220

Ile Leu Val Asn Ser Phe Glu Ser Leu Glu Arg Asn Ala Phe Asp Tyr
225                 230                 235                 240

Phe Asp Arg Arg Pro Asp Asn Tyr Pro Val Tyr Pro Ile Gly Pro
                245                 250                 255

Ile Leu Cys Ser Asn Asp Arg Pro Asn Leu Asp Leu Ser Glu Arg Asp
            260                 265                 270

Arg Ile Leu Lys Trp Leu Asp Asp Gln Pro Glu Ser Ser Val Val Phe
```

```
                275                 280                 285
Leu Cys Phe Gly Ser Leu Lys Ser Leu Ala Ala Ser Gln Ile Lys Glu
            290                 295                 300
Ile Ala Gln Ala Leu Glu Leu Val Gly Ile Arg Phe Leu Trp Ser Ile
305                 310                 315                 320
Arg Thr Asp Pro Lys Glu Tyr Ala Ser Pro Asn Glu Ile Leu Pro Asp
                325                 330                 335
Gly Phe Met Asn Arg Val Met Gly Leu Gly Leu Val Cys Gly Trp Ala
            340                 345                 350
Pro Gln Val Glu Ile Leu Ala His Lys Ala Ile Gly Gly Phe Val Ser
            355                 360                 365
His Cys Gly Trp Asn Ser Ile Leu Glu Ser Leu Arg Phe Gly Val Pro
        370                 375                 380
Ile Ala Thr Trp Pro Met Tyr Ala Glu Gln Gln Leu Asn Ala Phe Thr
385                 390                 395                 400
Ile Val Lys Glu Leu Gly Leu Ala Leu Glu Met Arg Leu Asp Tyr Val
                405                 410                 415
Ser Glu Tyr Gly Glu Ile Val Lys Ala Asp Glu Ile Ala Gly Ala Val
            420                 425                 430
Arg Ser Leu Met Asp Gly Glu Asp Val Pro Arg Arg Lys Leu Lys Glu
            435                 440                 445
Ile Ala Glu Ala Gly Lys Glu Ala Val Met Asp Gly Gly Ser Ser Phe
450                 455                 460
Val Ala Val Lys Arg Phe Ile Asp Gly Leu
465                 470

<210> SEQ ID NO 57
<211> LENGTH: 1425
<212> TYPE: DNA
<213> ORGANISM: Arabidopsis lyrata
<220> FEATURE:
<221> NAME/KEY: misc_feature
<223> OTHER INFORMATION: subsp. lyrata
<220> FEATURE:
<221> NAME/KEY: CDS
<222> LOCATION: (1)..(1425)

<400> SEQUENCE: 57 atg gag gag aag caa gaa gca gag ctc ata ttc atc cca ttt cca atc      48
Met Glu Glu Lys Gln Glu Ala Glu Leu Ile Phe Ile Pro Phe Pro Ile
1               5                   10                  15 cct gga cac atg ctt gcc aca atc gaa ctc gcg aaa cgt ctc atc aat      96
Pro Gly His Met Leu Ala Thr Ile Glu Leu Ala Lys Arg Leu Ile Asn
                20                  25                  30 cac aaa cct cgt cgg atc cat acc atc acc atc ctc cat tgg agc tta     144
His Lys Pro Arg Arg Ile His Thr Ile Thr Ile Leu His Trp Ser Leu
            35                  40                  45 cct ttt ctt cct caa tct gac act atc tcc ttc ctc aaa tcc cta atc     192
Pro Phe Leu Pro Gln Ser Asp Thr Ile Ser Phe Leu Lys Ser Leu Ile
        50                  55                  60 caa aca gag tct cgt atc cgt ctt gtt acc tta ccc gac gtc cca aac     240
Gln Thr Glu Ser Arg Ile Arg Leu Val Thr Leu Pro Asp Val Pro Asn
65                  70                  75                  80 cct cca cca atg gaa ctt ttc gtg aaa gct tca gaa tct tac att ctt     288
Pro Pro Pro Met Glu Leu Phe Val Lys Ala Ser Glu Ser Tyr Ile Leu
                85                  90                  95 gaa ttc gtc aag aaa atg gtt cct ttg gtt aaa aaa gct ctc tcc act     336
Glu Phe Val Lys Lys Met Val Pro Leu Val Lys Lys Ala Leu Ser Thr
                100                 105                 110
```

```
ctc ttg tct tct cgt gat gaa tcg gat tca gtt cgt gtc gcc gga tta      384
Leu Leu Ser Ser Arg Asp Glu Ser Asp Ser Val Arg Val Ala Gly Leu
        115                 120                 125 gtt ctc gat ttc ttc tgt gtc cct ttg att gat gtt gga aac gag ttt      432
Val Leu Asp Phe Phe Cys Val Pro Leu Ile Asp Val Gly Asn Glu Phe
130                 135                 140 aat ctc cct tct tac att ttc ttg acg tgt agc gca agt ttc ttg ggt      480
Asn Leu Pro Ser Tyr Ile Phe Leu Thr Cys Ser Ala Ser Phe Leu Gly
145                 150                 155                 160 atg atg aag tat ctc cca gag aga cac cgc aaa atc aaa ccg gaa ttt      528
Met Met Lys Tyr Leu Pro Glu Arg His Arg Lys Ile Lys Pro Glu Phe
                165                 170                 175 aac cgg agc tct ggc gag gaa aca ata ccg gtt cct ggc ttt gtt aac      576
Asn Arg Ser Ser Gly Glu Glu Thr Ile Pro Val Pro Gly Phe Val Asn
            180                 185                 190 tcc gtt ccg gtt aag gtt ttg cca ccg ggt ctg ttc atg aga gag tct      624
Ser Val Pro Val Lys Val Leu Pro Pro Gly Leu Phe Met Arg Glu Ser
        195                 200                 205 tac gaa gct tgg gtc gaa atg gcg gag agg ttc cct gaa gcc aag ggt      672
Tyr Glu Ala Trp Val Glu Met Ala Glu Arg Phe Pro Glu Ala Lys Gly
210                 215                 220 atc ttg gta aat tct ttc gaa tct cta gaa cgt aac gct ttt gat tat      720
Ile Leu Val Asn Ser Phe Glu Ser Leu Glu Arg Asn Ala Phe Asp Tyr
225                 230                 235                 240 ttc gat cat cgt ccg gat aat tac cca ccc gtt tac cca atc ggg ccg      768
Phe Asp His Arg Pro Asp Asn Tyr Pro Pro Val Tyr Pro Ile Gly Pro
                245                 250                 255 att cta tgc tcc aac gat cgt ccg aat ttg gat tta tcg gaa cga gat      816
Ile Leu Cys Ser Asn Asp Arg Pro Asn Leu Asp Leu Ser Glu Arg Asp
            260                 265                 270 cgg atc ttg aga tgg ctc gat gac caa ccc gag tca tca gtt gtg ttc      864
Arg Ile Leu Arg Trp Leu Asp Asp Gln Pro Glu Ser Ser Val Val Phe
        275                 280                 285 ttc tgc ttc ggg agc ttg aag agt ctc gct gct tct cag att aaa gag      912
Phe Cys Phe Gly Ser Leu Lys Ser Leu Ala Ala Ser Gln Ile Lys Glu
290                 295                 300 atc gct caa gcc att gaa ctc gtc gga ttc aga ttc ctc tgg tcg att      960
Ile Ala Gln Ala Ile Glu Leu Val Gly Phe Arg Phe Leu Trp Ser Ile
305                 310                 315                 320 cga aca gat ccg aac gag tac ccg aac ccg tac gag att tta ccg gac     1008
Arg Thr Asp Pro Asn Glu Tyr Pro Asn Pro Tyr Glu Ile Leu Pro Asp
                325                 330                 335 ggg ttt atg aac cgg gtc atg ggt ttg ggt ctt gtt tgt ggt tgg gct     1056
Gly Phe Met Asn Arg Val Met Gly Leu Gly Leu Val Cys Gly Trp Ala
            340                 345                 350 cct caa gtt gaa att ctg gcc cat aaa gca atc gga ggg ttc gtg tca     1104
Pro Gln Val Glu Ile Leu Ala His Lys Ala Ile Gly Gly Phe Val Ser
        355                 360                 365 cac tgc ggt tgg aac tcg att ttg gag agt ttg cgt ttc ggg gtt cca     1152
His Cys Gly Trp Asn Ser Ile Leu Glu Ser Leu Arg Phe Gly Val Pro
370                 375                 380 atc gcc acg tgg cca atg tac gca gaa caa caa cta aac gcg ttc acg     1200
Ile Ala Thr Trp Pro Met Tyr Ala Glu Gln Gln Leu Asn Ala Phe Thr
385                 390                 395                 400 att gtg aag gag ctt ggt ttg gcg ttg gag atg cgg ttg gat tac gtg     1248
Ile Val Lys Glu Leu Gly Leu Ala Leu Glu Met Arg Leu Asp Tyr Val
                405                 410                 415 tgg gct cat gga gaa atc gtg aaa gct gat gaa atc gca ggt gcc gta     1296
Trp Ala His Gly Glu Ile Val Lys Ala Asp Glu Ile Ala Gly Ala Val
```

```
                420                 425                 430
cga tct tta atg gac ggt gag gat gtg cgg agg agg aaa ctg aag gag    1344
Arg Ser Leu Met Asp Gly Glu Asp Val Arg Arg Arg Lys Leu Lys Glu
            435                 440                 445 att gcg gag gcg gca aaa gag gct gtg atg gac ggt gga tct tcg ttt    1392
Ile Ala Glu Ala Ala Lys Glu Ala Val Met Asp Gly Gly Ser Ser Phe
450                 455                 460 gtt gcg gtt aaa aga ttc ata gat ggg ctt tga                        1425
Val Ala Val Lys Arg Phe Ile Asp Gly Leu
465                 470
```

<210> SEQ ID NO 58
<211> LENGTH: 474
<212> TYPE: PRT
<213> ORGANISM: Arabidopsis lyrata

<400> SEQUENCE: 58

```
Met Glu Glu Lys Gln Glu Ala Glu Leu Ile Phe Ile Pro Phe Pro Ile
1               5                   10                  15

Pro Gly His Met Leu Ala Thr Ile Glu Leu Ala Lys Arg Leu Ile Asn
                20                  25                  30

His Lys Pro Arg Ile His Thr Ile Thr Ile Leu His Trp Ser Leu
            35                  40                  45

Pro Phe Leu Pro Gln Ser Asp Thr Ile Ser Phe Leu Lys Ser Leu Ile
    50                  55                  60

Gln Thr Glu Ser Arg Ile Arg Leu Val Thr Leu Pro Asp Val Pro Asn
65                  70                  75                  80

Pro Pro Pro Met Glu Leu Phe Val Lys Ala Ser Glu Ser Tyr Ile Leu
                85                  90                  95

Glu Phe Val Lys Lys Met Val Pro Leu Val Lys Lys Ala Leu Ser Thr
            100                 105                 110

Leu Leu Ser Ser Arg Asp Glu Ser Asp Ser Val Arg Val Ala Gly Leu
        115                 120                 125

Val Leu Asp Phe Phe Cys Val Pro Leu Ile Asp Val Gly Asn Glu Phe
    130                 135                 140

Asn Leu Pro Ser Tyr Ile Phe Leu Thr Cys Ser Ala Ser Phe Leu Gly
145                 150                 155                 160

Met Met Lys Tyr Leu Pro Glu Arg His Arg Lys Ile Lys Pro Glu Phe
                165                 170                 175

Asn Arg Ser Ser Gly Glu Glu Thr Ile Pro Val Pro Gly Phe Val Asn
            180                 185                 190

Ser Val Pro Val Lys Val Leu Pro Gly Leu Phe Met Arg Glu Ser
        195                 200                 205

Tyr Glu Ala Trp Val Glu Met Ala Glu Arg Phe Pro Glu Ala Lys Gly
    210                 215                 220

Ile Leu Val Asn Ser Phe Glu Ser Leu Glu Arg Asn Ala Phe Asp Tyr
225                 230                 235                 240

Phe Asp His Arg Pro Asp Asn Tyr Pro Pro Val Tyr Pro Ile Gly Pro
                245                 250                 255

Ile Leu Cys Ser Asn Asp Arg Pro Asn Leu Asp Leu Ser Glu Arg Asp
            260                 265                 270

Arg Ile Leu Arg Trp Leu Asp Asp Gln Pro Glu Ser Ser Val Val Phe
        275                 280                 285

Phe Cys Phe Gly Ser Leu Lys Ser Leu Ala Ala Ser Gln Ile Lys Glu
    290                 295                 300
```

| | | | | | | | | | | | | | | |
|---|---|---|---|---|---|---|---|---|---|---|---|---|---|---|
|Ile|Ala|Gln|Ala|Ile|Glu|Leu|Val|Gly|Phe|Arg|Phe|Leu|Trp|Ser|Ile|
|305| | | |310| | | |315| | | |320| | |

Arg Thr Asp Pro Asn Glu Tyr Pro Asn Pro Tyr Glu Ile Leu Pro Asp
                325                 330                 335

Gly Phe Met Asn Arg Val Met Gly Leu Gly Leu Val Cys Gly Trp Ala
            340                 345                 350

Pro Gln Val Glu Ile Leu Ala His Lys Ala Ile Gly Gly Phe Val Ser
        355                 360                 365

His Cys Gly Trp Asn Ser Ile Leu Glu Ser Leu Arg Phe Gly Val Pro
    370                 375                 380

Ile Ala Thr Trp Pro Met Tyr Ala Glu Gln Gln Leu Asn Ala Phe Thr
385                 390                 395                 400

Ile Val Lys Glu Leu Gly Leu Ala Leu Glu Met Arg Leu Asp Tyr Val
                405                 410                 415

Trp Ala His Gly Glu Ile Val Lys Ala Asp Glu Ile Ala Gly Ala Val
            420                 425                 430

Arg Ser Leu Met Asp Gly Glu Asp Val Arg Arg Lys Leu Lys Glu
        435                 440                 445

Ile Ala Glu Ala Ala Lys Glu Ala Val Met Asp Gly Gly Ser Ser Phe
450                 455                 460

Val Ala Val Lys Arg Phe Ile Asp Gly Leu
465                 470

<210> SEQ ID NO 59
<211> LENGTH: 1449
<212> TYPE: DNA
<213> ORGANISM: Arabidopsis lyrata
<220> FEATURE:
<221> NAME/KEY: misc_feature
<223> OTHER INFORMATION: subsp. lyrata
<220> FEATURE:
<221> NAME/KEY: CDS
<222> LOCATION: (1)..(1449)

<400> SEQUENCE: 59

```
atg ggg atg caa gaa gaa gca gag ctc gtc atc atc cct ttc ccc ttc      48
Met Gly Met Gln Glu Glu Ala Glu Leu Val Ile Ile Pro Phe Pro Phe
1               5                   10                  15 tcc ggg cac att ctc gca acc atc gaa ctc gcg aaa cgt ctc ata agt      96
Ser Gly His Ile Leu Ala Thr Ile Glu Leu Ala Lys Arg Leu Ile Ser
                20                  25                  30 caa gac aat cct cgg atc cac acc atc acc atc ctc tat tgg gga cta     144
Gln Asp Asn Pro Arg Ile His Thr Ile Thr Ile Leu Tyr Trp Gly Leu
            35                  40                  45 ccc ttt att cct caa gct gac aca atc gct ttc ctc caa tcc cta gtc     192
Pro Phe Ile Pro Gln Ala Asp Thr Ile Ala Phe Leu Gln Ser Leu Val
        50                  55                  60 aaa aat gag tct cgt atc cgt ctc gtt acg ttg ccc gag gtc caa aac     240
Lys Asn Glu Ser Arg Ile Arg Leu Val Thr Leu Pro Glu Val Gln Asn
65                  70                  75                  80 cct cca cca atg gaa ctc ttt gtg gaa ttt gct gaa tct tac att ctt     288
Pro Pro Pro Met Glu Leu Phe Val Glu Phe Ala Glu Ser Tyr Ile Leu
                85                  90                  95 gaa tac gtc aag aaa atg att ccc att gtg aga gat ggt ctc tcc act     336
Glu Tyr Val Lys Lys Met Ile Pro Ile Val Arg Asp Gly Leu Ser Thr
                100                 105                 110 ctc ttg tct tct cgc gat gaa tcg gat tca gtt cgt gtg gct gga ttg     384
Leu Leu Ser Ser Arg Asp Glu Ser Asp Ser Val Arg Val Ala Gly Leu
            115                 120                 125
```

```
gtt ctt gat ttc ttc tgc gtc cct atg atc gat gtg gga aac gag ttt       432
Val Leu Asp Phe Phe Cys Val Pro Met Ile Asp Val Gly Asn Glu Phe
    130             135                 140 aat ctc cct tct tac att ttc ttg acg tgt agc gca ggg ttc ttg ggt       480
Asn Leu Pro Ser Tyr Ile Phe Leu Thr Cys Ser Ala Gly Phe Leu Gly
145             150                 155                 160 atg atg aag tat ctt cca gag aga cac cgc aaa atc aaa tcg gaa ttt       528
Met Met Lys Tyr Leu Pro Glu Arg His Arg Lys Ile Lys Ser Glu Phe
                165                 170                 175 acc cgg agc tct aac gag gag tta aac cct att cct ggt ttt gtc aac       576
Thr Arg Ser Ser Asn Glu Glu Leu Asn Pro Ile Pro Gly Phe Val Asn
            180                 185                 190 tct gtt cca act aag gtt ttg ccg tca ggt ctg ttc atg aaa gag act       624
Ser Val Pro Thr Lys Val Leu Pro Ser Gly Leu Phe Met Lys Glu Thr
        195                 200                 205 tac gag cct tgg gtc gta cta gcc gag aga ttt cct gaa gct aag ggt       672
Tyr Glu Pro Trp Val Val Leu Ala Glu Arg Phe Pro Glu Ala Lys Gly
    210                 215                 220 att ttg gta aat tcc tac aca tct ctc gag cca aac ggt ttt aaa tat       720
Ile Leu Val Asn Ser Tyr Thr Ser Leu Glu Pro Asn Gly Phe Lys Tyr
225             230                 235                 240 ttc gat cgt tgt ccg gat aac tac cca acc gtt tac cca atc ggg ccg       768
Phe Asp Arg Cys Pro Asp Asn Tyr Pro Thr Val Tyr Pro Ile Gly Pro
                245                 250                 255 att tta tgc tcc aac gac cgt ccg aat ttg gac tca tcg gaa cgc gat       816
Ile Leu Cys Ser Asn Asp Arg Pro Asn Leu Asp Ser Ser Glu Arg Asp
            260                 265                 270 cgg atc ata aga tgg ctc gat gac caa ccc gag tca tca gtc gtg ttc       864
Arg Ile Ile Arg Trp Leu Asp Asp Gln Pro Glu Ser Ser Val Val Phe
        275                 280                 285 ctt tgt ttc ggg agc ttg aag aat ctc agt gct act cag atc aac gag       912
Leu Cys Phe Gly Ser Leu Lys Asn Leu Ser Ala Thr Gln Ile Asn Glu
    290                 295                 300 atc gct caa gcc tta gag ctc gtt gaa tgc aaa ttc atc tgg tcg ttc       960
Ile Ala Gln Ala Leu Glu Leu Val Glu Cys Lys Phe Ile Trp Ser Phe
305             310                 315                 320 cga acc aac ccg aag gag tac gca agc ccg tac gag gcc tta cca gac      1008
Arg Thr Asn Pro Lys Glu Tyr Ala Ser Pro Tyr Glu Ala Leu Pro Asp
                325                 330                 335 ggg ttc atg gac cgg gtc atg gat caa ggc ctc gtt tgt ggt tgg gct      1056
Gly Phe Met Asp Arg Val Met Asp Gln Gly Leu Val Cys Gly Trp Ala
            340                 345                 350 cct caa gtt gaa att tta gct cat aaa gct gtc gga gga ttt gta tcg      1104
Pro Gln Val Glu Ile Leu Ala His Lys Ala Val Gly Gly Phe Val Ser
        355                 360                 365 cac tgc ggt tgg aac tcg ata tta gaa agt ttg ggt ttc ggc gtt cca      1152
His Cys Gly Trp Asn Ser Ile Leu Glu Ser Leu Gly Phe Gly Val Pro
    370                 375                 380 atc gcc acg tgg cca atg tac gca gaa caa caa cta aac gcg ttc acg      1200
Ile Ala Thr Trp Pro Met Tyr Ala Glu Gln Gln Leu Asn Ala Phe Thr
385             390                 395                 400 atg gtg aag gaa ctt ggt tta gcc ttg gag atg cgg ttg gat tac gtg      1248
Met Val Lys Glu Leu Gly Leu Ala Leu Glu Met Arg Leu Asp Tyr Val
                405                 410                 415 tcg gaa gat gga gat ata gtg aaa gct gat gaa atc gca gga acc att      1296
Ser Glu Asp Gly Asp Ile Val Lys Ala Asp Glu Ile Ala Gly Thr Ile
            420                 425                 430 aga tct tta atg gac ggt gtg gat gtg cca aag agt aaa gtg aag gag      1344
Arg Ser Leu Met Asp Gly Val Asp Val Pro Lys Ser Lys Val Lys Glu
        435                 440                 445
```

```
att gct gag gcg gga aaa gaa gct gtt ctg gac ggt gga tct tcg ttt       1392
Ile Ala Glu Ala Gly Lys Glu Ala Val Leu Asp Gly Gly Ser Ser Phe
450                 455                 460 gtt gcg gtt aaa aga ttc att ggt gac ttg atc gac ggc gtt tct ata       1440
Val Ala Val Lys Arg Phe Ile Gly Asp Leu Ile Asp Gly Val Ser Ile
465                 470                 475                 480 agg aag tag                                                           1449
Arg Lys <210> SEQ ID NO 60
<211> LENGTH: 482
<212> TYPE: PRT
<213> ORGANISM: Arabidopsis lyrata

<400> SEQUENCE: 60

Met Gly Met Gln Glu Glu Ala Glu Leu Val Ile Ile Pro Phe Pro Phe
1               5                   10                  15

Ser Gly His Ile Leu Ala Thr Ile Glu Leu Ala Lys Arg Leu Ile Ser
                20                  25                  30

Gln Asp Asn Pro Arg Ile His Thr Ile Thr Ile Leu Tyr Trp Gly Leu
            35                  40                  45

Pro Phe Ile Pro Gln Ala Asp Thr Ile Ala Phe Leu Gln Ser Leu Val
        50                  55                  60

Lys Asn Glu Ser Arg Ile Arg Leu Val Thr Leu Pro Glu Val Gln Asn
65                  70                  75                  80

Pro Pro Pro Met Glu Leu Phe Val Glu Phe Ala Glu Ser Tyr Ile Leu
                85                  90                  95

Glu Tyr Val Lys Lys Met Ile Pro Ile Val Arg Asp Gly Leu Ser Thr
                100                 105                 110

Leu Leu Ser Ser Arg Asp Glu Ser Asp Ser Val Arg Val Ala Gly Leu
            115                 120                 125

Val Leu Asp Phe Phe Cys Val Pro Met Ile Asp Val Gly Asn Glu Phe
        130                 135                 140

Asn Leu Pro Ser Tyr Ile Phe Leu Thr Cys Ser Ala Gly Phe Leu Gly
145                 150                 155                 160

Met Met Lys Tyr Leu Pro Glu Arg His Arg Lys Ile Lys Ser Glu Phe
                165                 170                 175

Thr Arg Ser Ser Asn Glu Glu Leu Asn Pro Ile Pro Gly Phe Val Asn
            180                 185                 190

Ser Val Pro Thr Lys Val Leu Pro Ser Gly Leu Phe Met Lys Glu Thr
        195                 200                 205

Tyr Glu Pro Trp Val Val Leu Ala Glu Arg Phe Pro Glu Ala Lys Gly
    210                 215                 220

Ile Leu Val Asn Ser Tyr Thr Ser Leu Glu Pro Asn Gly Phe Lys Tyr
225                 230                 235                 240

Phe Asp Arg Cys Pro Asp Asn Tyr Pro Thr Val Tyr Pro Ile Gly Pro
                245                 250                 255

Ile Leu Cys Ser Asn Asp Arg Pro Asn Leu Asp Ser Ser Glu Arg Asp
            260                 265                 270

Arg Ile Ile Arg Trp Leu Asp Asp Gln Pro Glu Ser Ser Val Val Phe
        275                 280                 285

Leu Cys Phe Gly Ser Leu Lys Asn Leu Ser Ala Thr Gln Ile Asn Glu
    290                 295                 300

Ile Ala Gln Ala Leu Glu Leu Val Glu Cys Lys Phe Ile Trp Ser Phe
305                 310                 315                 320
```

-continued

```
Arg Thr Asn Pro Lys Glu Tyr Ala Ser Pro Tyr Glu Ala Leu Pro Asp
            325                 330                 335

Gly Phe Met Asp Arg Val Met Asp Gln Gly Leu Val Cys Gly Trp Ala
        340                 345                 350

Pro Gln Val Glu Ile Leu Ala His Lys Ala Val Gly Gly Phe Val Ser
    355                 360                 365

His Cys Gly Trp Asn Ser Ile Leu Glu Ser Leu Gly Phe Gly Val Pro
370                 375                 380

Ile Ala Thr Trp Pro Met Tyr Ala Glu Gln Gln Leu Asn Ala Phe Thr
385                 390                 395                 400

Met Val Lys Glu Leu Gly Leu Ala Leu Glu Met Arg Leu Asp Tyr Val
                405                 410                 415

Ser Glu Asp Gly Asp Ile Val Lys Ala Asp Glu Ile Ala Gly Thr Ile
            420                 425                 430

Arg Ser Leu Met Asp Gly Val Asp Val Pro Lys Ser Lys Val Lys Glu
        435                 440                 445

Ile Ala Glu Ala Gly Lys Glu Ala Val Leu Asp Gly Ser Ser Phe
    450                 455                 460

Val Ala Val Lys Arg Phe Ile Gly Asp Leu Ile Asp Gly Val Ser Ile
465                 470                 475                 480

Arg Lys

<210> SEQ ID NO 61
<211> LENGTH: 1785
<212> TYPE: DNA
<213> ORGANISM: Capsella rubella
<220> FEATURE:
<221> NAME/KEY: CDS
<222> LOCATION: (134)..(1576)

<400> SEQUENCE: 61
ctttaaaagt agctaacaat aagcatcaac acatacaaaa cacaactttc tagaaaaaaa      60
cagctttgca caatctcagt ttcattttga ttttgtcatt ttccttattg acttttgagt     120
ttctcagaac aca atg ggg aac caa gaa gca gag ctc gtc atc atc cct       169
            Met Gly Asn Gln Glu Ala Glu Leu Val Ile Ile Pro
            1               5                   10 cac ccg ttc tcc gga cat att ctc gca acc atc gaa ctg gcg aaa cgt       217
His Pro Phe Ser Gly His Ile Leu Ala Thr Ile Glu Leu Ala Lys Arg
            15                  20                  25 ctc atc agt caa gac aat cct cgg atc cac acc atc acc atc ctc tac       265
Leu Ile Ser Gln Asp Asn Pro Arg Ile His Thr Ile Thr Ile Leu Tyr
        30                  35                  40 tgg gga cta ccc ttt att cct caa gct gac acg atc gcc ttc ctc cag       313
Trp Gly Leu Pro Phe Ile Pro Gln Ala Asp Thr Ile Ala Phe Leu Gln
45                  50                  55                  60 tcc cta gtc aaa aat gag cca cgt atc cgt ctc gtt acc ttg ccc gac       361
Ser Leu Val Lys Asn Glu Pro Arg Ile Arg Leu Val Thr Leu Pro Asp
                65                  70                  75 gtc gag aac cct cca ccg atg gag ctc ttc ttg gaa gca gct gaa gct       409
Val Glu Asn Pro Pro Pro Met Glu Leu Phe Leu Glu Ala Ala Glu Ala
            80                  85                  90 tac att ctt gaa tac gtc aag aag atg gtt ccc atc gtg agg gat ggt       457
Tyr Ile Leu Glu Tyr Val Lys Lys Met Val Pro Ile Val Arg Asp Gly
        95                  100                 105 ctc tcc act ctc ttg tct tct cgt gac gaa tct gat cca gtt cgc gtg       505
Leu Ser Thr Leu Leu Ser Ser Arg Asp Glu Ser Asp Pro Val Arg Val
    110                 115                 120
```

-continued

```
gcg gga ttg gtt ctt gat ttc ttc tgc gtc ccc atg att gat gtt gga    553
Ala Gly Leu Val Leu Asp Phe Phe Cys Val Pro Met Ile Asp Val Gly
125                 130                 135                 140 aac gag ttc aac ctc cct tct tac att ttc ttg acg tgc agc gca ggt    601
Asn Glu Phe Asn Leu Pro Ser Tyr Ile Phe Leu Thr Cys Ser Ala Gly
                145                 150                 155 ttc ttg ggt atg atg aag tat ctc cca gag aga cac agc gaa acc aac    649
Phe Leu Gly Met Met Lys Tyr Leu Pro Glu Arg His Ser Glu Thr Asn
            160                 165                 170 tca gag ttt aac cgg agc tct aac gag gag tta aac cgg gtt cct ggt    697
Ser Glu Phe Asn Arg Ser Ser Asn Glu Glu Leu Asn Arg Val Pro Gly
        175                 180                 185 ttt gtc aac tct gtt cct acc aag gtt ttg ccg tca ggt ctg ttc atg    745
Phe Val Asn Ser Val Pro Thr Lys Val Leu Pro Ser Gly Leu Phe Met
    190                 195                 200 aaa gag act tac gag cct tgg gtc gtg cta gca gag agg ttt cct gaa    793
Lys Glu Thr Tyr Glu Pro Trp Val Val Leu Ala Glu Arg Phe Pro Glu
205                 210                 215                 220 gct aag ggt atc tta gta aat tca ttc acg tct tta gag cca aac gct    841
Ala Lys Gly Ile Leu Val Asn Ser Phe Thr Ser Leu Glu Pro Asn Ala
                225                 230                 235 ttt gaa tat ttt gat ggt tgt ccg gat aat tac cca ccc gtt tac cca    889
Phe Glu Tyr Phe Asp Gly Cys Pro Asp Asn Tyr Pro Pro Val Tyr Pro
            240                 245                 250 atc ggg ccg ata ctc tgc tcc aac gat cgt ccg aat ctg gac tca tcg    937
Ile Gly Pro Ile Leu Cys Ser Asn Asp Arg Pro Asn Leu Asp Ser Ser
        255                 260                 265 gaa cga gac cgg atc ata aca tgg ctc gat gat cag aca gag tca tcg    985
Glu Arg Asp Arg Ile Ile Thr Trp Leu Asp Asp Gln Thr Glu Ser Ser
    270                 275                 280 gtt gtg ttc ctt tgc ttc ggg agc ttg aag aat att tct cag aca cag   1033
Val Val Phe Leu Cys Phe Gly Ser Leu Lys Asn Ile Ser Gln Thr Gln
285                 290                 295                 300 atc aaa gag atc gct caa gcc ttg gag ctc gtt gac tgc aaa ttc ctc   1081
Ile Lys Glu Ile Ala Gln Ala Leu Glu Leu Val Asp Cys Lys Phe Leu
                305                 310                 315 tgg tca ata aga acc gac ccg aaa gag tac tcg agc ccg tac gaa gct   1129
Trp Ser Ile Arg Thr Asp Pro Lys Glu Tyr Ser Ser Pro Tyr Glu Ala
            320                 325                 330 tta cca gac ggg ttc atg gac cgg gtt atg gat caa ggt ctt gtt tgt   1177
Leu Pro Asp Gly Phe Met Asp Arg Val Met Asp Gln Gly Leu Val Cys
        335                 340                 345 ggt tgg gct cct caa gtt gag att ctg gcc cat aaa gca atc gga ggg   1225
Gly Trp Ala Pro Gln Val Glu Ile Leu Ala His Lys Ala Ile Gly Gly
    350                 355                 360 ttc gtg tct cac tgc ggt tgg aac tct att ttg gag agt ttg ggt tac   1273
Phe Val Ser His Cys Gly Trp Asn Ser Ile Leu Glu Ser Leu Gly Tyr
365                 370                 375                 380 ggc gtt ccc atc gcc acg tgg ccg atg tac gcg gaa cag cag cta aac   1321
Gly Val Pro Ile Ala Thr Trp Pro Met Tyr Ala Glu Gln Gln Leu Asn
                385                 390                 395 gcg ttc acg atg gtg aag gag ctt ggt atc gca ttg gag atg cgg ttg   1369
Ala Phe Thr Met Val Lys Glu Leu Gly Ile Ala Leu Glu Met Arg Leu
            400                 405                 410 gat tac gtg tcg gaa gat gga cat ata gtg aaa gct gat gag atc gca   1417
Asp Tyr Val Ser Glu Asp Gly His Ile Val Lys Ala Asp Glu Ile Ala
        415                 420                 425 gaa acc gta cga tct ttg atg gac ggt gag gat cgt gcg ctg aag aat   1465
Glu Thr Val Arg Ser Leu Met Asp Gly Glu Asp Arg Ala Leu Lys Asn
```

```
                430             435             440
aca gtg gag gag att gct aat gcg gga aaa gtg gct gtg atg gac ggt    1513
Thr Val Glu Glu Ile Ala Asn Ala Gly Lys Val Ala Val Met Asp Gly
445                 450                 455                 460 gga tct tcg ttt gct gcg att aaa aga ttt atc ggt gat ttg atc atc    1561
Gly Ser Ser Phe Ala Ala Ile Lys Arg Phe Ile Gly Asp Leu Ile Ile
                465                 470                 475 ggc gat ggt ttg tag aaacgtcgta gtttcacttg gcgtgtggtg accatgatgc    1616
Gly Asp Gly Leu
            480 tcggctcaga ttcctttgtt cgttattaaa taatagaaga ctgagtcttc ttacaagtat   1676 tttcaccagt tccatgtttt gtaaaggagt caacgattcc attatttgct tccacgtaat   1736 gttgtatact tgtatcatct catatttaag gatcaaaaac gagttattc               1785
```

<210> SEQ ID NO 62
<211> LENGTH: 480
<212> TYPE: PRT
<213> ORGANISM: Capsella rubella

<400> SEQUENCE: 62

```
Met Gly Asn Gln Glu Ala Glu Leu Val Ile Ile Pro His Pro Phe Ser
1               5                   10                  15

Gly His Ile Leu Ala Thr Ile Glu Leu Ala Lys Arg Leu Ile Ser Gln
            20                  25                  30

Asp Asn Pro Arg Ile His Thr Ile Thr Ile Leu Tyr Trp Gly Leu Pro
        35                  40                  45

Phe Ile Pro Gln Ala Asp Thr Ile Ala Phe Leu Gln Ser Leu Val Lys
    50                  55                  60

Asn Glu Pro Arg Ile Arg Leu Val Thr Leu Pro Asp Val Glu Asn Pro
65                  70                  75                  80

Pro Pro Met Glu Leu Phe Leu Glu Ala Ala Glu Ala Tyr Ile Leu Glu
                85                  90                  95

Tyr Val Lys Lys Met Val Pro Ile Val Arg Asp Gly Leu Ser Thr Leu
            100                 105                 110

Leu Ser Ser Arg Asp Glu Ser Asp Pro Val Arg Val Ala Gly Leu Val
        115                 120                 125

Leu Asp Phe Phe Cys Val Pro Met Ile Asp Val Gly Asn Glu Phe Asn
    130                 135                 140

Leu Pro Ser Tyr Ile Phe Leu Thr Cys Ser Ala Gly Phe Leu Gly Met
145                 150                 155                 160

Met Lys Tyr Leu Pro Glu Arg His Ser Glu Thr Asn Ser Glu Phe Asn
                165                 170                 175

Arg Ser Ser Asn Glu Glu Leu Asn Arg Val Pro Gly Phe Val Asn Ser
            180                 185                 190

Val Pro Thr Lys Val Leu Pro Ser Gly Leu Phe Met Lys Glu Thr Tyr
        195                 200                 205

Glu Pro Trp Val Val Leu Ala Glu Arg Phe Pro Glu Ala Lys Gly Ile
    210                 215                 220

Leu Val Asn Ser Phe Thr Ser Leu Glu Pro Asn Ala Phe Glu Tyr Phe
225                 230                 235                 240

Asp Gly Cys Pro Asp Asn Tyr Pro Pro Val Tyr Pro Ile Gly Pro Ile
                245                 250                 255

Leu Cys Ser Asn Asp Arg Pro Asn Leu Asp Ser Ser Glu Arg Asp Arg
            260                 265                 270
```

```
Ile Ile Thr Trp Leu Asp Asp Gln Thr Glu Ser Ser Val Val Phe Leu
            275                 280                 285

Cys Phe Gly Ser Leu Lys Asn Ile Ser Gln Thr Gln Ile Lys Glu Ile
290                 295                 300

Ala Gln Ala Leu Glu Leu Val Asp Cys Lys Phe Leu Trp Ser Ile Arg
305                 310                 315                 320

Thr Asp Pro Lys Glu Tyr Ser Ser Pro Tyr Glu Ala Leu Pro Asp Gly
                325                 330                 335

Phe Met Asp Arg Val Met Asp Gln Gly Leu Val Cys Gly Trp Ala Pro
                340                 345                 350

Gln Val Glu Ile Leu Ala His Lys Ala Ile Gly Gly Phe Val Ser His
            355                 360                 365

Cys Gly Trp Asn Ser Ile Leu Glu Ser Leu Gly Tyr Gly Val Pro Ile
370                 375                 380

Ala Thr Trp Pro Met Tyr Ala Glu Gln Gln Leu Asn Ala Phe Thr Met
385                 390                 395                 400

Val Lys Glu Leu Gly Ile Ala Leu Glu Met Arg Leu Asp Tyr Val Ser
                405                 410                 415

Glu Asp Gly His Ile Val Lys Ala Asp Glu Ile Ala Glu Thr Val Arg
                420                 425                 430

Ser Leu Met Asp Gly Glu Asp Arg Ala Leu Lys Asn Thr Val Glu Glu
            435                 440                 445

Ile Ala Asn Ala Gly Lys Val Ala Val Met Asp Gly Gly Ser Ser Phe
450                 455                 460

Ala Ala Ile Lys Arg Phe Ile Gly Asp Leu Ile Ile Gly Asp Gly Leu
465                 470                 475                 480
```

<210> SEQ ID NO 63
<211> LENGTH: 61
<212> TYPE: PRT
<213> ORGANISM: Artificial sequence
<220> FEATURE:
<223> OTHER INFORMATION: protein pattern
<220> FEATURE:
<221> NAME/KEY: Variant
<222> LOCATION: (3)..(3)
<223> OTHER INFORMATION: Xaa in position 3 is Leu or Phe
<220> FEATURE:
<221> NAME/KEY: Variant
<222> LOCATION: (10)..(10)
<223> OTHER INFORMATION: Xaa in position 10 is Ala or Thr
<220> FEATURE:
<221> NAME/KEY: Variant
<222> LOCATION: (14)..(14)
<223> OTHER INFORMATION: Xaa in position 14 is Leu or Met
<220> FEATURE:
<221> NAME/KEY: Variant
<222> LOCATION: (18)..(18)
<223> OTHER INFORMATION: Xaa in position 18 is any amino acid
<220> FEATURE:
<221> NAME/KEY: Variant
<222> LOCATION: (24)..(24)
<223> OTHER INFORMATION: Xaa in position 24 is any amino acid
<220> FEATURE:
<221> NAME/KEY: Variant
<222> LOCATION: (31)..(33)
<223> OTHER INFORMATION: Xaa in position 31 to 33 is any or no amino
      acid
<220> FEATURE:
<221> NAME/KEY: Variant
<222> LOCATION: (43)..(43)
<223> OTHER INFORMATION: Xaa in position 43 is Asn or Ser
<220> FEATURE:
<221> NAME/KEY: Variant
<222> LOCATION: (54)..(54)
<223> OTHER INFORMATION: Xaa in position 54 is any amino acid

```
<220> FEATURE:
<221> NAME/KEY: Variant
<222> LOCATION: (57)..(57)
<223> OTHER INFORMATION: Xaa in position 57 is Ile or Val
<220> FEATURE:
<221> NAME/KEY: Variant
<222> LOCATION: (58)..(58)
<223> OTHER INFORMATION: Xaa in position 58 is Ala, Glu or Ser
<220> FEATURE:
<221> NAME/KEY: Variant
<222> LOCATION: (59)..(59)
<223> OTHER INFORMATION: Xaa in position 59 is any amino acid

<400> SEQUENCE: 63

Gly Ser Xaa Val Ile Asn Ile Gly Asp Xaa Met Gln Ile Xaa Ser Asn
1               5                   10                  15

Gly Xaa Tyr Lys Ser Val Glu Xaa Arg Val Leu Ala Asn Gly Xaa Xaa
            20                  25                  30

Xaa Asn Arg Ile Ser Val Pro Ile Phe Val Xaa Pro Lys Pro Glu Ser
        35                  40                  45

Val Ile Gly Pro Leu Xaa Glu Val Xaa Xaa Xaa Gly Glu
    50                  55                  60

<210> SEQ ID NO 64
<211> LENGTH: 49
<212> TYPE: PRT
<213> ORGANISM: Artificial sequence
<220> FEATURE:
<223> OTHER INFORMATION: protein pattern
<220> FEATURE:
<221> NAME/KEY: Variant
<222> LOCATION: (1)..(1)
<223> OTHER INFORMATION: Xaa in position 1 is Lys or Gln
<220> FEATURE:
<221> NAME/KEY: Variant
<222> LOCATION: (4)..(4)
<223> OTHER INFORMATION: Xaa in position 4 is Ala or Asp
<220> FEATURE:
<221> NAME/KEY: Variant
<222> LOCATION: (11)..(11)
<223> OTHER INFORMATION: Xaa in position 11 is Asp or Glu
<220> FEATURE:
<221> NAME/KEY: Variant
<222> LOCATION: (15)..(15)
<223> OTHER INFORMATION: Xaa in position 15 is Phe or Tyr
<220> FEATURE:
<221> NAME/KEY: Variant
<222> LOCATION: (19)..(19)
<223> OTHER INFORMATION: Xaa in position 19 is any amino acid
<220> FEATURE:
<221> NAME/KEY: Variant
<222> LOCATION: (21)..(21)
<223> OTHER INFORMATION: Xaa in position 21 is any amino acid
<220> FEATURE:
<221> NAME/KEY: Variant
<222> LOCATION: (23)..(23)
<223> OTHER INFORMATION: Xaa in position 23 is Lys or Arg
<220> FEATURE:
<221> NAME/KEY: Variant
<222> LOCATION: (28)..(28)
<223> OTHER INFORMATION: Xaa in position 28 is Ile, Leu or Val
<220> FEATURE:
<221> NAME/KEY: Variant
<222> LOCATION: (31)..(31)
<223> OTHER INFORMATION: Xaa in position 31 is any amino acid
<220> FEATURE:
<221> NAME/KEY: Variant
<222> LOCATION: (36)..(36)
<223> OTHER INFORMATION: Xaa in position 36 is Ile or Leu
<220> FEATURE:
<221> NAME/KEY: Variant
<222> LOCATION: (49)..(49)
<223> OTHER INFORMATION: Xaa in position 49 is Leu or Met
```

```
<400> SEQUENCE: 64

Xaa Ser Asp Xaa Leu Tyr Gln Tyr Ile Leu Xaa Thr Ser Val Xaa Pro
1               5                   10                  15

Arg Glu Xaa Glu Xaa Met Xaa Glu Leu Arg Glu Xaa Thr Ala Xaa His
            20              25                  30

Pro Trp Asn Xaa Met Thr Thr Ser Ala Asp Glu Gly Gln Phe Leu Asn
            35                  40                  45

Xaa

<210> SEQ ID NO 65
<211> LENGTH: 60
<212> TYPE: PRT
<213> ORGANISM: Artificial sequence
<220> FEATURE:
<223> OTHER INFORMATION: protein pattern

<400> SEQUENCE: 65

Gly Asn Leu Glu Asn Asn Leu Lys Cys Ser Gly Glu Ile Ser Tyr Asn
1               5                   10                  15

Gly His Arg Leu Asp Glu Phe Val Pro Gln Lys Thr Ser Ala Tyr Ile
            20                  25                  30

Ser Gln Tyr Asp Leu His Ile Ala Glu Met Thr Val Arg Glu Thr Val
            35                  40                  45

Asp Phe Ser Ala Arg Cys Gln Gly Val Gly Ser Arg
        50                  55                  60

<210> SEQ ID NO 66
<211> LENGTH: 61
<212> TYPE: PRT
<213> ORGANISM: Artificial sequence
<220> FEATURE:
<223> OTHER INFORMATION: protein pattern
<220> FEATURE:
<221> NAME/KEY: Variant
<222> LOCATION: (21)..(21)
<223> OTHER INFORMATION: Xaa in position 21 is Ile or Val
<220> FEATURE:
<221> NAME/KEY: Variant
<222> LOCATION: (45)..(45)
<223> OTHER INFORMATION: Xaa in position 45 is any or no amino acid
<220> FEATURE:
<221> NAME/KEY: Variant
<222> LOCATION: (47)..(47)
<223> OTHER INFORMATION: Xaa in position 47 is any or no amino acid

<400> SEQUENCE: 66

Ala Gly Arg Lys Thr Ser Gly Tyr Ile Glu Gly Asp Ile Arg Ile Ser
1               5                   10                  15

Gly Phe Pro Lys Xaa Gln Glu Thr Phe Ala Arg Val Ser Gly Tyr Cys
            20                  25                  30

Glu Gln Thr Asp Ile His Ser Pro Asn Ile Thr Val Xaa Glu Xaa Ser
            35                  40                  45

Val Ile Tyr Ser Ala Trp Leu Arg Leu Ala Pro Glu Ile
        50                  55                  60

<210> SEQ ID NO 67
<211> LENGTH: 60
<212> TYPE: PRT
<213> ORGANISM: Artificial sequence
<220> FEATURE:
<223> OTHER INFORMATION: protein pattern
<220> FEATURE:
<221> NAME/KEY: Variant
<222> LOCATION: (6)..(6)
```

```
<223> OTHER INFORMATION: Xaa in position 6 is any amino acid

<400> SEQUENCE: 67

Asp Ile Cys Ala Glu Xaa Leu Ile Gly Asp Val Met Arg Arg Gly Ile
1               5                   10                  15

Ser Gly Gly Gln Lys Lys Arg Leu Thr Thr Ala Glu Met Ile Val Gly
            20                  25                  30

Pro Thr Lys Ala Leu Phe Met Asp Glu Ile Thr Asn Gly Leu Asp Ser
        35                  40                  45

Ser Thr Ala Phe Gln Ile Val Lys Ser Leu Gln Gln
    50                  55                  60

<210> SEQ ID NO 68
<211> LENGTH: 60
<212> TYPE: PRT
<213> ORGANISM: Artificial sequence
<220> FEATURE:
<223> OTHER INFORMATION: protein pattern
<220> FEATURE:
<221> NAME/KEY: Variant
<222> LOCATION: (2)..(2)
<223> OTHER INFORMATION: Xaa in position 2 is any amino acid

<400> SEQUENCE: 68

Gly Xaa Ser Gly Leu Ser Thr Glu Gln Arg Lys Arg Leu Thr Ile Ala
1               5                   10                  15

Val Glu Leu Val Ala Asn Pro Ser Ile Ile Phe Met Asp Glu Pro Thr
            20                  25                  30

Thr Gly Leu Asp Ala Arg Ala Ala Ala Ile Val Met Arg Ala Val Lys
        35                  40                  45

Asn Val Ala Asp Thr Gly Arg Thr Ile Val Cys Thr
    50                  55                  60

<210> SEQ ID NO 69
<211> LENGTH: 59
<212> TYPE: PRT
<213> ORGANISM: Artificial sequence
<220> FEATURE:
<223> OTHER INFORMATION: protein pattern
<220> FEATURE:
<221> NAME/KEY: Variant
<222> LOCATION: (3)..(3)
<223> OTHER INFORMATION: Xaa in position 3 is Asp or Gly
<220> FEATURE:
<221> NAME/KEY: Variant
<222> LOCATION: (4)..(4)
<223> OTHER INFORMATION: Xaa in position 4 is any amino acid
<220> FEATURE:
<221> NAME/KEY: Variant
<222> LOCATION: (6)..(6)
<223> OTHER INFORMATION: Xaa in position 6 is Ile or Leu
<220> FEATURE:
<221> NAME/KEY: Variant
<222> LOCATION: (22)..(22)
<223> OTHER INFORMATION: Xaa in position 22 is Ile or Val
<220> FEATURE:
<221> NAME/KEY: Variant
<222> LOCATION: (39)..(39)
<223> OTHER INFORMATION: Xaa in position 39 is any amino acid
<220> FEATURE:
<221> NAME/KEY: Variant
<222> LOCATION: (40)..(40)
<223> OTHER INFORMATION: Xaa in position 40 is Phe or Tyr

<400> SEQUENCE: 69

Val Met Xaa Xaa Gly Xaa Val Cys Gly Trp Ala Pro Gln Val Glu Ile
1               5                   10                  15
```

Leu Ala His Lys Ala Xaa Gly Gly Phe Val Ser His Cys Gly Trp Asn
                 20                  25                  30

Ser Ile Leu Glu Ser Leu Xaa Xaa Gly Val Pro Ile Ala Thr Trp Pro
             35                  40                  45

Met Tyr Ala Glu Gln Gln Leu Asn Ala Phe Thr
     50                  55

<210> SEQ ID NO 70
<211> LENGTH: 60
<212> TYPE: PRT
<213> ORGANISM: Artificial sequence
<220> FEATURE:
<223> OTHER INFORMATION: protein pattern
<220> FEATURE:
<221> NAME/KEY: Variant
<222> LOCATION: (11)..(11)
<223> OTHER INFORMATION: Xaa in position 11 is Asp or Gly
<220> FEATURE:
<221> NAME/KEY: Variant
<222> LOCATION: (12)..(12)
<223> OTHER INFORMATION: Xaa in position 12 is Pro or Ser
<220> FEATURE:
<221> NAME/KEY: Variant
<222> LOCATION: (14)..(14)
<223> OTHER INFORMATION: Xaa in position 14 is His or Arg
<220> FEATURE:
<221> NAME/KEY: Variant
<222> LOCATION: (27)..(27)
<223> OTHER INFORMATION: Xaa in position 27 is Leu or Met
<220> FEATURE:
<221> NAME/KEY: Variant
<222> LOCATION: (47)..(47)
<223> OTHER INFORMATION: Xaa in position 47 is Gly or Ser
<220> FEATURE:
<221> NAME/KEY: Variant
<222> LOCATION: (56)..(56)
<223> OTHER INFORMATION: Xaa in position 56 is Leu or Pro
<220> FEATURE:
<221> NAME/KEY: Variant
<222> LOCATION: (59)..(59)
<223> OTHER INFORMATION: Xaa in position 59 is any amino acid
<220> FEATURE:
<221> NAME/KEY: Variant
<222> LOCATION: (60)..(60)
<223> OTHER INFORMATION: Xaa in position 60 is Arg or Ser

<400> SEQUENCE: 70

Ser Thr Leu Leu Ser Ser Arg Asp Glu Ser Xaa Xaa Val Xaa Val Ala
1               5                   10                  15

Gly Leu Val Leu Asp Phe Phe Cys Val Pro Xaa Ile Asp Val Gly Asn
                 20                  25                  30

Glu Phe Asn Leu Pro Ser Tyr Ile Phe Leu Thr Cys Ser Ala Xaa Phe
             35                  40                  45

Leu Gly Met Met Lys Tyr Leu Xaa Glu Arg Xaa Xaa
     50                  55                  60

<210> SEQ ID NO 71
<211> LENGTH: 10304
<212> TYPE: DNA
<213> ORGANISM: Artificial Sequence
<220> FEATURE:
<223> OTHER INFORMATION: vector

<400> SEQUENCE: 71
gaagattagc ctcttcaatt tcagaaagaa tgctgaccca cagatggtta gagaggccta      60
cgcggcaggt ctcatcaaga cgatctaccc gagtaataat ctccaggaga tcaaatacct     120
tcccaagaag gttaaagatg cagtcaaaag attcaggact aactgcatca agaacacaga     180

```
gaaagatata tttctcaaga tcagaagtac tattccagta tggacgattc aaggcttgct    240
tcataaacca aggcaagtaa tagagattgg agtctctaag aaagtagttc ctactgaatc    300
aaaggccatg gagtcaaaaa ttcagatcga ggatctaaca gaactcgccg tgaagactgg    360
cgaacagttc atacagagtc ttttacgact caatgacaag aagaaaatct tcgtcaacat    420
ggtggagcac gacactctcg tctactccaa gaatatcaaa gatacagtct cagaagacca    480
aagggctatt gagacttttc aacaaagggt aatatcggga aacctcctcg gattccattg    540
cccagctatc tgtcacttca tcaaaaggac agtagaaaag gaaggtggca cctacaaatg    600
ccatcattgc gataaaggaa aggctatcgt tcaagatgcc tctgccgaca gtggtcccaa    660
agatggaccc ccacccacga ggagcatcgt ggaaaaagaa gacgttccaa ccacgtcttc    720
aaagcaagtg gattgatgtg atatctccac tgacgtaagg gatgacgcac aatcccacta    780
tccttcgcaa gacccttcct ctatataagg aagttcattt catttggaga ggactccggt    840
atttttacaa caataccaca acaaaacaaa caacaaacaa cattacaatt tactattcta    900
gtcgacctgc aggcggccgc actagtgata tcacaagttt gtacaaaaaa gcaggctcat    960
atttttacaa caattaccaa caacaacaaa caacaaacaa cattacaatt actatttaca   1020
attacaatta ccatggacta caaggacgac gatgacaaga caactttgta tacaaaagtt   1080
gcaatggctc caacactctt gacaacccaa ttctcaaatc cagctgaagt aaccgacttt   1140
gtagtctaca aggaaatggt gttaagggt ttatcagaaa caggaatcaa agctcttcca   1200
gaacaataca ttcagccact tgaagaacga ctcatcaaca aattcgtcaa cgaaacagat   1260
gaagccattc cagttatcga tatgtcgaac cctgatgagg acagagtcgc tgaagctgtt   1320
tgtgatgctg ctgagaaatg ggggttcttt caagtgatca atcatggagt tcctttggaa   1380
gttcttgatg acgtcaaggc tgcgactcac aagttcttca tctccctgt tgaagagaag   1440 cgcaagttca ctaaagagaa ttcgctgtcg acgactgtta ggtttgggac gagttttagt   1500
cctcttgcag agcaagcgct tgagtggaaa gattatctca gcctcttctt tgtctctgaa   1560
gctgaagctg aacagttctg gcctgatatc tgcaggaatg aaacgttaga gtacattaac   1620
aagtcaaaga gatggtgag gaggcttcta gagtatttgg gaaagaatct caatgttaaa   1680
gagcttgacg agacgaaaga atcactcttt atgggctcga ttcgagtcaa ccttaactac   1740
taccccatct gccctaatcc ggacctaaca gttggtgttg gtcgccactc agacgtctct   1800
tctctcacca ttctcttaca agaccagatc ggtggtctac acgtgcgttc tctggcttca   1860
gggaactggg ttcacgtgcc tccggttgct ggatcttttg tgatcaacat cggagatgcg   1920
atgcagatca tgagcaatgg tctgtacaag agcgtggagc atcgtgtctt agccaatggt   1980
tacaataata gaatctctgt tcctatcttt gtgaacccaa aaccagagtc agttattggt   2040
cctctacctg aggtgattgc aaacggagag gaaccgattt acagagacgt cctgtactct   2100
gattacgtca gtatttcctt caggaaggca cacgatggaa agaaaaccgt cgattacgcc   2160
aagatctgat acccagcttt cttgtacaaa gtggtgatat cccgcggcca tgctagagtc   2220
cgcaaaaatc accagtctct ctctacaaat ctatctctct ctatttttct ccagaataat   2280
gtgtgagtag ttcccagata agggaattag ggttcttata gggtttcgct catgtgttga   2340
gcatataaga aaccctagt atgtatttgt atttgtaaaa tacttctatc aataaaattt   2400
ctaattccta aaaccaaaat ccagtgacct gcaggcatgc gacgtcgggc ccaagcttag   2460
cttgagcttg gatcagattg tcgtttcccg ccttcagttt aaactatcag tgtttgacag   2520
gatatattgg cgggtaaacc taagagaaaa gagcgtttat tagaataacg gatatttaaa   2580
```

```
agggcgtgaa aaggtttatc cgttcgtcca tttgtatgtg catgccaacc acagggttcc   2640
cctcgggatc aaagtacttt gatccaaccc ctccgctgct atagtgcagt cggcttctga   2700
cgttcagtgc agccgtcttc tgaaaacgac atgtcgcaca agtcctaagt tacgcgacag   2760
gctgccgccc tgcccttttc ctggcgtttt cttgtcgcgt gttttagtcg cataaagtag   2820
aatacttgcg actagaaccg gagacattac gccatgaaca agagcgccgc cgctggcctg   2880
ctgggctatg cccgcgtcag caccgacgac caggacttga ccaaccaacg ggccgaactg   2940
cacgcggccg gctgcaccaa gctgttttcc gagaagatca ccggcaccag gcgcgaccgc   3000
ccggagctgg ccaggatgct tgaccaccta cgccctggcg acgttgtgac agtgaccagg   3060
ctagaccgcc tggcccgcag cacccgcgac ctactggaca ttgccgagcg catccaggag   3120
gccggcgcgg gcctgcgtag cctggcagag ccgtgggccg acaccaccac gccggccggc   3180
cgcatggtgt tgaccgtgtt cgccggcatt gccgagttcg agcgttccct aatcatcgac   3240
cgcacccgga gcgggcgcga ggccgccaag gcccgaggcg tgaagtttgg ccccgcgcct   3300
accctcaccc cggcacagat cgcgcacgcc cgcgagctga tcgaccagga aggccgcacc   3360
gtgaaagagg cggctgcact gcttggcgtg catcgctcga ccctgtaccg cgcacttgag   3420
cgcagcgagg aagtgacgcc caccgaggcc aggcggcgcg gtgccttccg tgaggacgca   3480
ttgaccgagg ccgacgccct ggcggccgcc gagaatgaac gccaagagga caagcatga   3540 aaccgcacca ggacggccag gacgaaccgt ttttcattac cgaagagatc gaggcggaga   3600
tgatcgcggc cgggtacgtg ttcgagccgc ccgcgcacgt ctcaaccgtg cggctgcatg   3660
aaatcctggc cggtttgtct gatgccaagc tggcggcctg gccggccagc ttggccgctg   3720
aagaaaccga gcgccgccgt ctaaaaaggt gatgtgtatt tgagtaaaac agcttgcgtc   3780
atgcggtcgc tgcgtatatg atgcgatgag taaataaaca aatacgcaag gggaacgcat   3840
gaaggttatc gctgtactta accagaaagg cgggtcaggc aagacgacca tcgcaaccca   3900
tctagcccgc gccctgcaac tcgccggggc cgatgttctg ttagtcgatt ccgatcccca   3960
gggcagtgcc cgcgattggg cggccgtgcg ggaagatcaa ccgctaaccg ttgtcggcat   4020
cgaccgcccg acgattgacc gcgacgtgaa ggccatcggc cggcgcgact tcgtagtgat   4080
cgacggagcg ccccaggcgg cggacttggc tgtgtccgcg atcaaggcag ccgacttcgt   4140
gctgattccg gtgcagccaa gcccttacga catatgggcc accgccgacc tggtggagct   4200
ggttaagcag cgcattgagg tcacggatgg aaggctacaa gcggcctttg tcgtgtcgcg   4260
ggcgatcaaa ggcacgcgca tcggcggtga ggttgccgag gcgctggccg gtacgagct   4320 gcccattctt gagtcccgta tcacgcagcg cgtgagctac ccaggcactg ccgccgccgg   4380
cacaaccgtt cttgaatcag aacccgaggg cgacgctgcc cgcgaggtcc aggcgctggc   4440
cgctgaaatt aaatcaaaac tcatttgagt taatgaggta agagaaaat gagcaaaagc   4500 acaaacacgc taagtgccgg ccgtccgagc gcacgcagca gcaaggctgc aacgttggcc   4560
agcctggcag acacgccagc catgaagcgg gtcaactttc agttgccggc ggaggatcac   4620
accaagctga agatgtacgc ggtacgccaa ggcaagacca ttaccgagct gctatctgaa   4680
tacatcgcgc agctaccaga gtaaatgagc aaatgaataa atgagtagat gaattttagc   4740
ggctaaagga ggcggcatgg aaaatcaaga acaaccaggc accgacgccg tggaatgccc   4800
catgtgtgga ggaacgggcg gttggccagg cgtaagcggc tgggttgtct gccggccctg   4860
caatggcact ggaaccccca gcccgaggga atcggcgtga cggtcgcaaa ccatccggcc   4920
```

```
cggtacaaat cggcgcggcg ctgggtgatg acctggtgga gaagttgaag gccgcgcagg    4980
ccgcccagcg gcaacgcatc gaggcagaag cacgccccgg tgaatcgtgg caagcggccg    5040
ctgatcgaat ccgcaaagaa tcccggcaac cgccggcagc cggtgcgccg tcgattagga    5100
agccgcccaa gggcgacgag caaccagatt ttttcgttcc gatgctctat gacgtgggca    5160
cccgcgatag tcgcagcatc atggacgtgg ccgttttccg tctgtcgaag cgtgaccgac    5220
gagctggcga ggtgatccgc tacgagcttc cagacgggca cgtagaggtt ccgcagggc     5280
cggccggcat ggccagtgtg tgggattacg acctggtact gatggcggtt tcccatctaa    5340
ccgaatccat gaaccgatac cgggaaggga agggagacaa gcccggccgc gtgttccgtc    5400
cacacgttgc ggacgtactc aagttctgcc ggcgagccga tggcggaaag cagaaagacg    5460
acctggtaga aacctgcatt cggttaaaca ccacgcacgt tgccatgcag cgtacgaaga    5520
aggccaagaa cggccgcctg gtgacggtat ccgagggtga agccttgatt agccgctaca    5580
agatcgtaaa gagcgaaacc gggcggccgg agtacatcga gatcgagcta gctgattgga    5640
tgtaccgcga gatcacagaa ggcaagaacc cggacgtgct gacggttcac cccgattact    5700
ttttgatcga tcccggcatc ggccgttttc tctaccgcct ggcacgccgc gccgcaggca    5760
aggcagaagc cagatggttg ttcaagacga tctacgaacg cagtggcagc gccggagagt    5820
tcaagaagtt ctgtttcacc gtgcgcaagc tgatcgggtc aaatgacctg ccggagtacg    5880
atttgaagga ggaggcgggg caggctggcc cgatcctagt catgcgctac cgcaacctga    5940
tcgagggcga agcatccgcc ggttcctaat gtacggagca gatgctaggg caaattgccc    6000
tagcagggga aaaggtcga aaaggtctct ttcctgtgga tagcacgtac attgggaacc    6060
caaagccgta cattgggaac cggaacccgt acattgggaa cccaaagccg tacattggga    6120
accggtcaca catgtaagtg actgatataa aagagaaaaa aggcgatttt tccgcctaaa    6180
actctttaaa acttattaaa actcttaaaa cccgcctggc ctgtgcataa ctgtctggcc    6240
agcgcacagc cgaagagctg caaaaagcgc ctacccttcg gtcgctgcgc tcctacgcc     6300
ccgccgcttc gcgtcggcct atcgcggccg ctggccgctc aaaaatggct ggcctacggc    6360
caggcaatct accagggcgc ggacaagccg cgccgtcgcc actcgaccgc cggcgcccac    6420
atcaaggcac cctgcctcgc gcgtttcggt gatgacggtg aaaacctctg acacatgcag    6480
ctcccggaga cggtcacagc ttgtctgtaa gcggatgccg ggagcagaca agcccgtcag    6540
ggcgcgtcag cgggtgttgg cgggtgtcgg ggcgcagcca tgacccagtc acgtagcgat    6600
agcggagtgt atactggctt aactatgcgg catcagagca gattgtactg agagtgcacc    6660
atatgcggtg tgaaataccg cacagatgcg taaggagaaa ataccgcatc aggcgctctt    6720
ccgcttcctc gctcactgac tcgctgcgct cggtcgttcg gctgcggcga gcggtatcag    6780
ctcactcaaa ggcggtaata cggttatcca cagaatcagg ggataacgca ggaaagaaca    6840
tgtgagcaaa aggccagcaa aaggccagga accgtaaaaa ggccgcgttg ctggcgtttt    6900
tccataggct ccgcccccct gacgagcatc acaaaaatcg acgctcaagt cagaggtggc    6960
gaaacccgac aggactataa agataccagg cgtttccccc tggaagctcc ctcgtgcgct    7020
ctcctgttcc gaccctgccg cttaccggat acctgtccgc ctttctccct tcgggaagcg    7080
tggcgctttc tcatagctca cgctgtaggt atctcagttc ggtgtaggtc gttcgctcca    7140
agctgggctg tgtgcacgaa ccccccgttc agcccgaccg ctgcgcctta tccggtaact    7200
atcgtcttga gtccaacccg gtaagacacg acttatcgcc actggcagca gccactggta    7260
acaggattag cagagcgagg tatgtaggcg gtgctacaga gttcttgaag tggtggccta    7320
```

```
actacggcta cactagaagg acagtatttg gtatctgcgc tctgctgaag ccagttacct   7380
tcggaaaaag agttggtagc tcttgatccg gcaaacaaac caccgctggt agcggtggtt   7440
tttttgtttg caagcagcag attacgcgca gaaaaaaagg atctcaagaa gatcctttga   7500
tcttttctac ggggtctgac gctcagtgga acgaaaactc acgttaaggg attttggtca   7560
tgcatgatat atctcccaat tgtgtaggg cttattatgc acgcttaaaa ataataaaag    7620
cagacttgac ctgatagttt ggctgtgagc aattatgtgc ttagtgcatc taatcgcttg   7680
agttaacgcc ggcgaagcgg cgtcggcttg aacgaatttc tagctagaca ttatttgccg   7740
actaccttgg tgatctcgcc tttcacgtag tggacaaatt cttccaactg atctgcgcgc   7800
gaggccaagc gatcttcttc ttgtccaaga taagcctgtc tagcttcaag tatgacgggc   7860
tgatactggg ccgcaggcg ctccattgcc cagtcggcag cgacatcctt cggcgcgatt    7920
ttgccggtta ctgcgctgta ccaaatgcgg gacaacgtaa gcactacatt tcgctcatcg   7980
ccagcccagt cgggcggcga gttccatagc gttaaggttt catttagcgc ctcaaataga   8040
tcctgttcag gaaccggatc aaagagttcc tccgccgctg gacctaccaa ggcaacgcta   8100
tgttctcttg cttttgtcag caagatagcc agatcaatgt cgatcgtggc tggctcgaag   8160
atacctgcaa gaatgtcatt gcgctgccat tctccaaatt gcagttcgcg cttagctgga   8220
taacgccacg gaatgatgtc gtcgtgcaca acaatggtga cttctacagc gcggagaatc   8280
tcgctctctc caggggaagc cgaagtttcc aaaaggtcgt tgatcaaagc tcgccgcgtt   8340
gtttcatcaa gccttacggt caccgtaacc agcaaatcaa tatcactgtg tggcttcagg   8400
ccgccatcca ctgcggagcc gtacaaatgt acggccagca acgtcggttc gagatggcgc   8460
tcgatgacgc caactacctc tgatagttga gtcgatactt cggcgatcac cgcttccccc   8520
atgatgttta actttgtttt agggcgactg ccctgctgcg taacatcgtt gctgctccat   8580
aacatcaaac atcgacccac ggcgtaacgc gcttgctgct tggatgcccg aggcatagac   8640
tgtaccccaa aaaacatgt cataacaaga agccatgaaa accgccactg cgccgttacc    8700
accgctgcgt tcggtcaagg ttctggacca gttgcgtgac ggcagttacg ctacttgcat   8760
tacagcttac gaaccgaacg aggcttatgt ccactgggtt cgtgccccgaa ttgatcacag  8820
gcagcaacgc tctgtcatcg ttacaatcaa catgctaccc tccgcgagat catccgtgtt   8880
tcaaacccgg cagcttagtt gccgttcttc cgaatagcat cggtaacatg agcaaagtct   8940
gccgccttac aacggctctc ccgctgacgc cgtcccggac tgatgggctg cctgtatcga   9000
gtggtgattt tgtgccgagc tgccggtcgg ggagctgttg gctggctggt ggcaggatat   9060
attgtggtgt aaacaaattg acgcttagac aacttaataa cacattgcgg acgtttttaa   9120
tgtactgaat taacgccgaa ttgaattatc agcttgcatg ccggtcgatc tagtaacata   9180
tagatgacac cgcgcgcgat aatttatcct agtttgcgcg ctatattttg ttttctatcg   9240
cgtattaaat gtataattgc gggactctaa tcataaaaac ccatctcata ataacgtca    9300
tgcattacat gttaattatt acatgcttaa cgtaattcaa cagaaattat atgataatca   9360
tcgcaagacc ggcaacagga ttcaatctta agaaacttta ttgccaaatg tttgaacgat   9420
ctgcttgact ctaggggtca tcagatttcg gtgacgggca ggaccggacg gggcggcacc   9480
ggcaggctga agtccagctg ccagaaaccc acgtcatgcc agttcccgtg cttgaagccg   9540
gccgcccgca gcatgccgcg gggggcatat ccgagcgcct cgtgcatgcg cacgctcggg   9600
tcgttgggca gcccgatgac agcgaccacg ctcttgaagc cctgtgcctc cagggacttc   9660
```

| | |
|---|---|
| agcaggtggg tgtagagcgt ggagcccagt cccgtccgct ggtggcgggg ggagacgtac | 9720 |
| acggtcgact cggccgtcca gtcgtaggcg ttgcgtgcct tccagggacc cgcgtaggcg | 9780 |
| atgccggcga cctcgccgtc cacctcggcg acgagccagg gatagcgctc ccgcagacgg | 9840 |
| acgaggtcgt ccgtccactc ctgccggttcc tgccggctcgg tacggaagtt gaccgtgctt | 9900 |
| gtctcgatgt agtggttgac gatggtgcag accgccggca tgtccgcctc ggtggcacgg | 9960 |
| cggatgtcgg ccgggcgtcg ttctgggctc atggtagatc ccctcgatcg agttgagagt | 10020 |
| gaatatgaga ctctaattgg ataccgaggg gaatttatgg aacgtcagtg gagcattttt | 10080 |
| gacaagaaat atttgctagc tgatagtgac cttaggcgac ttttgaacgc gcaataatgg | 10140 |
| tttctgacgt atgtgcttag ctcattaaac tccagaaacc cgcggctcag tggctccttc | 10200 |
| aacgttgcgg ttctgtcagt tccaaacgta aaacggcttg tcccgcgtca tcggcggggg | 10260 |
| tcataacgtg actcccttaa ttctcatgta tgataattcg agct | 10304 |

<210> SEQ ID NO 72
<211> LENGTH: 10317
<212> TYPE: DNA
<213> ORGANISM: Artificial Sequence
<220> FEATURE:
<223> OTHER INFORMATION: vector

<400> SEQUENCE: 72

| | |
|---|---|
| ctcccatatg gtcgactaga gccaagctga tctcctttgc cccggagatc accatggacg | 60 |
| actttctcta tctctacgat ctaggaagaa agttcgacgg agaaggtgac gataccatgt | 120 |
| tcaccaccga taatgagaag attagcctct tcaatttcag aaagaatgct gacccacaga | 180 |
| tggttagaga ggcctacgcg gcaggtctca tcaagacgat ctacccgagt aataatctcc | 240 |
| aggagatcaa ataccttccc aagaaggtta aagatgcagt caaaagattc aggactaact | 300 |
| gcatcaagaa cacagagaaa gatatatttc tcaagatcag aagtactatt ccagtatgga | 360 |
| cgattcaagg cttgcttcat aaaccaaggc aagtaataga gattggagtc tctaagaaag | 420 |
| tagttcctac tgaatcaaag gccatggagt caaaaattca gatcgaggat ctaacagaac | 480 |
| tcgccgtgaa gactggcgaa cagttcatac agagtctttt acgactcaat gacaagaaga | 540 |
| aaatcttcgt caacatggtg gagcacgaca ctctcgtcta ctccaagaat atcaaagata | 600 |
| cagtctcaga agaccaaagg gctattgaga cttttcaaca aagggtaata tcgggaaacc | 660 |
| tcctcggatt ccattgccca gctatctgtc acttcatcaa aaggacagta gaaaaggaag | 720 |
| gtggcaccta caaatgccat cattgcgata aaggaaaggc tatcgttcaa gatgcctctg | 780 |
| ccgacagtgg tcccaaagat ggacccccac ccacgaggag catcgtggaa aaagaagacg | 840 |
| ttccaaccac gtcttcaaag caagtggatt gatgtgatat ctccactgac gtaagggatg | 900 |
| acgcacaatc ccactatcct tcgcaagacc cttcctctat ataaggaagt tcatttcatt | 960 |
| tggagaggac tccggtatttt ttacaacaat accacaacaa acaaacaac aaacaacatt | 1020 |
| acaatttact attctagtcg acctgcaggc ggccgcacta gtgatatcac aagtttgtac | 1080 |
| aaaaaagcag gcttaatggc tccaacactc ttgacaaccc aattctcaaa tccagctgaa | 1140 |
| gtaaccgact ttgtagtcta caaggaaat ggtgttaagg gttatcaga acaggaatc | 1200 |
| aaagctcttc cagaacaata cattcagcca cttgaagaac gactcatcaa caaattcgtc | 1260 |
| aacgaaacag atgaagccat tccagttatc gatatgtcga accctgatga ggacagagtc | 1320 |
| gctgaagctg tttgtgatgc tgctgagaaa tgggggttct ttcaagtgat caatcatgga | 1380 |
| gttccttggg aagttcttga tgacgtcaag gctgcgactc acaagttctt caatctccct | 1440 |

```
gttgaagaga agcgcaagtt cactaaagag aattcgctgt cgacgactgt taggtttggg    1500
acgagtttta gtcctcttgc agagcaagcg cttgagtgga aagattatct cagcctcttc    1560
tttgtctctg aagctgaagc tgaacagttc tggcctgata tctgcaggaa tgaaacgtta    1620
gagtacatta acaagtcaaa gaagatggtg aggaggcttc tagagtattt gggaaagaat    1680
ctcaatgtta aagagcttga cgagacgaaa gaatcactct ttatgggctc gattcgagtc    1740
aaccttaact actacccat ctgccctaat ccgacctaa cagttggtgt tggtcgccac      1800
tcagacgtct cttctctcac cattctctta aagaccaga tcggtggtct acacgtgcgt    1860
tctctggctt cagggaactg ggttcacgtg cctccggttg ctggatcttt tgtgatcaac    1920
atcggagatg cgatgcagat catgagcaat ggtctgtaca agagcgtgga gcatcgtgtc    1980
ttagccaatg gttacaataa tagaatctct gttcctatct ttgtgaaccc aaaaccagag    2040
tcagttattg gtcctctacc tgaggtgatt gcaaacggag aggaaccgat ttacagagac    2100
gtcctgtact ctgattacgt caagtatttc ttcaggaagg cacacgatgg aaagaaaacc    2160
gtcgattacg ccaagatctg atacccagct ttcttgtaca aagtggtgat atcccgcggc    2220
catgctagag tccgcaaaaa tcaccagtct ctctctacaa atctatctct ctctattttt    2280
ctccagaata atgtgtgagt agttcccaga taagggaatt agggttctta tagggtttcg    2340
ctcatgtgtt gagcatataa gaaacccta gtatgtattt gtatttgtaa aatacttcta    2400
tcaataaaat ttctaattcc taaaaccaaa atccagtgac ctgcaggcat gcgacgtcgg    2460
gcccaagctt agcttgagct tggatcagat tgtcgtttcc cgccttcagt ttaaactatc    2520
agtgtttgac aggatatatt ggcgggtaaa cctaagagaa aagagcgttt attagaataa    2580
cggatattta aaagggcgtg aaaaggttta tccgttcgtc catttgtatg tgcatgccaa    2640
ccacagggtt cccctcggga tcaaagtact ttgatccaac ccctccgctg ctatagtgca    2700
gtcggcttct gacgttcagt gcagccgtct tctgaaaacg acatgtcgca caagtcctaa    2760
gttacgcgac aggctgccgc cctgcccttt tcctggcgtt ttcttgtcgc gtgttttagt    2820
cgcataaagt agaatacttg cgactagaac cggagacatt acgccatgaa caagagcgcc    2880
gccgctggcc tgctgggcta tgcccgcgtc agcaccgacg accaggactt gaccaaccaa    2940
cgggccgaac tgcacgcggc cggctgcacc aagctgtttt ccgagaagat caccggcacc    3000
aggcgcgacc gcccggagct ggccaggatg cttgaccacc tacgccctgg cgacgttgtg    3060
acagtgacca ggctagaccg cctggcccgc agcacccgcg acctactgga cattgccgag    3120
cgcatccagg aggccggcgc gggcctgcgt agcctggcag agccgtgggc cgacaccacc    3180
acgccggccg gccgcatggt gttgaccgtg ttcgccggca ttgccgagtt cgagcgttcc    3240
ctaatcatcg accgcacccg gagcgggcgc gaggccgcca ggcccgagg cgtgaagttt    3300 ggccccccgcc ctaccctcac cccggcacag atcgcgcacg cccgcgagct gatcgaccag    3360
gaaggccgca ccgtgaaaga gcggctgca ctgcttggcg tgcatcgctc gaccctgtac    3420
cgcgcacttg agcgcagcga ggaagtgacg cccaccgagg ccaggcggcg cggtgccttc    3480
cgtgaggacg cattgaccga ggccgacgcc ctggcggccg ccgagaatga acgccaagag    3540
gaacaagcat gaaaccgcac caggacggcc aggacgaacc gttttcatt accgaagaga    3600 tcgaggcgga gatgatcgcg gccgggtacg tgttcgagcc gcccgcgcac gtctcaaccg    3660
tgcggctgca tgaaatcctg gccggttttgt ctgatgccaa gctggcggcc tggccggcca    3720
gcttggccgc tgaagaaacc gagcgccgcc gtctaaaaag gtgatgtgta tttgagtaaa    3780
```

```
acagcttgcg tcatgcggtc gctgcgtata tgatgcgatg agtaaataaa caaatacgca   3840
aggggaacgc atgaaggtta tcgctgtact taaccagaaa ggcgggtcag gcaagacgac   3900
catcgcaacc catctagccc gcgccctgca actcgccggg gccgatgttc tgttagtcga   3960
ttccgatccc cagggcagtg cccgcgattg ggcggccgtg cgggaagatc aaccgctaac   4020
cgttgtcggc atcgaccgcc cgacgattga ccgcgacgtg aaggccatcg gccggcgcga   4080
cttcgtagtg atcgacggag cgccccaggc ggcggacttg gctgtgtccg cgatcaaggc   4140
agccgacttc gtgctgattc cggtgcagcc aagcccttac gacatatggg ccaccgccga   4200
cctggtggag ctggttaagc agcgcattga ggtcacggat ggaaggctac aagcggcctt   4260
tgtcgtgtcg cgggcgatca aaggcacgcg catcggcggt gaggttgccg aggcgctggc   4320
cgggtacgag ctgcccattc ttgagtcccg tatcacgcag cgcgtgagct acccaggcac   4380
tgccgccgcc ggcacaaccg ttcttgaatc agaacccgag ggcgacgctg cccgcgaggt   4440
ccaggcgctg gccgctgaaa ttaaatcaaa actcatttga gttaatgagg taaagagaaa   4500
atgagcaaaa gcacaaacac gctaagtgcc ggccgtccga gcgcacgcag cagcaaggct   4560
gcaacgttgg ccagcctggc agacacgcca gccatgaagc gggtcaactt tcagttgccg   4620
gcggaggatc acaccaagct gaagatgtac gcggtacgcc aaggcaagac cattaccgag   4680
ctgctatctg aatacatcgc gcagctacca gagtaaatga gcaaatgaat aaatgagtag   4740
atgaatttta gcggctaaag gaggcggcat ggaaaatcaa gaacaaccag gcaccgacgc   4800
cgtggaatgc cccatgtgtg gaggaacggg cggttggcca ggcgtaagcg gctgggttgt   4860
ctgccggccc tgcaatggca ctggaacccc aagcccgagg aatcggcgt gacggtcgca   4920 aaccatccgg cccggtacaa atcggcgcgg cgctgggtga tgacctggtg gagaagttga   4980
aggccgcgca ggccgcccag cggcaacgca tcgaggcaga agcacgcccc ggtgaatcgt   5040
ggcaagcggc cgctgatcga atccgcaaag aatcccggca accgccggca gccggtgcgc   5100
cgtcgattag gaagccgccc aagggcgacg agcaaccaga ttttttcgtt ccgatgctct   5160
atgacgtggg cacccgcgat agtcgcagca tcatggacgt ggccgttttc cgtctgtcga   5220
agcgtgaccg acgagctggc gaggtgatcc gctacgagct tccagacggg cacgtagagg   5280
tttccgcagg gccggccggc atggccagtg tgtgggatta cgacctggta ctgatggcgg   5340
tttcccatct aaccgaatcc atgaaccgat accgggaagg gaaggagac aagcccggcc   5400 gcgtgttccg tccacacgtt gcggacgtac tcaagttctg ccggcgagcc gatggcggaa   5460
agcagaaaga cgacctggta gaaacctgca ttcggttaaa caccacgcac gttgccatgc   5520
agcgtacgaa gaaggccaag aacggccgcc tggtgacggt atccgagggt gaagccttga   5580
ttagccgcta caagatcgta aagagcgaaa ccgggcggcc ggagtacatc gagatcgagc   5640
tagctgattg gatgtaccgc gagatcacag aaggcaagaa cccggacgtg ctgacggttc   5700
accccgatta cttttttgatc gatcccggca tcggccgttt tctctaccgc ctggcacgcc   5760
gcgccgcagg caaggcagaa gccagatggt tgttcaagac gatctacgaa cgcagtggca   5820
gcgccggaga gttcaagaag ttctgtttca ccgtgcgcaa gctgatcggg tcaaatgacc   5880
tgccggagta cgatttgaag gaggaggcgg ggcaggctgg cccgatccta gtcatgcgct   5940
accgcaacct gatcgagggc gaagcatccg ccggttccta atgtacggag cagatgctag   6000
ggcaaattgc cctagcaggg gaaaaaggtc gaaaaggtct ctttcctgtg gatagcacgt   6060
acattgggaa cccaaagccg tacattggga accggaaccc gtacattggg aacccaaagc   6120
cgtacattgg gaaccggtca cacatgtaag tgactgatat aaaagagaaa aaaggcgatt   6180
```

```
tttccgccta aaactctttta aaacttatta aaactcttaa aacccgcctg gcctgtgcat    6240
aactgtctgg ccagcgcaca gccgaagagc tgcaaaaagc gcctacccct cggtcgctgc    6300
gctccctacg ccccgccgct tcgcgtcggc ctatcgcggc cgctggccgc tcaaaaatgg    6360
ctggcctacg gccaggcaat ctaccagggc gcggacaagc cgcgccgtcg ccactcgacc    6420
gccggcgccc acatcaaggc accctgcctc gcgcgtttcg gtgatgacgg tgaaaacctc    6480
tgacacatgc agctcccgga gacggtcaca gcttgtctgt aagcggatgc cgggagcaga    6540
caagcccgtc agggcgcgtc agcgggtgtt ggcgggtgtc ggggcgcagc catgacccag    6600
tcacgtagcg atagcggagt gtatactggc ttaactatgc ggcatcagag cagattgtac    6660
tgagagtgca ccatatgcgg tgtgaaatac cgcacagatg cgtaaggaga aataccgca     6720 tcaggcgctc ttccgcttcc tcgctcactg actcgctgcg ctcggtcgtt cggctgcggc    6780
gagcggtatc agctcactca aaggcggtaa tacggttatc cacagaatca ggggataacg    6840
caggaaagaa catgtgagca aaaggccagc aaaaggccag gaaccgtaaa aaggccgcgt    6900
tgctggcgtt tttccatagg ctccgccccc ctgacgagca tcacaaaaat cgacgctcaa    6960
gtcagaggtg gcgaaacccg acaggactat aaagatacca ggcgtttccc cctggaagct    7020
ccctcgtgcg ctctcctgtt ccgaccctgc cgcttaccgg atacctgtcc gcctttctcc    7080
cttcgggaag cgtggcgctt tctcatagct cacgctgtag gtatctcagt tcggtgtagg    7140
tcgttcgctc caagctgggc tgtgtgcacg aaccccccgt tcagcccgac cgctgcgcct    7200
tatccggtaa ctatcgtctt gagtccaacc cggtaagaca cgacttatcg ccactggcag    7260
cagccactgg taacaggatt agcagagcga ggtatgtagg cggtgctaca gagttcttga    7320
agtggtggcc taactacggc tacactagaa ggacagtatt tggtatctgc gctctgctga    7380
agccagttac cttcggaaaa agagttggta gctcttgatc cggcaaacaa accaccgctg    7440
gtagcggtgg tttttttgtt tgcaagcagc agattacgcg cagaaaaaaa ggatctcaag    7500
aagatccttt gatcttttct acggggtctg acgctcagtg gaacgaaaac tcacgttaag    7560
ggattttggt catgcatgat atatctccca atttgtgtag gcttattat gcacgcttaa     7620 aaataataaa agcagacttg acctgatagt ttggctgtga gcaattatgt gcttagtgca    7680
tctaatcgct tgagttaacg ccggcgaagc ggcgtcggct tgaacgaatt tctagctaga    7740
cattatttgc cgactacctt ggtgatctcg cctttcacgt agtggacaaa ttcttccaac    7800
tgatctgcgc gcgaggccaa gcgatcttct tcttgtccaa gataagcctg tctagcttca    7860
agtatgacgg gctgatactg ggccggcagg cgctccattg cccagtcggc agcgacatcc    7920
ttcggcgcga ttttgccggt tactgcgctg taccaaatgc gggacaacgt aagcactaca    7980
tttcgctcat cgccagccca gtcgggcggc gagttccata gcgttaaggt ttcatttagc    8040
gcctcaaata gatcctgttc aggaaccgga tcaaagagtt cctccgccgc tggacctacc    8100
aaggcaacgc tatgttctct tgcttttgtc agcaagatag ccagatcaat gtcgatcgtg    8160
gctggctcga agatacctgc aagaatgtca ttgcgctgcc attctccaaa ttgcagttcg    8220
cgcttagctg gataacgcca cggaatgatg tcgtcgtgca caacaatggt gacttctaca    8280
gcgcggagaa tctcgctctc tccaggggaa gccgaagttt ccaaaaggtc gttgatcaaa    8340
gctcgccgcg ttgtttcatc aagccttacg gtcaccgtaa ccagcaaatc aatatcactg    8400
tgtggcttca ggccgccatc cactgcggag ccgtacaaat gtacggccag caacgtcggt    8460
tcgagatggc gctcgatgac gccaactacc tctgatagtt gagtcgatac ttcggcgatc    8520
```

```
accgcttccc ccatgatgtt taactttgtt ttagggcgac tgccctgctg cgtaacatcg      8580
ttgctgctcc ataacatcaa acatcgaccc acggcgtaac gcgcttgctg cttggatgcc      8640
cgaggcatag actgtacccc aaaaaaacat gtcataacaa gaagccatga aaaccgccac      8700
tgcgccgtta ccaccgctgc gttcggtcaa ggttctggac cagttgcgtg acggcagtta      8760
cgctacttgc attacagctt acgaaccgaa cgaggcttat gtccactggg ttcgtgcccg      8820
aattgatcac aggcagcaac gctctgtcat cgttacaatc aacatgctac cctccgcgag      8880
atcatccgtg tttcaaaccc ggcagcttag ttgccgttct tccgaatagc atcggtaaca      8940
tgagcaaagt ctgccgcctt acaacggctc tcccgctgac gccgtccggg actgatgggc      9000
tgcctgtatc gagtggtgat tttgtgccga gctgccggtc ggggagctgt tggctggctg      9060
gtggcaggat atattgtggt gtaaacaaat tgacgcttag acaacttaat aacacattgc      9120
ggacgttttt aatgtactga attaacgccg aattgaatta tcagcttgca tgccggtcga      9180
tctagtaaca tatagatgac accgcgcgcg ataatttatc ctagtttgcg cgctatattt      9240
tgttttctat cgcgtattaa atgtataatt gcgggactct aatcataaaa acccatctca      9300
taaataacgt catgcattac atgttaatta ttacatgctt aacgtaattc aacagaaatt      9360
atatgataat catcgcaaga ccggcaacag gattcaatct taagaaactt tattgccaaa      9420
tgtttgaacg atctgcttga ctctaggggt catcagattt cggtgacggg caggaccgga      9480
cggggcggca ccggcaggct gaagtccagc tgccagaaac ccacgtcatg ccagttcccg      9540
tgcttgaagc cggccgcccg cagcatgccg cgggggcat atccgagcgc ctcgtgcatg      9600
cgcacgctcg ggtcgttggg cagcccgatg acagcgacca cgctcttgaa gccctgtgcc      9660
tccagggact tcagcaggtg ggtgtagagc gtggagccca gtcccgtccg ctggtggcgg      9720
ggggagacgt acacggtcga ctcggccgtc cagtcgtagg cgttgcgtgc cttccaggga      9780
cccgcgtagg cgatgccggc gacctcgccg tccacctcgg cgacgagcca gggatagcgc      9840 tccccgcagac ggacgaggtc gtccgtccac tcctgcggtt cctgcggctc ggtacggaag      9900
ttgaccgtgc ttgtctcgat gtagtggttg acgatggtgc agaccgccgg catgtccgcc      9960
tcggtggcac ggcggatgtc ggccgggcgt cgttctgggc tcatggtaga tcccctcgat     10020
cgagttgaga gtgaatatga gactctaatt ggataccgag gggaatttat ggaacgtcag     10080
tggagcattt tgacaagaa atatttgcta gctgatagtg accttaggcg acttttgaac      10140
gcgcaataat ggtttctgac gtatgtgctt agctcattaa actccagaaa cccgcggctc     10200
agtggctcct tcaacgttgc ggttctgtca gttccaaacg taaaacggct tgtcccgcgt     10260
catcggcggg ggtcataacg tgactccctt aattctcatg tatgataatt cgagctc       10317
```

<210> SEQ ID NO 73
<211> LENGTH: 12323
<212> TYPE: DNA
<213> ORGANISM: Artificial Sequence
<220> FEATURE:
<223> OTHER INFORMATION: vector

<400> SEQUENCE: 73

```
aaaagttgcc atgattacgc caagcttggc cactaaggcc aatttaaatc tactaggccg       60
gccaaagtag gcgcctacta ccggtaattc ccgggattag cggccgctag tctgtgcgca      120
cttgtatcct gcaggtcaat cgtttaaaca ctgtacggac cgtggcctaa taggccggta      180
cccaagtttg tacaaaaaag caggctccat gattacgcca agcttggcca ctaaggccaa      240
tttaaatcta ctaggccggc caaagtaggc gcctactacc ggtaattccc gggattagcg      300
```

```
gccgctagtc tgtgcgcact tgtatcctgc aggtcaatcg tttaaacact gtacggaccg    360
tggcctaata ggccggtacc acccagcttt cttgtacaaa gtggccatga ttacgccaag    420
cttggccact aaggccaatt taaatctact aggccggccc aggtaccaat tcgaatccaa    480
aaattacgga tatgaatata ggcatatccg tatccgaatt atccgtttga cagctagcaa    540
cgattgtaca attgcttctt taaaaaagga agaaagaaag aaagaaaaga atcaacatca    600
gcgttaacaa acgcccccgt tacgcccaaa acggtcatat agagtaacgg cgttaagcgt    660
tgaaagactc ctatcgaaat acgtaaccgc aaacgtgtca tagtcagatc ccctcttcct    720
tcaccgcctc aaacacaaaa ataatcttct acagcctata tatacaaccc cccttctat    780 ctctcctttc tcacaattca tcatctttct ttctctaccc ccaatttaa gaaatcctct    840 cttctcctct tcattttcaa ggtaaatctc tctctctctc tctctctctg ttattccttg    900
ttttaattag gtatgtatta ttgctagttt gttaatctgc ttatcttatg tatgccttat    960
gtgaatatct ttatcttgtt catctcatcc gtttagaagc tataaatttg ttgatttgac   1020
tgtgtatcta cacgtggtta tgtttatatc taatcagata tgaatttctt catattgttg   1080
cgtttgtgtg taccaatccg aaatcgttga ttttttttcat ttaatcgtgt agctaattgt   1140
acgtatacat atggatctac gtatcaattg ttcatctgtt tgtgtttgta tgtatacaga   1200
tctgaaaaca tcacttctct catctgattg tgttgttaca tacatagata tagatctgtt   1260
atatcatttt ttttattaat tgtgtatata tatatgtgca tagatctgga ttacatgatt   1320
gtgattattt acatgatttt gttatttacg tatgtatata tgtagatctg gacttttttgg   1380 agttgttgac ttgattgtat ttgtgtgtgt atatgtgtgt tctgatcttg atatgttatg   1440
tatgtgcagt taattaacca tggctccaac actcttgaca acccaattct caaatccagc   1500
tgaagtaacc gactttgtag tctacaaagg aaatggtgtt aagggtttat cagaaacagg   1560
aatcaaagct cttccagaac aatacattca gccacttgaa gaacgactca tcaacaaatt   1620
cgtcaacgaa acagatgaag ccattccagt tatcgatatg tcgaaccctg atgaggacag   1680
agtcgctgaa gctgtttgtg atgctgctga gaaatggggg ttcttttcaag tgatcaatca   1740 tggagttcct ttggaagttc ttgatgacgt caaggctgcg actcacaagt tcttcaatct   1800
ccctgttgaa gagaagcgca agttcactaa agagaattcg ctgtcgacga ctgttaggtt   1860
tgggacgagt tttagtcctc ttgcagagca agcgcttgag tggaaagatt atctcagcct   1920
cttctttgtc tctgaagctg aagctgaaca gttctggcct gatatctgca ggaatgaaac   1980
gttagagtac attaacaagt caagaagat ggtgaggagg cttctagagt atttgggaaa   2040
gaatctcaat gttaaagagc ttgacgagac gaaagaatca ctctttatgg gctcgattcg   2100
agtcaaccct aactactacc ccatctgccc taatccggac ctaacagttg gtgttggtcg   2160
ccactcagac gtctcttctc tcaccattct cttacaagac cagatcggtg gtctacacgt   2220
gcgttctctg gcttcaggga actgggttca cgtgcctccg gttgctggat cttttgtgat   2280
caacatcgga gatgcgatgc agatcatgag caatggtctg tacaagagcg tggagcatcg   2340
tgtcttagcc aatggttaca ataatagaat ctctgttcct atctttgtga acccaaaacc   2400
agagtcagtt attggtcctc tacctgaggt gattgcaaac ggagaggaac cgatttacag   2460
agacgtcctg tactctgatt acgtcaagta tttcttcagg aaggcacacg atggaaagaa   2520
aaccgtcgat tacgccaaga tctgaggcgc gccctgcttt aatgagatat gcagacgcc   2580 tatgatcgca tgatatttgc tttcaattct gttgtgcacg ttgtaaaaaa cctgagcatg   2640
```

```
tgtagctcag atccttaccg ccggtttcgg ttcattctaa tgaatatatc accgttact    2700
atcgtatttt tatgaataat attctccgtt caatttactg attgtggcgc ctactaccgg   2760
taattcccgg gattagcggc cgctagtctg tgcgcacttg tatcctgcag gtcaatcgtt   2820
taaacactgt acggaccgtg gcctaatagg ccggtaccca actttattat acatagttga   2880
taattcactg gccggatgta ccgaattcgc ggccgcaagc ttggtacctt tctttacgag   2940
gtaattgatc tcgcattata tatctacatt ttggttatgt tacttgacat atagtcattg   3000
attcaatagt tctgttaatt cctttaaaga tcattttgac tagaccacat tcttggttca   3060
ttcctcaata atttgtaatc atattggtgg atatagaagt agattggtta tagatcagat   3120
agtggaagac tttaggatga atttcagcta gttttttttt ttggcttatt gtctcaaaag   3180
attagtgctt tgctgtctcc attgcttctg ctatcgacac gcttctgtct ccttgtatct   3240
ttattatatc tattcgtccc atgagttttg tttgttctgt attcgttcgc tctggtgtca   3300
tggatggagt ctctgttcca tgtttctgta atgcatgttg ggttgtttca tgcaagaaat   3360
gctgagataa acactcattt gtgaaagttt ctaaactctg aatcgcgcta caggcaatgc   3420
tccgaggagt aggaggagaa gaacgaacca aacgacatta tcagcccttt gaggaagctc   3480
ttagttttgt tattgttttt gtagccaaat tctccattct tattccattt tcacttatct   3540
cttgttcctt atagacctta taagtttttt attcatgtat acaaattata ttgtcatcaa   3600
gaagtatctt taaaatctaa atctcaaatc accaggacta tgttttttgtc caattcgtgg  3660
aaccaacttg cagcttgtat ccattctctt aaccaataaa aaagaaaga aagatcaatt    3720
tgataaattt ctcagccaca aattctacat ttaggtttta gcatatcgaa ggctcaatca   3780
caaatacaat agatagacta gagattccag cgtcacgtga gttttatcta taaataaagg   3840
accaaaaatc aaatcccgag ggcattttcg taatccaaca taaaacccctt aaacttcaag  3900
tctcattttt aaacaaatca tgttcacaag tctcttcttc ttctctgttt ctctatctct   3960
tgctcgggcc cttagatctc gtgccgtcgt gcgacgttgt tttccggtac gtttattcct   4020
gttgattcct tctctgtctc tctcgattca ctgctacttc tgtttggatt cctttcgcgc   4080
gatctctgga tccgtgcgtt attcattggc tcgtcgtttt cagatctgtt gcgtttcttc   4140
tgttttctgt tatgagtgga tgcgttttct tgtgattcgc ttgtttgtaa tgctggatct   4200
gtatctgcgt cgtgggaatt caaagtgata gtagttgata ttttttccag atcaggcatg   4260
ttctcgtata atcaggtcta atggttgatg attctgcgga attatagatc taagatcttg   4320
attgatttag atttgaggat atgaatgaga ttcgtaggtc cacaaaggtc ttgttatctc   4380
tgctgctaga tagatgatta tccaattgcg tttcgtagtt attttttatgg attcaaggaa  4440
ttgcgtgtaa ttgagagttt tactctgttt tgtgaacagg cttgatcaaa ctcgagatct   4500
ttctcctgaa ccatggcggc ggcaacaaca acaacaacaa catcttcttc gatctccttc   4560
tccaccaaac catctccttc ctcctccaaa tcaccattac caatctccag attctccctc   4620
ccattctccc taaaccccaa caaatcatcc tcctcctccc gccgccgcgg tatcaaatcc   4680
agctctccct cctccatctc cgccgtgctc aacacaacca ccaatgtcac aaccactccc   4740
tctccaacca aacctaccaa acccgaaaca ttcatctccc gattcgctcc agatcaaccc   4800
cgcaaaggcg ctgatatcct cgtcgaggct ttagaacgtc aaggcgtaga aaccgtattc   4860
gcttaccctg gaggtacatc aatggagatt caccaagcct taacccgctc ttcctcaatc   4920
cgtaacgtcc ttcctcgtca cgaacaagga ggtgtattcg cagcagaagg atacgctcga   4980
tcctcaggta aaccaggtat ctgtatagcc acttcaggtc ccggagctac aaatctcgtt   5040
```

```
agcggattag ccgatgcgtt gttagatagt gttcctcttg tagcaatcac aggacaagtc    5100
cctcgtcgta tgattggtac agatgcgttt caagagactc cgattgttga ggtaacgcgt    5160
tcgattacga agcataacta tcttgtgatg gatgttgaag atatcccaag gattattgaa    5220
gaggctttct ttttagctac ttctggtaga cctggacctg ttttggttga tgttcctaaa    5280
gatattcaac aacagcttgc gattcctaat tgggaacagg ctatgagatt acctggttat    5340
atgtctagga tgcctaaacc tccggaagat tctcatttgg agcagattgt taggttgatt    5400
tctgagtcta agaagcctgt gttgtatgtt ggtggtggtt gtcttaattc tagcgatgaa    5460
ttgggtaggt ttgttgagct tacgggcatc cctgttgcga gtacgttgat ggggctggga    5520
tcttatcctt gtgatgatga gttgtcgtta catatgcttg gaatgcatgg gactgtgtat    5580
gcaaattacg ctgtggagca tagtgatttg ttgttggcgt ttggggtaag gtttgatgat    5640
cgtgtcacgg gtaaacttga ggcttttgct agtagggcta agattgttca tattgatatt    5700
gactcggctg agattgggaa gaataagact cctcatgtgt ctgtgtgtgg tgatgttaag    5760
ctggctttgc aagggatgaa taaggttctt gagaaccgag cggaggagct taaacttgat    5820
tttggagttt ggaggaatga gttgaacgta cagaaacaga gtttccgtt gagctttaag    5880 acgtttgggg aagctattcc tccacagtat gcgattaagg tccttgatga gttgactgat    5940
ggaaaagcca taataagtac tggtgtcggg caacatcaaa tgtgggcggc gcagttctac    6000
aattacaaga aaccaaggca gtggctatca tcaggaggcc ttggagctat gggatttgga    6060
cttcctgctg cgattggagc gtctgttgct aaccctgatg cgatagttgt ggatattgac    6120
ggagatggaa gttttataat gaatgtgcaa gagctagcca ctattcgtgt agagaatctt    6180
ccagtgaagg tacttttatt aaacaaccag catcttggca tggttatgca atgggaagat    6240
cggttctaca aagctaaccg agctcacaca tttctcgggg acccggctca ggaggacgag    6300
atattcccga acatgttgct gtttgcagca gcttgcggga ttccagcggc gagggtgaca    6360
aagaaagcag atctccgaga agctattcag acaatgctgg atacaccagg accttacctg    6420
ttggatgtga tttgtccgca ccaagaacat gtgttgccga tgatcccgaa tggtggcact    6480
ttcaacgatg tcataacgga aggagatggc cggattaaat actgagagat gaaaccggtg    6540
attatcagaa cctttatgg tctttgtatg catatggtaa aaaaacttag tttgcaattt    6600
cctgtttgtt ttggtaattt gagtttcttt tagttgttga tctgcctgct ttttggttta    6660
cgtcagacta ctactgctgt tgttgtttgg tttcctttct ttcatttat aaataaataa    6720 tccggttcgg tttactcctt gtgactggct cagtttggtt attgcgaaat gcgaatggta    6780
aattgagtaa ttgaaattcg ttattagggt tctaagctgt tttaacagtc actgggttaa    6840
tatctctcga atcttgcatg gaaaatgctc ttaccattgg ttttaattg aaatgtgctc    6900 atatgggccg tggtttccaa attaaataaa actacgatgt catcgagaag taaaatcaac    6960
tgtgtccaca ttatcagttt tgtgtatacg atgaaatagg gtaattcaaa atctagcttg    7020
atatgccttt tggttcattt taaccttctg taaacatttt ttcagatttt gaacaagtaa    7080
atccaaaaaa aaaaaaaaa aatctcaact caacactaaa ttattttaat gtataaaga    7140 tgcttaaaac atttggctta aagaaagaa gctaaaaaca tagagaactc ttgtaaattg    7200
aagtatgaaa atatactgaa ttgggtatta tatgaatttt tctgatttag gattcacatg    7260
atccaaaaag gaaatccaga agcactaatc agacattgga agtaggattt aaatttaatc    7320
gcagtactta atcagtgatc agtaactaaa ttcagtacat taaagacgtc cgcaatgtgt    7380
```

```
tattaagttg tctaagcgtc aatttgttta caccacaata tatcctgcca ccagccagcc     7440
aacagctccc cgaccggcag ctcggcacaa aatcactgat catctaaaaa ggtgatgtgt     7500
atttgagtaa aacagcttgc gtcatgcggt cgctgcgtat atgatgcgat gagtaaataa     7560
acaaatacgc aaggggaacg catgaaggtt atcgctgtac ttaaccagaa aggcgggtca     7620
ggcaagacga ccatcgcaac ccatctagcc cgcgccctgc aactcgccgg ggccgatgtt     7680
ctgttagtcg attccgatcc ccagggcagt gcccgcgatt gggcggccgt gcgggaagat     7740
caaccgctaa ccgttgtcgg catcgaccgc ccgacgattg accgcgacgt gaaggccatc     7800
ggccggcgcg acttcgtagt gatcgacgga gcgcccagg cggcggactt ggctgtgtcc      7860
gcgatcaagg cagccgactt cgtgctgatt ccggtgcagc caagcccta cgacatttgg      7920 gccaccgccg acctggtgga gctggttaag cagcgcattg aggtcacgga tggaaggcta     7980
caagcggcct ttgtcgtgtc gcgggcgatc aaaggcacgc catcggcgg tgaggttgcc      8040 gaggcgctgg ccgggtacga gctgcccatt cttgagtccc gtatcacgca gcgcgtgagc     8100
tacccaggca ctgccgccgc cggcacaacc gttcttgaat cagaacccga gggcgacgct     8160
gcccgcgagg tccaggcgct ggccgctgaa attaaatcaa aactcatttg agttaatgag     8220
gtaaagagaa aatgagcaaa agcacaaaca cgctaagtgc cggccgtccg agcgcacgca     8280
gcagcaaggc tgcaacgttg gccagcctgg cagacacgcc agccatgaag cgggtcaact     8340
ttcagttgcc ggcggaggat cacaccaagc tgaagatgta cgcggtacgc caaggcaaga     8400
ccattaccga gctgctatct gaatacatcg cgcagctacc agagtaaatg agcaaatgaa     8460
taaatgagta gatgaatttt gcggctaaa ggaggcggca tggaaaatca agaacaacca      8520
ggcaccgacg ccgtggaatg ccccatgtgt ggaggaacgg gcggttggcc aggcgtaagc     8580
ggctgggttg tctgccggcc ctgcaatggc actggaaccc ccaagcccga ggaatcggcg     8640
tgagcggtcg caaaccatcc ggcccggtac aaatcggcgc ggcgctgggt gatgacctgg     8700
tggagaagtt gaaggccgcg caggccgccc agcggcaacg catcgaggca gaagcacgcc     8760
ccggtgaatc gtggcaaggg gccgctgatc gaatcgcaa agaatcccgg caaccgccgg      8820
cagccggtgc gccgtcgatt aggaagccgc ccaaggcga cgagcaacca gatttttcg       8880 ttccgatgct ctatgacgtg gcacccgcg atagtcgcag catcatggac gtggccgttt      8940
tccgtctgtc gaagcgtgac cgacgagctg gcgaggtgat ccgctacgag cttccagacg     9000
ggcacgtaga ggtttccgca ggcccgccg gcatggccag tgtgtgggat tacgacctgg      9060
tactgatggc ggtttcccat ctaaccgaat ccatgaaccg ataccgggaa gggaagggag     9120
acaagcccgg ccgcgtgttc cgtccacacg ttgcggacgt actcaagttc tgccggcgag     9180
ccgatgcgaa aaagcagaaa gacgacctgg tagaaacctg cattcggtta aacaccacgc     9240
acgttgccat gcagcgtacc aagaaggcca agaacggccg cctggtgacg gtatccgagg     9300
gtgaagcctt gattagccgc tacaagatcg taaagagcga aaccgggcgg ccggagtaca     9360
tcgagatcga gcttgctgat tggatgtacc gcgagatcac agaaggcaag aacccggacg     9420
tgctgacggt tcaccccgat tacttttttga tcgaccccgg catcggccgt tttctctacc     9480
gcctggcacg ccgcgccgca ggcaaggcag aagccagatg gttgttcaag acgatctacg     9540
aacgcagtgg cagcgccgga gagttcaaga agttctgttt caccgtgcgc aagctgatcg     9600
ggtcaaatga cctgccggag tacgatttga aggaggaggc ggggcaggct ggcccgatcc     9660
tagtcatgcg ctaccgcaac ctgatcgagg gcgaagcatc cgccggttcc taatgtacgg     9720
agcagatgct agggcaaatt gccctagcag gggaaaaagg tcgaaaaggt ctctttcctg     9780
```

```
tggatagcac gtacattggg aacccaaagc cgtacattgg gaaccggaac ccgtacattg   9840
ggaacccaaa gccgtacatt gggaaccggt cacacatgta agtgactgat ataaaagaga   9900
aaaaaggcga ttttttccgcc taaaactctt taaaacttat taaaactctt aaaacccgcc   9960
tggcctgtgc ataactgtct ggccagcgca cagccgaaga gctgcaaaaa gcgcctaccc  10020
ttcggtcgct gcgctcccta cgccccgccg cttcgcgtcg gcctatcgcg gcctatgcgg  10080
tgtgaaatac cgcacagatg cgtaaggaga aaataccgca tcaggcgctc ttccgcttcc  10140
tcgctcactg actcgctgcg ctcggtcgtt cggctgcggc gagcggtatc agctcactca  10200
aaggcggtaa tacggttatc cacagaatca ggggataacg caggaaagaa catgtgagca  10260
aaaggccagc aaaaggccag gaaccgtaaa aaggccgcgt tgctggcgtt tttccatagg  10320
ctccgccccc ctgacgagca tcacaaaaat cgacgctcaa gtcagaggtg gcgaaacccg  10380
acaggactat aaagatacca ggcgtttccc cctggaagct ccctcgtgcg ctctcctgtt  10440
ccgaccctgc cgcttaccgg atacctgtcc gcctttctcc cttcgggaag cgtggcgctt  10500
tctcatagct cacgctgtag gtatctcagt tcggtgtagg tcgttcgctc caagctgggc  10560
tgtgtgcacg aacccccccgt tcagcccgac cgctgcgcct tatccggtaa ctatcgtctt  10620
gagtccaacc cggtaagaca cgacttatcg ccactggcag cagccactgg taacaggatt  10680
agcagagcga ggtatgtagg cggtgctaca gagttcttga agtggtggcc taactacggc  10740
tacactagaa ggacagtatt tggtatctgc gctctgctga gccagttac cttcggaaaa  10800
agagttggta gctcttgatc cggcaaacaa accaccgctg gtagcggtgg tttttttgtt  10860
tgcaagcagc agattacgcg cagaaaaaaa ggatctcaag aagatccttt gatcttttct  10920
acggggtcct tcaactcatc gatagtttgg ctgtgagcaa ttatgtgctt agtgcatcta  10980
acgcttgagt taagccgcgc cgcgaagcgg cgtcggcttg aacgaatttc tagctagaca  11040
ttatttgcca acgaccttcg tgatctcgcc cttgacatag tggacaaatt cttcgagctg  11100
gtcggcccgg gacgcgagac ggtcttcttc ttggcccaga taggcttggc gcgcttcgag  11160
gatcacgggc tggtattgcg ccggaaggcg ctccatcgcc cagtcggcgg cgacatcctt  11220
cggcgcgatc ttgccggtaa ccgccgagta ccaaatccgg ctcagcgtaa ggaccacatt  11280
gcgctcatcg cccgcccaat ccggcgggga gttccacagg gtcagcgtct cgttcagtgc  11340
ttcgaacaga tcctgttccg gcaccgggtc gaaaagttcc tcggccgcgg ggccgacgag  11400
ggccacgcta tgctcccggg ccttggtgag caggatcgcc agatcaatgt cgatggtggc  11460
cggttcaaag atacccgcca gaatatcatt acgctgccat tcgccgaact ggagttcgcg  11520
tttggccgga tagcgccagg ggatgatgtc atcgtgcacc acaatcgtca cctcaaccgc  11580
gcgcaggatt tcgctctcgc cggggaggc ggacgtttcc agaaggtcgt tgataagcgc  11640
gcggcgcgtg gtctcgtcga cggacggt aacggtgaca agcaggtcga tgtccgaatg  11700
gggcttaagg ccgccgtcaa cggcgctacc atacagatgc acggcgagga gggtcggttc  11760
gaggtggcgc tcgatgacac ccacgacttc cgacagctgg gtggacacct cggcgatgac  11820
cgcttcaccc atgatgttta actttgtttt agggcgactg ccctgctgcg taacatcgtt  11880
gctgctccat aacatcaaac atcgacccac ggcgtaacgc gcttgctgct tggatgcccg  11940
aggcatagac tgtaccccaa aaaaacagtc ataacaagcc atgaaaaccg ccactgcgtt  12000
ccatgaatat tcaaacaaac acatacagcg cgacttatca tggatattga catacaaatg  12060
gacgaacgga taaacctttt cacgcccttt taaatatccg attattctaa taaacgctct  12120
```

```
tttctcttag gtttacccgc caatatatcc tgtcaaacac tgatagttta aactgaaggc   12180
gggaaacgac aatctgatca ctgattagta actaaggcct ttaattaatc tagaggcgcg   12240
ccgggccccc tgcagggagc tcggccggcc aatttaaatt gatatcggta catcgattac   12300
gccaagctat caactttgta tag                                          12323

<210> SEQ ID NO 74
<211> LENGTH: 14404
<212> TYPE: DNA
<213> ORGANISM: Artificial Sequence
<220> FEATURE:
<223> OTHER INFORMATION: vector

<400> SEQUENCE: 74
ttatacatag ttgataattc actggccgga tgtaccgaat tcgcggccgc aagcttggta     60
cctttcttta cgaggtaatt gatctcgcat tatatatcta cattttggtt atgttacttg    120
acatatagtc attgattcaa tagttctgtt aattccttta agatcatttt gactagacc     180 acattcttgg ttcattcctc aataatttgt aatcatattg tggatatag aagtagattg    240 gttatagatc agatagtgga agactttagg atgaatttca gctagttttt ttttttggct   300
tattgtctca aaagattagt gctttgctgt ctccattgct tctgctatcg acacgcttct   360
gtctccttgt atctttatta tatctattcg tcccatgagt tttgtttgtt ctgtattcgt   420
tcgctctggt gtcatggatg gagtctctgt tccatgtttc tgtaatgcat gttgggttgt   480
ttcatgcaag aaatgctgag ataaacactc atttgtgaaa gtttctaaac tctgaatcgc   540
gctacaggca atgctccgag gagtaggagg agaagaacga accaaacgac attatcagcc   600 cttttgaggaa gctcttagtt ttgttattgt ttttgtagcc aaattctcca ttcttattcc   660
atttcacctt atctcttgtt ccttatagac cttataagtt ttttattcat gtatacaaat   720
tatattgtca tcaagaagta tctttaaaat ctaaatctca aatcaccagg actatgtttt   780
tgtccaattc gtggaaccaa cttgcagctt gtatccattc tcttaaccaa taaaaaaaga   840
aagaaagatc aatttgataa atttctcagc cacaaattct acatttaggt tttagcatat   900
cgaaggctca atcacaaata caatagatag actagagatt ccagcgtcac gtgagtttta   960
tctataaata aaggaccaaa aatcaaatcc cgagggcatt ttcgtaatcc aacataaaac   1020
ccttaaactt caagtctcat ttttaaacaa atcatgttca caagtctctt cttcttctct   1080
gtttctctat ctcttgctcg ggcccttaga tctcgtgccg tcgtgcgacg ttgttttccg   1140
gtacgtttat tcctgttgat tccttctctg tctctctcga ttcactgcta cttctgtttg   1200
gattcctttc gcgcgatctc tggatccgtg cgttattcat tggctcgtcg ttttcagatc   1260
tgttgcgttt cttctgtttt ctgttatgag tggatgcgtt ttcttgtgat tcgcttgttt   1320
gtaatgctgg atctgtatct gcgtcgtggg aattcaaagt gatagtagtt gatattttt   1380 ccagatcagg catgttctcg tataatcagg tctaatggtt gatgattctg cggaattata   1440
gatctaagat cttgattgat ttagatttga ggatatgaat gagattcgta ggtccacaaa   1500
ggtcttgtta tctctgctgc tagatagatg attatccaat tgcgtttcgt agttattttt   1560
atggattcaa ggaattgcgt gtaattgaga gttttactct gttttgtgaa caggcttgat   1620
caaactcgag atctttctcc tgaaccatgg cggcggcaac aacaacaaca acaacatctt   1680
cttcgatctc cttctccacc aaaccatctc cttcctcctc caaatcacca ttaccaatct   1740
ccagattctc cctcccattc tccctaaacc ccaacaaatc atcctcctcc tccgccgcc   1800 gcggtatcaa atccagctct ccctcctcca tctccgccgt gctcaacaca accaccaatg   1860
```

```
tcacaaccac tccctctcca accaaaccta ccaaacccga aacattcatc tcccgattcg    1920
ctccagatca accccgcaaa ggcgctgata tcctcgtcga ggctttagaa cgtcaaggcg    1980
tagaaaccgt attcgcttac cctggaggta catcaatgga gattcaccaa gccttaaccc    2040
gctcttcctc aatccgtaac gtccttcctc gtcacgaaca aggaggtgta ttcgcagcag    2100
aaggatacgc tcgatcctca ggtaaaccag gtatctgtat agccacttca ggtcccggag    2160
ctacaaatct cgttagcgga ttagccgatg cgttgttaga tagtgttcct cttgtagcaa    2220
tcacaggaca agtccctcgt cgtatgattg gtacagatgc gtttcaagag actccgattg    2280
ttgaggtaac gcgttcgatt acgaagcata actatcttgt gatggatgtt gaagatatcc    2340
caaggattat tgaagaggct ttcttttttag ctacttctgg tagacctgga cctgttttgg    2400
ttgatgttcc taaagatatt caacaacagc ttgcgattcc taattgggaa caggctatga    2460
gattacctgg ttatatgtct aggatgccta aacctccgga agattctcat ttggagcaga    2520
ttgttaggtt gatttctgag tctaagaagc ctgtgttgta tgttggtggt ggttgtctta    2580
attctagcga tgaattgggt aggtttgttg agcttacggg catccctgtt gcgagtacgt    2640
tgatggggct gggatcttat ccttgtgatg atgagttgtc gttacatatg cttggaatgc    2700
atgggactgt gtatgcaaat tacgctgtgg agcatagtga tttgttgttg gcgtttgggg    2760
taaggtttga tgatcgtgtc acgggtaaac ttgaggcttt tgctagtagg gctaagattg    2820
ttcatattga tattgactcg gctgagattg ggaagaataa gactcctcat gtgtctgtgt    2880
gtggtgatgt taagctggct ttgcaaggga tgaataaggt tcttgagaac cgagcggagg    2940
agcttaaact tgattttgga gtttggagga atgagttgaa cgtacagaaa cagaagtttc    3000
cgttgagctt taagacgttt ggggaagcta ttcctccaca gtatgcgatt aaggtccttg    3060
atgagttgac tgatggaaaa gccataataa gtactggtgt cgggcaacat caaatgtggg    3120
cggcgcagtt ctacaattac aagaaaccaa ggcagtggct atcatcagga ggccttggag    3180
ctatgggatt tggacttcct gctgcgattg gagcgtctgt tgctaaccct gatgcgatag    3240
ttgtggatat tgacggagat ggaagtttta taatgaatgt gcaagagcta gccactattc    3300
gtgtagagaa tcttccagtg aaggtacttt tattaaacaa ccagcatctt ggcatggtta    3360
tgcaatggga agatcggttc tacaaagcta accgagctca cacatttctc ggggacccgg    3420
ctcaggagga cgagatattc ccgaacatgt tgctgtttgc agcagcttgc gggattccag    3480
cggcgagggt gacaaagaaa gcagatctcc gagaagctat tcagacaatg ctggatacac    3540
caggacctta cctgttggat gtgatttgtc cgcaccaaga acatgtgttg ccgatgatcc    3600
cgaatggtgg cactttcaac gatgtcataa cggaaggaga tggccggatt aaatactgag    3660
agatgaaacc ggtgattatc agaaccttt atggtctttg tatgcatatg gtaaaaaaac    3720
ttagtttgca atttcctgtt tgttttggta atttgagttt cttttagttg ttgatctgcc    3780
tgcttttttgg tttacgtcag actactactg ctgttgttgt ttggtttcct ttctttcatt    3840
ttataaataa ataatccggt tcggtttact ccttgtgact ggctcagttt ggttattgcg    3900
aaatgcgaat ggtaaattga gtaattgaaa ttcgttatta gggttctaag ctgttttaac    3960
agtcactggg ttaatatctc tcgaatcttg catggaaaat gctcttacca ttggttttta    4020
attgaaatgt gctcatatgg gccgtggttt ccaaattaaa taaaactacg atgtcatcga    4080
gaagtaaaat caactgtgtc cacattatca gttttgtgta tacgatgaaa tagggtaatt    4140
caaaatctag cttgatatgc cttttggttc attttaacct tctgtaaaca ttttttcaga    4200
```

```
ttttgaacaa gtaaatccaa aaaaaaaaaa aaaaaatctc aactcaacac taaattattt    4260
taatgtataa aagatgctta aaacatttgg cttaaaagaa agaagctaaa aacatagaga    4320
actcttgtaa attgaagtat gaaaatatac tgaattgggt attatatgaa tttttctgat    4380
ttaggattca catgatccaa aaaggaaatc cagaagcact aatcagacat tggaagtagg    4440
atttaaattt aatcgcagta cttaatcagt gatcagtaac taaattcagt acattaaaga    4500
cgtccgcaat gtgttattaa gttgtctaag cgtcaatttg tttacaccac aatatatcct    4560
gccaccagcc agccaacagc tccccgaccg gcagctcggc acaaaatcac tgatcatcta    4620 aaaggtgat gtgtatttga gtaaaacagc ttgcgtcatg cggtcgctgc gtatatgatg     4680
cgatgagtaa ataaacaaat acgcaagggg aacgcatgaa ggttatcgct gtacttaacc    4740
agaaaggcgg gtcaggcaag acgaccatcg caacccatct agcccgcgcc ctgcaactcg    4800
ccggggccga tgttctgtta gtcgattccg atccccaggg cagtgcccgc gattgggcgg    4860
ccgtgcggga agatcaaccg ctaaccgttg tcggcatcga ccgcccgacg attgaccgcg    4920
acgtgaaggc catcggccgg cgcgacttcg tagtgatcga cggagcgccc caggcggcg     4980 acttggctgt gtccgcgatc aaggcagccg acttcgtgct gattccggtg cagccaagcc    5040
cttacgacat ttgggccacc gccgacctgg tggagctggt taagcagcgc attgaggtca    5100
cggatggaag gctacaagcg gcctttgtcg tgtcgcgggc gatcaaaggc acgcgcatcg    5160
gcggtgaggt tgccgaggcg ctggccgggt acgagctgcc cattcttgag tcccgtatca    5220
cgcagcgcgt gagctaccca ggcactgccg ccgccggcac aaccgttctt gaatcagaac    5280
ccgagggcga cgctgcccgc gaggtccagg cgctggccgc tgaaattaaa tcaaaactca    5340
tttgagttaa tgaggtaaag agaaaatgag caaaagcaca aacacgctaa gtgccggccg    5400
tccgagcgca cgcagcagca aggctgcaac gttggccagc ctggcagaca cgccagccat    5460
gaagcgggtc aactttcagt tgccggcgga ggatcacacc aagctgaaga tgtacgcggt    5520
acgccaaggc aagaccatta ccgagctgct atctgaatac atcgcgcagc taccagagta    5580
aatgagcaaa tgaataaatg agtagatgaa ttttagcggc taaaggaggc ggcatggaaa    5640
atcaagaaca accaggcacc gacgccgtgg aatgccccat gtgtgaagga cgggcggtt    5700 ggccaggcgt aagcggctgg gttgtctgcc ggccctgcaa tggcactgga accccaagc    5760 ccgaggaatc ggcgtgagcg gtcgcaaacc atccggcccg gtacaaatcg cgcggcgct    5820 gggtgatgac ctggtggaga agttgaaggc cgcgcaggcc gcccagcggc aacgcatcga    5880
ggcagaagca cgccccggtg aatcgtggca agggccgct gatcgaatcc gcaaagaatc    5940
ccggcaaccg ccggcagccg gtgcgccgtc gattaggaag ccgcccaagg gcgacgagca    6000
accagatttt ttcgttccga tgctctatga cgtgggcacc cgcgatagtc gcagcatcat    6060
ggacgtggcc gttttccgtc tgtcgaagcg tgaccgacga gctggcgagg tgatccgcta    6120
cgagcttcca gacgggcacg tagaggtttc cgcaggcccc gccggcatgg ccagtgtgtg    6180
ggattacgac ctggtactga tggcggtttc ccatctaacc gaatccatga accgataccg    6240
ggaagggaag ggagacaagc ccggccgcgt gttccgtcca cacgttgcgg acgtactcaa    6300
gttctgccgg cgagccgatg gcggaaagca gaaagacgac ctggtagaaa cctgcattcg    6360
gttaaacacc acgcacgttg ccatgcagcg taccaagaag gccaagaacg gccgcctggt    6420
gacggtatcc gagggtgaag ccttgattag ccgctacaag atcgtaaaga gcgaaaccgg    6480
gcggccggag tacatcgaga tcgagcttgc tgattggatg taccgcgaga tcacagaagg    6540
caagaacccg gacgtgctga cggttcaccc cgattacttt ttgatcgacc ccggcatcgg    6600
```

```
ccgttttctc taccgcctgg cacgccgcgc cgcaggcaag gcagaagcca gatggttgtt    6660
caagacgatc tacgaacgca gtggcagcgc cggagagttc aagaagttct gtttcaccgt    6720
gcgcaagctg atcgggtcaa atgacctgcc ggagtacgat ttgaaggagg aggcggggca    6780
ggctggcccg atcctagtca tgcgctaccg caacctgatc gagggcgaag catccgccgg    6840
ttcctaatgt acggagcaga tgctagggca aattgcccta gcaggggaaa aaggtcgaaa    6900
aggtctcttt cctgtggata gcacgtacat tgggaaccca aagccgtaca ttgggaaccg    6960
gaacccgtac attgggaacc caaagccgta cattgggaac cggtcacaca tgtaagtgac    7020
tgatataaaa gagaaaaaag gcgattttc cgcctaaaac tctttaaaac ttattaaaac    7080
tcttaaaacc cgcctggcct gtgcataact gtctggccag cgcacagccg aagagctgca    7140
aaaagcgcct acccttcggt cgctgcgctc cctacgcccc gccgcttcgc gtcggcctat    7200
cgcggcctat gcggtgtgaa ataccgcaca gatgcgtaag gagaaaatac cgcatcaggc    7260
gctcttccgc ttcctcgctc actgactcgc tgcgctcggt cgttcggctg cggcgagcgg    7320
tatcagctca ctcaaaggcg gtaatacggt tatccacaga atcaggggat aacgcaggaa    7380
agaacatgtg agcaaaaggc cagcaaaagg ccaggaaccg taaaaaggcc gcgttgctgg    7440
cgttttccca taggctccgc cccctgacg agcatcacaa aaatcgacgc tcaagtcaga    7500
ggtggcgaaa cccgacagga ctataaagat accaggcgtt tccccctgga agctccctcg    7560
tgcgctctcc tgttccgacc ctgccgctta ccggatacct gtccgccttt ctcccttcgg    7620
gaagcgtggc gctttctcat agctcacgct gtaggtatct cagttcggtg taggtcgttc    7680
gctccaagct gggctgtgtg cacgaacccc ccgttcagcc cgaccgctgc gccttatccg    7740
gtaactatcg tcttgagtcc aacccggtaa gacacgactt atcgccactg gcagcagcca    7800
ctggtaacag gattagcaga gcgaggtatg taggcggtgc tacagagttc ttgaagtggt    7860
ggcctaacta cggctacact agaaggacag tatttggtat ctgcgctctg ctgaagccag    7920
ttaccttcgg aaaaagagtt ggtagctctt gatccggcaa acaaaccacc gctggtagcg    7980
gtggtttttt tgtttgcaag cagcagatta cgcgcagaaa aaaaggatct caagaagatc    8040
ctttgatctt ttctacgggg tccttcaact catcgatagt ttggctgtga gcaattatgt    8100
gcttagtgca tctaacgctt gagttaagcc gcgccgcgaa gcggcgtcgg cttgaacgaa    8160
tttctagcta gacattattt gccaacgacc ttcgtgatct cgcccttgac atagtggaca    8220
aattcttcga gctggtcggc ccgggacgcg agacggtctt cttcttggcc cagataggct    8280
tggcgcgctt cgaggatcac gggctggtat tgcgccggaa ggcgctccat cgcccagtcg    8340
gcggcgacat ccttcggcgc gatcttgccg gtaaccgccg agtaccaaat ccggctcagc    8400
gtaaggacca cattgcgctc atcgcccgcc caatccggcg gggagttcca cagggtcagc    8460
gtctcgttca gtgcttcgaa cagatcctgt tccggcaccg ggtcgaaaag ttcctcggcc    8520
gcggggccga cgagggccac gctatgctcc cgggccttgg tgagcaggat cgccagatca    8580
atgtcgatgg tggccggttc aaagataccc gccagaatat cattacgctg ccattcgccg    8640
aactggagtt cgcgttttgc cggatagcgc caggggatga tgtcatcgtg caccacaatc    8700
gtcacctcaa ccgcgcgcag gatttcgctc tcgccggggg aggcggacgt ttccagaagg    8760
tcgttgataa gcgcgcggcg cgtggtctcg tcgagacgga cggtaacggt gacaagcagg    8820
tcgatgtccg aatgggggctt aaggccgccg tcaacgcgc taccatacag atgcacggcg    8880
aggagggtcg gttcgaggtg gcgctcgatg acacccacga cttccgacag ctgggtggac    8940
```

```
acctcggcga tgaccgcttc acccatgatg tttaactttg ttttagggcg actgccctgc   9000
tgcgtaacat cgttgctgct ccataacatc aaacatcgac ccacggcgta acgcgcttgc   9060
tgcttggatg cccgaggcat agactgtacc ccaaaaaaac agtcataaca agccatgaaa   9120
accgccactg cgttccatga atattcaaac aaacacatac agcgcgactt atcatggata   9180
ttgacataca aatggacgaa cggataaacc ttttcacgcc cttttaaata tccgattatt   9240
ctaataaacg ctcttttctc ttaggtttac ccgccaatat atcctgtcaa acactgatag   9300
tttaaactga aggcgggaaa cgacaatctg atcactgatt agtaactaag gcctttaatt   9360
aatctagagg cgcgcggggc cccctgcagg gagctcggcc ggccaattta aattgatatc   9420
ggtacatcga ttacgccaag ctatcaactt tgtatagaaa agttgccatg attacgccaa   9480
gcttggccac taaggccaat ttaaatctac taggccggcc aaagtaggcg cctactaccg   9540
gtaattcccg ggattagcgg ccgctagtct gtgcgcactt gtatcctgca ggtcaatcgt   9600
ttaaacactg tacggaccgt ggcctaatag gccggtaccc aagtttgtac aaaaaagcag   9660
gctcccggga tacctgcagg ttaggccggc ccaggtaccc tagattcgac ggtatcgata   9720
agctcgcgga tccctgaaag cgacgttgga tgttaacatc tacaaattgc cttttcttat   9780
cgaccatgta cgtaagcgct tacgttttg gtggacccctt gaggaaactg gtagctgttg   9840
tgggcctgtg gtctcaagat ggatcattaa tttccacctt cacctacgat gggggcatc    9900
gcaccggtga gtaatattgt acggctaaga gcgaatttgg cctgtaggat ccctgaaagc   9960
gacgttggat gttaacatct acaaattgcc ttttcttatc gaccatgtac gtaagcgctt  10020
acgttttggg tggacccttg aggaaactgg tagctgttgt gggcctgtgg tctcaagatg  10080
gatcattaat ttccaccttc acctacgatg ggggcatcg caccggtgag taatattgta  10140
cggctaagag cgaatttggc ctgtaggatc cctgaaagcg acgttggatg ttaacatcta  10200
caaattgcct tttcttatcg accatgtacg taagcgctta cgttttggt ggacccttga  10260
ggaaactggt agctgttgtg ggcctgtggt ctcaagatgg atcattaatt tccaccttca  10320
cctacgatgg ggggcatcgc accggtgagt aatattgtac ggctaagagc gaatttggcc  10380
tgtaggatcc gcgagctggt caatcccatt gcttttgaag cagctcaaca ttgatctctt  10440
tctcgatcga gggagatttt tcaaatcagt gcgcaagacg tgacgtaagt atccgagtca  10500
gttttattt ttctactaat ttggtcgttt atttcggcgt gtaggacatg gcaaccgggc  10560
ctgaatttcg cgggtattct gtttctattc aacttttc ttgatccgca gccattaacg  10620
acttttgaat agatacgctg acacgccaag cctcgctagt caaagtgta ccaaacaacg  10680
cttacagca agaacggaat gcgcgtgacg ctcgcggtga cgccatttcg ccttttcaga  10740
aatggataaa tagccttgct tcctattata tcttcccaaa ttaccaatac attacactag  10800
catctgaatt tcataaccaa tctcgataca ccaaatcgat taattaacca tggcgacgac  10860
aacaacagaa gcaacgaaga catcatcgac caatggagaa gatcagaagc agtctcagaa  10920
tcttcgacat caagaagttg gtcacaagag tctcttacag agcgatgatc tctaccagta  10980
tatactggag acaagtgtgt atcctagaga accagaatca atgaaggaac tcagggaagt  11040
gacagcaaaa catccatgga acataatgac cacatcagct gatgaaggac agttcttaaa  11100
catgcttatc aagctcgtta acgccaagaa cacaatggag atcggagttt acactggcta  11160
ctctcttctc gccaccgctc ttgctctccc tgaagacggc aaaattctgg ctatggatgt  11220
caacagagag aattacgaat tgggtttacc gatcattgag aaagccggcg ttgctcacaa  11280
gatcgacttc agggaaggcc ctgctcttcc cgttcttgat gaaatcgttg ctgacgagaa  11340
```

```
gaaccatgga acatatgact ttatattcgt tgatgctgac aaagacaact acatcaacta    11400
ccacaagcgt tgatcgatc ttgtgaaaat tggaggagtg attggctacg acaacactct    11460
gtggaatggt tctgtcgtgg ctcctcctga tgcaccaatg aggaagtacg ttcgttacta    11520
cagagacttt gttcttgagc ttaacaaggc tcttgctgct gaccctcgga tcagatctg     11580 tatgctccct gttggtgatg gaatcactat ctgccgtcgg atcagttgag gcgcgccgat    11640
cgttcaaaca tttggcaata agtttctta agattgaatc ctgttgccgg tcttgcgatg     11700
attatcatat aatttctgtt gaattacgtt aagcatgtaa taattaacat gtaatgcatg    11760
acgttattta tgagatgggt ttttatgatt agagtcccgc aattatacat ttaatacgcg    11820
atagaaaaca aaatatagcg cgcaaactag gataaattat cgcgcgcggt gtcatctatg    11880
ttactagatc ggcgcctaag tttaaactaa gcggccgcac ccagctttct tgtacaaagt    11940
ggccatgatt acgccaagct tggccactaa ggccaattta aatctactag gccggcccag    12000
gtaccaattc gaatccaaaa attacggata tgaatatagg catatccgta tccgaattat    12060
ccgtttgaca gctagcaacg attgtacaat tgcttcttta aaaaggaag  aaagaaagaa     12120 agaaaagaat caacatcagc gttaacaaac ggcccgtta cggcccaaac ggtcatatag      12180
agtaacggcg ttaagcgttg aaagactcct atcgaaatac gtaaccgcaa acgtgtcata    12240
gtcagatccc ctcttccttc accgcctcaa acacaaaaat aatcttctac agcctatata    12300
tacaaccccc ccttctatct ctcctttctc acaattcatc atctttcttt ctctaccccc    12360 aatttttaaga aatcctctct tctcctcttc attttcaagg taaatctctc tctctctctc   12420
tctctctgtt attccttgtt ttaattaggt atgtattatt gctagtttgt taatctgctt    12480
atcttatgta tgccttatgt gaatatcttt atcttgttca tctcatccgt ttagaagcta    12540
taaatttgtt gatttgactg tgtatctaca cgtggttatg tttatatcta atcagatatg    12600
aatttcttca tattgttgcg tttgtgtgta ccaatccgaa atcgttgatt ttttttcattt   12660 aatcgtgtag ctaattgtac gtatacatat ggatctacgt atcaattgtt catctgtttg   12720
tgtttgtatg tatacagatc tgaaaacatc acttctctca tctgattgtg ttgttacata    12780
catagatata gatctgttat atcattttt ttattaattg tgtatatata tatgtgcata     12840
gatctggatt acatgattgt gattatttac atgattttgt tatttacgta tgtatatatg    12900
tagatctgga cttttttggag ttgttgactt gattgtattt gtgtgtgtat atgtgtgttc    12960
tgatcttgat atgttatgta tgtgcagtta attaaccatg gctccaacac tcttgacaac    13020
ccaattctca aatccagctg aagtaaccga ctttgtagtc tacaaaggaa atggtgttaa    13080
gggtttatca gaaacaggaa tcaaagctct tccagaacaa tacattcagc cacttgaaga    13140
acgactcatc aacaaattcg tcaacgaaac agatgaagcc attccagtta tcgatatgtc    13200
gaaccctgat gaggacagag tcgctgaagc tgtttgtgat gctgctgaga atgggggttt    13260
ctttcaagtg atcaatcatg gagttccttt ggaagttctt gatgacgtca aggctgcgac    13320
tcacaagttc ttcaatctcc ctgttgaaga gaagcgcaag ttcactaaag agaattcgct    13380
gtcgacgact gttaggtttg ggacgagttt tagtcctctt gcagagcaag cgcttgagtg    13440
gaaagattat ctcagcctct tctttgtctc tgaagctgaa gctgaacagt tctggcctga    13500
tatctgcagg aatgaaacgt tagagtacat taacaagtca agaagatgg tgaggaggct     13560 tctagagtat ttgggaaaga atctcaatgt taaagagctt gacgagacga aagaatcact    13620
ctttatgggc tcgattcgag tcaaccttaa ctactacccc atctgccta atccggacct      13680
```

```
aacagttggt gttggtcgcc actcagacgt ctcttctctc accattctct tacaagacca    13740
gatcggtggt ctacacgtgc gttctctggc ttcagggaac tgggttcacg tgcctccggt    13800
tgctggatct tttgtgatca acatcggaga tgcgatgcag atcatgagca atggtctgta    13860
caagagcgtg gagcatcgtg tcttagccaa tggttacaat aatagaatct ctgttcctat    13920
ctttgtgaac ccaaaaccag agtcagttat tggtcctcta cctgaggtga ttgcaaacgg    13980
agaggaaccg atttacagag acgtcctgta ctctgattac gtcaagtatt tcttcaggaa    14040
ggcacacgat ggaaagaaaa ccgtcgatta cgccaagatc tgaggcgcgc cctgctttaa    14100
tgagatatgc gagacgccta tgatcgcatg atatttgctt tcaattctgt tgtgcacgtt    14160
gtaaaaaacc tgagcatgtg tagctcagat ccttaccgcc ggtttcggtt cattctaatg    14220
aatatatcac ccgttactat cgtattttta tgaataatat tctccgttca atttactgat    14280
tgtggcgcct actaccggta attcccggga ttagcggccg ctagtctgtg cgcacttgta    14340
tcctgcaggt caatcgttta aacactgtac ggaccgtggc ctaataggcc ggtacccaac    14400
ttta                                                                 14404

<210> SEQ ID NO 75
<211> LENGTH: 20077
<212> TYPE: DNA
<213> ORGANISM: Artificial Sequence
<220> FEATURE:
<223> OTHER INFORMATION: vector

<400> SEQUENCE: 75
ttatacatag ttgataattc actggccgga tgtaccgaat tcgcggccgc aagcttggta      60 cctttctttta cgaggtaatt gatctcgcat tatatatcta cattttggtt atgttacttg     120
acatatagtc attgattcaa tagttctgtt aattccttta aagatcattt tgactagacc     180
acattcttgg ttcattcctc aataatttgt aatcatattg gtggatatag aagtagattg     240
gttatagatc agatagtgga agactttagg atgaatttca gctagttttt ttttttggct     300
tattgtctca aaagattagt gctttgctgt ctccattgct tctgctatcg acacgcttct     360
gtctccttgt atctttatta tatctattcg tcccatgagt tttgtttgtt ctgtattcgt     420
tcgctctggt gtcatggatg gagtctctgt tccatgtttc tgtaatgcat gttgggttgt     480
ttcatgcaag aaatgctgag ataaacactc atttgtgaaa gtttctaaac tctgaatcgc     540
gctacaggca atgctccgag gagtaggagg agaagaacga accaaacgac attatcagcc     600
ctttgaggaa gctcttagtt ttgttattgt ttttgtagcc aaattctcca ttcttattcc     660
attttcactt atctcttgtt ccttatagac cttataagtt ttttattcat gtatacaaat     720
tatattgtca tcaagaagta tctttaaaat ctaaatctca aatcaccagg actatgtttt     780
tgtccaattc gtggaaccaa cttgcagctt gtatccattc tcttaaccaa taaaaaaaga     840
aagaaagatc aatttgataa atttctcagc cacaaattct acatttaggt tttagcatat     900
cgaaggctca atcacaaata caatagatag actagagatt ccagcgtcac gtgagttta     960 tctataaata aaggaccaaa atcaaatcc cgagggcatt tcgtaatcc aacataaaac    1020 ccttaaactt caagtctcat ttttaaacaa atcatgttca caagtctctt cttcttctct    1080
gtttctctat ctcttgctcg ggcccttaga tctcgtgccg tcgtgcgacg ttgttttccg    1140
gtacgtttat tcctgttgat tccttctctg tctctctcga ttcactgcta cttctgtttg    1200
gattcctttc gcgcgatctc tggatccgtg cgttattcat tggctcgtcg ttttcagatc    1260
tgttgcgttt cttctgtttt ctgttatgag tggatgcgtt ttcttgtgat tcgcttgttt    1320
```

```
gtaatgctgg atctgtatct gcgtcgtggg aattcaaagt gatagtagtt gatatttttt    1380
ccagatcagg catgttctcg tataatcagg tctaatggtt gatgattctg cggaattata    1440
gatctaagat cttgattgat ttagatttga ggatatgaat gagattcgta ggtccacaaa    1500
ggtcttgtta tctctgctgc tagatagatg attatccaat gcgtttcgt agttattttt     1560
atggattcaa ggaattgcgt gtaattgaga gttttactct gttttgtgaa caggcttgat    1620
caaactcgag atctttctcc tgaaccatgg cggcggcaac aacaacaaca caacatctt     1680
cttcgatctc cttctccacc aaaccatctc cttcctcctc caaatcacca ttaccaatct    1740
ccagattctc cctcccattc tccctaaacc ccaacaaatc atcctcctcc tcccgccgcc    1800
gcggtatcaa atccagctct ccctcctcca tctccgccgt gctcaacaca accaccaatg    1860
tcacaaccac tccctctcca accaaaccta ccaaacccga acattcatc tcccgattcg     1920
ctccagatca accccgcaaa ggcgctgata tcctcgtcga ggctttagaa cgtcaaggcg    1980
tagaaaccgt attcgcttac cctggaggta catcaatgga gattcaccaa gccttaaccc    2040
gctcttcctc aatccgtaac gtccttcctc gtcacgaaca aggaggtgta ttcgcagcag    2100
aaggatacgc tcgatcctca ggtaaaccag gtatctgtat agccacttca ggtcccggag    2160
ctacaaatct cgttagcgga ttagccgatg cgttgttaga tagtgttcct cttgtagcaa    2220
tcacaggaca agtccctcgt cgtatgattg gtacagatgc gtttcaagag actccgattg    2280
ttgaggtaac gcgttcgatt acgaagcata actatcttgt gatggatgtt gaagatatcc    2340
caaggattat tgaagaggct ttcttttttag ctacttctgg tagacctgga cctgttttgg    2400
ttgatgttcc taaagatatt caacaacagc ttgcgattcc taattgggaa caggctatga    2460
gattacctgg ttatatgtct aggatgccta aacctccgga agattctcat ttggagcaga    2520
ttgttaggtt gatttctgag tctaagaagc ctgtgttgta tgttggtggt ggttgtctta    2580
attctagcga tgaattgggt aggtttgttg agcttacggg catccctgtt gcgagtacgt    2640
tgatggggct gggatcttat ccttgtgatg atgagttgtc gttacatatg cttggaatgc    2700
atgggactgt gtatgcaaat tacgctgtgg agcatagtga tttgttgttg gcgtttgggg    2760
taaggtttga tgatcgtgtc acgggtaaac ttgaggcttt tgctagtagg gctaagattg    2820
ttcatattga tattgactcg gctgagattg ggaagaataa gactcctcat gtgtctgtgt    2880
gtggtgatgt taagctggct ttgcaaggga tgaataaggt tcttgagaac cgagcggagg    2940
agcttaaaact tgattttgga gtttggagga tgagttgaa cgtacagaaa cagaagtttc    3000
cgttgagctt taagacgttt ggggaagcta ttcctccaca gtatgcgatt aaggtccttg    3060
atgagttgac tgatggaaaa gccataataa gtactggtgt cgggcaacat caaatgtggg    3120
cggcgcagtt ctacaattac aagaaaccaa ggcagtggct atcatcagga ggccttggag    3180
ctatgggatt tggacttcct gctgcgattg gagcgtctgt tgctaaccct gatgcgatag    3240
ttgtggatat tgacggagat ggaagttta taatgaatgt gcaagagcta gccactattc    3300
gtgtagagaa tcttccagtg aaggtacttt tattaaacaa ccagcatctt ggcatggtta    3360
tgcaatggga agatcggttc tacaaagcta accgagctca cacatttctc ggggacccgg    3420
ctcaggagga cgagatattc ccgaacatgt tgctgtttgc agcagcttgc gggattccag    3480
cggcgagggt gacaaagaaa gcagatctcc gagaagctat tcagacaatg ctggatacac    3540
caggacctta cctgttggat gtgatttgtc cgcaccaaga acatgtgttg ccgatgatcc    3600
cgaatggtgg cactttcaac gatgtcataa cggaaggaga tggccggatt aaatactgag    3660
```

```
agatgaaacc ggtgattatc agaacctttt atggtctttg tatgcatatg gtaaaaaaac  3720
ttagtttgca atttcctgtt tgttttggta atttgagttt cttttagttg ttgatctgcc  3780
tgcttttttgg tttacgtcag actactactg ctgttgttgt ttggtttcct ttctttcatt  3840
ttataaataa ataatccggt tcggtttact ccttgtgact ggctcagttt ggttattgcg  3900
aaatgcgaat ggtaaattga gtaattgaaa ttcgttatta gggttctaag ctgttttaac  3960
agtcactggg ttaatatctc tcgaatcttg catggaaaat gctcttacca ttggttttta  4020
attgaaatgt gctcatatgg gccgtggttt ccaaattaaa taaaactacg atgtcatcga  4080
gaagtaaaat caactgtgtc cacattatca gttttgtgta tacgatgaaa tagggtaatt  4140
caaaatctag cttgatatgc cttttggttc attttaacct tctgtaaaca ttttttcaga  4200
ttttgaacaa gtaaatccaa aaaaaaaaaa aaaaatctc aactcaacac taaattattt  4260
taatgtataa aagatgctta aaacatttgg cttaaaagaa agaagctaaa aacatagaga  4320
actcttgtaa attgaagtat gaaaatatac tgaattgggt attatatgaa ttttctgat  4380
ttaggattca catgatccaa aaaggaaatc cagaagcact aatcagacat tggaagtagg  4440
atttaaattt aatcgcagta cttaatcagt gatcagtaac taaattcagt acattaaaga  4500
cgtccgcaat gtgttattaa gttgtctaag cgtcaatttg tttacaccac aatatatcct  4560
gccaccagcc agccaacagc tccccgaccg gcagctcggc acaaaatcac tgatcatcta  4620
aaaaggtgat gtgtatttga gtaaaacagc ttgcgtcatg cggtcgctgc gtatatgatg  4680
cgatgagtaa ataaacaaat acgcaagggg aacgcatgaa ggttatcgct gtacttaacc  4740
agaaaggcgg gtcaggcaag acgaccatcg caacccatct agcccgcgcc ctgcaactcg  4800
ccggggccga tgttctgtta gtcgattccg atccccaggg cagtgcccgc gattgggcgg  4860
ccgtgcggga agatcaaccg ctaaccgttg tcggcatcga ccgcccgacg attgaccgcg  4920
acgtgaaggc catcggccgg cgcgacttcg tagtgatcga cggagcgccc caggcggcgg  4980
acttggctgt gtccgcgatc aaggcagccg acttcgtgct gattccggtg cagccaagcc  5040
cttacgacat ttgggccacc gccgacctgg tggagctggt taagcagcgc attgaggtca  5100
cggatggaag gctacaagcg gccttttgtcg tgtcgcgggc gatcaaaggc acgcgcatcg  5160
gcggtgaggt tgccgaggcg ctggccgggt acagctgcc cattcttgag tcccgtatca  5220
cgcagcgcgt gagctaccca ggcactgccg ccgccggcac aaccgttctt gaatcagaac  5280
ccgagggcga cgctgcccgc gaggtccagg cgctggccgc tgaaattaaa tcaaaactca  5340
tttgagttaa tgaggtaaag agaaaatgag caaaagcaca aacacgctaa gtgccggccg  5400
tccgagcgca cgcagcagca aggctgcaac gttggccagc ctggcagaca cgccagccat  5460
gaagcgggtc aactttcagt tgccggcgga ggatcacacc aagctgaaga tgtacgcggt  5520
acgccaaggc aagaccatta ccgagctgct atctgaatac atcgcgcagc taccagagta  5580
aatgagcaaa tgaataaatg agtagatgaa ttttagcggc taaaggaggc ggcatggaaa  5640
atcaagaaca accaggcacc gacgccgtgg aatgccccat gtgtggagga acgggcggtt  5700
ggccaggcgt aagcggctgg gttgtctgcc ggccctgcaa tggcactgga acccccaagc  5760
ccgaggaatc ggcgtgagcg gtcgcaaacc atccggcccg gtacaaatcg cgcggcgct  5820
gggtgatgac ctggtggaga gttgaaggc cgcgcaggcc gcccagcggc aacgcatcga  5880
ggcagaagca cgccccggtg aatcgtggca aggggccgct gatcgaatcc gcaaagaatc  5940
ccggcaaccg ccggcagccg gtgcgccgtc gattaggaag ccgcccaagg cgacgagca  6000
accagatttt ttcgttccga tgctctatga cgtgggcacc cgcgatagtc gcagcatcat  6060
```

```
ggacgtggcc gttttccgtc tgtcgaagcg tgaccgacga gctggcgagg tgatccgcta    6120
cgagcttcca gacgggcacg tagaggtttc cgcaggcccc gccggcatgg ccagtgtgtg    6180
ggattacgac ctggtactga tggcggtttc ccatctaacc gaatccatga accgataccg    6240
ggaagggaag ggagacaagc ccggccgcgt gttccgtcca cacgttgcgg acgtactcaa    6300
gttctgccgg cgagccgatg gcggaaagca gaaagacgac ctggtagaaa cctgcattcg    6360
gttaaacacc acgcacgttg ccatgcagcg taccaagaag gccaagaacg gccgcctggt    6420
gacggtatcc gagggtgaag ccttgattag ccgctacaag atcgtaaaga gcgaaaccgg    6480
gcggccggag tacatcgaga tcgagcttgc tgattggatg taccgcgaga tcacagaagg    6540
caagaacccg gacgtgctga cggttcaccc cgattacttt ttgatcgacc ccggcatcgg    6600
ccgtttctc taccgcctgg cacgccgcgc cgcaggcaag gcagaagcca gatggttgtt    6660
caagacgatc tacgaacgca gtggcagcgc cggagagttc aagaagttct gtttcaccgt    6720
gcgcaagctg atcgggtcaa atgacctgcc ggagtacgat ttgaaggagg aggcggggca    6780
ggctggcccg atcctagtca tgcgctaccg caacctgatc gagggcgaag catccgccgg    6840
ttcctaatgt acgagcaga tgctagggca aattgcccta gcaggggaaa aaggtcgaaa    6900
aggtctcttt cctgtggata gcacgtacat tgggaaccca aagccgtaca ttgggaaccg    6960
gaacccgtac attgggaacc caaagccgta cattgggaac cggtcacaca tgtaagtgac    7020
tgatataaaa gagaaaaaag gcgattttc cgcctaaaac tctttaaaac ttattaaaac    7080
tcttaaaacc cgcctggcct gtgcataact gtctggccag cgcacagccg aagagctgca    7140
aaaagcgcct acccttcggt cgctgcgctc cctacgcccc gccgcttcgc gtcggcctat    7200
cgcggcctat gcggtgtgaa ataccgcaca gatgcgtaag gagaaaatac cgcatcaggc    7260
gctcttccgc ttcctcgctc actgactcgc tgcgctcggt cgttcggctg cggcgagcgg    7320
tatcagctca ctcaaaggcg gtaatacggt tatccacaga atcaggggat aacgcaggaa    7380
agaacatgtg agcaaaaggc cagcaaaagg ccaggaaccg taaaaaggcc gcgttgctgg    7440
cgttttccca taggctccgc cccctgacg agcatcacaa aaatcgacgc tcaagtcaga    7500
ggtggcgaaa cccgacagga ctataaagat accaggcgtt tccccctgga agctccctcg    7560
tgcgctctcc tgttccgacc ctgccgctta ccggatacct gtccgccttt ctcccttcgg    7620
gaagcgtggc gctttctcat agctcacgct gtaggtatct cagttcggtg taggtcgttc    7680
gctccaagct gggctgtgtg cacgaacccc ccgttcagcc cgaccgctgc gccttatccg    7740
gtaactatcg tcttgagtcc aacccggtaa gacacgactt atcgccactg gcagcagcca    7800
ctggtaacag gattagcaga gcgaggtatg taggcggtgc tacagagttc ttgaagtggt    7860
ggcctaacta cggctacact agaaggacag tatttggtat ctgcgctctg ctgaagccag    7920
ttaccttcgg aaaaagagtt ggtagctctt gatccggcaa acaaaccacc gctggtagcg    7980
gtggtttttt tgtttgcaag cagcagatta cgcgcagaaa aaaaggatct caagaagatc    8040
ctttgatctt ttctacgggg tccttcaact catcgatagt ttggctgtga gcaattatgt    8100
gcttagtgca tctaacgctt gagttaagcc gcgccgcgaa gcggcgtcgg cttgaacgaa    8160
tttctagcta gacattattt gccaacgacc ttcgtgatct cgcccttgac atagtggaca    8220
aattcttcga gctggtcggc ccgggacgcg agacggtctt cttcttggcc cagataggct    8280
tggcgcgctt cgaggatcac gggctggtat tgcgccggaa ggcgctccat cgcccagtcg    8340
gcggcgacat ccttcggcgc gatcttgccg gtaaccgccg agtaccaaat ccggctcagc    8400
```

```
gtaaggacca cattgcgctc atcgcccgcc caatccggcg gggagttcca cagggtcagc    8460
gtctcgttca gtgcttcgaa cagatcctgt tccggcaccg ggtcgaaaag ttcctcggcc    8520
gcggggccga cgagggccac gctatgctcc cgggccttgg tgagcaggat cgccagatca    8580
atgtcgatgg tggccggttc aaagataccc gccagaatat cattacgctg ccattcgccg    8640
aactggagtt cgcgtttggc cggatagcgc caggggatga tgtcatcgtg caccacaatc    8700
gtcacctcaa ccgcgcgcag gatttcgctc tcgccggggg aggcggacgt ttccagaagg    8760
tcgttgataa gcgcgcggcg cgtggtctcg tcgagacgga cggtaacggt gacaagcagg    8820
tcgatgtccg aatggggctt aaggccgccg tcaacggcgc taccatacag atgcacggcg    8880
aggagggtcg gttcgaggtg gcgctcgatg acacccacga cttccgacag ctgggtggac    8940
acctcggcga tgaccgcttc acccatgatg tttaactttg ttttagggcg actgccctgc    9000
tgcgtaacat cgttgctgct ccataacatc aaacatcgac ccacggcgta acgcgcttgc    9060
tgcttggatg cccgaggcat agactgtacc ccaaaaaaac agtcataaca agccatgaaa    9120
accgccactg cgttccatga atattcaaac aaacacatac agcgcgactt atcatggata    9180
ttgacataca aatggacgaa cggataaacc ttttcacgcc cttttaaata tccgattatt    9240
ctaataaacg ctcttttctc ttaggtttac ccgccaatat atcctgtcaa acactgatag    9300
tttaaactga aggcgggaaa cgacaatctg atcactgatt agtaactaag gcctttaatt    9360
aatctagagg cgcgccgggc cccctgcagg gagctcggcc ggccaattta aattgatatc    9420
ggtacatcga ttacgccaag ctatcaactt tgtatagaaa agttgccatg attacgccaa    9480
gcttggccac taaggccaat ttaaatctac taggccggcc caggtaccat ttccaactcc    9540
tgactgagaa gtggatttca tatcaacatt agcaattagt agaatactat catctttcac    9600
gctacaaaac attggtactt tggtaggtaa agatttgcaa acacgaataa gtaattaaga    9660
aaggttcata cacattcaat gattctggat tcctaccttta cgttatttgt ttcgaaatac    9720
ctagatgaga gcatcttgtt atttattact acatattaat tttccctgtg taccttgtcg    9780
tagtttaaat ttattatttt ttcaatcata ataaatata  agaaatattt ttttcttaat    9840
ataattttat tttatattta aaaataaatc ataatttgaa agagctacaa atttatacca    9900
catgtgggaa gtattgttgg tttctccaac catacttatt gagaataact tgaatttata    9960
ttcaacgtat taattgcttc acctttaacg tgccaaaata ataataataa aaacttaaa    10020 actactgtat taatcgcgtg tggttgaatg gaggcaaatt ctattctaaa aaagaaaagc    10080
attaacaaaa ggagaaaaga aaaactgttg acacctgaca gcagtaacag ggaactggga    10140
agtagcagta ggagtatttg cgtgttggtt tccaactctg gaatccaccg tgccaaactg    10200
cgaatgcagg agaaatcgac acgtgtccat ttgcaggcgc gagttgaacg tgacaatgca    10260
ccaccgccca gcatcgaacg cagccaagga ccacgtcgaa accacagtaa tccacgttcc    10320
agtgctgcgc ggaacatggt cggtctttct aggagtggtt ggaatcacgc cagctaggac    10380
aaaccccatc aatcattggt cattatcaaa caaaacattt caaaaattca acatattacg    10440
cctcgggacc cacctcccac tacacctcac cctcacttct attaactcga acacattcgg    10500
gttataaatc cgcaacccctc cttctcactc actcactcac tcactcactc actcgcaagc    10560
aaaaagaaag aatcccaggc gaggagaaag ttaattaacc atggctcata tggttggagc    10620
agacgatatt gagtcattga gagtagagct tgcagagatc ggaagaagca tcagatcatc    10680
attccggaga catacttcga gtttcagaag cagctcttca atatatgaag ttgaaaatga    10740
tggtgatgtt aatgatcatg atgcagagta tgctctgcaa tgggctgaga ttgagagatt    10800
```

```
accaactgtc aagcgaatga gatcgactct ccttgatgat ggcgatgagt ccatgaccga   10860
gaaaggaaga agagtcgttg atgtcacaaa gcttggagcc gtggaacgtc atctgatgat   10920
tgagaaactc atcaaacaca ttgagaatga taatctcaag ttgctcaaga aaatcaggag   10980
aagaatagac agagtcggga tggagttacc gaccatagaa gtgaggtacg agagtttaaa   11040
agtggtggcc gagtgcgagg ttgtcgaagg gaaggcactt ccaacactgt ggaacactgc   11100
taagcgtgtt ttatctgaac tggtgaagct cactggtgca aaaacacatg aagccaagat   11160
aaacattatt aatgatgtta atggcattat aaagccagga aggttaacac tgttgcttgg   11220
tcctcctagc tgcggaaaaa caactttgtt aaaggccttg tctggaaatt tagaaaacaa   11280
tctaaagtgt tcaggtgaaa tatcttacaa tggacacaga ctggatgagt ttgttcctca   11340
gaaaacttca gcgtacataa gtcaatatga tctgcacatt gcagagatga cagtgaggga   11400
gacagttgac ttctcagctc gttgtcaggg cgttggtagc cgaacagata ttatgatgga   11460
agttagtaaa agagaaaagg aaaaaggaat cattcctgac acagaagtgg atgcttacat   11520
gaaagcaatt tctgttgaag gactccaaag aagtctgcaa acagattaca ttttgaagat   11580
tctcggactt gatatttgtg cagaaatatt gattggagat gtgatgagga gaggtatatc   11640
aggaggtcaa aagaagcgtc ttaccacagc tgagatgatc gttggcccga caaaggctct   11700
gtttatggat gaaataacaa atggcctaga cagctccaca gcttttcaga ttgtcaaatc   11760
tcttcagcag tttgctcaca tatcaagcgc tactgtactt gtttcgcttc ttcaacccgc   11820
cccagaatcc tatgacctct ttgatgcat tatgctgatg ccaaaggaa gaatcgtgta   11880
tcatggtcca cgcggtgaag tccttaactt cttttgagga ttgtggattcc gatgccctga   11940
aaggaagggt gttgcagact ttctccagga ggttatatcc aaaaaagatc aagcacaata   12000
ctggtggcac gaggatttac cttacagttt tgtctcggta gaaatgttgt cgaagaagtt   12060
caaggacttg agtattggga aaagatcga agacactctg tcaaagccat atgatagatc   12120
caaaagccat aaggatgctt tgtccttcag tgtgtattct cttccaaact gggagctgtt   12180
catagcatgc atatcaagag agtatcttct catgaagaga aactatttcg tctatatttt   12240
caagactgct cagcttgtta tggccgcatt catcactatg acagtgttta tccgaacacg   12300
gatgggtatt gatatcattc atggaaattc ttacatgagt gccctctttt tcgccctcat   12360
tatacttctt gttgacggat tcccagagtt gtctatgacg gctcaacgtc tagccgtgtt   12420
ttataagcag aagcagttgt gtttctatcc tgcatgggcg tatgcaatcc ctgcaacagt   12480
gttaaaggtc cctctctcgt tctttgaatc tctcgtttgg acctgcctct catactatgt   12540
cattggatac acccctgaag catccaggtt cttcaagcag ttcattctac tctttgctgt   12600
tcacttcacc tcgatatcca tgttccggtg tctagctgca atcttccaga cagtagttgc   12660
ttcaatcaca gctggcagtt ttggtatatt attcacattt gtctttgccg gtttcgtcat   12720
tccaccacct tctatgccag catggctcaa gtgggggtttc tgggcaaatc ctttgagtta   12780
cggtgagatt gggttatcag taaacgagtt tcttgctcca aggtggaatc agatgcaacc   12840
caataatttt accttaggac gaaccatact ccaaacccgt ggaatggact acaacggtta   12900
catgtactgg gtatcattat gtgccttgtt gggtttcact gtgctcttca acatcatttt   12960
cactctggct ctaacgttct tgaaatcacc cacatcatct cgagccatga tttcgcaaga   13020
caaactctct gagctgcaag gaacagaaaa gtcaacagaa gattcttctg tcaggaaaaa   13080
gaccacagac tcccctgtaa agaccgaaga agaagacaaa atggtcttac cattcaagcc   13140
```

```
tctcactgta acatttcaag acttgaacta tttcgttgac atgccagtgg agatgagaga    13200
ccaaggatat gatcagaaga aactacaact tctctcagat atcacaggag ctttccgtcc    13260
cggaatccta acggcactaa tgggagtgag tggagctgga aaaaccactc ttctcgacgt    13320
tctagccgga aggaaaacaa gcggatacat cgaaggagac attagaatca gtggcttccc    13380
taaagtccaa gaaacattcg ctagagtctc aggctactgt gaacaaacag atattcactc    13440
accaaacatc actgtagaag aatccgtaat ctactcggct tggcttcgtc tagctcctga    13500
gatcgatgcc acaacaaaaa ccaaattcgt gaagcaagtg cttgagacga tcgaattaga    13560
tgagattaaa gattcattgg tgggagtcac cggagttagt ggattatcga cggagcaaag    13620
gaagagattg acgattgcgg tggagttggt ggcgaatccg tcgattatat ttatggatga    13680
gccaacgacg gggctagacg caagagcagc tgccattgtt atgagagctg tgaagaacgt    13740
cgctgatact ggacgaacca tcgtctgtac tattcatcag cctagtatcg acatttttga    13800
agccttcgac gagctggtgc ttcttaaaag aggtggtcgc atgatctaca caggaccatt    13860
aggccaacat tcacgtcaca ttatcgagta ttttgagagt gttcctgaaa ttcctaaaat    13920
aaaagacaac cacaatccag caacatggat gcttgatgtt agttcacagt cggtagaaat    13980
tgaacttggt gtcgatttcg caaaaatcta ccatgactct gctctttaca agcgaaactc    14040
agagcttgtg aaacagttga gccagccaga ttcaggatca agtgatatac agtttaagag    14100
aacctttgca caaagctggt ggggacaatt caaatctatt ctatggaaaa tgaacttgtc    14160
ttattggaga agcccttctt ataacctaat gcgtatgatg cacactttag tctcttcttt    14220
gatcttcggc gcacttttct ggaaacaagg ccaaaatcta gatactcaac agagtatgtt    14280
cacagtattt ggagcgatct acggtttggt actcttctta gggataaaca attgtgcatc    14340
agctcttcaa tatttcgaaa cagagagaaa tgttatgtac cgggaaagat tcgcagggat    14400
gtactcagcg actgcttatg cattgggtca agtggtgact gagataccct atatattcat    14460
acaagctgcc gagtttgtga tcgtaacata tccaatgatc ggtttctatc cttcagccta    14520
caaagtcttt tggtcactct actctatgtt ttgctcacta ctcactttca actaccttgc    14580
gatgttcctc gtctccatca cgccaaactt catggttgcc gcgattcttc aatcgctctt    14640
ttatgttggt ttcaacccttt tttcggggtt tttgatcccc caaacgcaag taccagggtg    14700
gtggatttgg ttatattatc taacaccaac gtcttggaca ctcaacgggt ttatctcgtc    14760
ccaatacggc gatattcatg aagagatcaa tgtctttgga caatccacga cggttgcaag    14820
attcttgaaa gactattttg gatttcatca tgaccttttg gcggttaccg cggttgttca    14880
aatcgctttt cccattgcct tagcttctat gtttgcattc ttcgtgggca aactcaactt    14940
ccaacgaaga tgaggcgcgc ccctgcagat agactatact atgttttagc ctgcctgctg    15000
gctagctact atgttatgtt atgttgtaaa ataaacacct gctaaggtat atctatctat    15060
attttagcat ggctttctca ataaattgtc tttccttatc gtttactatc ttatacctaa    15120
taatgaaata ataatatcac atatgaggaa cggggcaggt ttaggcatat atatacgagt    15180
gtagggcgga gtggggtaag gcgcctacta ccggtaattc ccgggattag cggccgctag    15240
tctgtgcgca cttgtatcct gcaggtcaat cgtttaaaca ctgtacggac cgtgcctaa    15300 taggccggta cccaagtttg tacaaaaaag caggctcccg ggataccttgc aggttaggcc    15360 ggcccaggta ccctagattc gacggtatcg ataagctcgc ggatccctga aagcgacgtt    15420
ggatgttaac atctacaaat tgcctttcct tatcgaccat gtacgtaagc gcttacgttt    15480
ttggtggacc cttgaggaaa ctggtagctg ttgtgggcct gtggtctcaa gatggatcat    15540
```

```
taatttccac cttcacctac gatgggggc atcgcaccgg tgagtaatat tgtacggcta    15600
agagcgaatt tggcctgtag gatccctgaa agcgacgttg gatgttaaca tctacaaatt    15660
gccttttctt atcgaccatg tacgtaagcg cttacgtttt tggtggaccc ttgaggaaac    15720
tggtagctgt tgtgggcctg tggtctcaag atggatcatt aatttccacc ttcacctacg    15780 atgggggca tcgcaccggt gagtaatatt gtacggctaa gagcgaattt ggcctgtagg    15840
atccctgaaa gcgacgttgg atgttaacat ctacaaattg cctttctta tcgaccatgt    15900 acgtaagcgc ttacgttttt ggtggaccct tgaggaaact ggtagctgtt gtgggcctgt    15960
ggtctcaaga tggatcatta atttccacct tcacctacga tgggggcat cgcaccggtg    16020 agtaatattg tacggctaag agcgaatttg gcctgtagga tccgcgagct ggtcaatccc    16080 attgctttg aagcagctca acattgatct ctttctcgat cgagggagat ttttcaaatc    16140
agtgcgcaag acgtgacgta agtatccgag tcagttttta tttttctact aatttggtcg    16200
tttatttcgg cgtgtaggac atggcaaccg ggcctgaatt tcgcgggtat tctgtttcta    16260
ttccaacttt ttcttgatcc gcagccatta acgactttg aatagatacg ctgacacgcc    16320
aagcctcgct agtcaaaagt gtaccaaaca acgctttaca gcaagaacgg aatgcgcgtg    16380
acgctcgcgg tgacgccatt tcgccttttc agaaatggat aaatagcctt gcttcctatt    16440
atatcttccc aaattaccaa tacattacac tagcatctga atttcataac caatctcgat    16500
acaccaaatc gattaattaa ccatggcgac gacaacaaca gaagcaacga agacatcatc    16560
gaccaatgga gaagatcaga agcagtctca gaatcttcga catcaagaag ttggtcacaa    16620
gagtctctta cagagcgatg atctctacca gtatatactg gagacaagtg tgtatcctag    16680
agaaccagaa tcaatgaagg aactcaggga agtgacagca aaacatccat ggaacataat    16740
gaccacatca gctgatgaag gacagttctt aaacatgctt atcaagctcg ttaacgccaa    16800
gaacacaatg gagatcggag tttacactgg ctactctctt ctcgccaccg ctcttgctct    16860
ccctgaagac ggcaaaattc tggctatgga tgtcaacaga gagaattacg aattgggttt    16920
accgatcatt gagaaagccg gcgttgctca caagatcgac ttcagggaag ccctgctct    16980 tcccgttctt gatgaaatcg ttgctgacga gaagaaccat ggaacatatg actttatatt    17040
cgttgatgct gacaaagaca actacatcaa ctaccacaag cgtttgatcg atcttgtgaa    17100
aattggagga gtgattggct acgacaacac tctgtgaat ggtctgtcg tggctcctcc    17160 tgatgcacca atgaggaagt acgttcgtta ctacagagac tttgttcttg agcttaacaa    17220
ggctcttgct gctgaccctc ggatcgagat ctgtatgctc cctgttggtg atggaatcac    17280
tatctgccgt cggatcagtt gaggcgcgcc gatcgttcaa acatttggca ataaagtttc    17340
ttaagattga atcctgttgc cggtcttgcg atgattatca tataatttct gttgaattac    17400
gttaagcatg taataattaa catgtaatgc atgacgttat ttatgagatg ggttttatg    17460 attagagtcc cgcaattata catttaatac gcgatagaaa acaaaatata gcgcgcaaac    17520
taggataaat tatcgcgcgc ggtgtcatct atgttactag atcggcgcct aagtttaaac    17580
taagcggccg cacccagctt tcttgtacaa agtggccatg attacgccaa gcttggccac    17640
taaggccaat ttaaatctac taggccggcc caggtaccaa ttcgaatcca aaaattacgg    17700
atatgaatat aggcatatcc gtatccgaat tatccgtttg acagctagca acgattgtac    17760
aattgcttct ttaaaaaagg aagaaagaaa gaaagaaaag aatcaacatc agcgttaaca    17820
aacggccccg ttacggccca aacggtcata tagagtaacg gcgttaagcg ttgaaagact    17880
```

| | |
|---|---|
| cctatcgaaa tacgtaaccg caaacgtgtc atagtcagat ccccctcttcc ttcaccgcct | 17940 |
| caaacacaaa aataatcttc tacagcctat atatacaacc ccccccttcta tctctccttt | 18000 |
| ctcacaattc atcatctttc tttctctacc cccaatttta agaaatcctc tcttctcctc | 18060 |
| ttcattttca aggtaaatct ctctctctct ctctctctct gttattcctt gttttaatta | 18120 |
| ggtatgtatt attgctagtt tgttaatctg cttatcttat gtatgccttta tgtgaatatc | 18180 |
| tttatcttgt tcatctcatc cgtttagaag ctataaattt gttgatttga ctgtgtatct | 18240 |
| acacgtggtt atgtttatat ctaatcagat atgaatttct tcatattgtt gcgtttgtgt | 18300 |
| gtaccaatcc gaaatcgttg attttttttca tttaatcgtg tagctaattg tacgtataca | 18360 |
| tatggatcta cgtatcaatt gttcatctgt ttgtgtttgt atgtatacag atctgaaaac | 18420 |
| atcacttctc tcatctgatt gtgttgttac atacatagat atagatctgt tatatcattt | 18480 |
| tttttattaa ttgtgtatat atatatgtgc atagatctgg attacatgat tgtgattatt | 18540 |
| tacatgattt tgttatttac gtatgtatat atgtagatct ggacttttttg gagttgttga | 18600 |
| cttgattgta tttgtgtgtg tatatgtgtg ttctgatctt gatatgttat gtatgtgcag | 18660 |
| ttaattaacc atggctccaa cactcttgac aacccaattc tcaaatccag ctgaagtaac | 18720 |
| cgactttgta gtctacaaag gaaatggtgt taagggttta tcagaaacag gaatcaaagc | 18780 |
| tcttccagaa caatacattc agccacttga agaacgactc atcaacaaat tcgtcaacga | 18840 |
| aacagatgaa gccattccag ttatcgatat gtcgaaccct gatgaggaca gagtcgctga | 18900 |
| agctgtttgt gatgctgctg agaaatgggg gttctttcaa gtgatcaatc atggagttcc | 18960 |
| tttggaagtt cttgatgacg tcaaggctgc gactcacaag ttcttcaatc tccctgttga | 19020 |
| agagaagcgc aagttcacta aagagaattc gctgtcgacg actgttaggt ttgggacgag | 19080 |
| ttttagtcct cttgcagagc aagcgcttga gtggaaagat tatctcagcc tcttctttgt | 19140 |
| ctctgaagct gaagctgaac agttctggcc tgatatctgc aggaatgaaa cgttagagta | 19200 |
| cattaacaag tcaaagaaga tggtgaggag gcttctagag tatttgggaa agaatctcaa | 19260 |
| tgttaaagag cttgacgaga cgaaagaatc actctttatg ggctcgattc gagtcaacct | 19320 |
| taactactac cccatctgcc ctaatccgga cctaacagtt ggtgttggtc gccactcaga | 19380 |
| cgtctcttct ctcaccattc tcttacaaga ccagatcggt ggtctacacg tgcgttctct | 19440 |
| ggcttcaggg aactgggttc acgtgcctcc ggttgctgga tcttttgtga tcaacatcgg | 19500 |
| agatgcgatg cagatcatga gcaatggtct gtacaagagc gtggagcatc gtgtcttagc | 19560 |
| caatggttac aataatagaa tctctgttcc tatctttgtg aacccaaaac cagagtcagt | 19620 |
| tattggtcct ctacctgagg tgattgcaaa cggagaggaa ccgatttaca gagacgtcct | 19680 |
| gtactctgat tacgtcaagt atttcttcag gaaggcacac gatggaaaga aaaccgtcga | 19740 |
| ttacgccaag atctgaggcg cgccctgctt taatgagata tgcgagacgc ctatgatcgc | 19800 |
| atgatatttg ctttcaattc tgttgtgcac gttgtaaaaa acctgagcat gtgtagctca | 19860 |
| gatccttacc gccggtttcg gttcattcta atgaatatat cacccgttac tatcgtattt | 19920 |
| ttatgaataa tattctccgt tcaatttact gattgtggcg cctactaccg gtaattcccg | 19980 |
| ggattagcgg ccgctagtct gtgcgcactt gtatcctgca ggtcaatcgt ttaaacactg | 20040 |
| tacggaccgt ggcctaatag gccggtaccc aacttta | 20077 |

<210> SEQ ID NO 76
<211> LENGTH: 51
<212> TYPE: DNA
<213> ORGANISM: Artificial

```
-continued

<220> FEATURE:
<223> OTHER INFORMATION: primer

<400> SEQUENCE: 76
ggggacaagt ttgtacaaaa aagcaggctt aatggctcca acactcttga c         51

<210> SEQ ID NO 77
<211> LENGTH: 49
<212> TYPE: DNA
<213> ORGANISM: Artificial
<220> FEATURE:
<223> OTHER INFORMATION: primer

<400> SEQUENCE: 77
ggggaccact ttgtacaaga aagctgggta tcagatcttg gcgtaatcg            49

<210> SEQ ID NO 78
<211> LENGTH: 55
<212> TYPE: DNA
<213> ORGANISM: Artificial
<220> FEATURE:
<223> OTHER INFORMATION: primer

<400> SEQUENCE: 78
ggggacaagt ttgtacaaaa aagcaggctc atatttttac aacaattacc aacaa     55

<210> SEQ ID NO 79
<211> LENGTH: 47
<212> TYPE: DNA
<213> ORGANISM: Artificial
<220> FEATURE:
<223> OTHER INFORMATION: primer

<400> SEQUENCE: 79
ggggacaact tttgtataca aagttgtctt gtcatcgtcg tccttgt              47

<210> SEQ ID NO 80
<211> LENGTH: 48
<212> TYPE: DNA
<213> ORGANISM: Artificial
<220> FEATURE:
<223> OTHER INFORMATION: primer

<400> SEQUENCE: 80
ggggacaact tttgtataca aagttgcaat ggctccaaca ctcttgac             48

<210> SEQ ID NO 81
<211> LENGTH: 20
<212> TYPE: DNA
<213> ORGANISM: Artificial
<220> FEATURE:
<223> OTHER INFORMATION: primer

<400> SEQUENCE: 81
ctcagcctct tctttgtctc                                            20

<210> SEQ ID NO 82
<211> LENGTH: 19
<212> TYPE: DNA
<213> ORGANISM: Artificial
<220> FEATURE:
<223> OTHER INFORMATION: primer

<400> SEQUENCE: 82
aagcctcctc accatcttc                                             19
```

```
<210> SEQ ID NO 83
<211> LENGTH: 23
<212> TYPE: DNA
<213> ORGANISM: Artificial
<220> FEATURE:
<223> OTHER INFORMATION: primer

<400> SEQUENCE: 83
atggcgacga caacaacaga agc                                              23

<210> SEQ ID NO 84
<211> LENGTH: 25
<212> TYPE: DNA
<213> ORGANISM: Artificial
<220> FEATURE:
<223> OTHER INFORMATION: primer

<400> SEQUENCE: 84
gccaatcact cctccaattt tcaca                                            25

<210> SEQ ID NO 85
<211> LENGTH: 25
<212> TYPE: DNA
<213> ORGANISM: Artificial
<220> FEATURE:
<223> OTHER INFORMATION: primer

<400> SEQUENCE: 85
gatcgactct ccttgatgat ggcga                                            25

<210> SEQ ID NO 86
<211> LENGTH: 25
<212> TYPE: DNA
<213> ORGANISM: Artificial
<220> FEATURE:
<223> OTHER INFORMATION: primer

<400> SEQUENCE: 86
cgcactcggc caccactttt aaact                                            25

<210> SEQ ID NO 87
<211> LENGTH: 24
<212> TYPE: DNA
<213> ORGANISM: Artificial
<220> FEATURE:
<223> OTHER INFORMATION: primer

<400> SEQUENCE: 87
ctcgcaacaa tcgaactcgc caaa                                             24

<210> SEQ ID NO 88
<211> LENGTH: 25
<212> TYPE: DNA
<213> ORGANISM: Artificial
<220> FEATURE:
<223> OTHER INFORMATION: primer

<400> SEQUENCE: 88
tcggcaaatt ccacaaagag ttcca                                            25
```